US 9,975,887 B2

United States Patent
Das et al.

(10) Patent No.: US 9,975,887 B2
(45) Date of Patent: May 22, 2018

(54) COMPOUNDS AS ROR GAMMA MODULATORS

(71) Applicant: Glenmark Pharmaceuticals S.A., La Chaux-de-Fonds (CH)

(72) Inventors: Sanjib Das, West Bengal (IN); Laxmikant A. Gharat, Maharashtra (IN); Rajendra L. Harde, Maharashtra (IN); Sandeep Y. Shelke, Maharashtra (IN); Shailesh R. Pardeshi, Maharashtra (IN); Abraham Thomas, Maharashtra (IN); Neelima Khairatkar-Joshi, Maharashtra (IN); Daisy M. Shah, Maharashtra (IN); Malini Bajpai, Uttra Pradesh (IN)

(73) Assignee: GLENMARK PHARMACEUTICALS S.A., La Chaux-de-Fonds (CH)

( * ) Notice: Subject to any disclaimer, the term of this patent is extended or adjusted under 35 U.S.C. 154(b) by 0 days. days.

(21) Appl. No.: 15/318,513

(22) PCT Filed: Aug. 2, 2016

(86) PCT No.: PCT/IB2016/054639
§ 371 (c)(1),
(2) Date: Dec. 13, 2016

(87) PCT Pub. No.: WO2017/021879
PCT Pub. Date: Feb. 9, 2017

(65) Prior Publication Data
US 2017/0233380 A1 Aug. 17, 2017

(30) Foreign Application Priority Data
Aug. 3, 2015 (IN) .......................... 2930/MUM/2015

(51) Int. Cl.
| | |
|---|---|
| A61K 31/497 | (2006.01) |
| A61K 31/4427 | (2006.01) |
| A61K 31/4965 | (2006.01) |
| C07D 241/18 | (2006.01) |
| C07D 241/20 | (2006.01) |
| C07D 401/04 | (2006.01) |
| C07D 403/04 | (2006.01) |
| C07D 417/12 | (2006.01) |
| C07D 231/12 | (2006.01) |
| C07D 239/26 | (2006.01) |
| C07D 239/36 | (2006.01) |
| C07D 239/42 | (2006.01) |
| C07D 413/04 | (2006.01) |
| C07D 413/12 | (2006.01) |
| C07D 213/40 | (2006.01) |
| C07D 241/12 | (2006.01) |
| C07D 405/14 | (2006.01) |

(52) U.S. Cl.
CPC ......... *C07D 417/12* (2013.01); *C07D 213/40* (2013.01); *C07D 231/12* (2013.01); *C07D 239/26* (2013.01); *C07D 239/36* (2013.01); *C07D 239/42* (2013.01); *C07D 241/12* (2013.01); *C07D 241/18* (2013.01); *C07D 241/20* (2013.01); *C07D 401/04* (2013.01); *C07D 403/04* (2013.01); *C07D 405/14* (2013.01); *C07D 413/04* (2013.01); *C07D 413/12* (2013.01)

(58) Field of Classification Search
CPC .. C07D 241/18; C07D 241/20; C07D 401/04; C07D 403/04
See application file for complete search history.

(56) References Cited

FOREIGN PATENT DOCUMENTS

| | | |
|---|---|---|
| WO | WO-2012027965 A1 | 3/2012 |
| WO | WO-2012028100 A1 | 3/2012 |
| WO | WO-2012064744 A2 | 5/2012 |
| WO | WO-2012100732 A1 | 8/2012 |
| WO | WO-2012100734 A1 | 8/2012 |
| WO | WO-2012139775 A1 | 10/2012 |
| WO | WO-2013171729 A2 | 11/2013 |
| WO | WO-2015008234 A1 | 1/2015 |

*Primary Examiner* — Brian McDowell
(74) *Attorney, Agent, or Firm* — Blank Rome LLP

(57) ABSTRACT

The present disclosure is directed to compounds of formula (I) and pharmaceutically acceptable salts thereof, wherein ring A, ring B, L, $R^1$, $R^2$, $R^3$, $R^4$, $R^5$, $R^a$, $R^b$, n, m, p and q are as defined herein, which are active as modulators of retinoid-related orphan receptor gamma t (RORγt). These compounds prevent, inhibit, or suppress the action of RORγt and are therefore useful in the treatment of RORγt mediated diseases, disorders, syndromes or conditions such as, e.g., pain, inflammation, COPD, asthma, rheumatoid arthritis, colitis, multiple sclerosis, psoriasis, neurodegenerative diseases and cancer.

27 Claims, No Drawings

COMPOUNDS AS ROR GAMMA MODULATORS

RELATED APPLICATIONS

This application is the U.S. national stage of International Patent Application No. PCT/IB2016/054639, filed Aug. 2, 2016, which claims the benefit of Indian Provisional Application No. 2930/MUM/2015 filed on Aug. 3, 2015 which is hereby incorporated by reference in its entirety.

TECHNICAL FIELD

The present patent application is directed to novel compounds which may be useful as retinoid-related orphan receptor gamma t (RORγt) modulators.

BACKGROUND OF THE INVENTION

Retinoid-related orphan receptors (RORs) are transcription factors which belong to the steroid hormone nuclear receptor super family. The ROR family consists of three members, ROR alpha (RORα), ROR beta (RORβ) and ROR gamma (RORγ), also known as NR1F1, NR1F2 and NR1F3 respectively (and each encoded by a separate gene RORA, RORB and RORC, respectively). RORs contain four principal domains shared by the majority of nuclear receptors: an N-terminal A/B domain, a DNA-binding domain, a hinge domain, and a ligand binding domain. Each ROR gene generates several isoforms which differ only in their N-terminal A/B domain. Two isoforms of RORγ, RORγ1 and RORγt (also known as RORγ2) have been identified.

RORγt is a truncated form of RORγ, lacking the first N-terminal 21 amino acids and is exclusively expressed in cells of the lymphoid lineage and embryonic lymphoid tissue inducers (Sun et al., *Science*, 2000, 288, 2369-2372; Eberl et al., *Nat Immunol.*, 2004, 5: 64-73) in contrast to RORγ which is expressed in multiple tissues (heart, brain, kidney, lung, liver and muscle).

RORγt has been identified as a key regulator of Th17 cell differentiation. Th17 cells are a subset of T helper cells which produce IL-17 and other proinflammatory cytokines and have been shown to have key functions in several mouse autoimmune disease models including experimental autoimmune encephalomyelitis (EAE) and collagen-induced arthritis (CIA). In addition, Th17 cells have also been associated in the pathology of a variety of human inflammatory and autoimmune disorders including multiple sclerosis, rheumatoid arthritis, psoriasis, Crohn's disease and asthma (Jetten et al., *Nucl. Recept. Signal*, 2009, 7:e003; Manel et al., *Nat. Immunol.*, 2008, 9, 641-649). The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (Steinman et al., *J. Exp. Med.*, 2008, 205: 1517-1522; Leung et al., *Cell. Mol. Immunol.*, 2010 7: 182-189). Th17 cells are activated during the disease process and are responsible for recruiting other inflammatory cell types, especially neutrophils, to mediate pathology in the target tissues (Kom et al., *Annu. Rev. Immunol.*, 2009, 27:485-517) and RORγt has been shown to play a critical role in the pathogenic responses of Th17 cells (Ivanov et al., *Cell*, 2006 126: 1121-1133). RORγt deficient mice have shown no Th17 cells and also resulted in amelioration of EAE. The genetic disruption of RORγ in a mouse colitis model also prevented colitis development (Buonocore et al., *Nature*, 2010, 464: 1371-1375). The role of RORγt in the pathogenesis of autoimmune or inflammatory diseases has been well documented in the literature. (Jetten et al., *Adv. Dev. Biol.*, 2006, 16:313-355; Meier et al. Immunity, 2007, 26:643-654; Aloisi et al., *Nat. Rev. Immunol.*, 2006, 6:205-217; Jager et al., *J. Immunol.*, 2009, 183:7169-7177; Serafmi et al., *Brain Pathol.*, 2004, 14: 164-174; Magliozzi et al., *Brain*, 2007, 130: 1089-1104; Barnes et al., *Nat. Rev. Immunol.*, 2008, 8: 183-192).

In addition, RORγt is also shown to play a crucial role in other non-Th17 cells, such as mast cells (Hueber et al., *J Immunol.*, 2010, 184: 3336-3340). RORγt expression and secretion of Th17-type of cytokines has also been reported in NK T-cells (Eberl et al., *Nat. Immunol.*, 2004, 5: 64-73) and gamma-delta T-cells (Sutton et al, *Nat. Immunol.*, 2009, 31: 331-341; Louten et al., *J Allergy Clin. Immunol.*, 2009, 123: 1004-1011), suggesting an important function for RORγt in these cells.

PCT Publication Nos. WO 2012/139775, WO 2012/027965, WO 2012/028100, WO 2012/100732, WO 2012/100734, WO2012/064744, WO 2013/171729 and WO 2015/008234 disclose heterocyclic compounds which are modulators of retinoid-related orphan receptor gamma (RORγ) receptor activity.

In view of the above, a need exists for new therapeutic agents that modulate the activity of RORγt and thus will provide new methods for treating diseases or conditions associated with the modulation of RORγt.

The present application is directed to compounds that are modulators of the RORγt receptor.

SUMMARY OF THE INVENTION

In one aspect, the present invention relates to a compound of formula (I)

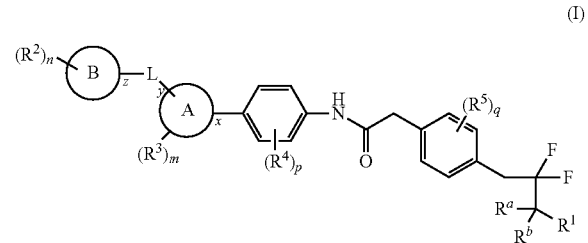

(I)

or a tautomer thereof, stereoisomer thereof or pharmaceutically acceptable salt thereof,
wherein
Ring A is selected from

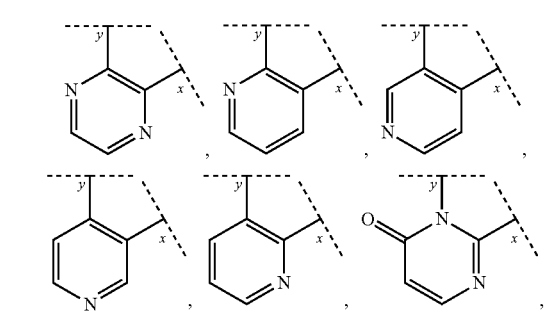

-continued

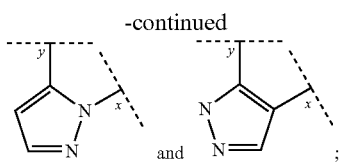

and

Ring B is selected from $C_{3-6}$cycloalkyl, $C_{6-14}$aryl, 3-15 membered heterocyclyl and 5 to 14 membered heteroaryl;

L is absent or is $_y*$—X—$(CR^xR^y)_t$—$*_z$; X is selected from O, $NR^{x1}$ and

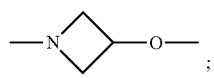

each of x, y and z represents a point of attachment;

$R^1$ is selected from hydroxyl, $C_{1-8}$alkyl and $C_{1-8}$alkoxy;

each occurrence of $R^2$ is independently selected from cyano, halogen, hydroxyl, $C_{1-8}$ alkyl, $C_{1-8}$alkoxy, $C_{1-8}$alkoxy$C_{1-8}$alkyl, halo$C_{1-8}$alkyl, halo$C_{1-8}$alkoxy, hydroxy$C_{1-8}$alkyl, $C(O)C_{1-8}$alkyl, $C_{3-6}$cycloalkyl, $C(O)C_{3-6}$cycloalkyl and 3 to 15 membered heterocyclic ring; each occurrence of $R^3$ is independently selected from halogen, cyano, $C_{1-8}$alkyl; halo$C_{1-8}$alkyl and $C_{3-6}$cycloalkyl;

each occurrence of $R^4$ is independently selected from halogen, cyano, $C_{1-8}$alkyl; halo$C_{1-8}$alkyl and $C_{3-6}$cycloalkyl;

each occurrence of $R^5$ is independently selected from halogen, cyano, $C_{1-8}$alkyl; halo$C_{1-8}$alkyl and $C_{3-6}$cycloalkyl;

$R^a$ and $R^b$, which may be the same or different, are each independently selected from hydrogen and $C_{1-8}$alkyl;

$R^x$ and $R^y$ which may be the same or different, are each independently selected from hydrogen, $C_{1-8}$alkyl and hydroxy$C_{1-8}$alkyl; or $R^x$ and $R^y$ together with the carbon atom to which they are attached, form a 3 to 6 membered cycloalkyl ring;

$R^{x1}$ is selected from hydrogen or $C_{1-8}$alkyl;

'n' is 0, 1, 2 or 3;

'm' is 0, 1 or 2;

'p' is 0, 1 or 2;

'q' is 0, 1, 2 or 3 and

't' is 0, 1, 2 or 3.

The compounds of formula (I) may involve one or more embodiments. Embodiments of formula (I) include compounds of formula (II) and formula (III) as described hereinafter. It is to be understood that the embodiments below are illustrative of the present invention and are not intended to limit the claims to the specific embodiments exemplified. It is also to be understood that the embodiments defined herein may be used independently or in conjunction with any definition and any other embodiment defined herein. Thus the invention contemplates all possible combinations and permutations of the various independently described embodiments. For example, the invention provides compounds of formula (I) as defined above wherein L is absent (according to an embodiment defined below), $R^1$ is hydroxyl, methyl or methoxy (according to another embodiment defined below) and 'p' is 0 (according to yet another embodiment defined below).

According to one embodiment, specifically provided are compounds of formula (I), in which ring B is $C_{3-6}$cycloalkyl (e.g. cyclohexyl), $C_{6-14}$aryl (e.g. phenyl), 3-15 membered heterocyclyl (e.g. 6-oxo-1,6-dihydropyridinyl, piperidinyl, piperazinyl or morpholinyl) or 5 to 14 membered heteroaryl (e.g. isoxazolyl, pyrazolyl, thiazolyl, pyridinyl or pyrimidinyl).

According to another embodiment, specifically provided are compounds of formula (I), in which ring B is cyclohexyl, phenyl, 6-oxo-1,6-dihydropyridinyl, piperidinyl, piperazinyl, morpholinyl, isoxazolyl, pyrazolyl, thiazolyl, pyridinyl or pyrimidinyl.

According to yet another embodiment, specifically provided are compounds of formula (I), in which L is absent.

According to yet another embodiment, specifically provided are compounds of formula (I), in which L is $_y*$—X—$(CR^xR^y)_t$—$*_z$ and 't' is 0.

According to yet another embodiment, specifically provided are compounds of formula (I), in which L is $_y*$—X—$(CR^xR^y)_t$—$*_z$ and 't' is 1. In this embodiment, $R^x$ is hydrogen and $R^y$ is hydrogen, methyl or hydroxymethyl or $R^x$ and $R^y$ together form a cyclopropyl ring.

According to yet another embodiment, specifically provided are compounds of formula (I), in which L is $_y*$—X—$(CR^xR^y)_t$—$*_z$ and 't' is 2. In this embodiment, $R^x$ and $R^y$ are hydrogen.

According to yet another embodiment, specifically provided are compounds of formula (I), in which L is

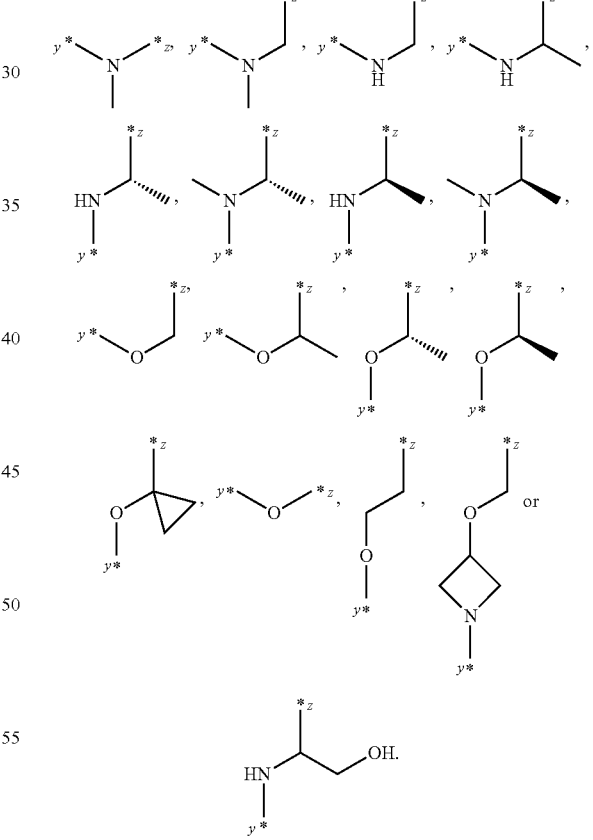

According to yet another embodiment, specifically provided are compounds of formula (I), in which $R^1$ is hydroxyl, $C_{1-8}$alkyl (e.g. methyl) or $C_{1-8}$alkoxy (e.g. methoxy).

According to yet another embodiment, specifically provided are compounds of formula (I), in which $R^1$ is hydroxyl, methyl or methoxy.

According to yet another embodiment, specifically provided are compounds of formula (I), in which each $R^2$ is cyano, halogen (e.g. F or Cl), $C_{1-8}$alkyl (e.g. methyl or ethyl), $C_{1-8}$alkoxy (e.g. methoxy), $C_{1-8}$alkoxy$C_{1-8}$alkyl (e.g. methoxyethyl), halo$C_{1-8}$alkyl (e.g. trifluoromethyl), $C_{3-6}$cycloalkyl (e.g. cyclopropyl), C(O)$C_{1-8}$alkyl (e.g. C(O)methyl), C(O)$C_{3-6}$cycloalkyl (e.g. C(O)cyclopropyl) or 3 to 15 membered heterocyclic ring (e.g. oxetan-3-yl).

According to yet another embodiment, specifically provided are compounds of formula (I), in which each $R^2$ is cyano, F, Cl, methyl, ethyl, methoxy, methoxyethyl, trifluoromethyl, cyclopropyl, C(O)methyl, C(O)cyclopropyl or oxetan-3-yl.

According to yet another embodiment, specifically provided are compounds of formula (I), in each which $R^2$ is cyano, F, Cl, methyl, ethyl, methoxy, methoxyethyl, trifluoromethyl, cyclopropyl, C(O)methyl, C(O)cyclopropyl or oxetan-3-yl and 'n' is 1 or 2.

According to yet another embodiment, specifically provided are compounds of formula (I), in which each $R^3$ is $C_{1-8}$alkyl (e.g. methyl or tert. butyl) or halo$C_{1-8}$alkyl (e.g. trifluoromethyl).

According to yet another embodiment, specifically provided are compounds of formula (I), in which each $R^3$ is methyl, tert-butyl or trifluoromethyl.

According to yet another embodiment, specifically provided are compounds of formula (I), in which $R^3$ is methyl, tert-butyl or trifluoromethyl and 'm' is 1.

According to yet another embodiment, specifically provided are compounds of formula (I), in which $R^4$ is halogen (e.g. F or Cl).

According to yet another embodiment, specifically provided are compounds of formula (I), in which $R^4$ is F.

According to yet another embodiment specifically provided are compounds of formula (I), in which $R^4$ is F and p is 1.

According to yet another embodiment, specifically provided are compounds of formula (I), in which one of $R^a$ and $R^b$ is hydrogen and the other is hydrogen or $C_{1-8}$alkyl (e.g. methyl).

According to yet another embodiment, specifically provided are compounds of formula (I), in which one of $R^a$ and $R^b$ is hydrogen and the other is hydrogen or methyl.

According to yet another embodiment, specifically provided are compounds of formula (I), in which $R^a$ and $R^b$ are hydrogen.

According to yet another embodiment, specifically provided are compounds of formula (I), in which $R^a$ is hydrogen and $R^b$ is $C_{1-8}$alkyl (e.g. methyl).

According to yet another embodiment, specifically provided are compounds of formula (I), in which $R^a$ is hydrogen and $R^b$ is methyl.

According to yet another embodiment, specifically provided are compounds of formula (I), in which $R^1$ is methyl; $R^a$ is hydrogen and $R^b$ is hydrogen.

According to yet another embodiment, specifically provided are compounds of formula (I), in which $R^1$ is methoxy; $R^a$ is hydrogen and $R^b$ is hydrogen.

According to yet another embodiment, specifically provided are compounds of formula (I), in which $R^1$ is hydroxyl; $R^a$ is hydrogen and $R^b$ is methyl.

According to yet another embodiment, specifically provided are compounds of formula (I), in which

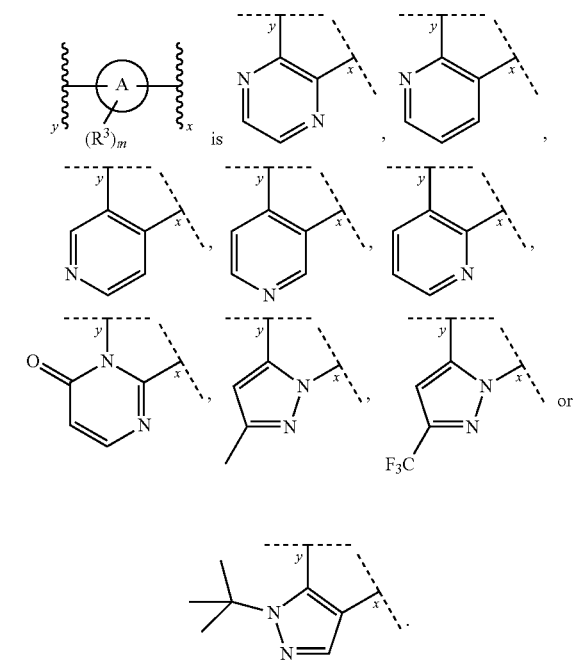

According to yet another embodiment, specifically provided are compounds of formula (I), in which

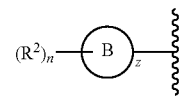

is cyclohexyl, phenyl, 2-chlorophenyl, 3-chlorophenyl, 4-chlorophenyl, 4-cyanophenyl, 2-cyclopropylphenyl, 2,4-dichlorophenyl, 2-chloro-4-fluorophenyl, 4-chloro-2-fluorophenyl, 2-chloro-4-methylphenyl, 2,4-difluorophenyl, 3,4-difluorophenyl, 2,4-dimethylphenyl, 2-ethylphenyl, 2-fluorophenyl, 4-fluorophenyl, 2-fluoro-4-methylphenyl, 4-fluoro-2-methylphenyl, 4-methoxyphenyl, 4-(trifluoromethyl)phenyl, o-tolyl, p-tolyl, 4-acetylpiperazin-1-yl, 4-acetyl-2-methylpiperazin-1-yl, 4-(cyclopropanecarbonyl)piperazin-1-yl, 4,4-difluoropiperidin-1-yl, 4-ethylpiperazin-1-yl, 4-methylpiperazin-1-yl, 4-(2-methoxyethyl)piperazin-1-yl, 1-methyl-6-oxo-1,6-dihydropyridin-3-yl, 4-(oxetan-3-yl)piperazin-1-yl, morpholin-4-yl, (2S,6R)-2,6-dimethylmorpholin-4-yl, 3,5-dimethylisoxazol-4-yl, 1-methyl-1H-pyrazol-4-yl, 4-methylthiazol-5-yl, pyridin-4-yl or pyrimidin-5-yl.

According to yet another embodiment, specifically provided are compounds of formula (I), in which 'n' is 0, 1 or 2.

According to yet another embodiment, specifically provided are compounds of formula (I), in which 'm' is 0 or 1.

According to yet another embodiment, specifically provided are compounds of formula (I), in which 'p' is 0 or 1.

According to yet another embodiment, specifically provided are compounds of formula (I), in which 'q' is 0.

According to yet another embodiment, specifically provided are compounds of formula (I), in which Ring A is

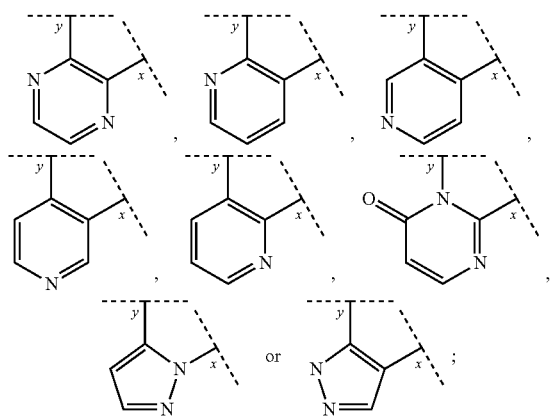

Ring B is cyclohexyl, phenyl, 6-oxo-1,6-dihydropyridinyl, piperidinyl, piperazinyl, morpholinyl, isoxazolyl, pyrazolyl, thiazolyl, pyridinyl or pyrimidinyl;

L is absent or is

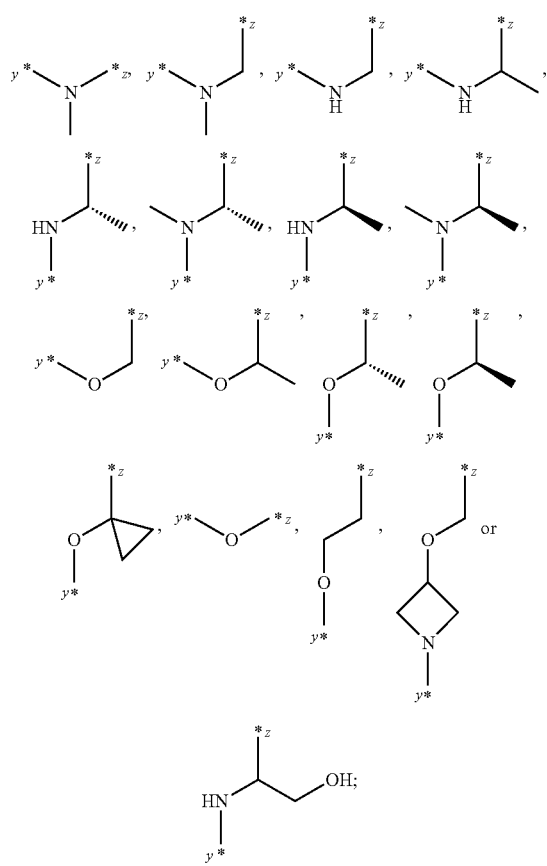

$R^1$ is hydroxyl, methyl or methoxy;
$R^2$ is cyano, F, Cl, methyl, ethyl, methoxy, methoxyethyl, trifluoromethyl, cyclopropyl, C(O)methyl, C(O)cyclopropyl or oxetan-3-yl;
$R^3$ is methyl, tert. butyl or trifluoromethyl;
$R^4$ is F;
$R^a$ is hydrogen;
$R^b$ is hydrogen or methyl;
'n' is 0, 1 or 2;
'm' is 0 or 1;
'p' is 0 or 1; and
'q' is 0.

According to yet another embodiment, specifically provided are compounds of formula (I), in which

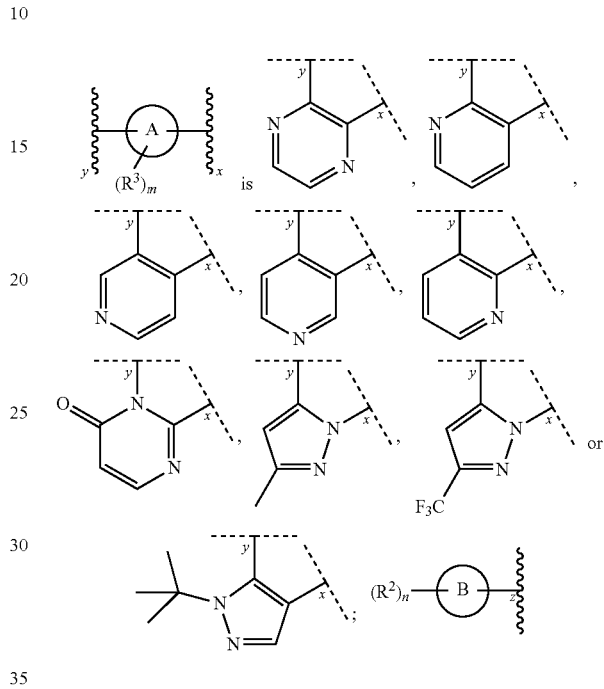

is cyclohexyl, phenyl, 2-chlorophenyl, 3-chlorophenyl, 4-chlorophenyl, 4-cyanophenyl, 2-cyclopropylphenyl, 2,4-dichlorophenyl, 2-chloro-4-fluorophenyl, 4-chloro-2-fluorophenyl, 2-chloro-4-methylphenyl, 2,4-difluorophenyl, 3,4-difluorophenyl, 2,4-dimethylphenyl, 2-ethylphenyl, 2-fluorophenyl, 4-fluorophenyl, 2-fluoro-4-methylphenyl, 4-fluoro-2-methylphenyl, 4-methoxyphenyl, 4-(trifluoromethyl)phenyl, o-tolyl, p-tolyl, 4-acetylpiperazin-1-yl, 4-acetyl-2-methylpiperazin-1-yl, 4-(cyclopropanecarbonyl)piperazin-1-yl, 4,4-difluoropiperidin-1-yl, 4-ethylpiperazin-1-yl, 4-methylpiperazin-1-yl, 4-(2-methoxyethyl)piperazin-1-yl, 1-methyl-6-oxo-1,6-dihydropyridin-3-yl, 4-(oxetan-3-yl)piperazin-1-yl, morpholin-4-yl, (2S,6R)-2,6-dimethylmorpholin-4-yl, 3,5-dimethylisoxazol-4-yl, 1-methyl-1H-pyrazol-4-yl, 4-methylthiazol-5-yl, pyridin-4-yl or pyrimidin-5-yl;

L is absent or is

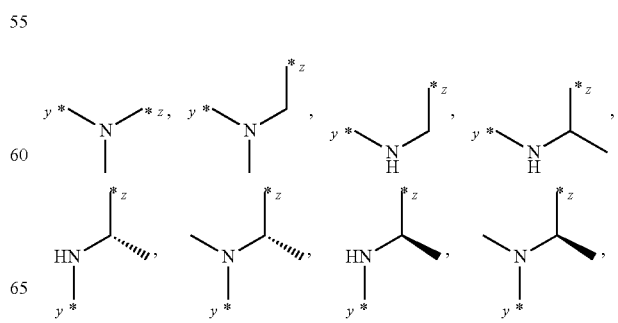

-continued

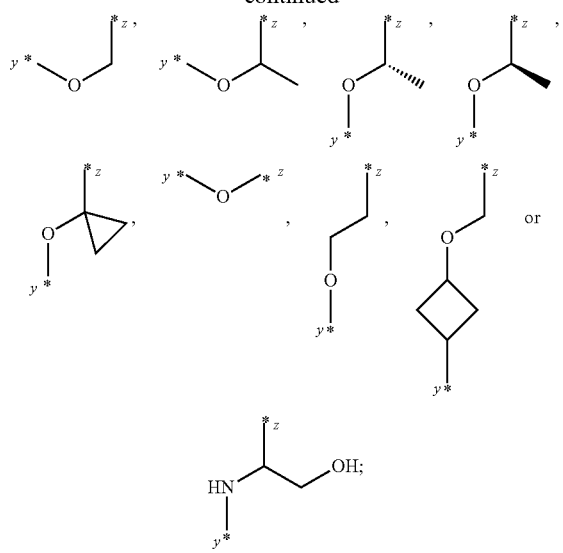

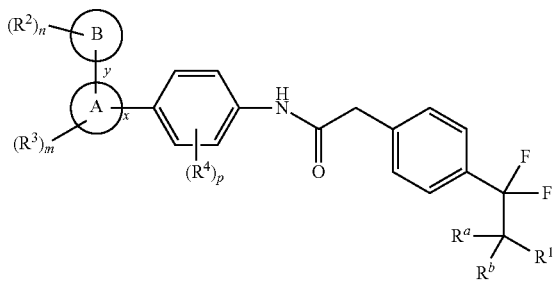

$R^1$ is hydroxyl, methyl or methoxy;
$R^4$ is F;
$R^a$ is hydrogen;
$R^b$ is hydrogen or methyl;
'p' is 0 or 1; and
'q' is 0.

According to an embodiment, specifically provided are compounds of formula (I) with an $IC_{50}$ value of less than 1000 nM, preferably less than 500 nM, more preferably less than 100 nM, with respect to RORγt activity.

Further embodiments relating to groups ring A, ring B, L, $R^1$, $R^2$, $R^3$, $R^4$, $R^5$, $R^a$, $R^b$, n, m, p and q (and groups defined therein) are described hereinafter in relation to the compounds of formula (II), or compounds of Formula (III). It is to be understood that these embodiments are not limited to use in conjunction with formula (II) or (III), but apply independently and individually to the compounds of formula (I). For example, in an embodiment described hereinafter, the invention specifically provides compounds of formula (II) or (III) in which 'm' is 0 or 1 and consequently there is also provided a compound of formula (I) in which 'm' is 0 or 1.

The invention also provides a compound of formula (II), which is an embodiment of a compound of formula (I).

Accordingly the invention provides a compound of formula (II)

(II)

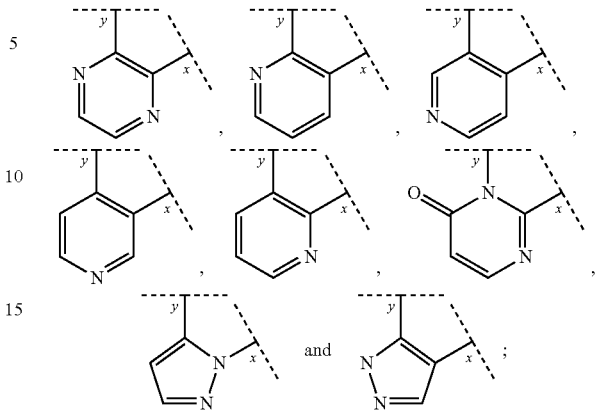

or a tautomer thereof, stereoisomer thereof or pharmaceutically acceptable salt thereof, wherein Ring A is selected from Ring B is selected from $C_{3-6}$cycloalkyl, $C_{6-14}$aryl, 3-15 membered heterocyclyl and 5 to 14 membered heteroaryl;
each of x and y represents a point of attachment;
$R^1$ is selected from hydroxyl, $C_{1-8}$alkyl and $C_{1-8}$alkoxy;
each occurrence of $R^2$ is independently selected from cyano, halogen, hydroxyl, $C_{1-8}$alkyl, $C_{1-8}$alkoxy, $C_{1-8}$alkoxy$C_{1-8}$alkyl, halo$C_{1-8}$alkyl, halo$C_{1-8}$alkoxy, hydroxy$C_{1-8}$alkyl, C(O)$C_{1-8}$alkyl, $C_{3-6}$cycloalkyl, C(O)$C_{3-6}$cycloalkyl and 3 to 15 membered heterocyclic ring; each occurrence of $R^3$ is independently selected from halogen, cyano, $C_{1-8}$alkyl; halo$C_{1-8}$alkyl and $C_{3-6}$cycloalkyl;
each occurrence of $R^4$ is independently selected from halogen, cyano, $C_{1-8}$alkyl; halo$C_{1-8}$alkyl and $C_{3-6}$cycloalkyl;
$R^a$ and $R^b$, which may be same or different, are each independently selected from hydrogen and $C_{1-8}$alkyl;
'n' is 0, 1, 2 or 3;
'm' is 0, 1 or 2; and
'p' is 0, 1 or 2.

The compounds of formula (II) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, any other embodiment defined herein. Thus the invention contemplates all possible combinations and permutations of the various independently described embodiments. For example, the invention provides compounds of formula (II) as defined above wherein $R^1$ is hydroxyl, methyl or methoxy (according to an embodiment defined below), $R^a$ is hydrogen (according to another embodiment defined below) and 'm' is 0 or 1 (according to yet another embodiment defined below).

According to one embodiment, specifically provided are compounds of formula (II), in which ring B is $C_{6-14}$aryl (e.g. phenyl), 3-15 membered heterocyclyl (e.g. 6-oxo-1,6-dihydropyridinyl, piperidinyl, piperazinyl or morpholinyl) or 5 to 14 membered heteroaryl (e.g. pyrazolyl, pyridinyl or pyrimidinyl).

According to another embodiment, specifically provided are compounds of formula (II), in which ring B is phenyl, 6-oxo-1,6-dihydropyridin-3-yl, piperidinyl, piperazinyl, morpholinyl, pyrazolyl, pyridinyl or pyrimidinyl.

According to yet another embodiment, specifically provided are compounds of formula (II), in which $R^1$ is hydroxyl, $C_{1-8}$alkyl (e.g. methyl) or $C_{1-8}$alkoxy (e.g. methoxy).

According to yet another embodiment specifically provided are compounds of formula (II), in which $R^1$ is hydroxyl, methyl or methoxy.

According to yet another embodiment, specifically provided are compounds of formula (II), in which each $R^2$ is cyano, halogen (e.g. F or Cl), $C_{1-8}$alkyl (e.g. methyl or ethyl), $C_{1-8}$alkoxy (e.g. methoxy), $C_{1-8}$alkoxy$C_{1-8}$alkyl (e.g. methoxyethyl), halo$C_{1-8}$alkyl (e.g. trifluoromethyl), C(O)$C_{1-8}$alkyl (e.g. C(O)methyl), C(O)$C_{3-6}$cycloalkyl (e.g. C(O)cyclopropyl) or 3 to 15 membered heterocyclic ring (e.g. oxetan-3-yl).

According to yet another embodiment, specifically provided are compounds of formula (II), in which each $R^2$ is cyano, F, Cl, methyl, ethyl, methoxy, methoxyethyl, trifluoromethyl, C(O)methyl, C(O)cyclopropyl or oxetan-3-yl.

According to yet another embodiment, specifically provided are compounds of formula (II), in each which $R^2$ is cyano, F, Cl, methyl, ethyl, methoxy, methoxyethyl, trifluoromethyl, C(O)methyl, C(O)cyclopropyl or oxetan-3-yl, and 'n' is 1 or 2.

According to yet another embodiment, specifically provided are compounds of formula (II), in which each $R^3$ is $C_{1-8}$alkyl (e.g. methyl or tert-butyl) or halo$C_{1-8}$alkyl (e.g. trifluoromethyl).

According to yet another embodiment, specifically provided are compounds of formula (II), in which each $R^3$ is methyl, tert-butyl or trifluoromethyl.

According to yet another embodiment, specifically provided are compounds of formula (II), in which $R^3$ is methyl, tert-butyl or trifluoromethyl and 'm' is 1.

According to yet another embodiment specifically provided are compounds of formula (II), in which $R^4$ is halogen (e.g. F or Cl).

According to yet another embodiment, specifically provided are compounds of formula (II), in which $R^4$ is F.

According to yet another embodiment, specifically provided are compounds of formula (II), in which $R^4$ is F and 'p' is 1.

According to yet another embodiment, specifically provided are compounds of formula (II), in which one of $R^a$ and $R^b$ is hydrogen and the other is hydrogen or $C_{1-8}$alkyl (e.g. methyl).

According to yet another embodiment, specifically provided are compounds of formula (II), in which one of $R^a$ and $R^b$ is hydrogen and the other is hydrogen or methyl.

According to yet another embodiment specifically provided are compounds of formula (II), in which $R^a$ and $R^b$ are hydrogen.

According to yet another embodiment, specifically provided are compounds of formula (II), in which $R^a$ is hydrogen and $R^b$ is $C_{1-8}$alkyl (e.g. methyl).

According to yet another embodiment, specifically provided are compounds of formula (II), in which $R^a$ is hydrogen and $R^b$ is methyl.

According to yet another embodiment, specifically provided are compounds of formula (II), in which $R^1$ is methyl; $R^a$ is hydrogen and $R^b$ is hydrogen.

According to yet another embodiment specifically provided are compounds of formula (II), in which $R^1$ is methoxy; $R^a$ is hydrogen and $R^b$ is hydrogen.

According to yet another embodiment, specifically provided are compounds of formula (II), in which $R^1$ is hydroxyl; $R^a$ is hydrogen and $R^b$ is methyl.

According to yet another embodiment, specifically provided are compounds of formula (II), in which

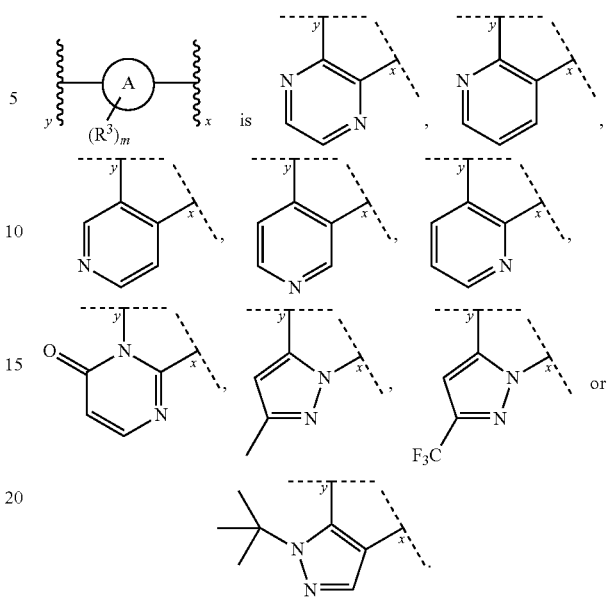

According to yet another embodiment, specifically provided are compounds of formula (II), in which

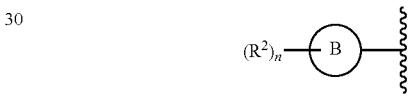

is phenyl, 2-chlorophenyl, 3-chlorophenyl, 4-chlorophenyl, 4-cyanophenyl, 2,4-dichlorophenyl, 2-chloro-4-fluorophenyl, 4-chloro-2-fluorophenyl, 2,4-difluorophenyl, 3,4-difluorophenyl, 2,4-dimethylphenyl, 2-ethylphenyl, 2-fluorophenyl, 4-fluorophenyl, 2-fluoro-4-methylphenyl, 4-fluoro-2-methylphenyl, 4-methoxyphenyl, 4-(trifluoromethyl)phenyl, o-tolyl, p-tolyl, 4-acetylpiperazin-1-yl, 4-acetyl-2-methylpiperazin-1-yl, 4-(cyclopropanecarbonyl)piperazin-1-yl, 4,4-difluoropiperidin-1-yl, 4-ethylpiperazin-1-yl, 4-methylpiperazin-1-yl, 4-(2-methoxyethyl)piperazin-1-yl, 1-methyl-6-oxo-1,6-dihydropyridin-3-yl, 4-(oxetan-3-yl)piperazin-1-yl, morpholin-4-yl, (2S,6R)-2,6-dimethylmorpholin-4-yl, 1-methyl-1H-pyrazol-4-yl, pyridin-4-yl or pyrimidin-5-yl.

According to yet another embodiment, specifically provided are compounds of formula (II), in which 'n' is 0, 1 or 2.

According to yet another embodiment, specifically provided are compounds of formula (II), in which 'm' is 0 or 1.

According to yet another embodiment, specifically provided are compounds of formula (II), in which 'p' is 0 or 1.

According to yet another embodiment, specifically provided are compounds of formula (II), in which
Ring A

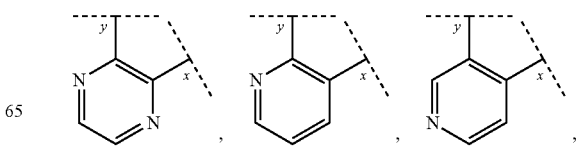

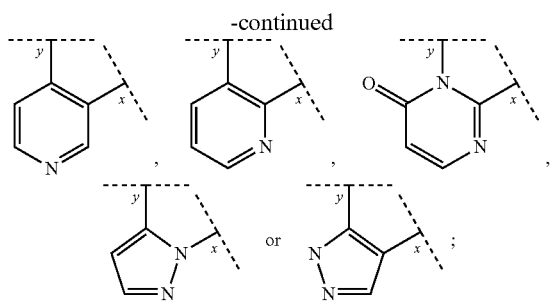

Ring B is phenyl, 6-oxo-1,6-dihydropyridinyl, piperidinyl, piperazinyl, morpholinyl, pyrazolyl, pyridinyl or pyrimidinyl;

$R^1$ is hydroxyl, methyl or methoxy;

$R^2$ is cyano, F, Cl, methyl, ethyl, methoxy, methoxyethyl, trifluoromethyl, C(O)methyl, C(O)cyclopropyl or oxetan-3-yl;

$R^3$ is methyl, tert. butyl or trifluoromethyl;

$R^4$ is F;

$R^a$ is hydrogen;

$R^b$ is hydrogen or methyl;

'n' is 0, 1 or 2;

'm' is 0 or 1; and

'p' is 0 or 1.

According to yet another embodiment, specifically provided are compounds of formula (II), in which

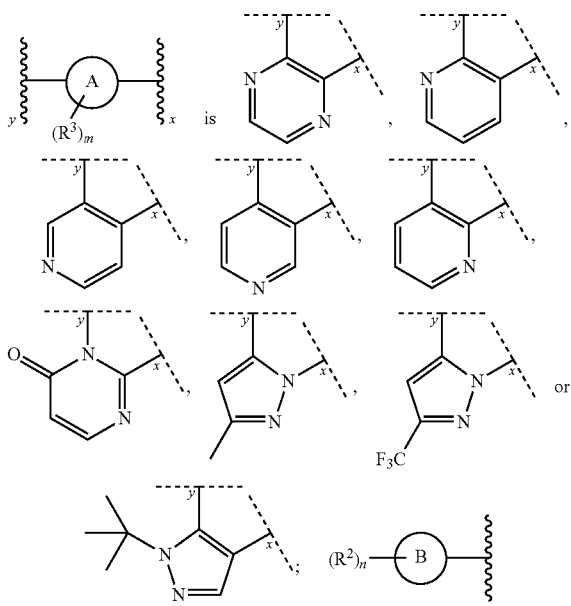

is phenyl, 2-chlorophenyl, 3-chlorophenyl, 4-chlorophenyl, 4-cyanophenyl, 2,4-dichlorophenyl, 2-chloro-4-fluorophenyl, 4-chloro-2-fluorophenyl, 2,4-difluorophenyl, 3,4-difluorophenyl, 2,4-dimethylphenyl, 2-ethylphenyl, 2-fluorophenyl, 4-fluorophenyl, 2-fluoro-4-methylphenyl, 4-fluoro-2-methylphenyl, 4-methoxyphenyl, 4-(trifluoromethyl)phenyl, o-tolyl, p-tolyl, 4-acetylpiperazin-1-yl, 4-acetyl-2-methylpiperazin-1-yl, 4-(cyclopropanecarbonyl)piperazin-1-yl, 4,4-difluoropiperidin-1-yl, 4-ethylpiperazin-1-yl, 4-methylpiperazin-1-yl, 4-(2-methoxyethyl)piperazin-1-yl, 1-methyl-6-oxo-1,6-dihydropyridin-3-yl, 4-(oxetan-3-yl) piperazin-1-yl, morpholin-4-yl, (2S,6R)-2,6-dimethylmorpholin-4-yl, 1-methyl-1H-pyrazol-4-yl, pyridin-4-yl or pyrimidin-5-yl;

$R^1$ is hydroxyl, methyl or methoxy;

$R^4$ is F;

$R^a$ is hydrogen;

$R^b$ is hydrogen or methyl; and

'p' is 0 or 1.

According to an embodiment, specifically provided are compounds of formula (II) with an $IC_{50}$ value of less than 1000 nM, preferably less than 500 nM, more preferably less than 100 nM, with respect to RORγt activity.

The invention also provides a compound of formula (III), which is an embodiment of a compound of formula (I).

Accordingly the invention provides a compound of formula (III)

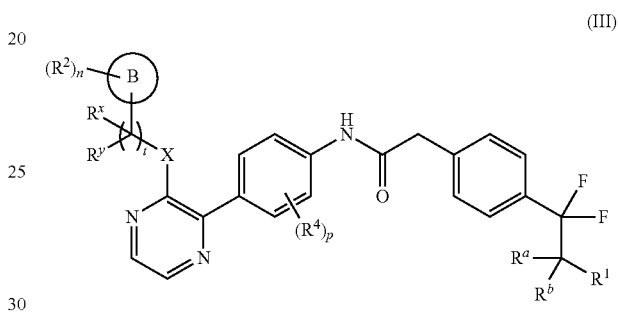

or a tautomer thereof, a stereoisomer thereof or a pharmaceutically acceptable salt thereof, wherein Ring B is selected from $C_{3-6}$cycloalkyl, $C_{6-14}$aryl, 3-15 membered heterocyclyl and 5 to 14 membered heteroaryl;

X is selected from —O—, —NR$^{x1}$— and

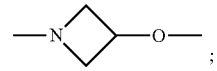

$R^1$ is selected from hydroxyl, $C_{1-8}$alkyl and $C_{1-8}$alkoxy;

each occurrence of $R^2$ is independently selected from cyano, halogen, hydroxyl, $C_{1-8}$alkyl, $C_{1-8}$alkoxy, $C_{1-8}$alkoxyC$_{1-8}$alkyl, haloC$_{1-8}$alkyl, haloC$_{1-8}$alkoxy, hydroxyC$_{1-8}$alkyl, C(O)C$_{1-8}$alkyl, $C_{3-6}$cycloalkyl, C(O)C$_{3-6}$cycloalkyl and 3 to 15 membered heterocyclic ring;

each occurrence of $R^4$ is independently selected from halogen, cyano, $C_{1-8}$alkyl; haloC$_{1-8}$alkyl and $C_{3-6}$cycloalkyl;

$R^a$ and $R^b$, which may be the same or different, are each independently selected from hydrogen and $C_{1-8}$alkyl;

$R^x$ and $R^y$ which may be the same or different, are each independently selected from hydrogen, $C_{1-8}$alkyl and hydroxyC$_{1-8}$alkyl; or $R^x$ and $R^y$ together with the carbon atom to which they are attached, form a 3 to 6 membered cycloalkyl ring;

$R^{x1}$ is selected from hydrogen or $C_{1-8}$alkyl;

'n' is 0, 1, 2 or 3;

'p' is 0, 1 or 2; and

't' is 0, 1, 2 or 3.

The compounds of formula (III) may involve one or more embodiments. It is to be understood that the embodiments below are illustrative of the present invention and are not intended to limit the claims to the specific embodiments exemplified. It is also to be understood that the embodiments defined herein may be used independently or in conjunction with any other embodiment defined herein. Thus the invention contemplates all possible combinations and permutations of the various independently described embodiments. For example, the invention provides compounds of formula (III) as defined above wherein X is O (according to an embodiment defined below), $R^1$ is hydroxyl or methyl (according to another embodiment defined below) and 'n' is 0, 1 or 2 (according to yet another embodiment defined below).

According to one embodiment, specifically provided are compounds of formula (III), in which ring B is $C_{3-6}$cycloalkyl (e.g. cyclohexyl), $C_{6-14}$aryl (e.g. phenyl), 3-15 membered heterocyclyl (e.g. piperazinyl) or 5 to 14 membered heteroaryl (e.g. isoxazolyl or thiazolyl).

According to another embodiment, specifically provided are compounds of formula (III), in which ring B is cyclohexyl, phenyl, piperazinyl, isoxazolyl or thiazolyl.

According to yet another embodiment specifically provided are compounds of formula (III), in which X is O.

According to yet another embodiment specifically provided are compounds of formula (III), in which X is $NR^{x1}$. In this embodiment $NR^{x1}$ is hydrogen or methyl.

According to yet another embodiment specifically provided are compounds of formula (III), in which X is —O—, —NH—, —N(CH$_3$)— or

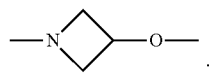

According to yet another embodiment specifically provided are compounds of formula (III), in which $R^x$ is hydrogen; $R^y$ is hydrogen; and t is 1 or 2.

According to yet another embodiment specifically provided are compounds of formula (III), in which $R^x$ is hydrogen; $R^y$ is methyl or hydroxymethyl; or $R^x$ and $R^y$ together with the carbon atom to which they are attached, form a cyclopropyl ring; and 't' is 1.

According to yet another embodiment, specifically provided are compounds of formula (III), in which

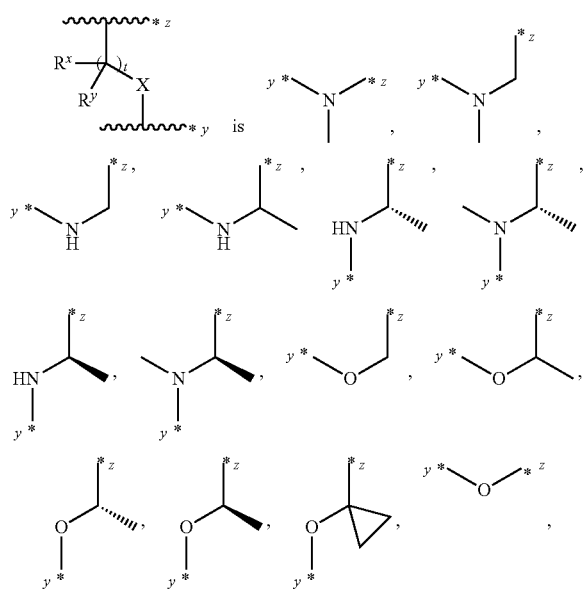

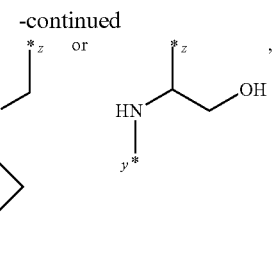

wherein y and z represents point of attachment.

According to yet another embodiment, specifically provided are compounds of formula (III), in which $R^1$ is hydroxyl or $C_{1-8}$alkyl (e.g. methyl).

According to yet another embodiment, specifically provided are compounds of formula (III), in which $R^1$ is hydroxyl or methyl.

According to yet another embodiment, specifically provided are compounds of formula (III), in which each $R^2$ is halogen (e.g. F or Cl), $C_{1-8}$alkyl (e.g. methyl) or $C_{3-6}$cycloalkyl (e.g. cyclopropyl).

According to yet another embodiment, specifically provided are compounds of formula (III), in which each $R^2$ is F, Cl, methyl or cyclopropyl.

According to yet another embodiment specifically provided are compounds of formula (III), in which each $R^2$ is F, Cl, methyl or cyclopropyl and 'n' is 1 or 2.

According to yet another embodiment specifically provided are compounds of formula (III), in which $R^4$ is halogen (e.g. F or Cl).

According to yet another embodiment specifically provided are compounds of formula (III), in which $R^4$ is F.

According to yet another embodiment specifically provided are compounds of formula (III), in which $R^4$ is F and 'p' is 1.

According to yet another embodiment, specifically provided are compounds of formula (III), in which one of $R^a$ and $R^b$ is hydrogen and the other is hydrogen or $C_{1-8}$alkyl (e.g. methyl).

According to yet another embodiment specifically provided are compounds of formula (III), in which one of $R^a$ and $R^b$ is hydrogen and the other is hydrogen or methyl.

According to yet another embodiment specifically provided are compounds of formula (III), in which $R^a$ and $R^b$ are hydrogen.

According to yet another embodiment, specifically provided are compounds of formula (III), in which $R^a$ is hydrogen and $R^b$ is $C_{1-8}$alkyl (e.g. methyl).

According to yet another embodiment, specifically provided are compounds of formula (III), in which $R^a$ is hydrogen and $R^b$ is methyl.

According to yet another embodiment specifically provided are compounds of formula (III), in which $R^1$ is methyl; $R^a$ is hydrogen and $R^b$ is hydrogen.

According to yet another embodiment specifically provided are compounds of formula (III), in which $R^1$ is methoxy; $R^a$ is hydrogen and $R^b$ is hydrogen.

According to yet another embodiment specifically provided are compounds of formula (III), in which $R^1$ is hydroxyl; $R^a$ is hydrogen and $R^b$ is methyl.

According to yet another embodiment, specifically provided are compounds of formula (III), in which

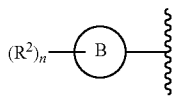

is cyclohexyl, phenyl, 2-chlorophenyl, 3-chlorophenyl, 4-chlorophenyl, 2-cyclopropylphenyl, 2-chloro-4-fluorophenyl, 2-chloro-4-methylphenyl, 2,4-dimethylphenyl, 4-fluoro-2-methylphenyl, 3,5-dimethylisoxazol-4-yl or 4-methylthiazol-5-yl.

According to yet another embodiment, specifically provided are compounds of formula (III), in which 'n' is 0, 1 or 2.

According to yet another embodiment, specifically provided are compounds of formula (III), in which Ring B is cyclohexyl, phenyl, piperazinyl, isoxazolyl or thiazolyl;

X is —O—, —NH—, —N(CH$_3$)— or

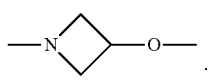

$R^1$ is hydroxyl, methyl or methoxy;
$R^2$ is F, Cl, methyl or cyclopropyl;
$R^4$ is F;
$R^a$ is hydrogen; $R^b$ is hydrogen or methyl;
$R^x$ is hydrogen; $R^y$ is hydrogen, methyl or hydroxymethyl; or $R^x$ and $R^y$ together form a cyclopropyl ring;
'n' is 0, 1 or 2;
'p' is 0 or 1; and
't' is 0, 1 or 2.

According to yet another embodiment, specifically provided are compounds of formula (III), in which

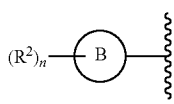

is cyclohexyl, phenyl, 2-chlorophenyl, 3-chlorophenyl, 4-chlorophenyl, 2-cyclopropylphenyl, 2-chloro-4-fluorophenyl, 2-chloro-4-methylphenyl, 2,4-dimethylphenyl, 4-fluoro-2-methylphenyl, 3,5-dimethylisoxazol-4-yl or 4-methylthiazol-5-yl;

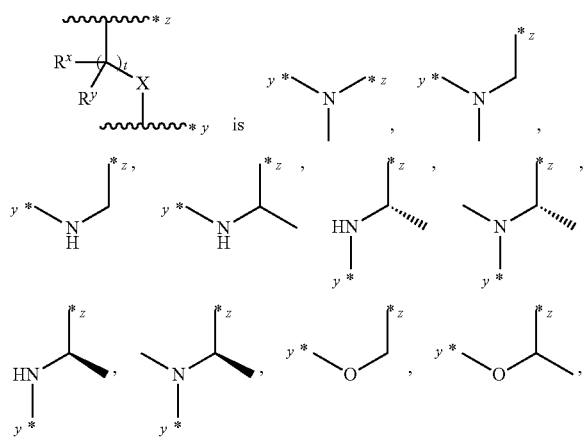

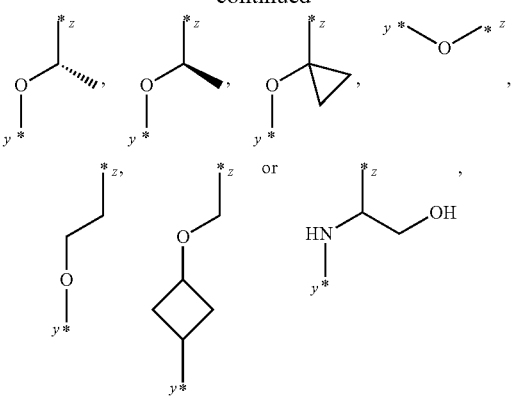

y and z represents point of attachment;
$R^1$ is hydroxyl, methyl or methoxy;
$R^4$ is F;
$R^a$ is hydrogen;
$R^b$ is hydrogen or methyl; and
'p' is 0 or 1.

According to an embodiment, specifically provided are compounds of formula (III) with an IC$_{50}$ value of less than 1000 nM, preferably less than 500 nM, more preferably less than 100 nM, with respect to RORγt activity.

Compounds of the present invention include the compounds in Examples 1-99. It should be understood that the formulas (I), (II) and (III) structurally encompasses all geometrical isomers, stereoisomers, enantiomers and diastereomers, N-oxides, and pharmaceutically acceptable salts that may be contemplated from the chemical structure of the genera described herein.

The present application also provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described herein may be associated with a pharmaceutically acceptable excipient (such as a carrier or a diluent) or be diluted by a carrier, or enclosed within a carrier which can be in the form of a tablet, capsule, sachet, paper or other container.

The compounds and pharmaceutical compositions of the present invention are useful for inhibiting the activity of RORγt. Thus, the present invention further provides a method of inhibiting RORγt in a subject in need thereof by administering to the subject one or more compounds described herein in an amount effective to cause inhibition of such receptor.

In a further aspect, the present invention relates to a method of treating a disease, disorder or condition modulated by RORγt, such as an autoimmune disease, inflammatory disease, respiratory disorder, pain and cancer comprising administering to a subject in need thereof a compound according to any of the embodiments described herein.

In another aspect, the present invention relates to a method of treating a disease, disorder or condition modulated by RORγt, such as chronic obstructive pulmonary disease (COPD), asthma, cough, pain, inflammatory pain, chronic pain, acute pain, arthritis, osteoarthritis, multiple sclerosis, rheumatoid arthritis, colitis, ulcerative colitis and inflammatory bowel disease, comprising administering to a subject in need thereof a compound according to any of the embodiments described herein.

DETAILED DESCRIPTION OF THE INVENTION

Definitions

The terms "halogen" or "halo" means fluorine (fluoro), chlorine (chloro), bromine (bromo), or iodine (iodo).

The term "alkyl" refers to a hydrocarbon chain radical that includes solely carbon and hydrogen atoms in the backbone, containing no unsaturation, having from one to eight carbon atoms (i.e. $C_{1-8}$alkyl), and which is attached to the rest of the molecule by a single bond, such as, but not limited to, methyl, ethyl, n-propyl, 1-methylethyl (isopropyl), n-butyl, n-pentyl, and 1,1-dimethylethyl (t-butyl). The term "$C_{1-8}$alkyl" refers to an alkyl chain having 1 to 8 carbon atoms. The term "$C_{1-4}$alkyl" refers to an alkyl chain having 1 to 4 carbon atoms.

Unless set forth or recited to the contrary, all alkyl groups described or claimed herein may be straight chain or branched.

The term "alkoxy" denotes an alkyl group attached via an oxygen linkage to the rest of the molecule (e.g. $C_{1-8}$ alkoxy). Representative examples of such groups are —$OCH_3$ and —$OC_2H_5$. Unless set forth or recited to the contrary, all alkoxy groups described or claimed herein may be straight chain or branched.

The term "haloalkyl" refers to at least one halo group (selected from F, Cl, Br or I), linked to an alkyl group as defined above (i.e. halo$C_{1-8}$alkyl). Examples of such haloalkyl groups include, but are not limited to, trifluoromethyl, difluoromethyl and fluoromethyl groups. The term "halo$C_{1-8}$alkyl" refers to at least one halo group linked an alkyl chain having 1 to 8 carbon atoms. Unless set forth or recited to the contrary, all haloalkyl groups described herein may be straight chain or branched.

The term "haloalkoxy" refers to an alkoxy group substituted with one or more halogen atoms (i.e. halo$C_{1-8}$alkoxy). Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichlorormethoxy, trichloromethoxy and 1-bromoethoxy. Unless set forth or recited to the contrary, all haloalkoxy groups described herein may be straight chain or branched.

The term "hydroxy$C_{1-8}$alkyl" refers to an $C_{1-8}$alkyl group as defined above wherein one to three hydrogen atoms on different carbon atoms are replaced by hydroxyl groups (i.e. hydroxy$C_{1-4}$alkyl). Examples of hydroxy$C_{1-8}$alkyl moieties include, but are not limited to —$CH_2OH$ and —$C_2H_4OH$.

The term "$C_{1-8}$alkoxy$C_{1-8}$alkyl" refers to an $C_{1-8}$alkyl group as defined above wherein one to three hydrogen atoms on different carbon atoms are replaced by alkoxy group as defined above. Examples of $C_{1-8}$alkoxy$C_{1-8}$alkyl moieties include, but are not limited to —$CH_2OCH_3$ and —$C_2H_4OCH_3$.

The term "cycloalkyl" denotes a non-aromatic mono or multicyclic ring system of 3 to about 12 carbon atoms, (i.e. $C_{3-12}$cycloalkyl). Examples of monocyclic cycloalkyl include but are not limited to cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups or spirobicyclic groups, e.g., spiro(4,4)non-2-yl. The term "$C_{3-6}$cycloalkyl" refers to the cyclic ring having 3 to 6 carbon atoms. Examples of "$C_{3-6}$ cycloalkyl" include but are not limited to cyclopropyl, cyclobutyl, cyclopentyl, or cyclohexyl.

The term "cycloalkylalkyl" refers to a cyclic ring-containing radical having 3 to about 6 carbon atoms directly attached to an alkyl group (e.g. $C_{3-6}$cycloalkyl$C_{1-8}$alkyl). The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "aryl" refers to an aromatic radical having 6 to 14 carbon atoms (i.e. $C_{6-14}$aryl), including monocyclic, bicyclic and tricyclic aromatic systems, such as phenyl, naphthyl, tetrahydronapthyl, indanyl, and biphenyl.

The term "heterocyclic ring" or "heterocyclyl" unless otherwise specified refers to substituted or unsubstituted non-aromatic 3 to 15 membered ring radical (i.e. 3 to 15 membered heterocyclyl) which consists of carbon atoms and from one to five hetero atoms selected from nitrogen, phosphorus, oxygen and sulfur. The heterocyclic ring radical may be a mono-, bi- or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; also, unless otherwise constrained by the definition the heterocyclic ring or heterocyclyl may optionally contain one or more olefinic bond(s). Examples of such heterocyclic ring radicals include, but are not limited to azepinyl, azetidinyl, benzodioxolyl, benzodioxanyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, 6-oxo-1,6-dihydropyridin-3-yl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl or tetrahydrofuranyl, tetrahydropyranyl, thiazolinyl, thiazolidinyl, thiamorpholinyl, thiamorpholinyl sulfoxide and thiamorpholinyl sulfone. The heterocyclic ring radical may be attached to the main structure at any heteroatom or carbon atom that results in the creation of a stable structure. Unless set forth or recited to the contrary, all heterocyclyl groups described or claimed herein may be substituted or unsubstituted.

The term "heteroaryl" unless otherwise specified refers to 5 to 14 membered aromatic heterocyclic ring radical with one or more heteroatom(s) independently selected from N, O or S (i.e. 5 to 14 membered heteroaryl). The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, oxadiazolyl, thiazolyl, isothiazolyl, pyridyl, pyrimidinyl, pyrazinyl, pyridazinyl, pyrazolyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl and phthalazinyl.

The term "pharmaceutically acceptable salt" includes salts prepared from pharmaceutically acceptable bases or acids including inorganic or organic bases and inorganic or organic acids. Examples of such salts include, but are not limited to, acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide and valerate. Examples of salts derived from inorganic bases include, but are not limited to, aluminum, ammonium, calcium, copper, ferric, ferrous, lithium, magnesium, manganic, mangamous, potassium, sodium, and zinc.

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

The compounds of formula (I), (II) or (III) may contain asymmetric or chiral centers, and, therefore, exist in different stereoisomeric forms. It is intended that all stereoisomeric forms of the compounds of formula (I), (II) or (III) as well as mixtures thereof, including racemic mixtures, form part of the present invention. In addition, the present invention embraces all geometric and positional isomers. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by the reaction with an appropriate optically active compound (e.g., chiral auxiliary such as a chiral alcohol or Mosher's acid chloride), separating the diastereomers and converting (e.g., hydrolysing) the individual diastereomers to the corresponding pure enantiomers. Enantiomers can also be separated by use of chiral HPLC column. The chiral centers of the present invention can have the S or R configuration as defined by the IUPAC 1974.

Pharmaceutical Compositions

The compounds of the invention are typically administered in the form of a pharmaceutical composition. The pharmaceutical compositions described herein comprise one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents, solvents and the like.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The pharmaceutical compositions described herein may also include one or more pharmaceutically acceptable auxiliary agents, wetting agents, suspending agents, preserving agents, buffers, sweetening agents, flavouring agents, colorants or any combination of the foregoing.

Administration of the compounds of the invention, in pure form or in an appropriate pharmaceutical composition, can be carried out using any of route of administration, such as orally or parenterally. The route of administration may be any route which effectively transports the active compound of the patent application to the appropriate or desired site of action.

Methods of Treatment

The compounds of the present invention are particularly useful because they inhibit the activity of retinoid-related orphan receptor gamma, particularly retinoid-related orphan receptor gamma t (RORγt), i.e., they prevent, inhibit, or suppress the action of RORγt, and/or may elicit a RORγt modulating effect. Compounds of the invention are therefore useful in the treatment of those conditions in which inhibition of ROR gamma activity, and particularly RORγt, is beneficial.

The compounds of the present patent application are modulators of RORγt and can be useful in the treatment of diseases or disorder mediated by RORγt. Accordingly, the compounds and the pharmaceutical compositions of this invention may be useful in the treatment of inflammatory, metabolic and autoimmune diseases mediated by RORγt.

The term "autoimmune diseases" will be understood by those skilled in the art to refer to a condition that occurs when the immune system mistakenly attacks and destroys healthy body tissue. An autoimmune disorder may result in the destruction of one or more types of body tissue, abnormal growth of an organ, and changes in organ function. An autoimmune disorder may affect one or more organ or tissue types which include, but are not limited to, blood vessels, connective tissues, endocrine glands such as the thyroid or pancreas, joints, muscles, red blood cells, and skin. Examples of autoimmune (or autoimmune-related) disorders include multiple sclerosis, arthritis, rheumatoid arthritis, psoriasis, Crohn's disease, gastrointestinal disorder, inflammatory bowel disease, irritable bowel syndrome, colitis, ulcerative colitis, Sjorgen's syndrome, atopic dermatitis, optic neuritis, respiratory disorder, chronic obstructive pulmonary disease (COPD), asthma, type I diabetes, neuromyelitis optica, Myasthenia Gavis, uveitis, Guillain-Barre syndrome, psoriatic arthritis, Gaves' disease, allergy, osteoarthritis, Kawasaki disease, mucosal leishmaniasis, Hashimoto's thyroiditis, Pernicious anemia, Addison's disease, Systemic lupus erythematosus, Dermatomyositis, Sjogren syndrome, Lupus erythematosus, Myasthenia gravis, Reactive arthritis, Celiac disease—sprue (gluten-sensitive enteropathy), Graves's disease, thymopoiesis and Lupus.

Compounds of the present patent application may also be useful in the treatment of inflammation. The term "inflammation" will be understood by those skilled in the art to include any condition characterized by a localized or a systemic protective response, which may be elicited by physical trauma, infection, chronic diseases, and/or chemical and/or physiological reactions to external stimuli (e.g. as part of an allergic response). Any such response, which may serve to destroy, dilute or sequester both the injurious agent and the injured tissue, may be manifest by, for example, heat, swelling, pain, redness, dilation of blood vessels and/or increased blood flow, invasion of the affected area by white.

The term "inflammation" is also understood to include any inflammatory disease, disorder or condition per se, any condition that has an inflammatory component associated with it, and/or any condition characterized by inflammation as a symptom, including inter alia acute, chronic, ulcerative, specific, allergic, infection by pathogens, immune reactions due to hypersensitivity, entering foreign bodies, physical injury, and necrotic inflammation, and other forms of inflammation known to those skilled in the art. The term thus also includes, for the purposes of this present patent application, inflammatory pain, pain generally and/or fever.

The compounds of the present invention may be used for treatment of arthritis, including, but are not limited to, rheumatoid arthritis, osteoarthritis, psoriatic arthritis, septic arthritis, spondyloarthropathies, gouty arthritis, systemic lupus erythematosus and juvenile arthritis, osteoarthritis, collagen-induced arthritis (CIA) and other arthritic conditions.

The compounds of the present invention may be used for treatment of respiratory disorders including, but are not limited to, chronic obstructive pulmonary disease (COPD), asthma, bronchospasm, and cough.

Other respiratory disorders include, but are not limited to, bronchitis, bronchiolitis, bronchiectasis, acute nasoparyngitis, acute and chronic sinusitis, maxillary sinusitis, pharyngitis, tonsillitis, laryngitis, tracheitis, epiglottitis, croup, chronic disease of tonsils and adenoids, hypertrophy of tonsils and adenoids, peritonsillar abscess, rhinitis, abscess or ulcer and nose, pneumonia, viral and bacterial pneumonia, bronchopneumonia, influenza, extrinsic allergic alveolitis, coal workers' pneumoconiosis, asbestosis, pneumoconiosis, pneumonopathy, respiratory conditions due to chemical fumes, vapors and other external agents, emphysema, pleurisy, pneumothorax, abscess of lung and mediastinum, pulmonary congestion and hypostasis, postinflammatory pulmonary fibrosis, other alveolar and parietoalveolar pneumonopathy, idiopathic fibrosing alveolitis, Hamman-Rich syndrome, atelectasis, ARDS, acute respiratory failure, and mediastinitis.

The compounds of the present invention may also be used for treatment of pain conditions. The pain can be acute or chronic pain. Thus, the compounds of the present invention may be used for treatment of e.g., inflammatory pain, arthritic pain, neuropathic pain, post-operative pain, surgical pain, visceral pain, dental pain, premenstrual pain, central pain, cancer pain, pain due to burns, migraine or cluster headaches, nerve injury, neuritis, neuralgias, poisoning, ischemic injury, interstitial cystitis, viral, parasitic or bacterial infection, post-traumatic injury, or pain associated with irritable bowel syndrome.

The compounds of the present invention may further be used for treatment of gastrointestinal disorder such as, but not limited to, irritable bowel syndrome, inflammatory bowel disease, colitis, ulcerative colitis, biliary colic and other biliary disorders, renal colic, diarrhea-dominant IBS, and pain associated with gastrointestinal distension.

In addition, the compounds of the present invention may be useful in the treatment of cancer, and pain associated with cancer. Such cancers include, e.g., multiple myeloma and bone disease associated with multiple myeloma, melanoma, medulloblastoma, acute myelogenous leukemia (AML), head and neck squamous cell carcinoma, hepatocellular carcinoma, gastric cancer, bladder carcinoma and colon cancer.

The compounds of the present invention may be useful in a treatment of disease, disorder, syndrome or condition selected from the group consisting of chronic obstructive pulmonary disease (COPD), asthma, cough, pain, inflammatory pain, chronic pain, acute pain, arthritis, osteoarthritis, multiple sclerosis, rheumatoid arthritis, colitis, ulcerative colitis and inflammatory bowel disease.

Any of the methods of treatment described herein comprise administering an effective amount of a compound according to Formula (I), (II) or (III), or a pharmaceutically-acceptable salt thereof, to a subject (particularly a human) in need thereof.

The present inventions further relates to the use of the compounds described herein in the preparation of a medicament for the treatment of diseases mediated by RORγt.

The compounds of the invention are effective both in the therapeutic and/or prophylactic treatment of the above-mentioned conditions. For the above-mentioned therapeutic uses the dosage administered may vary with the compound employed, the mode of administration, the treatment desired and the disorder.

The daily dosage of the compound of the invention administered may be in the range from about 0.05 mg/kg to about 100 mg/kg.

General Methods of Preparation

The compounds, described herein, including those of general formula (Ia), (Ib) and (II), intermediates and specific examples are prepared through the synthetic methods as depicted in Schemes 1 to 14. Furthermore, in the following schemes, where specific acids, bases, reagents, coupling reagents, solvents, etc. are mentioned, it is understood that other suitable acids, bases, reagents, coupling reagents, solvents etc. may be used and are included within the scope of the present invention. The modifications to reaction conditions, for example, temperature, duration of the reaction or combinations thereof, are envisioned as part of the present invention. The compounds obtained using the general reaction sequences may be of insufficient purity. These compounds can be purified using any of the methods for purification of organic compounds known to persons skilled in the art, for example, crystallization or silica gel or alumina column chromatography using different solvents in suitable ratios. All possible geometrical isomers and stereoisomers are envisioned within the scope of this invention.

The starting materials used herein are commercially available or were prepared by methods known in the art to those of ordinary skill or by methods disclosed herein. In general, the intermediates and compounds of the present invention can be prepared through the reaction schemes as follows. In some cases the final product may be further modified, for example, by manipulation of substituents. These manipulations may include, but are not limited to, reduction, oxidation, alkylation, acylation, hydrolysis, and cleavage of protecting groups etc., by following procedures known in the art of organic synthesis.

A general approach for the preparation of compounds of the formulae (Ia) and (Ib) (wherein ring A and ring B, L, $R^1$, $R^2$, $R^3$, $R^4$, $R^5$, $R^b$, 'n', 'm', 'p' and 'q', are as defined in the general description) is depicted in Synthetic scheme 1.

3-oxid hexafluorophosphate) (HATU). The suitable base used in the reaction may be $Et_3N$, DIPEA, pyridine or DMAP. The coupling reaction may be carried out in a suitable solvent or mixture thereof. The suitable solvent may be selected from $CH_2Cl_2$, $CHCl_3$, DMF and THF or a combination thereof. Alternatively, the coupling of an amine compound of formula (1) with a carboxylic acid compound of formula (3) in the presence of a suitable coupling agent(s) and suitable base gives the amide compound of formula (4). The reduction of the ketone group of the compound of formula (4) using a suitable reducing agent in a suitable

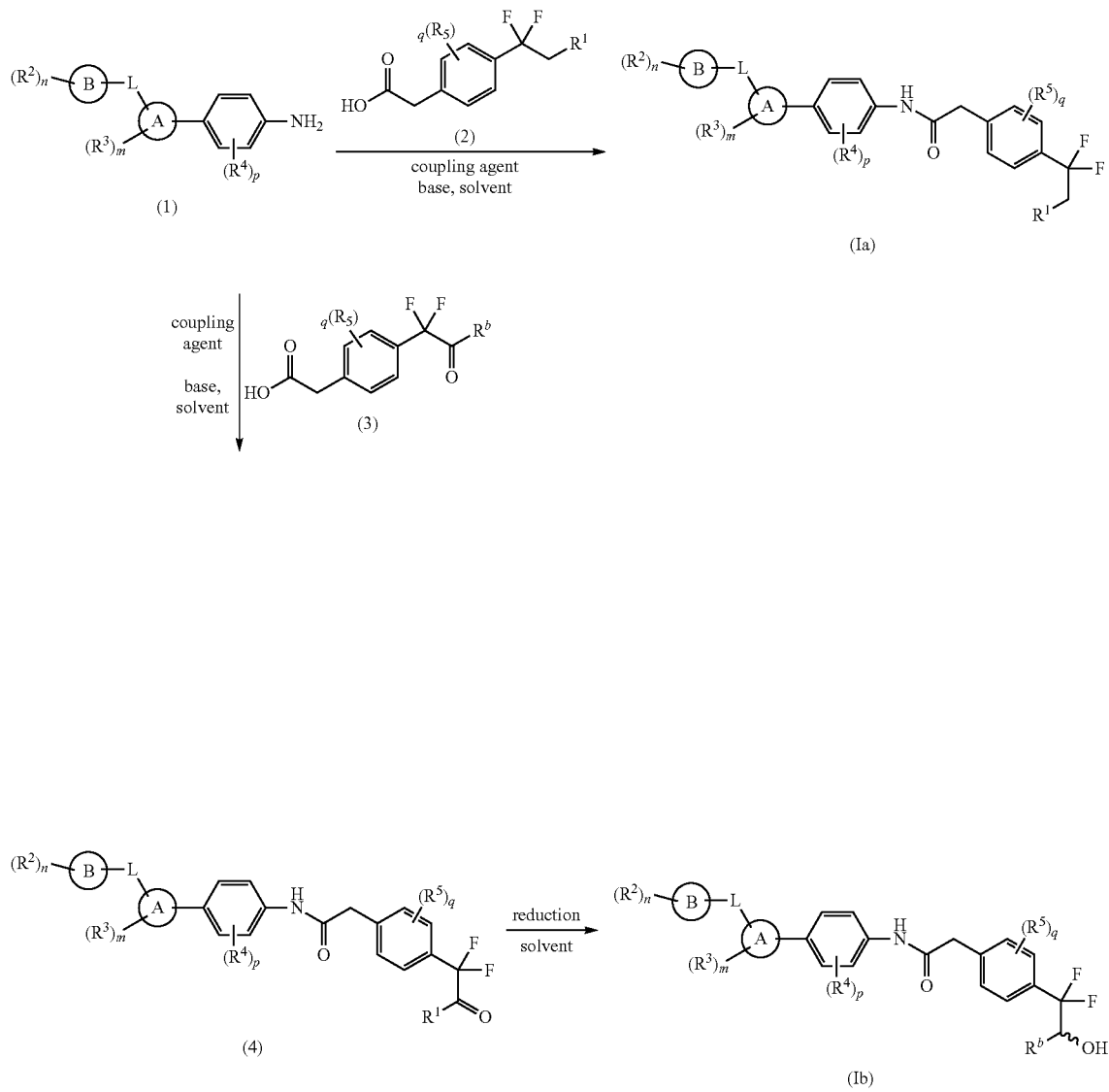

The coupling of an amine compound of formula (1) with a carboxylic acid compound of formula (2) in the presence of a suitable coupling agent(s) and a base gives the compound of formula (Ia). The suitable coupling agent(s) used in the reaction may be 1-ethyl-3-(3-dimethylaminopropyl)carbodiimide (EDCI), propylphosphonic anhydride ($T_3P$), N,N'-dicyclohexylcarbodiimide (DCC) or (1-[Bis(dimethylamino)methylene]-1H-1,2,3-triazolo[4,5-b]pyridinium solvent gives the corresponding racemic hydroxyl compound of formula (Ib). The suitable reducing agent used in the reaction may be sodium borohydride and the suitable solvent may be methanol or THF of combination thereof.

A general approach for the preparation of compounds of general formula (II) (wherein ring A, ring B, L, $R^2$, $R^3$, $R^4$, $R^5$, 'n', 'm', 'q' and 'p' are as defined in the general description and $R^6$ is $C_{1-8}$alkyl) is depicted in Synthetic scheme 2.

Synthetic scheme 2

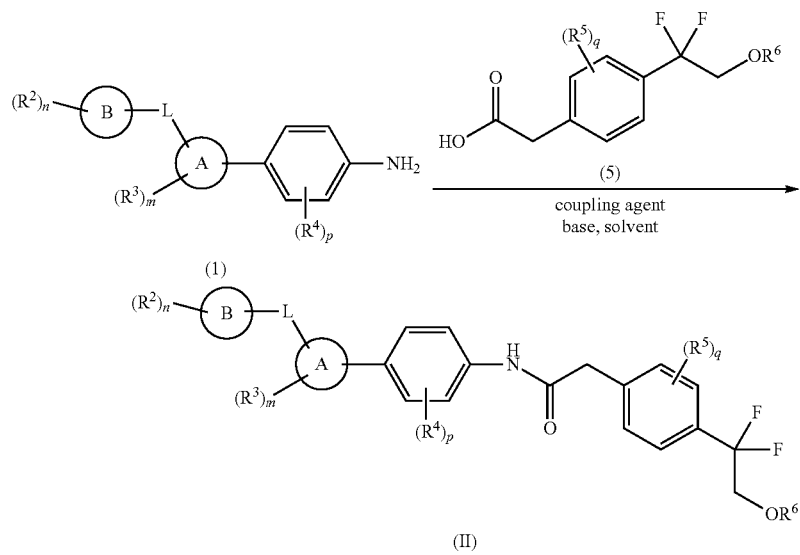

(II)

The coupling of an amine compound of formula (1) with a carboxylic acid compound of formula (5) in the presence of a suitable coupling agent(s) and base gives the compound of formula (Ia). The suitable coupling agent used in the reaction may be propylphosphonic anhydride ($T_3P$) or HATU. The suitable base used may be DIPEA, pyridine or DMAP. The coupling reaction may be carried out in a suitable solvent or mixture thereof. The suitable solvent may be selected from $CHCl_3$, DMF, $CH_2Cl_2$ and THF or combination thereof.

A general approach for the preparation of compound of formula (1a) (wherein ring B, $R^2$, $R^3$, $R^4$ 'm', 'n' and 'p' are as defined in the general description and any one or two of $X^1$, $X^2$, $X^3$ and $X^4$ is/are N and the others are CH) is depicted in Synthetic scheme 3.

Synthetic Scheme 3

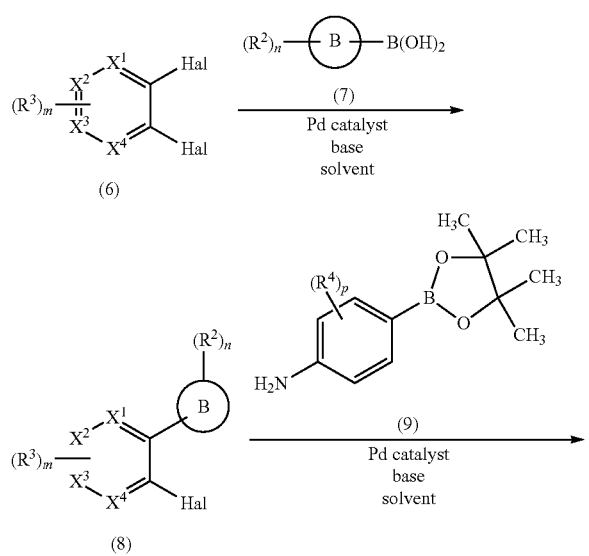

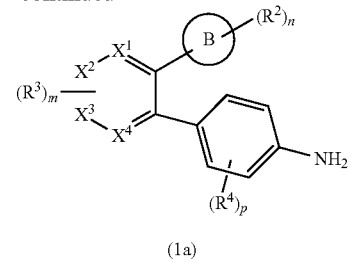

(1a)

The reaction of a suitably substituted dihalo compound of formula (6) (wherein Hal is halogen) with a substituted boronic acid compound of formula (7) using a palladium catalyst in the presence of a suitable base and in a suitable solvent gives a compound of formula (8). The suitable base used in the reaction may be sodium carbonate, potassium carbonate or cesium carbonate. The suitable solvent used in the reaction may be independently selected from THF, DMSO, water and $CH_2Cl_2$, or combination thereof. The reaction of a compound of formula (8) with a suitably substituted 4-aminophenylboronic acid, pinacol ester compound of formula (9) using a palladium catalyst in the presence of a suitable base gives the substituted aniline compound of formula (1a). The suitable base used in the reaction may be $Na_2CO_3$, $K_2CO_3$, DIPEA, pyridine or DMAP. The reaction may be carried out in a suitable solvent or mixture thereof. The suitable solvent may be selected from 1,4-dioxane, DMSO, water, DMF and THF or combination thereof.

Another approach for the preparation of compound of formula (Ia) (wherein ring B, $R^2$, $R^3$, $R^4$, 'm', 'n', and 'p' are as defined in the general description and any one or two of $X^1$, $X^2$, $X^3$ and $X^4$ is/are N and the others are CH) is depicted in synthetic scheme 4.

Synthetic Scheme 4

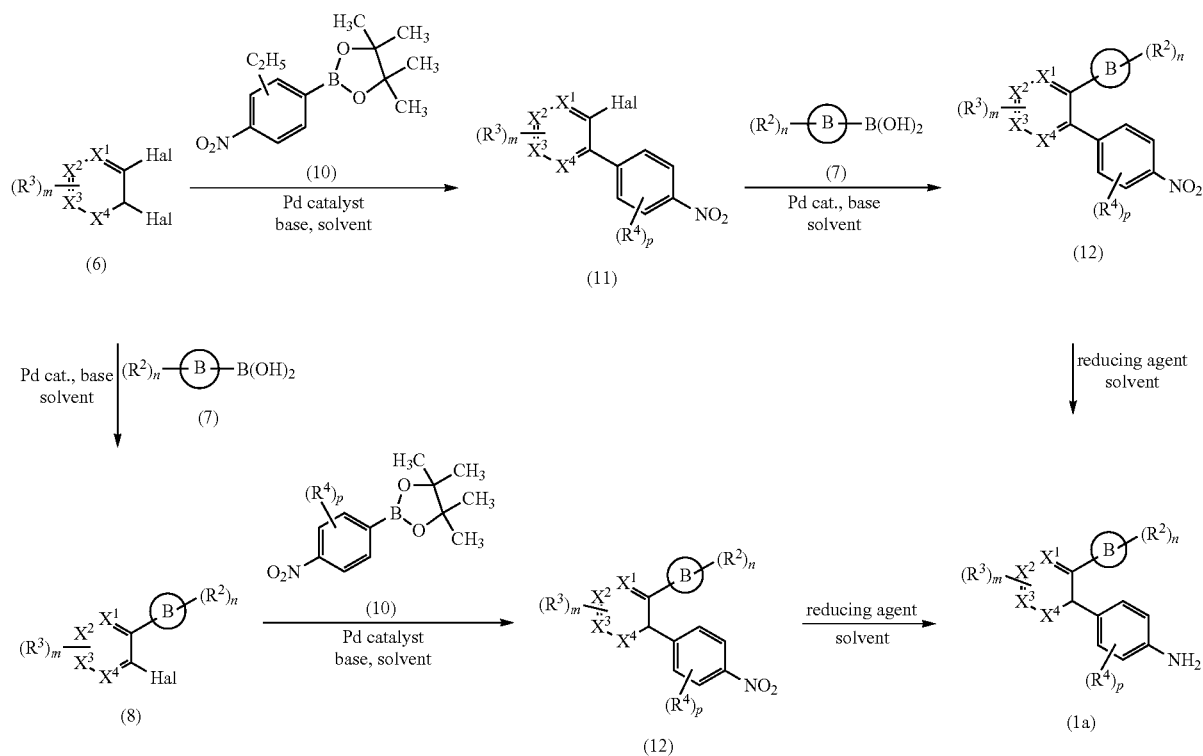

The reaction of a suitably substituted di-halo compound of formula (6) (wherein Hal is halogen) with a suitably substituted 4-nitrophenylboronic acid, pinacol ester compound of formula (10) using a palladium catalyst in the presence of a suitable base and in a suitable solvent gives the compound of formula (11). The suitable base used in the reaction may be sodium carbonate, potassium carbonate or cesium carbonate. The solvent may be selected from DMSO, DMF, water or a mixture thereof. The reaction of the nitro compound of formula (11) with a substituted boronic acid compound of formula (7) using a palladium catalyst in the presence of a suitable base and in a suitable solvent gives the compound of formula (12). The suitable base used in the reaction may be sodium carbonate. The suitable solvent may be selected from DMSO, water, DMF and THF or combination thereof. Alternatively, the reaction of a substituted di-halo compound of formula (6) with a substituted boronic acid compound of formula (7) using a palladium catalyst in the presence of a suitable base and in a suitable solvent gives the compound of general formula (8) which on reaction with a 4-nitrophenylboronic acid, pinacol ester compound of formula (10) using a palladium catalyst in the presence of a suitable base and in a suitable solvent furnishes compound of formula (12) under the same reaction conditions as mentioned above. The reduction of the nitro group of the compound of formula (12) using iron powder in the presence of aqueous acetic acid or ammonium chloride gives the corresponding amine compound of formula (1a). The solvent used in the reaction can be selected from ethanol, water, DMF, DMSO or a mixture thereof.

A general approach for the preparation of compound of formula (1b) (wherein $R^2$, $R^3$, $R^4$, 'm', 'n' and 'p' are as defined in the general description and $X^5$ is C, N or O) is depicted in the Synthetic Scheme 5.

Synthetic scheme 5

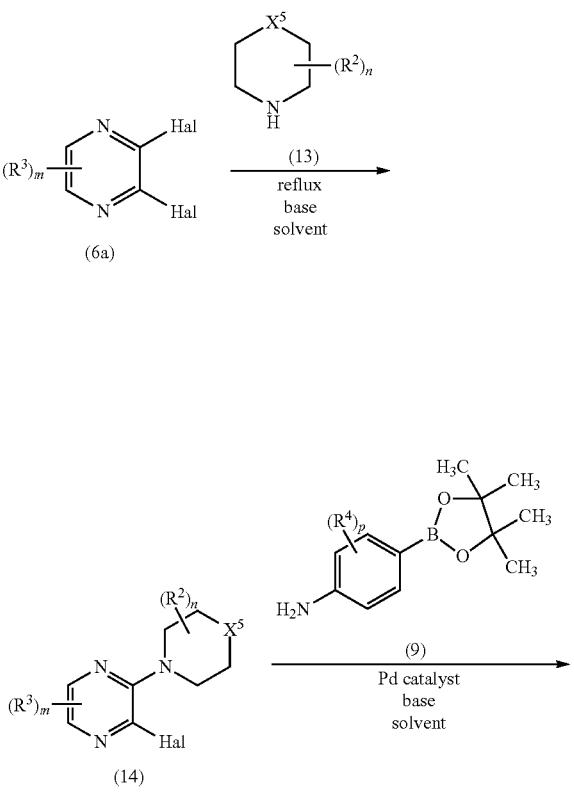

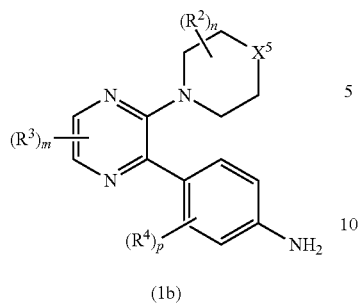

(1b)

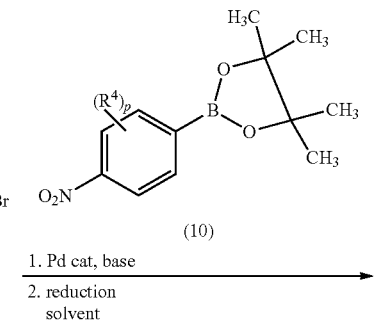

1. Pd cat, base
2. reduction
solvent (18)

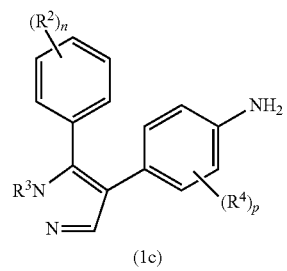

(1c)

The reaction of a suitably substituted di-halo compound of formula (6a) (wherein Hal is halogen) with the hetero alicyclic compound of formula (13) in the presence of a base and in a suitable solvent gives the compound of formula (14). The suitable base used in the reaction may be potassium carbonate, sodium carbonate or cesium fluoride. The reaction may be carried out in a suitable solvent or mixture thereof. The suitable solvent may be selected from $CH_2Cl_2$, $CHCl_3$, DMF and THF or combination thereof. The compound of formula (14) on reaction with a suitably substituted 4-aminophenylboronic acid, pinacol ester compound of formula (9) using a palladium catalyst in the presence of a suitable base gives the aniline compound of formula (1b). The suitable base used in the reaction may be potassium carbonate, sodium carbonate, triethylamine or DIPEA. The reaction may be carried out in a suitable solvent or mixture thereof. The suitable solvent may be selected from $CH_2Cl_2$, $CHCl_3$, DMF, acetonitrile or THF or combination thereof.

A general approach for the preparation of compound of formula (1c) (wherein $R^2$, $R^3$, $R^4$, 'n' and 'p' are as defined in the general description) is depicted in the Synthetic Scheme 6.

The condensation of a suitably substituted acetophenone compound of formula (15) with a hydrazine derivative (16) in a suitable solvent gives the pyrazole coupled substituted phenyl compound of formula (17). The reaction may be carried out in a suitable solvent or mixture thereof. The suitable solvent may be selected from ethanol, $CH_2Cl_2$, $CHCl_3$, DMF and THF or combination thereof. The selective bromination of a compound of formula (17) using N-bromosuccinimide (NBS) in a suitable solvent such as DMF or THF yields a compound of formula (18). The reaction of a compound of formula (18) with a suitably substituted 4-nitrophenylboronic acid, pinacol ester compound of formula (10) in the presence of a suitable base and solvent followed by the reduction of the nitro group using iron powder in the presence of aqueous acetic acid or ammonium chloride gives the corresponding amine compound of formula (1c). The suitable base used in the coupling reaction may be $Na_2CO_3$, $Et_3N$, DIPEA, pyridine or DMAP. The suitable solvent may be selected from ethanol, DMSO, water, $CH_2Cl_2$, DMF and THF or combination thereof.

A general approach for the preparation of compound of formula (1d) (wherein $R^2$, $R^4$, 'n', and 'p' are as defined in the general description and $R^7$ is $C_{1-8}$alkyl or halo$C_{1-8}$alkyl) is depicted in the Synthetic Scheme 7.

Synthetic Scheme 6

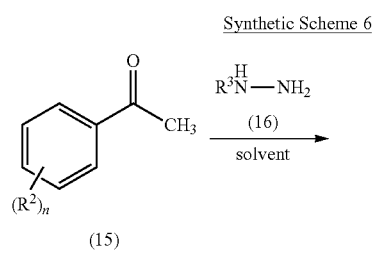

(15)

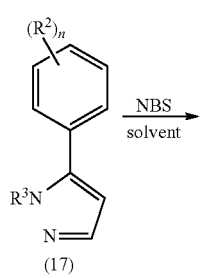

(17)

Synthetic scheme 7

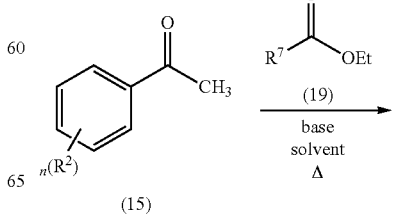

(15)

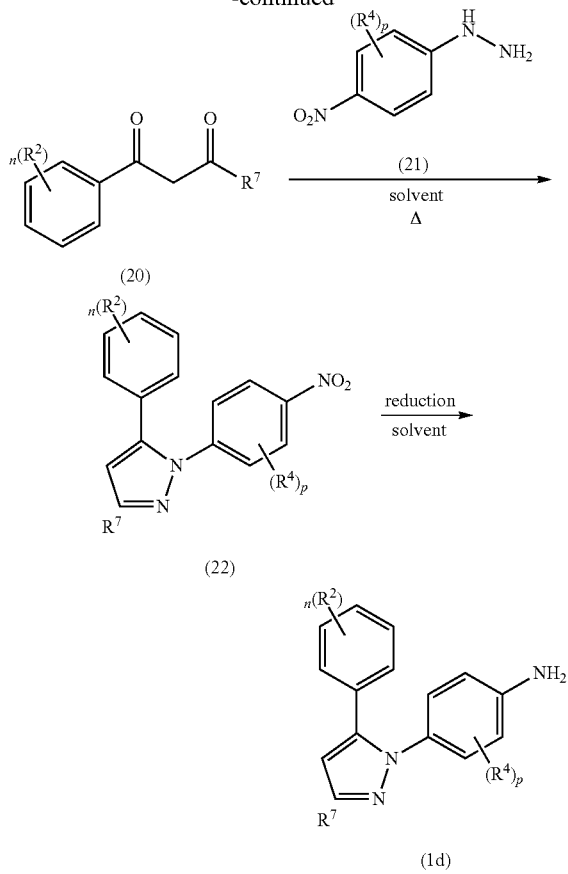

The reaction of a suitably substituted acetophenone compound of formula (15) with an ethyl ester compound of formula (19) in the presence of a base and in a suitable solvent gives the compound of formula (20). The suitable base used in the reaction may be sodium hydride, sodium methoxide (25% in methanol), DIPEA or pyridine. The suitable solvent may be selected from methyl tert-butyl ether, CHCl₃, DMF and THF or combination thereof. The reaction of compound of formula (20) with a suitably substituted phenyl hydrazine compound of formula (21) in a suitable solvent gives the pyrazole coupled substituted phenyl compound of formula (22). The suitable solvent may be selected from ethanol, 2,2,2-trifluoroethanol, DMF and THF or combination thereof. The reduction of the nitro group of the compound of formula (22) using iron powder in the presence of aqueous acetic acid or ammonium chloride gives the corresponding amine compound of formula (1d). The reaction may be carried out in a suitable solvent selected from ethanol, water, CH₂Cl₂, CHCl₃, DMF and THF or combination thereof.

An approach for the preparation of compound of formula (1e) (wherein R², R³, R⁴, Rˣ, Rʸ, X, 'm', 'n', 'p' and 't' are defined in the general description) is depicted in synthetic scheme 8.

Synthetic Scheme 8

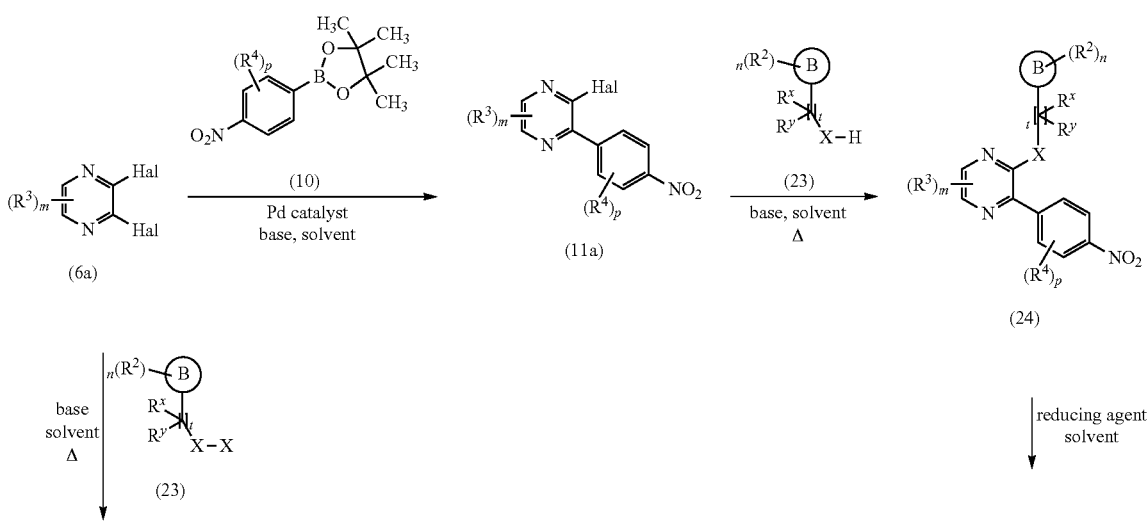

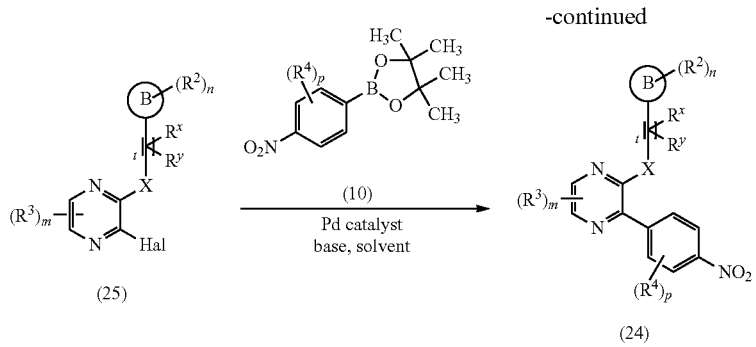
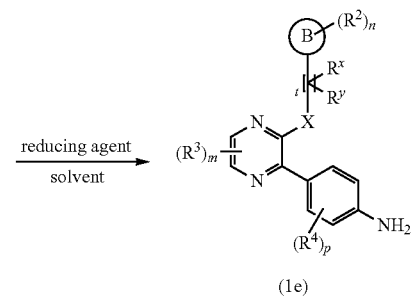

The reaction of a suitably substituted di-halo compound of formula (6a) (wherein Hal is halogen) with a suitably substituted 4-nitrophenylboronic acid, pinacol ester compound of formula (10) using a palladium catalyst in the presence of a suitable base and in a suitable solvent gives the compound of formula (11a). The suitable base used in the reaction may be sodium carbonate, potassium carbonate or cesium carbonate. The solvent may be selected from DMSO, DMF, water or a mixture thereof. Halide substitution of the compound of formula (1a) with a compound of formula (23) using a suitable base and in a solvent yields the compound of formula (24). The suitable base used in the reaction may be sodium carbonate, potassium carbonate, and cesium carbonate or cesium fluoride. The suitable solvent may be selected from DMSO, water, DMF and THF or combination thereof. Alternatively, the substitution reaction of a suitably substituted dihalopyrazine compound of formula (6a) with a compound of formula (23) using a suitable base and in a solvent yields a compound of formula (25) which on reaction with an appropriately substituted 4-nitrophenylboronic acid, pinacol ester compound of formula (10) using a palladium catalyst in the presence of a suitable base and in a suitable solvent furnishes the compound of formula (24) under the same reaction conditions as described above. The reduction of the nitro group of the compound of formula (24) using iron powder in the presence of aqueous acetic acid or ammonium chloride gives the corresponding amine compound of formula (1e). The solvent used in the reaction can be selected from ethanol, water, DMF, DMSO or a mixture thereof.

Another approach for the preparation of compound of formula (1e) (wherein $R^2$, $R^3$, $R^4$, $R^x$, $R^y$, X, 'm', 'n', 'p' and 't' are as defined in the general description) is depicted in Synthetic scheme 9.

The substitution reaction of a suitably substituted di-halo compound of formula (6a) (wherein Hal is halogen) with a compound of formula (23) using a suitable base and solvent yields a compound of formula (25). The suitable base used in the reaction may be sodium carbonate, potassium carbonate, and cesium carbonate or cesium fluoride. The suitable solvent may be selected from DMSO, water, DMF and THF or combination thereof. The reaction of the compound of formula (25) with a suitably substituted 4-aminophenylboronic acid, pinacol ester compound of formula (9) using a palladium catalyst in the presence of a base and suitable solvent gives the aniline compound of formula (1e). The suitable base used in the reaction may be $Na_2CO_3$, $K_2CO_3$ or cesium carbonate. The reaction may be carried out in solvent selected from 1,4-dioxane, DMSO, water, DMF and THF or combination thereof.

An approach for the preparation of compound of formula (1f) (wherein $R^2$, $R^3$, $R^4$, $R^x$, $R^y$, X, 'm', 'n', 'p' and 't' are as defined in the general description and $R^8$ is $C_{1-8}$alkyl) is depicted in Synthetic scheme 10.

Synthetic Scheme 10

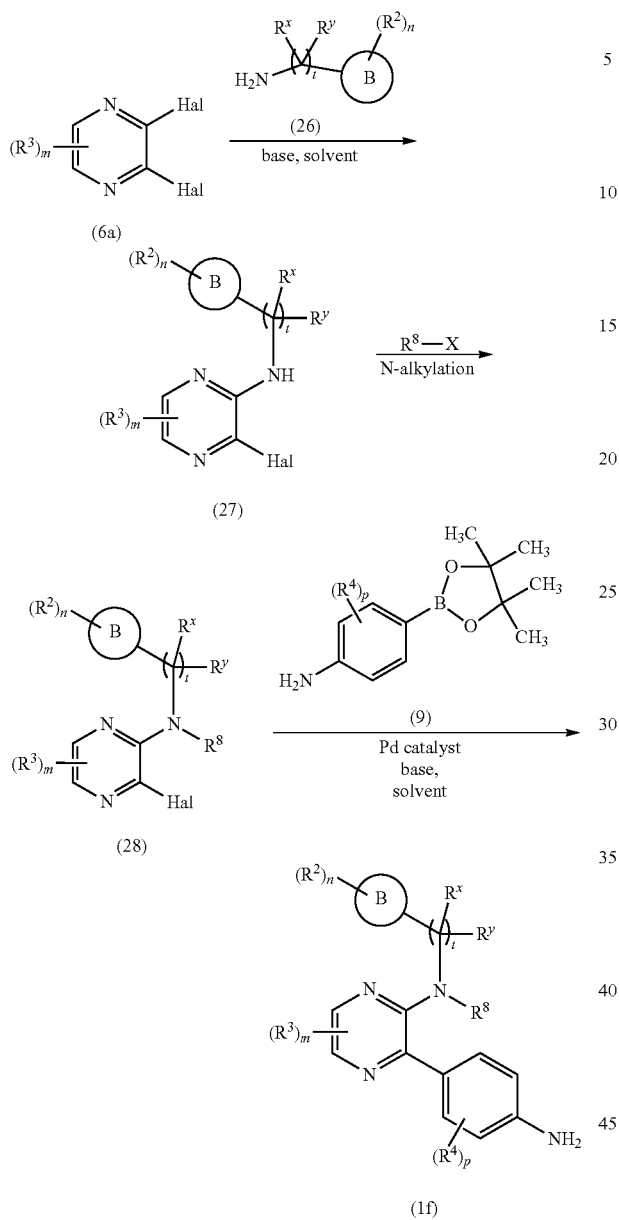

(1f)

The substitution reaction of a suitably substituted di-halo compound of formula (6a) (wherein Hal is halogen) with a compound of formula (26) using a suitable base and solvent yields the compound of formula (27). The suitable base used in the reaction may be sodium carbonate, potassium carbonate, and cesium carbonate or cesium fluoride. The suitable solvent may be selected from DMSO, water, DMF and THF or combination thereof. N-Alkylation of the amine derivative of formula (27) with an appropriate alkyl halide ($R^8$—X) in the presence of a suitable base such as sodium hydride and solvent such as THF, DMF or 1,4-dioxane furnishes the compound of formula (28). The coupling reaction of the compound of formula (28) with a suitably substituted 4-aminophenylboronic acid, pinacol ester compound of formula (9) using a palladium catalyst in the presence of a base and suitable solvent gives the aniline compound of formula (1f). The suitable base used in the reaction may be $Na_2CO_3$, $K_2CO_3$ or cesium carbonate. The reaction may be carried out in a solvent selected from 1,4-dioxane, DMSO, water, DMF and THF or combination thereof.

A general approach for the preparation of compound of formula (2) (wherein $R^1$, $R^5$ and 'q' are as defined in the general description) is depicted in the Synthetic Scheme 11.

Synthetic scheme 11

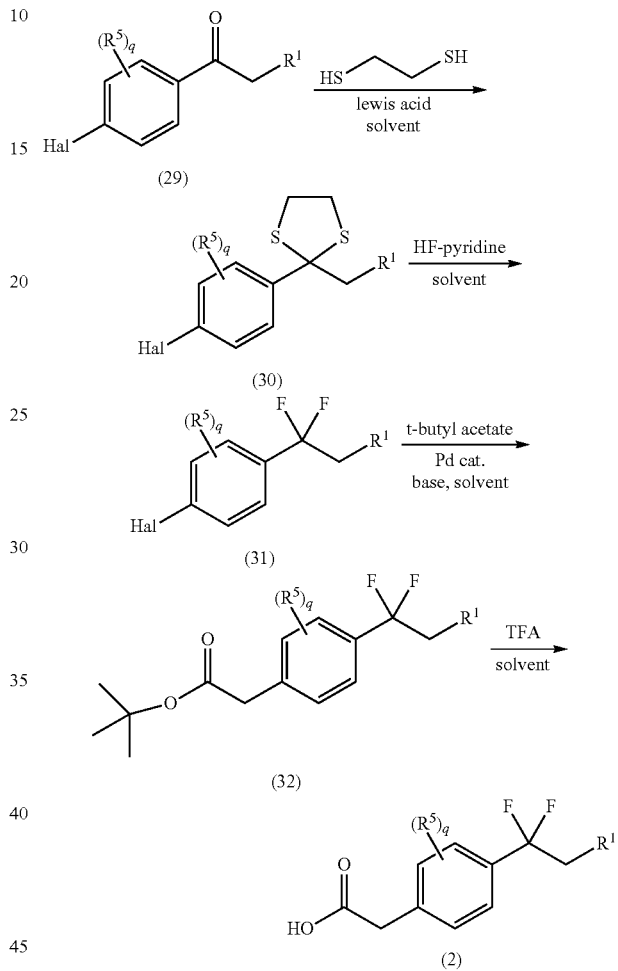

The reaction of a suitably substituted phenyl ketone compound of formula (29) (wherein Hal is halogen) with an ethane 1,2-dithiol in the presence of a suitable Lewis acid in a suitable solvent gives the thioacetal compound of formula (30). The suitable Lewis acid used in the reaction may be boron trifluoride diethyletherate and suitable solvent may be selected from $CH_2Cl_2$, $CHCl_3$, DMF and THF. The compound of formula (30) on reaction with a HF-pyridine complex in the presence of N-iodosuccinimide in a suitable solvent gives the difluoro compound of formula (31). The suitable solvent used in the reaction may be pyridine. The substitution of a halogen group in the compound of formula (31) with tert-butyl acetate in the presence of a palladium catalyst and suitable base in a suitable solvent gives the ester compound of formula (32). The suitable base may be lithium dicyclohexylamine and the suitable solvent may be toluene. The compound of formula (32) on deprotection using trifluoroacetic acid in a suitable solvent gives the compound of formula (2). The suitable solvent may be selected from $CH_2Cl_2$, $CHCl_3$, DMF and THF.

A general approach for the preparation of compound of formula (3) (wherein $R^b$, $R^5$ and 'q' are as defined in the general description) is depicted in the Synthetic Scheme 12.

Synthetic scheme 12

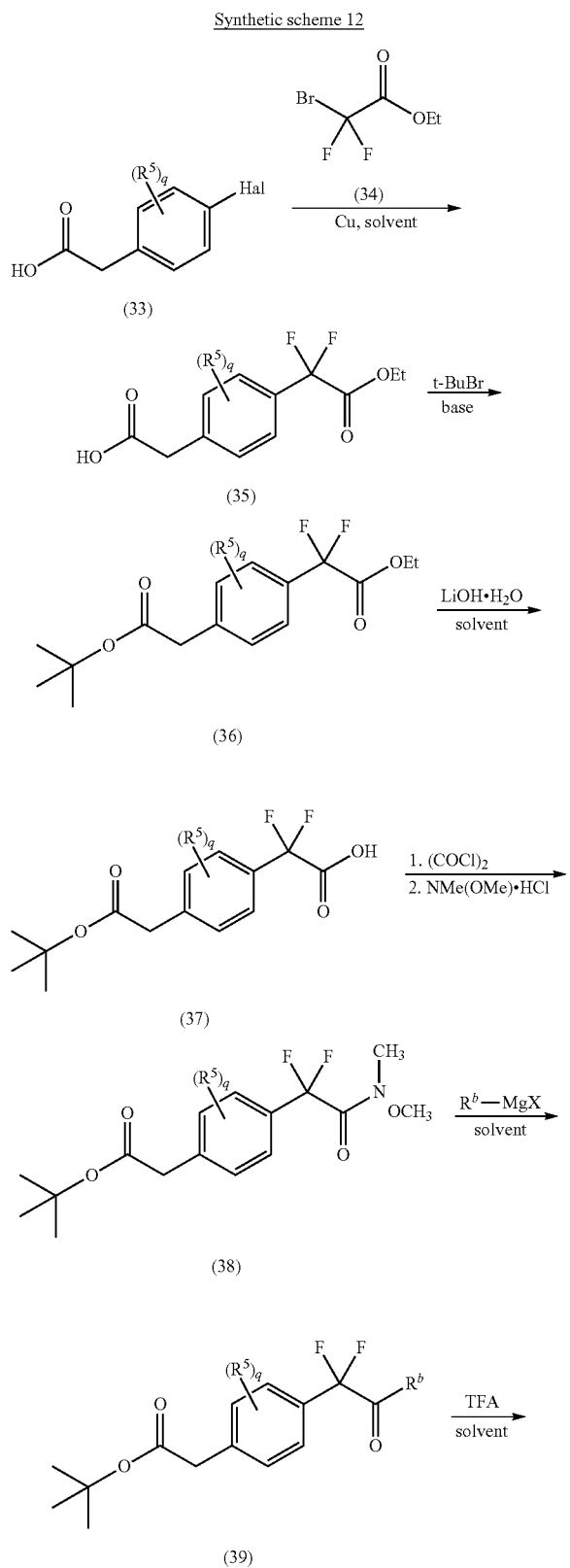

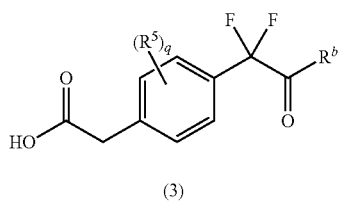

(3)

The condensation of a suitably substituted phenyl acetic acid compound of formula (33) (wherein Hal is halogen) with ethyl bromo(difluoro)acetate (34) in the presence of copper powder and in a suitable solvent gives the difluoro ester compound of formula (35). The suitable solvent used in this reaction may be DMSO or DMF. The protection of the carboxylic acid (35) with tert-butyl bromide in the presence of silver carbonate as a base and using a suitable solvent yields compound of formula (36). The suitable solvent may be $CH_2Cl_2$, THF or a mixture thereof. Selective hydrolysis of the ethyl ester in the compound of formula (36) using lithium hydroxide monohydrate in a suitable solvent gives the acid compound of formula (37). The suitable solvent may be THF, $CH_3OH$, water or mixture thereof. The reaction of compound (37) with oxalyl chloride gives the corresponding acid chloride which on reaction with N,O-dimethylhydroxylamine hydrochloride in the presence of a base and in a suitable solvent gives the Weinreb amide compound of formula (38). The suitable solvent used may be $CH_2Cl_2$ or THF. The Grignard reaction of the compound of formula (38) with a suitable alkyl magnesium halide of formula $R^bMgX$ in a suitable solvent such as THF gives the difluoroketone compound of formula (39). The ester hydrolysis of compound (39) using trifluoroacetic acid in a suitable solvent gives the acid of formula (3). The suitable solvent may be selected from $CH_2Cl_2$, $CHCl_3$, DMF and THF or combination thereof.

A general approach for the preparation of compound of formula (5) (wherein $R^5$ and 'q' are as defined in the general description and $R^6$ is $C_{1-8}$alkyl) is depicted in the Synthetic Scheme 13.

Synethetic scheme 13

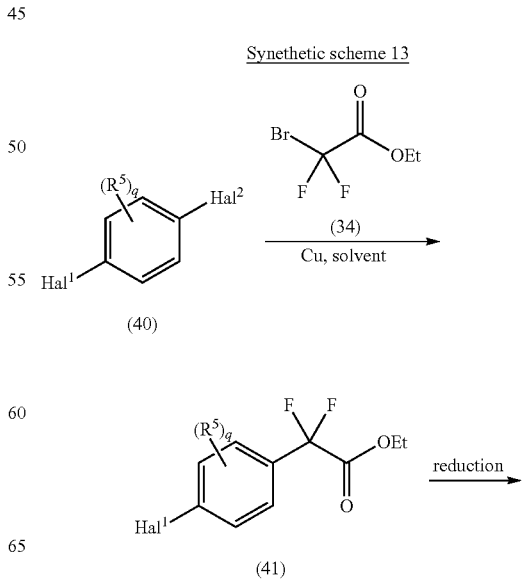

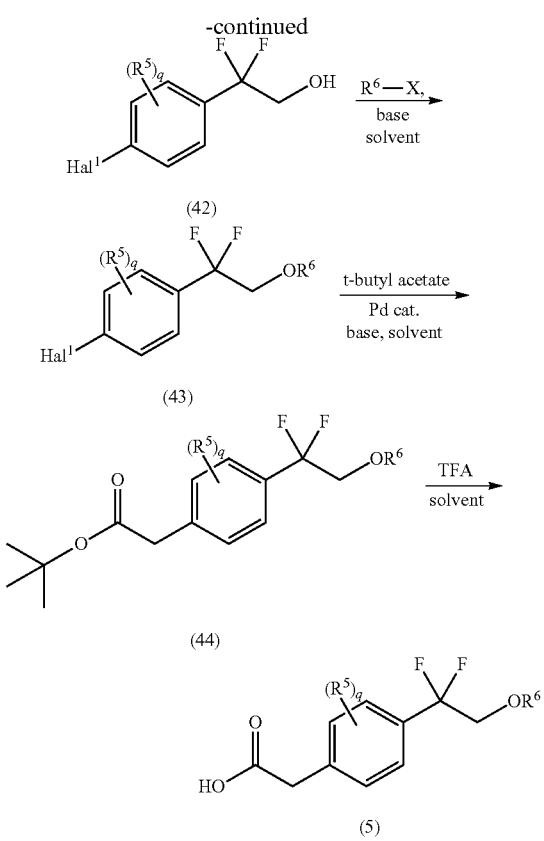

The reaction of a suitably substituted di-halo compound of formula (40) (wherein Hal¹ and Hal² are halogen) with ethyl bromo(difluoro)acetate of formula (34) in the presence of copper powder and in a suitable solvent gives the difluoro ester compound of formula (41). The suitable solvent used in this reaction may be DMSO or DMF. The compound of formula (41) on reduction using a suitable reducing agent and in a suitable solvent gives the hydroxyl compound of formula (42). The suitable solvent used may be ethanol or methanol and the suitable reducing agent may be sodium borohydride. The reaction of the compound of formula (42) with an alkylating compound of formula ($R^6$—X) (where X is halogen) using a suitable base in a suitable solvent gives the compound of formula (43). The suitable base may be sodium hydride and the solvent may be selected from $CH_2Cl_2$, $CHCl_3$, DMF and THF or combination thereof. Halide substitution of the compound of formula (43) with tert-butyl acetate in the presence of palladium catalyst in the presence of base and in a suitable solvent gives the compound of formula (44). The suitable base used in the reaction may be $Et_3N$, DIPEA, pyridine or DMAP. The deprotection of compound (44) using trifluoroacetic acid gives the carboxylic acid of formula (5). The reaction may be carried out in a suitable solvent or a mixture thereof. The suitable solvent may be selected from $CH_2Cl_2$, $CHCl_3$, DMF and THF or combination thereof.

A general approach for the preparation of compounds of the formulae (Ib-i) (wherein ring A, ring B, L, $R^b$, $R^2$, $R^3$, $R^4$, $R^5$, 'n', 'm', 'p' and 'q', are as defined in the general description) is depicted in Synthetic scheme 14.

Synthetic scheme 14

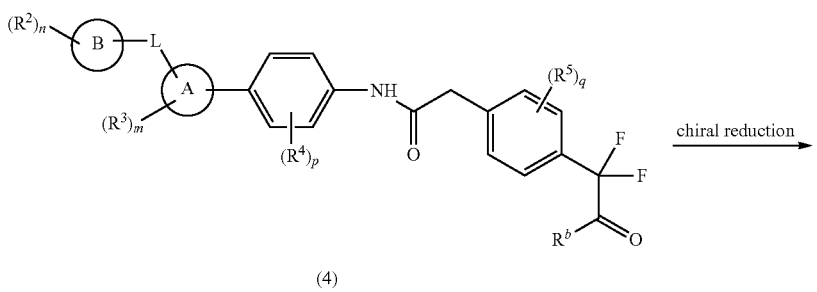

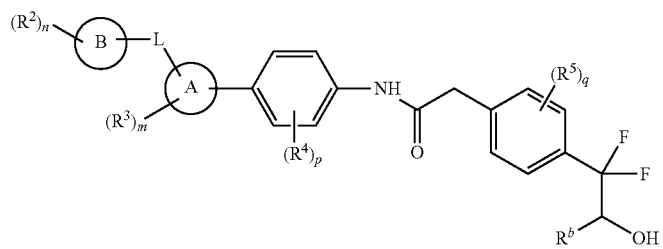

The reduction of the ketone group of the compound of formula (4) using a suitable chiral reducing agent in a suitable solvent gives one of the isomers of the hydroxyl compound of formula (Ib-i) as a major product. The suitable chiral reducing agent may be selected from (R or S)-2-methyl-CBS-oxazaborolidine in the presence of borane dimethyl sulfide, hydrogenation using BINAP-Ru dihalide, H$_2$/ruthenium (diphosphane)$_2$ (diamine)$_2$ complex, etc. The suitable solvent may be THF, DCM or DMF. The obtained isomer may be further purified according to various purification techniques known in the art.

Experimental Section

Unless otherwise stated, work-up includes distribution of the reaction mixture between the organic and aqueous phase indicated within parentheses, separation of layers and drying the organic layer over sodium sulfate, filtration and evaporation of the solvent. Purification, unless otherwise mentioned, includes purification by silica gel chromatographic techniques, generally using ethyl acetate/petroleum ether mixture of a suitable polarity as the mobile phase. Use of a different eluent system is indicated within parentheses.

The abbreviations, symbols and terms used in the examples and assays have the following meanings throughout: DCM: dichloromethane; DMSO-d$_6$: Hexadeuterodimethyl sulfoxide; DMSO dimethyl sulfoxide; $^1$H NMR: Proton Nuclear Magnetic Resonance; DMF: N,N-dimethyl formamide; EDCI.HCl: 1-ethyl-3-(3-dimethylaminopropyl) carbodiimide hydrochloride; HOBT: 1-hydroxybenzotriazole; NaOH: Sodium Hydroxide; KOH: Potassium Hydroxide; LiOH: Lithium Hydroxide; DIPEA: N,N-diisopropylethylamine; THF: Tetrahydofuran; HCl: hydrochloric acid; Na$_2$SO$_4$: Sodium sulfate; NaHCO$_3$: Sodium bicarbonate; J: Coupling constant in units of Hz; h: hour(s); mins: minutes; RT or rt: Room temperature (22-26° C.); o: ortho; m: meta; p: para; APCI-MS: Atmospheric Pressure Chemical Ionization Mass Spectrometry; MHz: Megahertz; aq.: aqueous

INTERMEDIATES

Intermediate 1

4-[3-(4-Chlorophenyl)pyrazin-2-yl]aniline

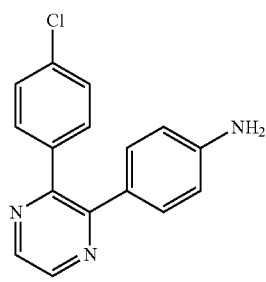

Step 1: 2-Chloro-3-(4-chlorophenyl)pyrazine

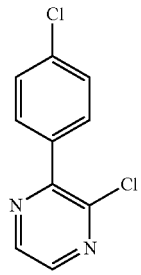

To a stirred solution of 2,3-dichloropyrazine (500 mg, 3.35 mmol), 4-chlorophenyl boronic acid (472 mg, 3.02 mmol) and sodium carbonate monohydrate (1.2 g, 10.05 mmol) in a mixture of DMSO and water (10 mL, 3:1) was added [1,1'-bis(diphenylphosphino)ferrocene]dichloropalladium (II) (122 mg, 0.16 mmol) at RT. The reaction mixture was degassed and bubbled with nitrogen thrice before heating at 80° C. for 16 h. The mixture was cooled to RT and diluted with ethyl acetate (30 mL). The organic solution was washed with water (30 mL) and brine (30 mL). The solvent was removed under reduced pressure and the residue obtained was purified by silica gel column chromatography to obtain 320 mg of the desired product; $^1$H NMR (300 MHz, CDCl$_3$) δ 7.47 (d, J=7.2 Hz, 2H), 7.76 (d, J=7.2 Hz, 2H), 8.35 (d, J=1.8 Hz, 1H), 8.58 (d, J=1.8 Hz, 1H).

Step 2: 4-[3-(4-Chlorophenyl)pyrazin-2-yl]aniline

The titled compound was prepared by the reaction of Step 1 intermediate (310 mg, 1.38 mmol) with 4-aminophenylboronic acid pinacol ester (302 mg, 1.38 mmol) using sodium carbonate monohydrate (513 mg, 4.14 mmol) and [1,1'-bis(diphenylphosphino)ferrocene]dichloropalladium (II) (50 mg, 0.06 mmol) in a mixture of DMSO and water (10 mL, 2:1) at RT as per the procedure described in Step 1 of Intermediate 1 to yield 270 mg of the product; $^1$H NMR (300 MHz, DMSO-d$_6$) δ 5.42 (s, 2H), 6.46 (d, J=8.4 Hz, 2H), 7.09 (d, J=8.4 Hz, 2H), 7.38-7.47 (m, 4H), 8.51 (s, 1H), 8.57 (s, 1H); APCI-MS (m/z) 282 (M+H)$^+$.

Intermediate 2

[4-(1,1-Difluoropropyl)phenyl]acetic acid

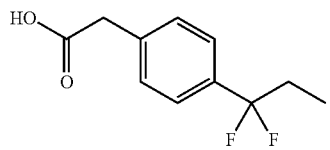

Step 1: 2-(4-Bromophenyl)-2-ethyl-1,3-dithiolane

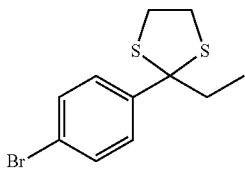

To a stirred solution of 4-bromopropiophenone (2.01 g, 9.43 mmol) in anhydrous dichloromethane (20 mL) were added boron trifluoride diethyl etherate (0.49 mL, 4.71 mmol) and ethane 1,2-dithiol (1.57 mL, 18.8 mmol). The reaction mixture was stirred overnight at RT. The mixture was diluted with dichloromethane (10 mL), washed with 10% sodium hydroxide solution (10 mL), water (20 mL) and brine (20 mL). The organic layer was dried over anhydrous sodium sulfate and concentrated under reduced pressure to give 2.21 g of the titled product; $^1$H NMR (300 MHz, CDCl$_3$) δ 0.89 (t, J=7.5 Hz, 3H), 2.33 (q, J=7.5 Hz, 2H), 3.19-3.32 (m, 2H), 3.34-3.41 (m, 2H), 7.41 (d, J=8.1 Hz, 2H), 7.56 (d, J=8.1 Hz, 2H); APCI-MS (m/z) 288 (M)$^+$.

Step 2: 1-Bromo-4-(1,1-difluoropropyl)benzene

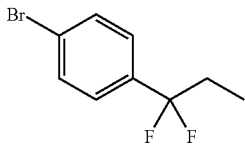

To a stirred solution of N-iodosuccinimide (704 mg, 3.13 mmol) in dichloromethane (5.0 mL) at −20° C. was added hydrogen fluoride in pyridine (70% w/w, 520 μL, 20.88 mmol) and the solution was stirred at the same temperature for 2 min. A solution of Step 1 intermediate (302 mg, 1.04 mmol) in dichloromethane (5.0 mL) was added to the reaction mixture. The resulting mixture was stirred at −20° C. for 30 min. The mixture was diluted with n-hexane (5.0 mL), filtered through basic alumina and washed with n-hexane (30 mL). Filtrate was concentrated and the residue was diluted with ethyl acetate (50 mL). The combined filtrates were washed with 10% sodium thiosulfate (20 mL), 2% potassium permanganate (20 mL), water (20 mL) and brine (20 mL). The organic layer was dried over anhydrous sodium sulfate and concentrated. The residue was purified by silica gel column chromatography to obtain 203 mg of the titled product; $^1$H NMR (300 MHz, CDCl$_3$) δ 0.97 (t, J=7.5 Hz, 3H), 2.02-2.21 (m, 2H), 7.33 (d, J=8.1 Hz, 2H), 7.56 (d, J=8.1 Hz, 2H); APCI-MS (m/z) 231 (M−H)$^-$.

Step 3: tert-Butyl [4-(1,1-difluoropropyl)phenyl]acetate

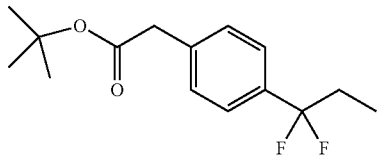 [SMILES: CCC(F)(F)c1ccc(CC(=O)OC(C)(C)C)cc1]

To a stirred solution of dicyclohexylamine (2.04 mL, 10.25 mmol) in anhydrous toluene (20 mL) at 0° C. was added n-butyl lithium (1.6 M, 6.41 mL, 10.26 mmol). After 5 min, tert-butyl acetate (1.15 mL, 8.55 mmol) was added to the mixture and stirred for 15 min at 0° C. In a separate flask, tri-tert-butylphosphonium tetrafluoroborate (248 mg, 0.85 mmol) and bis(dibenzylideneacetone) palladium (0) (245 mg, 0.42 mmol) were mixed and the flask was evacuated and refilled with nitrogen thrice. The solid mixture was taken in toluene (10 mL) and to the resulting suspension was added Step 2 intermediate (2.01 g, 8.55 mmol) followed by the first mixture. The resulting reaction mixture was stirred overnight at RT. The mixture was diluted with diethyl ether (50 mL), filtered through celite bed and washed with diethyl ether (30 mL). The filtrate was concentrated and the residue obtained was purified by silica gel column chromatography to obtain 1.43 g of the desired product; $^1$H NMR (300 MHz, CDCl$_3$) δ 0.98 (t, J=7.5 Hz, 3H), 1.44 (s, 9H), 2.04-2.22 (m, 2H), 3.55 (s, 2H), 7.31 (d, J=8.1 Hz, 2H), 7.41 (d, J=8.1 Hz, 2H).

Step 4: [4-(1,1-Difluoropropyl)phenyl]acetic acid

To a stirred solution of step 3 intermediate (1.42 g, 5.25 mmol) in dichloromethane (20 mL) at 0° C. was added trifluoroacetic acid (10 mL) and the mixture was stirred for 1 h at RT. The solvent in the reaction mixture was evaporated and the residue obtained was purified by silica gel column chromatography to yield 491 mg of the desired product; $^1$H NMR (300 MHz, DMSO-d$_6$) δ 0.90 (t, J=6.0 Hz, 3H), 2.11-2.28 (m, 2H), 3.63 (s, 2H), 7.33 (d, J=8.4 Hz, 2H), 7.42 (d, J=8.4 Hz, 2H), 12.42 (br s, 1H); APCI-MS (m/z) 213 (M−H)$^-$.

Intermediate 3

4-(1,1-Difluoro-2-oxopropyl)phenyl]acetic acid

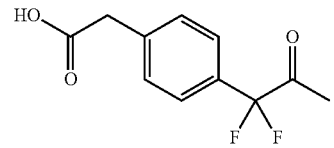 [SMILES: CC(=O)C(F)(F)c1ccc(CC(=O)O)cc1]

Step 1: [4-(2-Ethoxy-1,1-difluoro-2-oxoethyl)phenyl]acetic acid

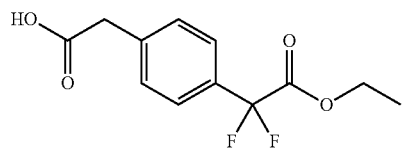 [SMILES: CCOC(=O)C(F)(F)c1ccc(CC(=O)O)cc1]

To a stirred suspension of 4-iodophenylacetic acid (203 mg, 0.76 mmol) and copper powder (193 mg, 3.05 mmol) in DMSO (8.0 mL) in a sealed tube was added ethyl bromodifluoroacetate (196 mg, 1.52 mmol). The reaction mixture was stirred overnight at 60° C. The mixture was cooled to RT, quenched with aqueous ammonium chloride (30 mL), and extracted with ethyl acetate (50 mL×2). The combined organic layers were dried over anhydrous sodium sulfate and concentrated under reduced pressure. The residue obtained was purified by silica gel column chromatography to obtain 171 mg of the titled product; $^1$H NMR (300 MHz, DMSO-d$_6$) δ 1.22 (t, J=6.0 Hz, 3H), 3.67 (s, 2H), 4.31 (q, J=7.2 Hz, 2H), 7.44 (d, J=8.1 Hz, 2H), 7.53 (d, J=8.1 Hz, 2H), 12.45 (s, 1H).

Step 2. Ethyl 2-(4-(2-(tert-butoxy)-2-oxoethyl)phenyl)-2,2-difluoroacetate

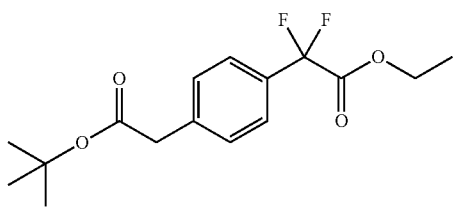 [SMILES: CCOC(=O)C(F)(F)c1ccc(CC(=O)OC(C)(C)C)cc1]

To a stirred solution of Step 1 intermediate (3.3 g, 12.77 mmol) in a mixture of dichloromethane and THF (2:1, 90 mL) were added molecular sieves (4 Å, 3.3 g) and silver carbonate (10.6 g, 38.33 mmol). The reaction mixture was stirred for 15 min, cooled to 0° C. tert-Butyl bromide (7.3 mL, 63.89 mmol) was added drop wise to the reaction mixture. The mixture was allowed to attain room temperature and was stirred overnight. The mixture was filtered through celite bed and washed with dichloromethane (100 mL). The filtrate was concentrated under reduced pressure and the residue obtained was purified by column chromatography to yield 1.82 g of the product; $^1$H NMR (300 MHz, DMSO-d$_6$) δ 1.19 (t, J=6.9 Hz, 3H), 1.37 (s, 9H), 3.64 (s, 2H), 4.28 (q, J=7.2 Hz, 2H), 7.41 (d, J=8.4 Hz, 2H), 7.52 (d, J=7.8 Hz, 2H).

Step 3: 2-(4-(2-(tert-Butoxy)-2-oxoethyl)phenyl)-2,2-difluoroacetic acid

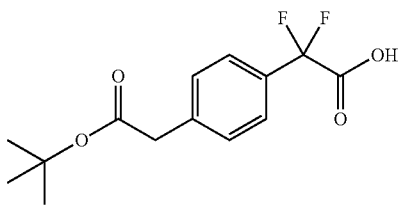 [SMILES: CC(C)(C)OC(=O)Cc1ccc(C(F)(F)C(=O)O)cc1]

To a stirred solution of step 2 intermediate (915 mg, 2.91 mmol) in a mixture of THF, methanol and water (3:2:1, 30 mL) at 0° C. was added lithium hydroxide monohydrate (366 mg, 8.73 mmol) and the mixture was stirred for 1 h at RT. The reaction mixture was acidified with 1 N HCl till pH 2-3 and extracted with ethyl acetate (50 mL×2). The combined organic layers were dried over anhydrous sodium sulfate and concentrated under reduced pressure to afford 839 mg of the desired product; $^1$H NMR (300 MHz, DMSO-d$_6$) δ 1.40 (s, 9H), 3.64 (s, 2H), 7.40 (d, J=8.4 Hz, 2H), 7.52 (d, J=8.1 Hz, 2H).

Step 4: tert-Butyl (4-{1,1-difluoro-2-[methoxy(methyl)amino]-2-oxoethyl}phenyl)acetate

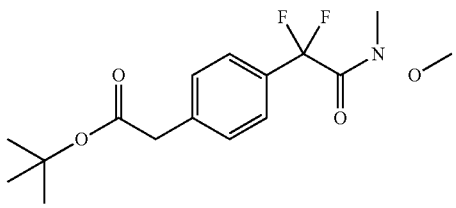

To a stirred solution of step 3 intermediate (833 mg, 2.90 mmol) in dichloromethane (15 mL) at 0° C. were added oxalyl chloride (2.2 mL, 4.36 mmol) and catalytic amount of DMF. The reaction mixture was allowed to gradually attain RT and was stirred for 3 h. The reaction mixture was concentrated under inert atmosphere to give a residue, which was diluted with dichloromethane (15 mL) and cooled to 0° C. Thereafter, N,O-dimethyl hydroxylamine hydrochloride (425 mg, 4.36 mmol) was added followed by triethyl amine (1.6 mL, 11.63 mmol) and the mixture was stirred overnight at RT. The mixture was diluted with dichloromethane (15 mL), washed with aq. saturated NaHCO$_3$ solution (20 mL) and brine (20 mL). The organic layer was concentrated and the crude obtained was purified by silica gel column chromatography to yield 581 mg of the titled product; $^1$H NMR (300 MHz, CDCl$_3$) δ 1.43 (s, 9H), 3.21 (s, 2H), 3.56 (s, 5H), 7.34 (d, J=7.8 Hz, 2H), 7.50 (d, J=7.8 Hz, 2H).

Step 5: tert-Butyl [4-(1,1-difluoro-2-oxopropyl)phenyl]acetate

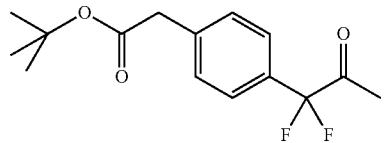 [SMILES: CC(=O)C(F)(F)c1ccc(CC(=O)OC(C)(C)C)cc1]

To a stirred solution of step 4 intermediate (572 mg, 1.73 mmol) in THF (15 mL) at 0° C. was added methylmagnesium bromide (1.15 mL, 3.47 mmol) and the mixture was stirred for 2 h. The reaction mixture was quenched with aqueous ammonium chloride solution (20 mL) and extracted with ethyl acetate (50 mL×2). The combined organic layers were washed with brine (50 mL) and concentrated under reduced pressure. The crude obtained was purified by silica gel column chromatography to yield 369 mg of the product; $^1$H NMR (300 MHz, CDCl$_3$) δ 1.43 (s, 9H), 2.31 (s, 3H), 3.56 (s, 2H), 7.36 (d, J=8.4 Hz, 2H), 7.50 (d, J=7.8 Hz, 2H), APCI-MS (m/z) 285 (M+H)$^+$.

Step 6: 4-(1,1-Difluoro-2-oxopropyl)phenyl]acetic acid

The titled compound was prepared by the reaction of step 5 intermediate (501 mg, 1.76 mmol) with trifluoroacetic acid (10 mL) in dichloromethane (10 mL) as per the procedure described in Step 4 of Intermediate 2 to afford 379 mg of the product; $^1$H NMR (300 MHz, DMSO-d$_6$) δ 2.36 (s, 3H), 3.66 (s, 2H), 7.43 (d, J=7.8 Hz, 2H), 7.52 (d, J=8.4 Hz, 2H), 12.22 (br s, 1H).

Intermediate 4

4-[3-(3-Chlorophenyl)pyrazin-2-yl]aniline

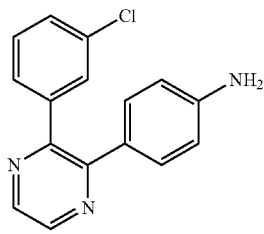 [SMILES: Nc1ccc(-c2nccnc2-c2cccc(Cl)c2)cc1]

Step 1: 2-Chloro-3-(3-chlorophenyl)pyrazine

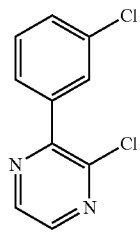 [SMILES: Clc1cccc(-c2nccnc2Cl)c1]

The titled compound was prepared by the reaction of 2,3-dichloropyrazine (500 mg, 3.35 mmol) with 3-chlorophenylboronic acid (472 mg, 3.02 mmol) using sodium carbonate monohydrate (1.2 g, 10.05 mmol) and [1,1'-bis(diphenylphosphino)ferrocene]dichloropalladium (II) (122 mg, 0.16 mmol) in a mixture of DMSO and water (15 mL, 3:1) at RT as per the procedure described in Step 1 of Intermediate 1 to yield 350 mg of the product; $^1$H NMR (300 MHz, CDCl$_3$) δ 7.41-7.50 (m, 2H), 7.71 (d, J=7.4 Hz, 1H), 7.81 (s, 1H), 8.38 (d, J=1.5 Hz, 1H), 8.60 (d, J=1.8 Hz, 1H).

Step 2: 4-[3-(3-Chlorophenyl)pyrazin-2-yl]aniline

The titled compound was prepared by the reaction of step 1 intermediate (250 mg, 1.11 mmol) with 4-aminophenylboronic acid pinacol ester (243 mg, 1.11 mmol) using sodium carbonate monohydrate (412 mg, 3.33 mmol) and [1,1'-bis(diphenylphosphino)ferrocene]dichloropalladium (II) (36 mg, 0.05 mmol) in a mixture of DMSO (15 mL) and water (5.0 mL) at RT as per the procedure described in Step 1 of Intermediate 1 to yield 273 mg of the product. The product was used further without characterization.

Intermediate 5

4-[3-(4-Fluorophenyl)pyrazin-2-yl]aniline

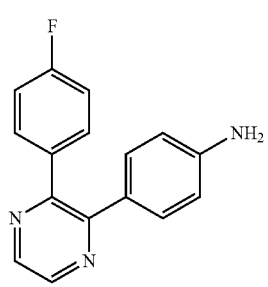 [SMILES: Nc1ccc(-c2nccnc2-c2ccc(F)cc2)cc1]

Step 1: 2-Chloro-3-(4-fluorophenyl)pyrazine

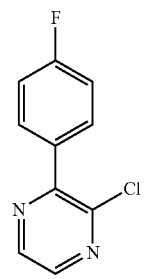 [SMILES: Fc1ccc(-c2nccnc2Cl)cc1]

The titled compound was prepared by the reaction of 2,3-dichloropyrazine (3.0 g, 20.13 mmol) with 4-fluorophenylboronic acid (2.68 g, 19.13 mmol) using 2M sodium carbonate solution (30 mL, 60.40 mmol) and [1,1'-bis(diphenylphosphino)ferrocene]dichloropalladium (II) (1.16 g, 1.00 mmol) in 1,4-dioxane (60 mL) at 90° C. as per the procedure described in Step 1 of Intermediate 1 to yield 1.74 g of the product; $^1$H NMR (300 MHz, DMSO-d$_6$) δ 7.37 (t, J=9.3 Hz, 2H), 7.83 (t, J=8.1 Hz, 2H), 8.54 (s, 1H), 8.76 (s, 1H); APCI-MS (m/z) 209 (M+H)$^+$.

Step 2: 4-[3-(4-Fluorophenyl)pyrazin-2-yl]aniline

The titled compound was prepared by the reaction of step 1 intermediate (503 mg, 2.39 mmol) with 4-aminophenylboronic acid pinacol ester (787 mg, 3.59 mmol) in the presence of bis(dibenzylidene)acetone palladium (0) (276 mg, 0.23 mmol) using 2M sodium carbonate solution (2.9 mL, 5.99 mmol) in a mixture of 1,4-dioxane and water (15 mL, 2:1) at 80° C. as per the procedure described in Step 1 of Intermediate 1 to yield 321 mg of the product; $^1$H NMR (300 MHz, DMSO-d$_6$) δ 5.38 (s, 2H), 6.44 (d, J=9.0 Hz, 2H), 7.06 (d, J=8.4 Hz, 2H), 7.17 (t, J=9.0 Hz, 2H), 7.44 (t, J=8.1 Hz, 2H), 7.46-7.61 (m, 2H).

Intermediate 6

4-[3-(3,4-Difluorophenyl)pyrazin-2-yl]aniline

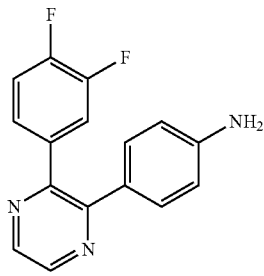 [SMILES: Nc1ccc(-c2nccnc2-c2ccc(F)c(F)c2)cc1]

Step 1: 2-Chloro-3-(3,4-difluorophenyl)pyrazine

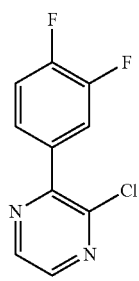 [SMILES: Fc1ccc(-c2nccnc2Cl)cc1F]

The titled compound was prepared by the reaction of 2,3-dichloropyrazine (500 mg, 3.35 mmol) with 3,4-difluorophenylboronic acid (477 mg, 3.02 mmol) using sodium carbonate monohydrate (1.2 g, 10.05 mmol) and [1,1'-bis(diphenylphosphino)ferrocene]dichloropalladium (II) (122 mg, 0.16 mmol) in a mixture of DMSO and water (15 mL, 3:1) at RT as per the procedure described in Step 1 of Intermediate 1 to yield 347 mg of the product; $^1$H NMR (300 MHz, CDCl$_3$) δ 7.23-7.34 (m, 1H), 7.59-7.72 (m, 2H), 8.37 (d, J=1.8 Hz, 1H), 8.58 (d, J=2.4 Hz, 1H).

Step 2: 4-[3-(3,4-Difluorophenyl)pyrazin-2-yl]aniline

The titled compound was prepared by the reaction of step 1 intermediate (250 mg, 1.10 mmol) with 4-aminophenylboronic acid pinacol ester (290 mg, 1.10 mmol) using sodium carbonate monohydrate (409 mg, 3.33 mmol) and [1,1'-bis(diphenylphosphino)ferrocene]dichloropalladium (II) (40 mg, 0.05 mmol) in a mixture of DMSO and water (15 mL, 3:1) at RT as per the procedure described in Step 1 of Intermediate 1 to yield 256 mg of the product; $^1$H NMR (300 MHz, DMSO-d$_6$) δ 5.44 (s, 2H), 6.48 (d, J=8.4 Hz, 2H), 7.09 (d, J=8.4 Hz, 2H), 7.20-7.26 (m, 1H), 7.40-7.50 (m, 2H), 8.54 (s, 1H), 8.60 (s, 1H).

Intermediate 7

4-[3-(4,4-Difluoropiperidin-1-yl)pyrazin-2-yl]aniline

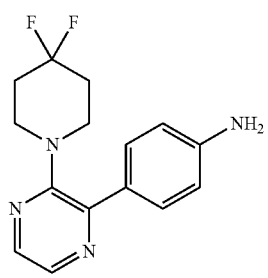 [SMILES: Nc1ccc(-c2nccnc2N2CCC(F)(F)CC2)cc1]

Step 1: 2-Chloro-3-(4,4-difluoropiperidin-1-yl)pyrazine

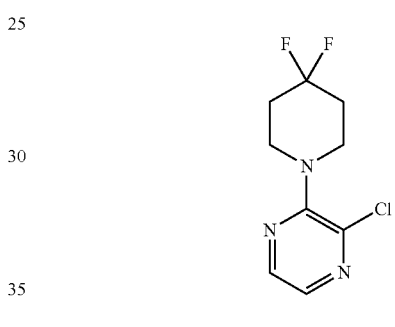

To the stirred solution of 2,3-dichloropyrazine (973 mg, 6.53 mmol) in DMF (10 mL) was added 4,4-difluoropiperidine hydrochloride (1.03 g, 6.53 mmol) and potassium carbonate (2.7 g, 19.59 mmol) and the resultant mixture was stirred for 16 h at 60° C. The reaction mixture was cooled to RT, diluted with water (50 mL) and extracted with ethyl acetate (100 mL). The organic layer was washed with brine (30 mL) and concentrated under reduced pressure. The crude compound was purified by silica gel column chromatography to obtain 1.12 g of the titled product; 1H NMR (300 MHz, CDCl$_3$) δ 2.08-2.21 (m, 4H), 3.58 (q, J=6.6 Hz, 4H), 7.92 (d, J=2.4 Hz, 1H), 8.12 (d, J=2.4 Hz, 1H).

Step 2: 4-[3-(4,4-Difluoropiperidin-1-yl)pyrazin-2-yl]aniline

The titled compound was prepared by the reaction of step 1 intermediate (500 mg, 2.14 mmol) with 4-aminophenylboronic acid pinacol ester (703 mg, 3.21 mmol) using sodium carbonate monohydrate (796 mg, 6.42 mmol) in the presence of tetrakis(triphenylphosphine)palladium(0) (247 mg, 0.21 mmol) in a mixture of 1,4-dioxane and water (10 mL, 2:1) at 80° C. as per the procedure described in Step 1 of Intermediate 1 to yield 316 mg of the product; $^1$H NMR (300 MHz, DMSO-d$_6$) δ 1.90-2.12 (m, 4H), 3.18-3.26 (m, 4H), 5.46 (s, 2H), 6.62 (d, J=8.4 Hz, 2H), 7.68 (d, J=8.1 Hz, 2H), 8.02 (d, J=1.8 Hz, 1H), 8.13 (d, J=2.4 Hz, 1H).

Intermediate 8

4-[3-(Morpholin-4-yl)pyrazin-2-yl]aniline

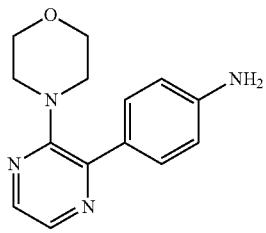 [SMILES: Nc1ccc(-c2nccnc2N2CCOCC2)cc1]

Step 1: 4-(3-Chloropyrazin-2-yl)morpholine

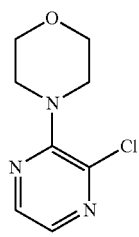

A mixture of 2,3-dichloropyrazine (1.2 g, 8.05 mmol) and morpholine (700 mg, 8.05 mmol) in ethanol (10 mL) was refluxed overnight. The mixture was cooled to RT, diluted with ethyl acetate (30 mL) and washed with water (30 mL) followed by brine (40 mL). The organic layer was dried over anhydrous sodium sulfate and concentrated under reduced pressure. The residue obtained was purified by silica gel column chromatography to yield 1.57 g of the desired product; $^1$H NMR (300 MHz, CDCl$_3$) δ 3.46 (t, J=6.9 Hz, 4H), 3.86 (t, J=6.9 Hz, 4H), 7.91 (d, J=2.4 Hz, 1H), 8.12 (d, J=2.4 Hz, 1H).

Step 2: 4-[3-(Morpholin-4-yl)pyrazin-2-yl]aniline

The titled compound was prepared by the reaction of step 1 intermediate (500 mg, 2.36 mmol) with 4-aminophenylboronic acid pinacol ester (518 mg, 2.36 mmol) using sodium carbonate monohydrate (879 mg, 7.09 mmol) and [1,1'-bis(diphenylphosphino)ferrocene]dichloropalladium (II) (86 mg, 0.11 mmol) in a mixture of DMSO and water (15 mL, 3:1) at RT as per the procedure described in Step 1 of Intermediate 1 to yield 150 mg of the product; $^1$H NMR (300 MHz, DMSO-d$_6$) δ 3.05 (t, J=4.8 Hz, 4H), 3.63 (t, J=4.8 Hz, 4H), 5.45 (s, 2H), 6.62 (d, J=8.4 Hz, 2H), 7.68 (d, J=8.4 Hz, 1H), 8.02 (d, J=2.4 Hz, 1H), 8.11 (d, J=2.4 Hz, 1H).

Intermediate 9

4-[1-tert-Butyl-5-(4-fluorophenyl)-1H-pyrazol-4-yl]aniline

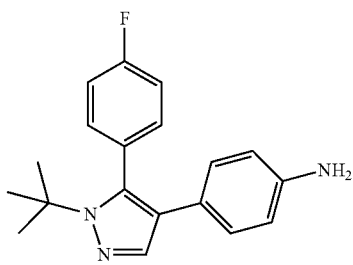 [SMILES: CC(C)(C)n1ncc(-c2ccc(N)cc2)c1-c1ccc(F)cc1]

Step 1: 1-tert-Butyl-5-(4-fluorophenyl)-1H-pyrazole

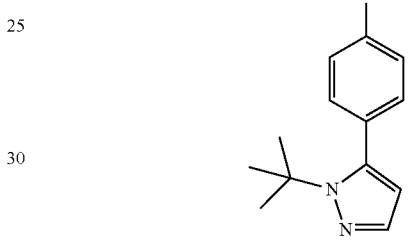

A mixture of 4-fluoroacetophenone (2.01 g, 14.47 mmol) and N,N'-dimethylformamide dimethyl acetal (2.07 g, 17.4 mmol) in DMF (20 mL) was heated at 80° C. for 1.5 h. The mixture was concentrated under reduced pressure. To the residue were added ethanol (20 mL) and tert-butyl hydrazine hydrochloride (5.41 g, 43.61 mmol). The mixture was heated at 70° C. for 5 h before cooled to RT and poured into water (70 mL). The precipitated solid was filtered, washed with water (20 mL) and dried under vacuum to give 841 mg of the desired product; $^1$H NMR (300 MHz, CDCl$_3$) δ 1.46 (s, 9H), 6.14 (s, 1H), 7.08 (t, J=8.4 Hz, 2H), 7.25-7.34 (m, 2H), 7.47 (s, 1H).

Step 2: 4-Bromo-1-tert-butyl-5-(4-fluorophenyl)-1H-pyrazole

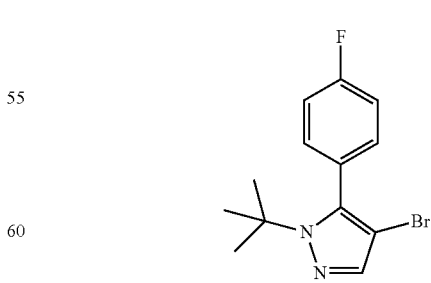

To a stirred solution of step 1 intermediate (803 mg, 3.67 mmol) in anhydrous DMF (8.0 mL) was added N-bromosuccinimide (720 mg, 4.04 mmol) and the mixture was stirred at RT for 1 h. The reaction mixture was poured into water (50 mL), the precipitated solid was filtered, washed with water (10 mL) and dried well to obtain 981 mg of the titled product; $^1$H NMR (300 MHz, CDCl$_3$) δ 1.43 (s, 9H), 7.15 (t, J=8.7, 2H), 7.25-7.30 (m, 2H), 7.49 (s, 1H)

Step 3: 1-tert-Butyl-5-(4-fluorophenyl)-4-(4-nitrophenyl)-1H-pyrazole

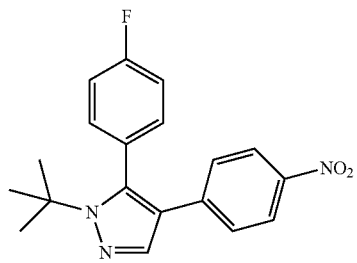 [SMILES: CC(C)(C)n1ncc(-c2ccc([N+](=O)[O-])cc2)c1-c1ccc(F)cc1]

The titled compound was prepared by the reaction of step 2 intermediate (603 mg, 2.02 mmol) with 4-nitrophenylboronic acid pinacol ester (505 mg, 2.02 mmol) using sodium carbonate monohydrate (754 mg, 6.08 mmol) and [1,1'-bis(diphenylphosphino)ferrocene]dichloropalladium (II) (74 mg, 0.10 mmol) in a mixture of DMSO and water (3:1, 10 mL) at RT as per the procedure described in Step 1 of Intermediate 1 to yield 321 mg of the product; 1H NMR (300 MHz, DMSO-d$_6$) δ 1.4 (s, 9H), 7.24-7.38 (m, 4H), 7.51 (t, J=5.7 Hz, 2H), 7.97-8.09 (m, 3H).

Step 4: 4-[1-tert-Butyl-5-(4-fluorophenyl)-1H-pyrazol-4-yl]aniline

To a suspension of step 3 intermediate (306 mg, 0.90 mmol) and ammonium chloride (482 mg, 9.01 mmol) in a mixture of ethanol and water (1:1, 10 mL) at 70° C. was added iron powder (151 mg, 2.70 mmol) and the resulting mixture was stirred at 100° C. for 1 h. The reaction mixture was cooled to RT, poured into saturated aqueous NaHCO$_3$ solution and extracted with ethyl acetate (50 mL×2). The organic layer was dried well and concentrated. The residue obtained was purified by silica gel column chromatography to yield 210 mg of the titled compound; $^1$H NMR (300 MHz, DMSO-d$_6$) δ 1.35 (s, 9H), 4.89 (s, 2H), 6.31 (d, J=8.1 Hz, 2H), 6.66 (d, J=7.8 Hz, 2H), 7.24 (t, J=8.7 Hz, 2H), 7.38 (t, J=8.1 Hz, 2H), 7.54 (s, 1H).

Intermediate 10

[4-(1,1-Difluoro-2-methoxyethyl)phenyl]acetic acid

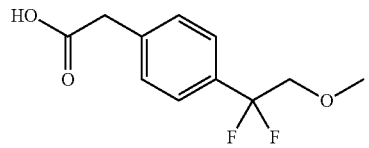 [SMILES: COCC(F)(F)c1ccc(CC(=O)O)cc1]

Step 1: Ethyl (4-bromophenyl)(difluoro)acetate

The titled compound was prepared by the reaction of 1-bromo-4-iodobenzene (1.0 g, 3.55 mmol) with ethyl bromodifluoroacetate (1.43 g, 7.06 mmol) using copper powder (903 mg, 14.2 mmol) in DMSO (10 mL) as per the procedure described in Step 1 of Intermediate 3 to give 623 mg of the product; $^1$H NMR (300 MHz, CDCl$_3$) δ 1.30 (t, J=7.2 Hz, 3H), 4.29 (q, J=7.2 Hz, 2H), 7.47 (d, J=8.4 Hz, 2H), 7.59 (d, J=8.4 Hz, 2H).

Step 2: 2-(4-Bromophenyl)-2,2-difluoroethanol

To a stirred solution of Step 1 intermediate (206 mg, 0.73 mmol) in ethanol (4.0 mL) at −10° C. was added calcium chloride (25 mg, 0.22 mmol) followed by sodium borohydride (70 mg, 1.84 mmol). The resulting mixture was stirred at RT for 2 h. The reaction mixture was quenched with aq. saturated NaHCO$_3$ solution (10 mL) and extracted with ethyl acetate (40 mL×2). The combined organic layers were washed with brine (50 mL), dried over anhydrous sodium sulfate and concentrated under reduced pressure. The crude compound was purified by silica gel column chromatography to obtain 176 mg of the titled product; $^1$H NMR (300 MHz, CDCl$_3$) δ 3.95 (t, J=13.2 Hz, 2H), 7.40 (d, J=8.4 Hz, 2H), 7.58 (d, J=8.1 Hz, 2H).

Step 3: 1-Bromo-4-(1,1-difluoro-2-methoxyethyl)benzene

To a stirred solution of Step 2 intermediate (170 mg, 0.71 mmol) in anhydrous DMF (20 mL) was added sodium hydride (60% w/w, 37 mg, 0.93 mmol) at 0° C. After 15 min was added methyl iodide (68 μL, 1.07 mmol) and the mixture was stirred at RT for 2 h. The reaction mixture was quenched with water (30 mL) and extracted with ethyl acetate (2×50 mL). The combined organic layers were washed with brine (100 mL), dried over anhydrous sodium sulfate and concentrated under reduced pressure. The residue obtained was purified by silica gel column chromatography to yield 141 mg of the titled product; $^1$H NMR (300 MHz, CDCl$_3$) δ 3.42 (s, 3H), 3.78 (t, J=12.6 Hz, 2H), 7.39 (d, J=8.1 Hz, 2H), 7.56 (d, J=8.4 Hz, 2H).

Step 4: tert-Butyl [4-(1,1-difluoro-2-methoxyethyl)phenyl]acetate

The titled compound was prepared by the reaction of Step 3 intermediate (506 mg, 2.01 mmol) with tert-butyl acetate (272 μL, 2.01 mmol) in the presence of n-butyl lithium (1.51 mL, 2.41 mmol), tri-tert-butylphosphonium tetrafluoroborate (58 mg, 0.20 mmol), bis(dibenzylidene)acetone palladium (0) (58 mg, 0.10 mmol) and dicyclohexylamine (782 μL, 2.41 mmol) in toluene (10 mL) as per the procedure described in Step 3 of Intermediate 2 to yield 398 mg of the product; $^1$H NMR (300 MHz, CDCl$_3$) δ 1.44 (s, 9H), 3.43 (s, 3H), 3.55 (s, 3H), 3.79 (t, J=13.2 Hz, 2H), 7.36 (d, J=13.8 Hz, 2H), 7.46 (d, J=8.4 Hz, 2H); ESI-MS (m/z) 283 (M−H)$^−$.

Step 5: [4-(1,1-Difluoro-2-methoxyethyl)phenyl]acetic acid

The titled compound was prepared by the reaction of Step 4 intermediate (386 mg, 1.38 mmol) with trifluoroacetic acid (3.0 mL) in dichloromethane (6.0 mL) as per the procedure described in Step 4 of Intermediate 2 to afford 161 mg of the product; $^1$H NMR (300 MHz, DMSO-d$_6$) δ 3.31 (s, 3H), 3.62 (s, 2H), 3.86 (t, J=14.1 Hz, 2H), 7.35 (d, J=7.8 Hz, 2H), 7.46 (d, J=8.1 Hz, 2H), 12.41 (br s, 1H).

Intermediate 11

4-[3-(2-Chlorophenyl)pyrazin-2-yl]aniline

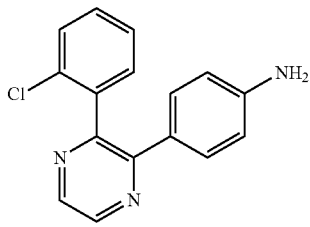

Step 1: 2-Chloro-3-(4-nitrophenyl)pyrazine

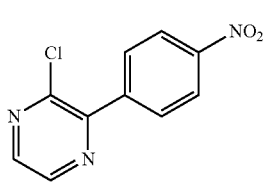 [SMILES: O=[N+]([O-])c1ccc(-c2nccnc2Cl)cc1]

The titled compound was prepared by the reaction of 2,3-dichloropyrazine (1.44 g, 9.62 mmol) with 4-nitrophenylboronic acid pinacol ester (2.01 g, 8.05 mmol) using sodium carbonate (2.99 g, 24.19 mmol) and [1,1'-bis(diphenylphosphino)ferrocene]dichloropalladium (II) (294 mg, 0.40 mmol) in a mixture of DMSO and water (20 mL, 3:1) at RT as per the procedure described in Step 1 of Intermediate 1 to yield 1.12 g of the product; $^1$H NMR (300 MHz, CDCl$_3$) δ 8.00 (d, J=9.0 Hz, 2H), 8.35 (d, J=8.7 Hz, 2H), 8.44 (d, J=2.4 Hz, 1H), 8.65 (d, J=2.1 Hz, 1H).

Step 2: 2-(2-Chlorophenyl)-3-(4-nitrophenyl)pyrazine

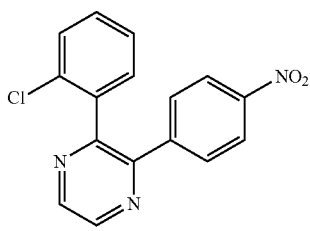

The titled compound was prepared by the reaction of Step 1 intermediate (305 mg, 3.35 mmol) with 2-chlorophenylboronic acid (246 mg, 1.57 mmol) using sodium carbonate monohydrate (417 mg, 3.93 mmol) and [1,1'-bis(diphenylphosphino)ferrocene]dichloropalladium (II) (48 mg, 0.06 mmol) in a mixture of DMSO and water (10 mL, 3:1) at RT as per the procedure described in Step 1 of Intermediate 1 to yield 149 mg of the product; $^1$H NMR (300 MHz, CDCl$_3$) δ 7.34-7.42 (m, 4H), 7.59 (d, J=8.7 Hz, 2H), 8.12 (d, J=9.3 Hz, 2H), 8.74 (d, J=5.4 Hz, 2H).

Step 3: 4-[3-(2-Chlorophenyl)pyrazin-2-yl]aniline

The titled compound was prepared by the reduction of Step 2 intermediate (140 mg, 0.44 mmol) using iron powder (75 mg, 1.34 mmol) and ammonium chloride (240 mg, 4.49 mmol) in a mixture of ethanol and water (10 mL, 1:1) as per the procedure described in Step 4 of Intermediate 9 to yield 110 mg of the product; $^1$H NMR (300 MHz, DMSO-d$_6$) δ 5.36 (s, 2H), 6.36 (d, J=7.8 Hz, 2H), 7.02 (d, J=8.4 Hz, 2H), 7.42 (br s, 4H), 8.53 (s, 1H), 8.65 (s, 1H).

Intermediate 12

4-[3-(4-Chloro-2-fluorophenyl)pyrazin-2-yl]aniline

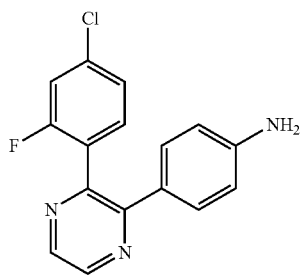

Step 1: 2-(4-Chloro-2-fluorophenyl)-3-(4-nitrophenyl)pyrazine

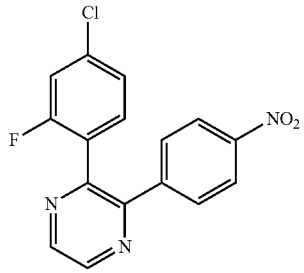

The titled compound was prepared by the reaction of 2-chloro-3-(4-nitrophenyl)pyrazine (Step 1 of intermediate 11) (403 mg, 1.73 mmol) with 4-chloro-2-fluorophenylboronic acid (362 mg, 2.07 mmol) using sodium carbonate monohydrate (550 mg, 5.19 mmol) and [1,1'-bis(diphenylphosphino)ferrocene]dichloropalladium (II) (63.3 mg, 0.08 mmol) in a mixture of DMSO and water (10 mL, 3:1) at RT as per the procedure described in Step 1 of Intermediate 1 to yield 376 mg of the product; $^1$H NMR (300 MHz, CDCl$_3$) δ 6.99 (d, J=9.6 Hz, 1H), 7.29 (t, J=8.1 Hz, 1H), 7.55-7.65 (m, 3H), 8.18 (d, J=8.7 Hz, 2H), 8.73 (s, 2H).

Step 2: 4-[3-(4-Chloro-2-fluorophenyl)pyrazin-2-yl]aniline

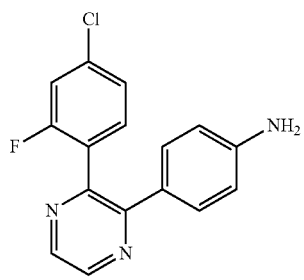 [SMILES: Nc1ccc(-c2nccnc2-c2ccc(Cl)cc2F)cc1]

The titled compound was prepared by the reduction of Step 1 intermediate (367 mg, 1.11 mmol) using iron powder (186 mg, 3.33 mmol) and ammonium chloride (595 mg, 11.13 mmol) in a mixture of ethanol and water (10 mL, 4:1) as per the procedure described in Step 4 of Intermediate 9 to yield 240 mg of the product; $^1$H NMR (300 MHz, DMSO-$d_6$) δ 5.42 (s, 2H), 6.44 (d, J=8.1 Hz, 2H), 7.07 (d, J=8.7 Hz, 2H), 7.41 (d, J=8.7 Hz, 2H), 7.59 (t, J=7.2 Hz, 1H), 8.57 (s, 1H), 8.66 (s, 1H).

Intermediate 13

4-[3-(2,4-Difluorophenyl)pyrazin-2-yl]aniline

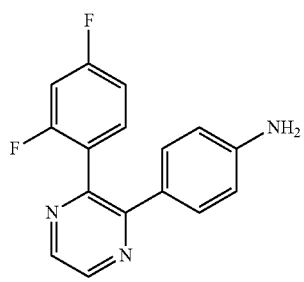

Step 1: 2-(2,4-Difluorophenyl)-3-(4-nitrophenyl)pyrazine

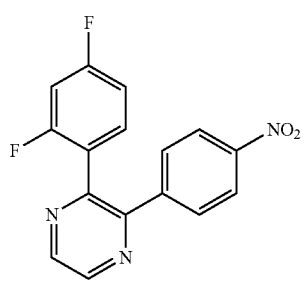 [SMILES: O=[N+]([O-])c1ccc(-c2nccnc2-c2ccc(F)cc2F)cc1]

The titled compound was prepared by the reaction of 2-chloro-3-(4-nitrophenyl)pyrazine (Step 1 of intermediate 11) (503 mg, 2.16 mmol) with 2,4-difluorophenylboronic acid (409 mg, 2.59 mmol) using sodium carbonate monohydrate (687 mg, 6.48 mmol) and [1,1'-bis(diphenylphosphino)ferrocene]dichloropalladium (II) (79 mg, 0.10 mmol) in a mixture of DMSO and water (10 mL, 3:1) at RT as per the procedure described in Step 1 of Intermediate 1 to yield 365 mg of the product; $^1$H NMR (300 MHz, CDCl$_3$) δ 6.66-6.75 (m, 1H), 7.04 (t, J=6.3 Hz, 1H), 7.60-7.68 (m, 3H), 8.17 (d, J=9.0 Hz, 2H), 8.72 (s, 2H).

Step 2: 4-[3-(2,4-Difluorophenyl)pyrazin-2-yl]aniline

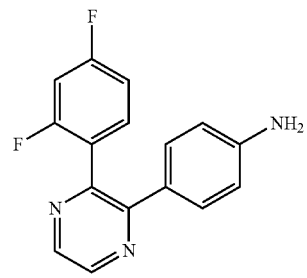 [SMILES: Nc1ccc(-c2nccnc2-c2ccc(F)cc2F)cc1]

The titled compound was prepared by the reduction of Step 1 intermediate (351 mg, 1.12 mmol) using iron powder (187 mg, 3.36 mmol) and ammonium chloride (600 mg, 11.20 mmol) in a mixture of ethanol and water (10 mL, 4:1) as per the procedure described in Step 4 of Intermediate 9 to yield 203 mg of the product; $^1$H NMR (300 MHz, DMSO-$d_6$) δ 5.36 (s, 2H), 6.42 (d, J=8.1 Hz, 2H), 7.06 (d, J=8.1 Hz, 2H), 7.18 (t, J=8.7 Hz, 3H), 7.58 (q, J=6.9 Hz, 1H), 8.54 (d, J=1.8 Hz, 1H), 8.62 (d, J=2.4 Hz, 1H).

Intermediate 14

4-[3-(4-Chlorophenyl)pyridin-2-yl]aniline

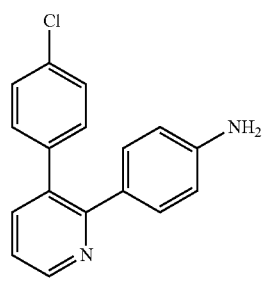

Step 1: 3-Bromo-2-(4-nitrophenyl)pyridine

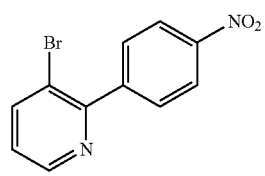 [SMILES: O=[N+]([O-])c1ccc(-c2ncccc2Br)cc1]

The titled compound was prepared by the reaction of 2,3-dibromopyridine (1.0 g, 4.22 mmol) with 4-nitrophenylboronic acid pinacol ester (1.26 g, 5.06 mmol) using potassium carbonate (1.75 g, 12.66 mmol) and [1,1'-bis(diphenylphosphino)ferrocene]dichloropalladium (II) (172 mg, 0.21 mmol) in a mixture of DMSO and water (25 mL, 4:1) at RT as per the procedure described in Step 1 of Intermediate 1 to yield 658 mg of the product; $^1$H NMR (300 MHz, CDCl$_3$) δ 7.21-7.28 (m, 1H), 7.88 (d, J=9.0 Hz, 2H), 8.06 (d, J=7.8 Hz, 1H), 8.34 (d, J=8.7 Hz, 2H), 8.68 (d, J=4.5 Hz, 1H).

Step 2:
3-(4-Chlorophenyl)-2-(4-nitrophenyl)pyridine

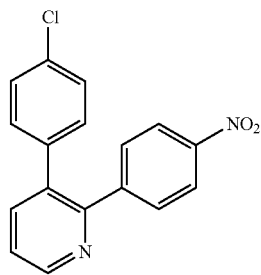

The titled compound was prepared by the reaction of Step 1 intermediate (250 mg, 0.89 mmol) with 4-chlorophenylboronic acid (209 mg, 1.34 mmol) using potassium carbonate (371 mg, 2.69 mmol) and [1,1'-bis(diphenylphosphino)ferrocene]dichloropalladium (II) (73 mg, 0.08 mmol) in a mixture of DMSO and water (12 mL, 3:1) at RT as per the procedure described in Step 1 of Intermediate 1 to yield 227 mg of the product; $^1$H NMR (300 MHz, DMSO-d$_6$) δ 7.23 (d, J=8.1 Hz, 2H), 7.40 (d, J=8.4 Hz, 2H), 7.57 (t, J=8.4 Hz, 3H), 7.92 (d, J=8.4 Hz, 1H), 8.16 (d, J=8.4 Hz, 2H), 8.74 (d, J=4.8 Hz, 1H).

Step 3: 4-[3-(4-Chlorophenyl)pyridin-2-yl]aniline

The titled compound was prepared by the reduction of Step 2 intermediate (220 mg, 0.70 mmol) using iron powder (198 mg, 3.54 mmol) and ammonium chloride (379 mg, 7.08 mmol) in a mixture of ethanol (15 mL) and water (3.0 mL) as per the procedure described in Step 4 of Intermediate 9 to yield 178 mg of the product; $^1$H NMR (300 MHz, DMSO-d$_6$) δ 5.25 (br s, 2H), 6.41 (d, J=8.4 Hz, 2H), 6.97 (d, J=8.1 Hz, 2H), 7.21 (d, J=8.4 Hz, 2H), 7.30-7.41 (m, 3H), 7.70 (d, J=6.3 Hz, 1H), 8.58 (d, J=4.5 Hz, 1H).

Intermediate 15

4-[3-(2-Fluorophenyl)pyrazin-2-yl]aniline

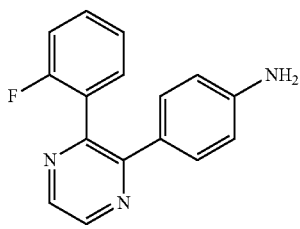 [SMILES: O=[N+]([O-])c1ccc(-c2nccnc2-c2ccccc2F)cc1]

Step 1:
2-(2-Fluorophenyl)-3-(4-nitrophenyl)pyrazine

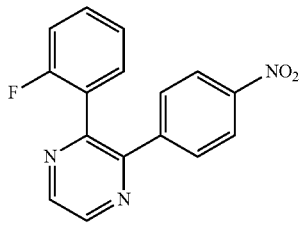

The titled compound was prepared by the reaction of 2-chloro-3-(4-nitrophenyl)pyrazine (Step 1 of intermediate 11) (306 mg, 1.31 mmol) with 2-fluorophenylboronic acid (221 mg, 1.57 mmol) using sodium carbonate monohydrate (419 mg, 3.95 mmol) and [1,1'-bis(diphenylphosphino)ferrocene]dichloropalladium (II) (48 mg, 0.06 mmol) in a mixture of DMSO and water (10 mL, 3:1) at RT as per the procedure described in Step 1 of Intermediate 1 to yield 348 mg of the product; 1H NMR (300 MHz, CDCl$_3$) δ 6.94 (t, J=9.0 Hz, 1H), 7.29 (t, J=9.3 Hz, 1H), 7.38-7.45 (m, 1H), 7.62 (d, J=8.7 Hz, 3H), 8.15 (d, J=9.0 Hz, 2H), 8.72 (d, J=2.1 Hz, 2H).

Step 2: 4-[3-(2-Fluorophenyl)pyrazin-2-yl]aniline

The titled compound was prepared by the reduction of Step 1 intermediate (312 mg, 1.05 mmol) using iron powder (177 mg, 3.16 mmol) and ammonium chloride (565 mg, 10.56 mmol) in a mixture of ethanol and water (10 mL, 4:1) as per the procedure described in Step 4 of Intermediate 9 to yield 211 mg of the product; $^1$H NMR (300 MHz, DMSO-d$_6$) δ 5.38 (s, 2H), 6.40 (d, J=8.4 Hz, 2H), 7.04-7.17 (m, 3H), 7.29 (t, J=7.2 Hz, 1H), 7.42-7.57 (m, 2H), 8.55 (s, 1H), 8.64 (d, J=2.1 Hz, 1H); APCI-MS (m/z) 266 (M+H)$^+$.

Intermediate 16

4-{3-[4-(Trifluoromethyl)phenyl]pyrazin-2-yl}aniline

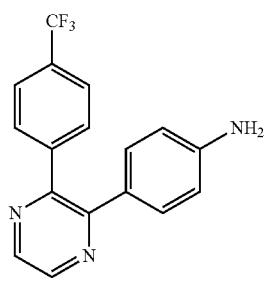 [SMILES: O=[N+]([O-])c1ccc(-c2nccnc2-c2ccc(C(F)(F)F)cc2)cc1]

Step 1: 2-(4-Nitrophenyl)-3-[4-(trifluoromethyl) phenyl]pyrazine

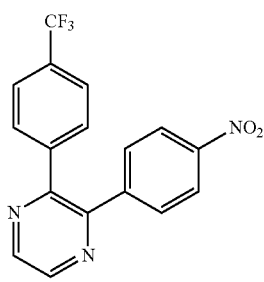

The titled compound was prepared by the reaction of 2-chloro-3-(4-nitrophenyl)pyrazine (Step 1 of intermediate 11) (308 mg, 1.32 mmol) with 4-trifluoromethyl phenylboronic acid (301 mg, 1.58 mmol) using sodium carbonate monohydrate (421 mg, 3.97 mmol) and [1,1'-bis(diphenylphosphino)ferrocene]dichloropalladium (II) (48 mg, 0.06 mmol) in a mixture of DMSO and water (10 mL, 3:1) at RT as per the procedure described in Step 1 of Intermediate 1 to yield 371 mg of the product; $^1$H NMR (300 MHz, CDCl$_3$) δ 7.53-7.67 (m, 6H), 8.19 (d, J=9.0 Hz, 2H), 8.71 (s, 2H).

Step 2: 4-{3-[4-(Trifluoromethyl)phenyl]pyrazin-2-yl}aniline

The titled compound was prepared by the reduction of Step 1 intermediate (346 mg, 1.00 mmol) using iron powder (167 mg, 3.00 mmol) and ammonium chloride (536 mg, 10.02 mmol) in a mixture of ethanol and water (10 mL, 4:1) as per the procedure described in Step 4 of Intermediate 9 to yield 241 mg of the product; $^1$H NMR (300 MHz, DMSO-d$_6$) δ 5.42 (s, 2H), 6.44 (d, J=8.4 Hz, 2H), 7.05 (d, J=7.8 Hz, 2H), 7.62 (d, J=8.1 Hz, 2H), 7.71 (d, J=8.4 Hz, 2H), 8.56 (s, 1H), 8.61 (s, 1H); APCI-MS (m/z) 316 (M+H)$^+$.

Intermediate 17

4-[3-(4-Methylphenyl)pyrazin-2-yl]aniline

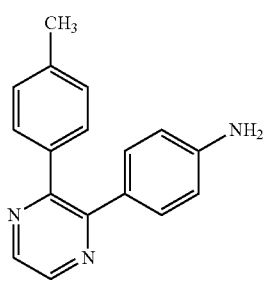

Step 1: 2-(4-Methylphenyl)-3-(4-nitrophenyl)pyrazine

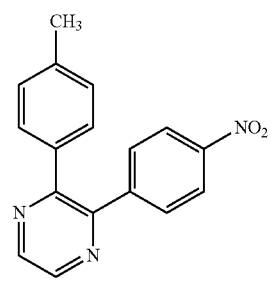

The titled compound was prepared by the reaction of 2-chloro-3-(4-nitrophenyl)pyrazine (Step 1 of intermediate 11) (300 mg, 1.28 mmol) with 4-methyl phenylboronic acid (210 mg, 1.54 mmol) using sodium carbonate monohydrate (410 mg, 3.86 mmol) and [1,1'-bis(diphenylphosphino)ferrocene]dichloropalladium (II) (47.14 mg, 0.06 mmol) in a mixture of DMSO and water (10 mL, 3:1) at RT as per the procedure described in Step 1 of Intermediate 1 to yield 248 mg of the product; $^1$H NMR (300 MHz, CDCl$_3$) δ 2.38 (s, 3H), 7.15 (d, J=7.8 Hz, 2H), 7.30 (t, J=7.8 Hz, 2H), 8.18 (d, J=8.7 Hz, 2H), 8.65 (d, J=11.4 Hz, 2H).

Step 2: 4-[3-(4-Methylphenyl)pyrazin-2-yl]aniline

The titled compound was prepared by the reduction of Step 1 intermediate (240 mg, 0.83 mmol) using iron powder (139 mg, 2.49 mmol) and ammonium chloride (445 mg, 8.32 mmol) in a mixture of ethanol and water (10 mL, 4:1) as per the procedure described in Step 4 of Intermediate 9 to yield 176 mg of the product; $^1$H NMR (300 MHz, DMSO-d$_6$) δ 2.31 (s, 3H), 5.37 (s, 2H), 6.44 (d, J=7.8 Hz, 2H), 7.08 (d, J=7.8 Hz, 2H), 7.14 (d, J=8.7 Hz, 2H), 7.31 (d, J=7.8 Hz, 2H), 8.51 (d, J=9.0 Hz, 2H).

Intermediate 18

4-[3-(4-Fluorophenyl)pyridin-2-yl]aniline

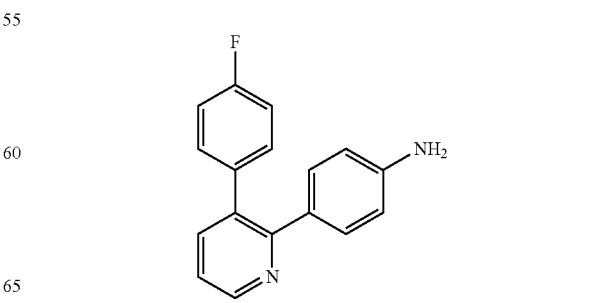

Step 1:
3-(4-Fluorophenyl)-2-(4-nitrophenyl)pyridine

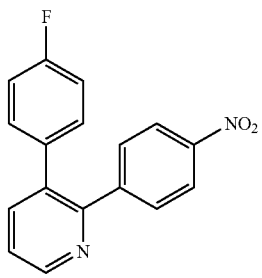 [SMILES: O=[N+]([O-])c1ccc(-c2ncccc2-c2ccc(F)cc2)cc1]

The titled compound was prepared by the reaction of 3-bromo-2-(4-nitrophenyl)pyridine (Step 1 of Intermediate 14) (250 mg, 0.89 mmol) with 4-fluorophenyl boronic acid (188 mg, 1.34 mmol) using potassium carbonate (371 mg, 2.69 mmol) and [1,1'-bis(diphenylphosphino)ferrocene]dichloropalladium (II) (73 mg, 0.08 mmol) in a mixture of DMSO and water (12 mL, 3:1) at RT as per the procedure described in Step 1 of Intermediate 1 to yield 238 mg of the product; $^1$H NMR (300 MHz, CDCl$_3$) δ 7.02 (t, J=8.7 Hz, 2H), 7.10-7.17 (m, 2H), 7.41-7.46 (m, 1H), 7.52 (d, J=8.7 Hz, 2H), 7.77 (d, J=7.8 Hz, 1H), 8.12 (d, J=8.4 Hz, 2H), 8.74 (d, J=4.5 Hz, 1H).

Step 2: 4-[3-(4-Fluorophenyl)pyridin-2-yl]aniline

The titled compound was prepared by the reduction of Step 1 intermediate (230 mg, 0.78 mmol) using iron powder (218 mg, 3.91 mmol) and ammonium chloride (418 mg, 7.81 mmol) in a mixture of ethanol and water (18 mL, 5:1) as per the procedure described in Step 4 of Intermediate 9 to yield 164 mg of the product; $^1$H NMR (300 MHz, DMSO-d$_6$) δ 5.22 (s, 2H), 6.39 (d, J=8.7 Hz, 2H), 6.96 (d, J=7.8 Hz, 2H), 7.13-7.24 (m, 4H), 7.29-7.33 (m, 1H), 7.69 (d, J=7.2 Hz, 1H), 8.55 (s, 1H).

Intermediate 19

4-(3-Phenylpyrazin-2-yl)aniline

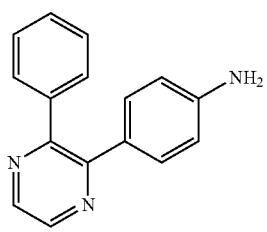

Step 1: 2-(4-Nitrophenyl)-3-phenylpyrazine

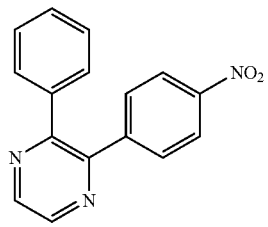 [SMILES: O=[N+]([O-])c1ccc(-c2nccnc2-c2ccccc2)cc1]

The titled compound was prepared by the reaction of 2-chloro-3-(4-nitrophenyl)pyrazine (Step 1 of Intermediate 11) (403 mg, 1.73 mmol) with phenylboronic acid (253 mg, 2.07 mmol) using sodium carbonate monohydrate (550 mg, 5.19 mmol) and [1,1'-bis(diphenylphosphino)ferrocene]dichloropalladium (II) (63 mg, 0.08 mmol) in a mixture of DMSO and water (10 mL, 3:1) at RT as per the procedure described in Step 1 of Intermediate 1 to yield 356 mg of the product; $^1$H NMR (300 MHz, CDCl$_3$) δ 7.26-7.45 (m, 5H), 7.64 (d, J=8.7 Hz, 2H), 8.16 (d, J=9.0 Hz, 2H), 8.68 (d, J=9.0 Hz, 2H).

Step 2: 4-(3-Phenylpyrazin-2-yl)aniline

The titled compound was prepared by the reduction of Step 1 intermediate (341 mg, 1.22 mmol) using iron powder (206 mg, 3.68 mmol) and ammonium chloride (657 mg, 12.29 mmol) in a mixture of ethanol and water (10 mL, 4:1) as per the procedure described in Step 4 of Intermediate 9 to yield 219 mg of the product; $^1$H NMR (300 MHz, DMSO-d$_6$) δ 5.39 (s, 2H), 6.44 (d, J=8.4 Hz, 2H), 7.08 (d, J=8.7 Hz, 2H), 7.33-7.42 (m, 5H), 8.52 (s, 1H), 8.57 (s, 1H).

Intermediate 20

4-[3-(4-Aminophenyl)pyrazin-2-yl]benzonitrile

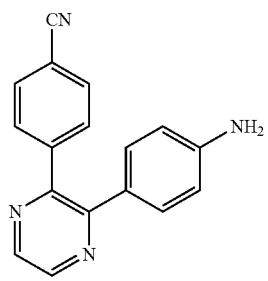 [SMILES: N#Cc1ccc(-c2nccnc2-c2ccc(N)cc2)cc1]

Step 1: 4-(3-Chloropyrazin-2-yl)benzonitrile

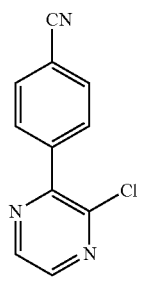 [SMILES: N#Cc1ccc(-c2nccnc2Cl)cc1]

The titled compound was prepared by the reaction of 2,3-dichloropyrazine (1.0 g, 6.77 mmol) with 4-cyanophenylboronic acid (896 mg, 6.10 mmol) using sodium carbonate monohydrate (2.5 g, 20.32 mmol) and [1,1'-bis(diphenylphosphino)ferrocene]dichloropalladium (II) (245 mg, 0.33 mmol) in a mixture of DMSO and water (25 mL, 3:1) at RT as per the procedure described in Step 1 of Intermediate 1 to yield 810 mg of the product; $^1$H NMR (300 MHz, CDCl$_3$) δ 7.80 (d, J=8.1 Hz, 2H), 7.95 (d, J=8.4 Hz, 2H), 8.43 (d, J=2.4 Hz, 1H), 8.65 (d, J=2.4 Hz, 1H).

Step 2: 4-[3-(4-Nitrophenyl)pyrazin-2-yl]benzonitrile

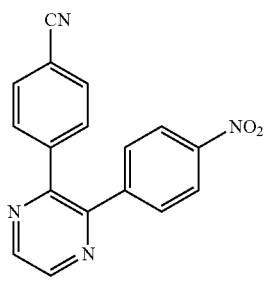 [SMILES: N#Cc1ccc(-c2nccnc2-c2ccc([N+](=O)[O-])cc2)cc1]

The titled compound was prepared by the reaction of Step 1 intermediate (503 mg, 2.33 mmol) with 4-nitrophenylboronic acid pinacol ester (581 mg, 2.33 mmol) using sodium carbonate monohydrate (867 mg, 6.99 mmol) and [1,1'-bis(diphenylphosphino)ferrocene]dichloropalladium (II) (85 mg, 0.11 mmol) in a mixture of DMSO and water (3:1, 10 mL) at RT as per the procedure described in Step 1 of Intermediate 1 to yield 526 mg of the product; $^1$H NMR (300 MHz, CDCl$_3$) δ 7.55-7.66 (m, 6H), 8.20 (d, J=8.1 Hz, 2H), 8.73 (s, 2H).

Step 3: 4-[3-(4-Aminophenyl)pyrazin-2-yl]benzonitrile

The titled compound was prepared by the reduction of Step 2 intermediate (503 mg, 1.66 mmol) using iron powder (279 mg, 4.99 mmol) and ammonium chloride (890 mg, 16.64 mmol) in a mixture of ethanol and water (10 mL, 3:1) as per the procedure described in Step 4 of Intermediate 9 to yield 313 mg of the product; $^1$H NMR (300 MHz, DMSO-d$_6$) δ 5.42 (s, 2H), 6.45 (d, J=8.1 Hz, 2H), 7.06 (d, J=8.4 Hz, 2H), 7.59 (d, J=7.8 Hz, 2H), 7.80 (d, J=8.1 Hz, 2H), 8.55 (s, 1H), 8.62 (s, 1H).

Intermediate 21

4-[3-(Pyridin-4-yl)pyrazin-2-yl]aniline

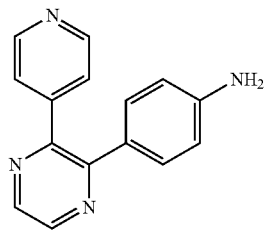 [SMILES: Nc1ccc(-c2nccnc2-c2ccncc2)cc1]

Step 1: 2-(4-Nitrophenyl)-3-(pyridin-4-yl)pyrazine

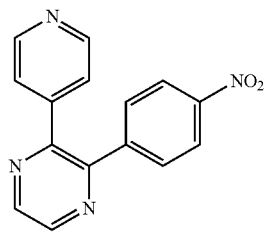 [SMILES: O=[N+]([O-])c1ccc(-c2nccnc2-c2ccncc2)cc1]

The titled compound was prepared by the reaction of 2-chloro-3-(4-nitrophenyl)pyrazine (Step 1 of Intermediate 11) (300 mg, 1.27 mmol) with pyridine 4-boronic acid (188 mg, 1.52 mmol) using potassium carbonate (528 mg, 3.82 mmol) and [1,1'-bis(diphenylphosphino)ferrocene]dichloropalladium (II) (52 mg, 0.06 mmol) in a mixture of DMSO and water (16 mL, 3:1) at RT as per the procedure described in Step 1 of Intermediate 1 to yield 208 mg of the product; 1H NMR (300 MHz, DMSO-d$_6$) δ 7.40 (d, J=4.2 Hz, 2H), 7.69 (d, J=8.1 Hz, 2H), 8.22 (d, J=8.4 Hz, 2H), 8.58 (s, 2H), 8.87 (s, 2H).

Step 2: 4-[3-(Pyridin-4-yl)pyrazin-2-yl]aniline

The titled compound was prepared by the reduction of Step 1 intermediate (200 mg, 0.71 mmol) using iron powder (200 mg, 3.69 mmol) and ammonium chloride (384 mg, 7.18 mmol) in a mixture of ethanol and water (18 mL, 5:1) as per the procedure described in Step 4 of Intermediate 9 to yield 132 mg of the product; $^1$H NMR (300 MHz, DMSO-d$_6$) δ 5.48 (s, 2H), 6.47 (d, J=8.1 Hz, 2H), 7.09 (d, J=8.1 Hz, 2H), 7.40 (d, J=5.7 Hz, 2H), 8.54-8.65 (m, 4H).

Intermediate 22

4-[5-(4-Fluorophenyl)-3-methyl-1H-pyrazol-1-yl]aniline

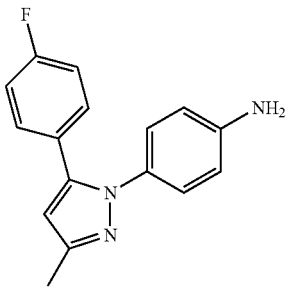 [SMILES: Cc1cc(-c2ccc(F)cc2)n(-c2ccc(N)cc2)n1]

Step 1: 1-(4-Fluorophenyl)butane-1,3-dione

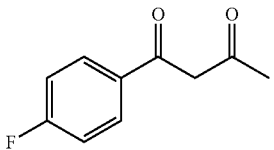

To a stirred solution of 4-fluoroacetophenone (1.02 g, 7.38 mmol) in anhydrous THF (10 mL) was added sodium hydride (60% w/w, 886 mg, 22.15 mmol) portion wise at RT. The mixture was stirred for 30 min, to it was added ethyl acetate (3.0 mL, 29.5 mmol) and it was further stirred at 40° C. for 3 h. The mixture was cooled to RT, quenched with 1N HCl and extracted with ethyl acetate (100 mL×2). The combined organic layers were washed with brine (100 mL), dried over anhydrous sodium sulfate and concentrated under reduced pressure. The crude compound obtained was purified by silica gel column chromatography to yield 813 mg of the desired product; $^1$H NMR (300 MHz, CDCl$_3$) δ 2.19 (s, 3H), 6.13 (s, 1H), 7.12 (t, J=8.4 Hz, 2H), 7.89 (t, J=5.4 Hz, 2H), 16.16 (br s, 1H).

Step 2: 5-(4-Fluorophenyl)-3-methyl-1-(4-nitrophenyl)-1H-pyrazole

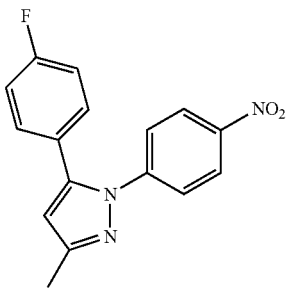 [SMILES: Cc1cc(-c2ccc(F)cc2)n(-c2ccc([N+](=O)[O-])cc2)n1]

A mixture of Step 1 intermediate (202 mg, 1.12 mmol) and 4-nitrophenyl hydrazine (206 mg, 1.34 mmol) in ethanol (10 mL) was refluxed for 3 h. The solvent was distilled off and the residue thus obtained was purified by silica gel column chromatography to yield 231 mg of the titled product; $^1$H NMR (300 MHz, DMSO-d$_6$) δ 2.29 (s, 3H), 6.54 (s, 1H), 7.21-7.33 (m, 4H), 7.46 (d, J=9.0 Hz, 2H), 8.22 (d, J=8.7 Hz, 2H); ESI-MS (m/z) 298 (M+H)$^+$.

Step 3: 4-[5-(4-Fluorophenyl)-3-methyl-1H-pyrazol-1-yl]aniline

The titled compound was prepared by the reduction of Step 2 intermediate (221 mg, 0.74 mmol) using iron powder (125 mg, 2.23 mmol) and ammonium chloride (408 mg, 7.43 mmol) in a mixture of ethanol and water (10 mL, 4:1) as per the procedure described in Step 4 of Intermediate 9 to yield 151 mg of the product; $^1$H NMR (300 MHz, DMSO-d$_6$) δ 2.20 (s, 3H), 5.27 (s, 2H), 6.33 (s, 1H), 6.48 (d, J=9.0 Hz, 2H), 6.82 (d, J=9.0 Hz, 2H), 7.10-7.21 (m, 4H); ESI-MS (m/z) 268 (M+H)$^+$.

Intermediate 23

4-[3-(1-Methyl-1H-pyrazol-4-yl)pyrazin-2-yl]aniline

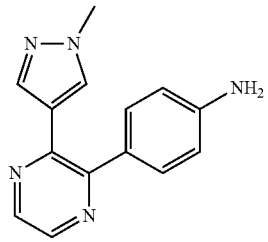 [SMILES: Cn1cc(-c2nccnc2-c2ccc(N)cc2)cn1]

Step 1: 2-Chloro-3-(1-methyl-1H-pyrazol-4-yl)pyrazine

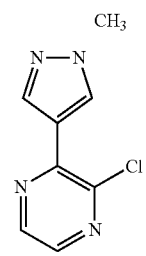

The titled compound was prepared by the reaction of 2,3-dichloropyrazine (200 mg, 1.34 mmol) with 1-methylpyrazole-4-boronic acid pinacol ester (335 mg, 1.61 mmol) using potassium carbonate (557 mg, 4.02 mmol) and [1,1'-bis(diphenylphosphino)ferrocene]dichloropalladium (II) (55 mg, 0.06 mmol) in a mixture of DMSO and water (16 mL, 3:1) at 90° C. as per the procedure described in Step 1 of Intermediate 1 to yield 156 mg of the product; $^1$H NMR (300 MHz, DMSO-d$_6$) δ 3.92 (s, 3H), 8.13 (s, 1H), 8.30 (s, 1H), 8.52 (s, 1H), 8.61 (s, 1H).

Step 2: 4-[3-(1-Methyl-1H-pyrazol-4-yl)pyrazin-2-yl]aniline

The titled compound was prepared by the reaction of step 1 intermediate (150 mg, 0.77 mmol) with 4-aminophenylboronic acid pinacol ester (203 mg, 0.92 mmol) using 2M sodium carbonate solution (1.2 mL, 2.31 mmol) and tetrakis(triphenylphosphine)palladium(0) (89 mg, 0.07 mmol) in 1,4 dioxane (2.3 mL) at 90° C. as per the procedure described in Step 1 of Intermediate 1 to yield 86 mg of the product; $^1$H NMR (300 MHz, DMSO-d$_6$) δ 3.78 (s, 3H), 5.43 (s, 2H), 6.60 (d, J=8.4 Hz, 2H), 7.17 (t, J=8.1 Hz, 3H), 7.74 (s, 1H), 8.41 (d, J=9.3 Hz, 2H).

Intermediate 24

1-{4-[3-(4-Aminophenyl)pyrazin-2-yl]piperazin-1-yl}ethanone

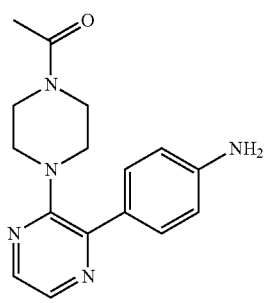

Step 1: 1-[4-(3-Chloropyrazin-2-yl)piperazin-1-yl]ethanone

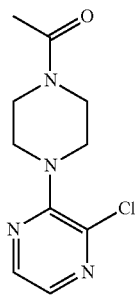

The titled compound was prepared by the reaction of 2,3-dichloropyrazine (300 mg, 2.01 mmol) with 1-acetylpiperazine (258 mg, 2.01 mmol) using potassium carbonate (278 mg, 2.01 mmol) in acetonitrile (20 mL) at 100° C. as per the procedure described in Step 1 of Intermediate 7 to yield 247 mg of the product; $^1$H NMR (300 MHz, CDCl$_3$) δ 2.15 (s, 3H), 3.44 (br s, 4H), 3.64 (br s, 2H), 3.77 (br s, 2H), 7.94 (s, 1H), 8.13 (s, 1H).

Step 2: 1-{4-[3-(4-Nitrophenyl)pyrazin-2-yl]piperazin-1-yl}ethanone

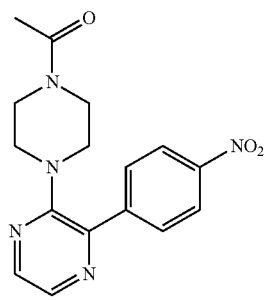 [SMILES: CC(=O)N1CCN(c2nccnc2-c2ccc([N+](=O)[O-])cc2)CC1]

The titled compound was prepared by the reaction of Step 1 intermediate (200 mg, 0.83 mmol) with 4-nitrophenylboronic acid pinacol ester (248 mg, 0.99 mmol) using potassium carbonate (344 mg, 2.49 mmol) and [1,1'-bis(diphenylphosphino)ferrocene]dichloropalladium (II) (34 mg, 0.04 mmol) in a mixture of DMSO and water (12 mL, 3:1) at RT as per the procedure described in Step 1 of Intermediate 1 to yield 127 mg of the product; $^1$H NMR (300 MHz, CDCl$_3$) δ 2.08 (s, 3H), 3.15-3.26 (m, 4H), 3.48 (br s, 2H), 3.61 (br s, 2H), 8.15 (t, J=8.7 Hz, 3H), 8.30 (t, J=8.7 Hz, 3H).

Step 3: 1-{4-[3-(4-Aminophenyl)pyrazin-2-yl]piperazin-1-yl}ethanone

The titled compound was prepared by the reduction of Step 2 intermediate (100 mg, 0.30 mmol) using iron powder (85 mg, 1.52 mmol) and ammonium chloride (163 mg, 3.05 mmol) in a mixture of ethanol and water (18 mL, 5:1) as per the procedure described in Step 4 of Intermediate 9 to yield 87 mg of the product; $^1$H NMR (300 MHz, DMSO-d$_6$) δ 1.98 (s, 3H), 3.06 (br s, 4H), 3.47 (br s, 4H), 5.46 (s, 2H), 6.62 (d, J=8.4 Hz, 2H), 7.70 (d, J=8.4 Hz, 2H), 8.03 (s, 1H), 8.12 (s, 1H); ESI-MS (m/z) 298 (M+H)$^+$.

Intermediate 25

5-[3-(4-Aminophenyl)pyrazin-2-yl]-1-methylpyridin-2(1H)-one

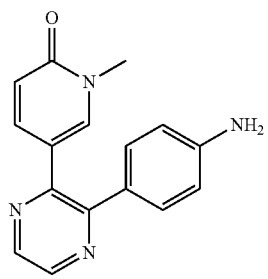

Step 1: 1-Methyl-5-(4,4,5,5-tetramethyl-1,3,2-dioxaborolan-2-yl)pyridin-2(1H)-one

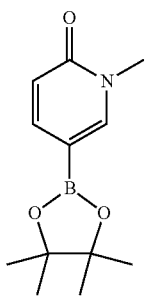

To a stirred suspension of 5-bromo-1-methylpyridin-2(1H)-one (470 mg, 2.49 mmol), potassium acetate (736 mg, 7.49 mmol) and bis(pinacolato)diboron (952 mg, 3.74 mmol) in degassed polyethylene glycol-400 (15 mL) was added [1,1'-bis(diphenylphosphino)ferrocene]dichloropalladium (II) (204 mg, 0.24 mmol) at RT. The resultant suspension was stirred for 3 h at 80° C. The reaction mixture was cooled to RT, diluted with ethyl acetate (100 mL) and washed with water (100 mL) followed by brine (100 mL). The organic layer was concentrated and the residue obtained purified by flash column chromatography to afford 160 mg of the titled product; $^1$H NMR (300 MHz, CDCl$_3$) δ 1.30 (s, 12H), 3.54 (s, 3H), 6.53 (d, J=9.3 Hz, 1H), 7.60 (d, J=9.0 Hz, 1H), 7.75 (s, 1H); APCI-MS (m/z) 236 (M+H)$^+$.

Step 2: 1-Methyl-5-[3-(4-nitrophenyl)pyrazin-2-yl]pyridin-2(1H)-one

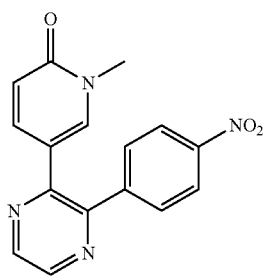 [SMILES: Cn1cc(-c2nccnc2-c2ccc([N+](=O)[O-])cc2)ccc1=O]

The titled compound was prepared by the reaction of 2-chloro-3-(4-nitrophenyl)pyrazine (Step 1 of intermediate 11) (90 mg, 0.38 mmol) with Step 1 intermediate (100 mg, 0.42 mmol) using potassium carbonate (176 mg, 1.27 mmol) and [1,1'-bis(diphenylphosphino)ferrocene]dichloropalladium (II) (35 mg, 0.04 mmol) in a mixture of DMSO and water (12 mL, 3:1) at RT as per the procedure described in Step 1 of Intermediate 1 to yield 63 mg of the product. $^1$H NMR (300 MHz, CDCl$_3$) δ 3.59 (s, 3H), 6.40 (d, J=9.3 Hz, 1H), 7.08 (d, J=9.6 Hz, 1H), 7.78 (d, J=8.7 Hz, 2H), 7.86 (s, 1H), 8.28 (d, J=8.7 Hz, 2H), 8.61 (s, 2H).

Step 3: 5-[3-(4-Aminophenyl)pyrazin-2-yl]-1-methylpyridin-2(1H)-one

The titled compound was prepared by the reduction of Step 2 intermediate (160 mg, 0.51 mmol) using iron powder (145 mg, 2.59 mmol) and ammonium chloride (278 mg, 5.19 mmol) in a mixture of ethanol and water (18 mL, 5:1) as per the procedure described in Step 4 of Intermediate 9 to yield 93 mg of the product; $^1$H NMR (300 MHz, CDCl$_3$) δ 3.44-3.58 (m, 3H), 6.38-6.42 (m, 1H), 7.04 (d, J=7.5 Hz, 1H), 7.14 (d, J=8.7 Hz, 1H), 7.26 (s, 1H), 7.42 (d, J=8.1 Hz, 2H), 7.50-7.53 (m, 1H), 7.78 (br s, 1H), 8.45-8.56 (m, 2H).

Intermediate 26

4-[3-(4-Chlorophenyl)pyrazin-2-yl]-2-fluoroaniline

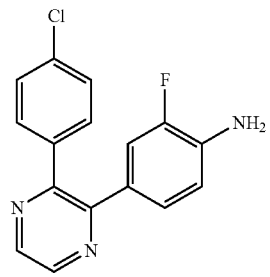 [SMILES: Nc1ccc(-c2nccnc2-c2ccc(Cl)cc2)cc1F]

The titled compound was prepared by the reaction of 2-chloro-3-(4-chlorophenyl)pyrazine (Step 1 of Intermediate 1) (300 mg, 1.33 mmol) with 4-amino-3-fluorophenylboronic acid pinacol ester (380 mg, 1.63 mmol) using potassium carbonate (552 mg, 3.99 mmol) and [1,1'-bis(diphenylphosphino)ferrocene]dichloropalladium (II) (109 mg, 0.13 mmol) in a mixture of DMSO and water (20 mL, 3:1) at RT as per the procedure described in Step 1 of Intermediate 1 to yield 196 mg of the product; $^1$H NMR (300 MHz, CDCl$_3$) δ 3.85-3.89 (m, 2H), 6.82-6.86 (m, 1H), 7.03 (d, J=7.2 Hz, 1H), 7.21-7.31 (m, 3H), 7.42 (d, J=8.4 Hz, 2H), 8.56 (s, 2H).

Intermediate 27

4-[3-(4-Methoxyphenyl)pyrazin-2-yl]aniline

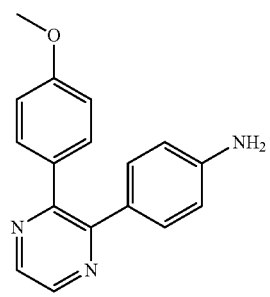 [SMILES: COc1ccc(-c2nccnc2-c2ccc(N)cc2)cc1]

Step:
2-(4-Methoxyphenyl)-3-(4-nitrophenyl)pyrazine

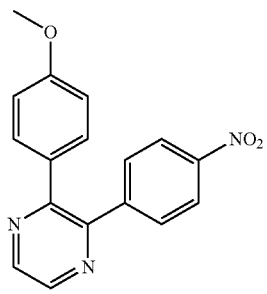 [SMILES: COc1ccc(-c2nccnc2-c2ccc([N+](=O)[O-])cc2)cc1]

The titled compound was prepared by the reaction of 2-chloro-3-(4-nitrophenyl)pyrazine (Step 1 of Intermediate 11) (300 mg, 1.28 mmol) with 4-methoxyphenylboronic acid (235 mg, 1.54 mmol) using sodium carbonate monohydrate (410 mg, 3.86 mmol) and [1,1'-bis(diphenylphosphino)ferrocene]dichloropalladium (II) (47 mg, 0.06 mmol) in a mixture of DMSO and water (10 mL, 3:1) at RT as per the procedure described in Step 1 of Intermediate 1 to yield 298 mg of the product; $^1$H NMR (300 MHz, CDCl$_3$) δ 3.82 (s, 3H), 6.85 (d, J=8.7 Hz, 2H), 7.37 (d, J=8.1 Hz, 2H), 7.66 (d, J=8.1 Hz, 2H), 8.19 (d, J=8.7 Hz, 2H), 8.64 (d, J=10.2 Hz, 2H).

Step 2: 4-[3-(4-Methoxyphenyl)pyrazin-2-yl]aniline

The titled compound was prepared by the reduction of Step 1 intermediate (277 mg, 0.90 mmol) using iron powder (151 mg, 2.70 mmol) and ammonium chloride (482 mg, 9.13 mmol) in a mixture of ethanol and water (10 mL, 3:1) as per the procedure described in Step 4 of Intermediate 9 to yield 199 mg of the product; $^1$H NMR (300 MHz, DMSO-d$_6$) δ δ 3.76 (s, 3H), 5.37 (s, 2H), 6.45 (d, J=8.7 Hz, 2H), 6.89 (d, J=8.1 Hz, 2H), 7.10 (d, J=8.1 Hz, 2H), 7.37 (d, J=8.7 Hz, 2H), 8.49 (d, J=10.2 Hz, 2H).

Intermediate 28

4-[5-(4-Fluorophenyl)-3-(trifluoromethyl)-1H-pyrazol-1-yl]aniline

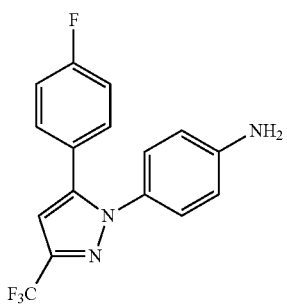

Step 1:
4,4,4-Trifluoro-1-(4-fluorophenyl)butane-1,3-dione

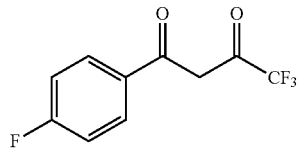 [SMILES: O=C(CC(=O)C(F)(F)F)c1ccc(F)cc1]

The titled compound was prepared by the reaction of 4-fluoroacetophenone (2.1 g, 15.23 mmol) with ethyl trifluoroacetate (2.0 mL, 16.79 mmol) using sodium methoxide (25% in CH$_3$OH, 1.14 mL, 18.2 mmol) in methyl t-butyl ether (4.5 mL) as per the procedure described in Step 1 of Intermediate 22 to afford 2.10 g of the product; $^1$H NMR (300 MHz, CDCl$_3$) δ 6.53 (s, 1H), 7.10-7.26 (m, 2H), 7.95-8.01 (m, 2H).

Step 2: 5-(4-Fluorophenyl)-1-(4-nitrophenyl)-3-(trifluoromethyl)-1H-pyrazole

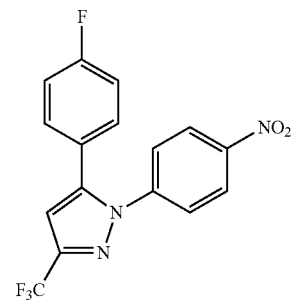 [SMILES: O=[N+]([O-])c1ccc(-n2nc(C(F)(F)F)cc2-c2ccc(F)cc2)cc1]

The titled compound was prepared by the reaction of Step 1 intermediate (1.02 g, 4.35 mmol) with 4-nitrophenylhydrazine (667 mg, 4.35 mmol) in 2,2,2-trifluoroethanol (10 mL) as per the procedure described in Step 2 of Intermediate 22 to yield 613 mg of the product; 1H NMR (300 MHz, CDCl$_3$) δ 6.77 (s, 1H), 7.10 (t, J=8.4 Hz, 2H), 7.23 (t, J=4.8 Hz, 2H), 7.50 (d, J=8.7 Hz, 2H), 8.24 (d, J=8.4 Hz, 2H).

Step 3: 4-[5-(4-Fluorophenyl)-3-(trifluoromethyl)-1H-pyrazol-1-yl]aniline

The titled compound was prepared by the reduction of Step 2 intermediate (511 mg, 1.59 mmol) using iron powder (266 mg, 4.77 mmol) and ammonium chloride (850 mg, 15.90 mmol) in a mixture of ethanol and water (10 mL, 3:1) as per the procedure described in Step 4 of Intermediate 9 to yield 314 mg of the product; $^1$H NMR (300 MHz, DMSO-d$_6$) δ 5.48 (s, 2H), 6.53 (d, J=8.4 Hz, 2H), 6.95 (d, J=8.7 Hz, 2H), 7.10 (s, 1H), 7.21-7.26 (m, 2H), 7.30-7.33 (m, 2H).

Intermediate 29

4-[5-(2-Chlorophenyl)-3-(trifluoromethyl)-1H-pyrazol-1-yl]aniline

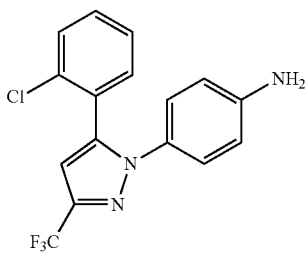 [SMILES: Nc1ccc(-n2nc(C(F)(F)F)cc2-c2ccccc2Cl)cc1]

Step 1:
1-(2-Chlorophenyl)-4,4,4-trifluorobutane-1,3-dione

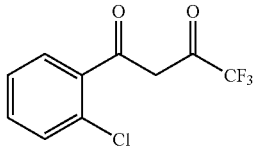 [SMILES: O=C(CC(=O)C(F)(F)F)c1ccccc1Cl]

The titled compound was prepared by the reaction of 2-chloroacetophenone (1.10 g, 7.11 mmol) with ethyl trifluoroacetate (929 μL, 7.82 mmol) using sodium methoxide (25% in CH$_3$OH, 1.84 mL, 8.53 mmol) in methyl tert-butyl ether (10 mL) as per the procedure described in Step 1 of Intermediate 22 to afford 1.05 g of the product; $^1$H NMR (300 MHz, CDCl$_3$) δ 6.57 (s, 1H), 7.32-7.49 (m, 3H), 7.67 (d, J=7.5 Hz, 1H).

Step 2: 5-(2-Chlorophenyl)-1-(4-nitrophenyl)-3-(trifluoromethyl)-1H-pyrazole

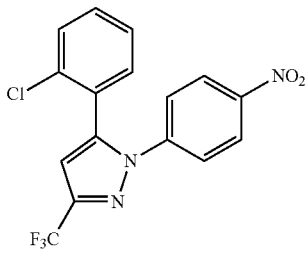 [SMILES: O=[N+]([O-])c1ccc(-n2nc(C(F)(F)F)cc2-c2ccccc2Cl)cc1]

The titled compound was prepared by the reaction of Step 1 intermediate (1.12 g, 4.86 mmol) with 4-nitrophenylhydrazine (745 mg, 4.86 mmol) in 2,2,2-trifluoroethanol (10 mL) as per the procedure described in Step 2 of Intermediate 22 to yield 813 mg of the product; $^1$H NMR (300 MHz, CDCl$_3$) δ 6.80 (s, 1H), 7.25 (s, 2H), 7.35-7.47 (m, 4H), 8.16 (d, J=9.3 Hz, 2H).

Step 3: 4-[5-(2-Chlorophenyl)-3-(trifluoromethyl)-1H-pyrazol-1-yl]aniline

The titled compound was prepared by the reduction of Step 2 intermediate (709 mg, 1.93 mmol) using iron powder (323 mg, 5.79 mmol) and ammonium chloride (1.33 g, 19.32 mmol) in a mixture of ethanol and water (10 mL, 3:1) as per the procedure described in Step 4 of Intermediate 9 to yield 412 mg of the product; $^1$H NMR (300 MHz, DMSO-d$_6$) δ 5.38 (s, 2H), 6.44 (d, J=8.7 Hz, 2H), 6.88 (d, J=8.7 Hz, 2H), 7.03 (s, 1H), 7.40-7.51 (m, 4H); APCI-MS (m/z) 338 (M+H)$^+$

Intermediate 30

4-[3-(2-Chlorophenyl)pyridin-2-yl]aniline

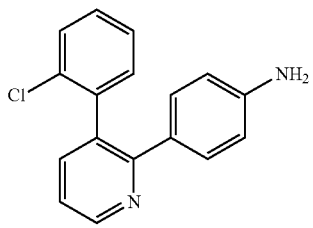 [SMILES: Nc1ccc(-c2ncccc2-c2ccccc2Cl)cc1]

Step 1:
3-(2-Chlorophenyl)-2-(4-nitrophenyl)pyridine

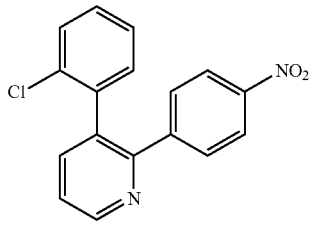 [SMILES: O=[N+]([O-])c1ccc(-c2ncccc2-c2ccccc2Cl)cc1]

The titled compound was prepared by the reaction of 3-bromo-2-(4-nitrophenyl)pyridine (Step 1 of Intermediate 14) (250 mg, 0.89 mmol) with 2-chlorophenylboronic acid (209 mg, 1.34 mmol) using potassium carbonate (371 mg, 2.69 mmol) and [1,1'-bis(diphenylphosphino)ferrocene]dichloropalladium (II) (73 mg, 0.08 mmol) in a mixture of DMSO and water (12 mL, 3:1) at RT as per the procedure described in Step 1 of Intermediate 1 to yield 193 mg of the product; $^1$H NMR (300 MHz, DMSO-d$_6$) δ 7.40-7.62 (m, 7H), 7.86 (d, J=7.8 Hz, 1H), 8.11 (d, J=9.0 Hz, 2H), 8.79 (d, J=3.0 Hz, 1H).

Step 2: 4-[3-(2-Chlorophenyl)pyridin-2-yl]aniline

The titled compound was prepared by the reduction of Step 1 intermediate (184 mg, 0.59 mmol) using iron powder (165 mg, 2.96 mmol) and ammonium chloride (316 mg, 5.92 mmol) in a mixture of ethanol and water (12 mL, 3:1) as per the procedure described in Step 4 of Intermediate 9 to yield 127 mg of the product; $^1$H NMR (300 MHz, DMSO-d$_6$) δ 5.17 (s, 2H), 6.31 (d, J=8.4 Hz, 2H), 6.94 (d, J=7.8 Hz, 2H), 7.23-7.32 (m, 4H), 7.40-7.43 (m, 1H), 7.60 (d, J=7.5 Hz, 1H), 8.58 (s, 1H).

Intermediate 31

4-[3-(2-Methylphenyl)pyrazin-2-yl]aniline

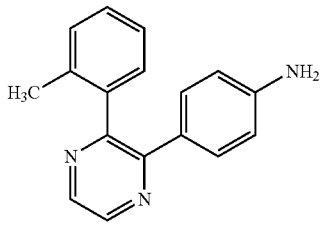

Step 1: 2-(2-Methylphenyl)-3-(4-nitrophenyl)pyrazine

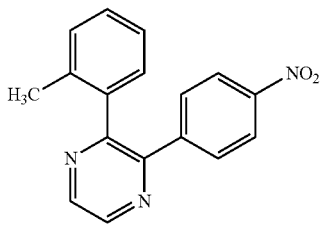 [SMILES: Cc1ccccc1-c1nccnc1-c1ccc([N+](=O)[O-])cc1]

The titled compound was prepared by the reaction of 2-chloro-3-(4-nitrophenyl)pyrazine (Step 1 of intermediate 11) (309 mg, 1.28 mmol) with o-tolylboronic acid (210 mg, 1.54 mmol) using sodium carbonate monohydrate (410 mg, 3.86 mmol) and [1,1'-bis(diphenylphosphino)ferrocene]dichloropalladium (II) (47 mg, 0.06 mmol) in a mixture of DMSO and water (10 mL, 3:1) at 100° C. as per the procedure described in Step 1 of Intermediate 1 to yield 258 mg of the product; $^1$H NMR (300 MHz, CDCl$_3$) δ 2.01 (s, 3H), 7.20-7.33 (s, 4H), 7.58 (d, J=8.7 Hz, 2H), 8.10 (d, J=9.0 Hz, 2H), 8.71 (s, 2H); APCI-MS (m/z) 292 (M+H)$^+$.

Step 2: 4-[3-(2-Methylphenyl)pyrazin-2-yl]aniline

The titled compound was prepared by the reduction of Step 1 intermediate (223 mg, 0.76 mmol) using iron powder (128 mg, 2.29 mmol) and ammonium chloride (410 mg, 7.65 mmol) in a mixture of ethanol and water (10 mL, 1:1) as per the procedure described in Step 4 of Intermediate 9 to yield 153 mg of the product; $^1$H NMR (300 MHz, DMSO-d$_6$) δ 1.89 (s, 3H), 5.36 (s, 2H), 6.36 (d, J=8.4 Hz, 2H), 7.03 (d, J=8.1 Hz, 2H), 7.20-7.27 (m, 4H), 8.52 (s, 1H), 8.61 (s, 1H); APCI-MS (m/z) 262 (M+H)$^+$.

Intermediate 32

4-[3-(4-Methylpiperazin-1-yl)pyrazin-2-yl]aniline

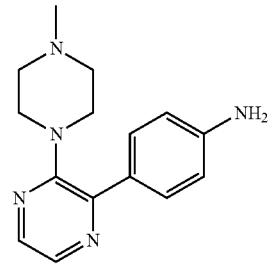 [SMILES: CN1CCN(c2nccnc2-c2ccc(N)cc2)CC1]

Step 1: 2-Chloro-3-(4-methylpiperazin-1-yl)pyrazine

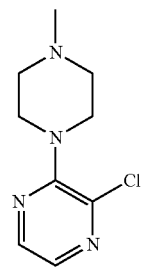

The titled compound was prepared by the reaction of 2,3-dichloropyrazine (1.0 g, 6.71 mmol) with N-methylpiperazine (988 mg, 9.86 mmol) in acetonitrile (25 mL) at RT as per the procedure described in Step 1 of Intermediate 7 to yield 658 mg of the product; $^1$H NMR (300 MHz, CDCl$_3$) δ 2.40 (s, 3H), 2.58-2.65 (m, 4H), 3.52 (s, 4H), 7.86 (d, J=2.1 Hz, 1H), 8.09 (s, 1H).

Step 2: 2-(4-Methylpiperazin-1-yl)-3-(4-nitrophenyl)pyrazine

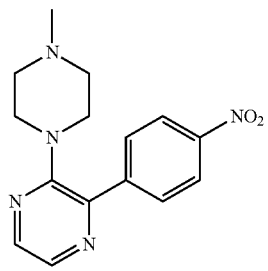 [SMILES: CN1CCN(c2nccnc2-c2ccc([N+](=O)[O-])cc2)CC1]

The titled compound was prepared by the reaction of Step 1 intermediate (300 mg, 1.41 mmol) with 4-nitrophenylboronic acid pinacol ester (422 mg, 1.69 mmol) using potassium carbonate (585 mg, 4.23 mmol) and [1,1'-bis(diphenylphosphino)ferrocene]dichloropalladium (II) (58 mg, 0.07 mmol) in a mixture of DMSO and water (12 mL, 3:1) at 80° C. as per the procedure described in Step 1 of Intermediate 1 to yield 208 mg of the product; $^1$H NMR (300 MHz, CDCl$_3$) δ 2.38 (s, 3H), 2.53 (s, 4H), 3.30 (s, 4H), 8.12-8.21 (m, 4H), 8.32 (d, J=8.7 Hz, 2H).

Step 3: 4-[3-(4-Methylpiperazin-1-yl)pyrazin-2-yl] aniline

The titled compound was prepared by the reduction of Step 2 intermediate (200 mg, 0.66 mmol) using iron powder (186 mg, 3.34 mmol) and ammonium chloride (358 mg, 6.68 mmol) in a mixture of ethanol and water (18 mL, 5:1) as per the procedure described in Step 4 of Intermediate 9 to yield 129 mg of the product; $^1$H NMR (300 MHz, CDCl$_3$) δ 2.41 (s, 4H), 2.60 (s, 4H), 3.34 (s, 3H), 3.85 (br s, 2H), 6.73 (d, J=8.7 Hz, 2H), 7.74 (d, J=7.8 Hz, 2H), 8.01 (s, 1H), 8.12 (s, 1H); APCI-MS (m/z) 270 (M+H)$^+$.

Intermediate 33

4-[3-(4-Ethylpiperazin-1-yl)pyrazin-2-yl]aniline

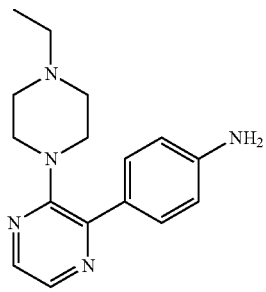

Step 1: 2-Chloro-3-(4-ethylpiperazin-1-yl)pyrazine

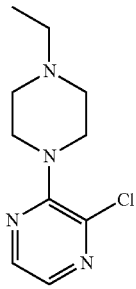

The titled compound was prepared by the reaction of 2,3-dichloropyrazine (1.0 g, 6.71 mmol) with N-ethylpiperazine (1.13 g, 9.86 mmol) in acetonitrile (25 mL) as per the procedure described in Step 1 of Intermediate 7 to yield 958 mg of the product; ESI-MS (m/z) 227 (M+H)$^+$.

Step 2: 2-(4-Ethylpiperazin-1-yl)-3-(4-nitrophenyl) pyrazine

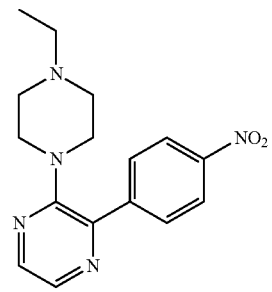 [SMILES: CCN1CCN(c2nccnc2-c2ccc([N+](=O)[O-])cc2)CC1]

The titled compound was prepared by the reaction of Step 1 intermediate (300 mg, 1.32 mmol) with 4-nitrophenylboronic acid pinacol ester (396 mg, 1.59 mmol) using potassium carbonate (549 mg, 3.97 mmol) and [1,1'-bis(diphenylphosphino)ferrocene]dichloropalladium (II) (54 mg, 0.06 mmol) in a mixture of DMSO and water (12 mL, 3:1) at 80° C. as per the procedure described in Step 1 of Intermediate 1 to yield 196 mg of the product; $^1$H NMR (300 MHz, CDCl$_3$) δ 1.14 (t, J=8.4 Hz, 3H), 2.49-2.56 (m, 6H), 3.31 (s, 4H), 8.10-8.22 (m, 4H), 8.30 (d, J=8.4 Hz, 2H); APCI-MS (m/z) 314 (M+H)$^+$.

Step 3: 4-[3-(4-Ethylpiperazin-1-yl)pyrazin-2-yl] aniline

The titled compound was prepared by the reduction of Step 2 intermediate (190 mg, 0.60 mmol) using iron powder (169 mg, 3.03 mmol) and ammonium chloride (324 mg, 6.06 mmol) in a mixture of ethanol and water (18 mL, 5:1) as per the procedure described in Step 4 of Intermediate 9 to yield 108 mg of the product; $^1$H NMR (300 MHz, CDCl$_3$) δ 1.13 (t, J=6.9 Hz, 3H), 2.48-2.57 (m, 6H), 3.30 (s, 4H), 3.83 (br s, 2H), 6.72 (d, J=7.8 Hz, 2H), 7.73 (d, J=8.4 Hz, 2H), 7.98 (s, 1H), 8.09 (s, 1H); APCI-MS (m z) 285 (M+H)$^+$.

Intermediate 34

4-(2-(4-Chlorophenyl)pyridin-3-yl)aniline

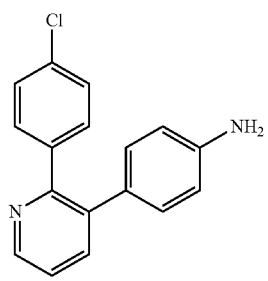

Step 1: 3-Bromo-2-(4-chlorophenyl)pyridine

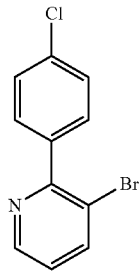

The titled compound was prepared by the reaction of 2,3-dibromopyridine (803 mg, 3.39 mmol) with 4-chlorophenylboronic acid (530 mg, 3.39 mmol) using sodium carbonate (1.06 g, 10.16 mmol) and [1,1'-bis(diphenylphosphino)ferrocene]dichloropalladium (II) (124 mg, 0.17 mmol) in a mixture of DMSO and water (10 mL, 1:1) as per the procedure described in Step 1 of Intermediate 1 to yield 378 mg of the product; $^1$H NMR (300 MHz, CDCl$_3$) δ 7.12-7.19 (m, 1H), 7.43 (d, J=8.7 Hz, 2H), 7.63 (d, J=8.4 Hz, 2H), 7.99 (d, J=7.8 Hz, 1H), 8.61 (d, J=4.5 Hz, 1H); APCI-MS (m/z) 268 (M)$^+$, 270 (M+2H)$^+$.

Step 2: 4-(2-(4-Chlorophenyl)pyridin-3-yl)aniline

The titled compound was prepared by the reaction of Step 1 intermediate (203 mg, 0.76 mmol) with 4-aminophenylboronic acid pinacol ester (264 mg, 0.91 mmol) using sodium carbonate (238 mg, 2.27 mmol) and [1,1'-bis(diphenylphosphino)ferrocene]dichloropalladium (II) (28 mg, 0.04 mmol) in a mixture of DMSO and water (10 mL, 4:1) at RT as per the procedure described in Step 1 of Intermediate 1 to yield 137 mg of the product; $^1$H NMR (300 MHz, DMSO-d$_6$) δ 5.20 (s, 2H), 6.48 (d, J=8.1 Hz, 2H), 7.81 (d, J=8.1 Hz, 2H), 7.32 (s, 4H), 7.38-7.42 (m, 1H), 7.72 (d, J=7.2 Hz, 1H), 8.56 (s, 1H); APCI-MS (m/z) 281 (M+H)$^+$,

Intermediate 35

4-(4-(4-Chlorophenyl)pyridin-3-yl)aniline

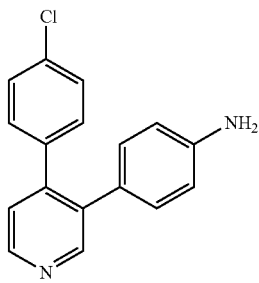 [SMILES: Nc1ccc(-c2cnccc2-c2ccc(Cl)cc2)cc1]

Step 1: 3-Bromo-4-(4-chlorophenyl)pyridine

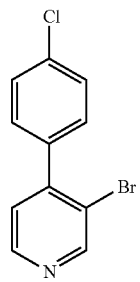 [SMILES: Clc1ccc(-c2ccncc2Br)cc1]

The titled compound was prepared by the reaction of 3,4-dibromopyridine (1.02 g, 4.30 mmol) with 4-chlorophenylboronic acid (673 mg, 4.30 mmol) using cesium carbonate (2.10 g, 6.45 mmol) and [1,1'-bis(diphenylphosphino)ferrocene]dichloropalladium (II) (157 mg, 0.22 mmol) in a mixture of DMSO and water (20 mL, 3:1) as per the procedure described in Step 1 of Intermediate 1 to yield 513 mg of the product; $^1$H NMR (300 MHz, CDCl$_3$) δ 7.25 (d, J=6.9 Hz, 1H), 7.37 (d, J=8.4 Hz, 2H), 7.44 (d, J=8.4 Hz, 2H), 8.54 (d, J=5.1 Hz, 1H), 8.81 (s, 1H); APCI-MS (m/z) 268 (M)$^+$, 270 (M+2H)$^+$.

Step 2: 4-(4-(4-Chlorophenyl)pyridin-3-yl)aniline

The titled compound was prepared by the reaction of Step 1 intermediate (251 mg, 0.93 mmol) with 4-aminophenylboronic acid pinacol ester (326 mg, 1.12 mmol) using sodium carbonate (294 mg, 2.80 mmol) and [1,1'-bis(diphenylphosphino)ferrocene]dichloropalladium (II) (34 mg, 0.05 mmol) in a mixture of DMSO and water (10 mL, 4:1) at RT as per the procedure described in Step 1 of Intermediate 1 to yield 123 mg of the product; $^1$H NMR (300 MHz, DMSO-d$_6$) δ 5.20 (s, 2H), 6.47 (d, J=8.4 Hz, 2H), 6.79 (d, J=7.8 Hz, 2H), 7.20 (t, J=8.4 Hz, 2H), 7.33-7.41 (m, 3H), 8.51 (s, 2H).

Intermediate 36

4-(3-((2S,6R)-2,6-Dimethylmorpholino)pyrazin-2-yl)aniline

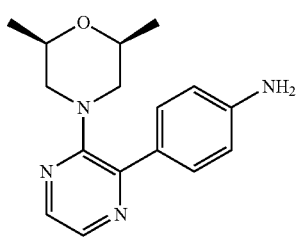 [SMILES: C[C@@H]1CN(c2nccnc2-c2ccc(N)cc2)C[C@H](C)O1]

Step 1: (2S,6R)-4-(3-Chloropyrazin-2-yl)-2,6-dimethylmorpholine

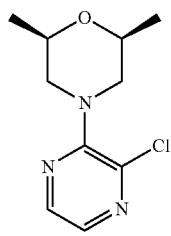

The titled compound was prepared by the reaction of 2,3-dichloropyrazine (200 mg, 1.34 mmol) with (2R,6S)-2,6-dimethylmorpholine (186 mg, 1.61 mmol) in the presence of potassium carbonate (278 mg, 2.01 mmol) in acetonitrile (15 mL) as per the procedure described in Step 1 of Intermediate 7 to yield 252 mg of the product; $^1$H NMR (300 MHz, CDCl$_3$) δ 1.24 (d, J=5.7 Hz, 6H), 2.64 (t, J=11.4 Hz, 2H), 3.85 (d, J=12.3 Hz, 4H), 7.88 (s, 1H), 8.10 (s, 1H); APCI-MS (m/z) 228 (M+H)$^+$.

Step 2: (2S,6R)-2,6-Dimethyl-4-(3-(4-nitrophenyl)pyrazin-2-yl)morpholine

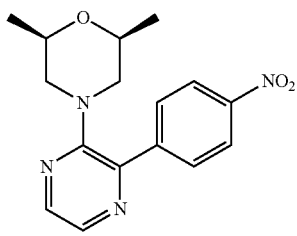 [SMILES: C[C@@H]1CN(c2nccnc2-c2ccc([N+](=O)[O-])cc2)C[C@H](C)O1]

The titled compound was prepared by the reaction of Step 1 intermediate (252 mg, 1.11 mmol) with 4-nitrophenylboronic acid pinacol ester (330 mg, 1.33 mmol) using potassium carbonate (459 mg, 3.32 mmol) and [1,1'-bis(diphenylphosphino)ferrocene]dichloropalladium (II). dichloromethane complex (45 mg, 0.06 mmol) in a mixture of DMSO and water (12 mL, 3:1) at 80° C. as per the procedure described in Step 1 of Intermediate 1 to yield 228 mg of the product; $^1$H NMR (300 MHz, CDCl$_3$) δ 1.11 (d, J=5.7 Hz, 6H), 2.55 (t, J=11.1 Hz, 2H), 3.41 (d, J=12.3 Hz, 2H), 3.64-3.68 (m, 2H), 8.10-8.22 (m, 4H), 8.32 (d, J=8.4 Hz, 2H).

Step 3: 4-(3-((2S,6R)-2,6-Dimethylmorpholino)pyrazin-2-yl)aniline

The titled compound was prepared by the reduction of Step 2 intermediate (215 mg, 0.68 mmol) using iron powder (190 mg, 3.42 mmol) and ammonium chloride (366 mg, 6.84 mmol) in a mixture of ethanol and water (18 mL, 5:1) as per the procedure described in Step 4 of Intermediate 9 to yield 137 mg of the product; $^1$H NMR (300 MHz, CDCl$_3$) δ 1.11 (d, J=6.3 Hz, 6H), 2.45 (t, J=12.3 Hz, 2H), 3.48 (d, J=12.3 Hz, 4H), 3.68 (br s, 2H), 6.85 (d, J=7.8 Hz, 2H), 7.80 (d, J=7.8 Hz, 2H), 8.03 (s, 1H), 8.11 (s, 1H); APCI-MS (m/z) 285 (M+H)$^+$.

Intermediate 37

4-(5-(2,4-Dichlorophenyl)-3-methyl-1H-pyrazol-1-yl)aniline

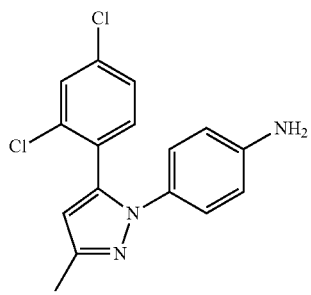 [SMILES: Cc1cc(-c2ccc(Cl)cc2Cl)n(-c2ccc(N)cc2)n1]

Step 1: 1-(2,4-Dichlorophenyl)butane-1,3-dione

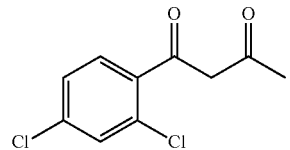

The titled compound was prepared by the reaction of 2,4-dichloroacetophenone (1.03 g, 5.44 mmol) with ethyl acetate (2.1 mL, 21.7 mmol) in the presence of sodium hydride (60% w/w, 653 mg, 16.3 mmol) in anhydrous THF (10 mL) as per the procedure described in Step 1 of Intermediate 22 to yield 561 mg of the product; $^1$H NMR (300 MHz, CDCl$_3$) δ 2.19 (s, 3H), 6.04 (s, 2H), 7.32 (d, J=6.3 Hz, 1H), 7.45 (s, 1H), 7.55 (d, J=8.4 Hz, 1H).

Step 2: 5-(2,4-Dichlorophenyl)-3-methyl-1-(4-nitrophenyl)-1H-pyrazole

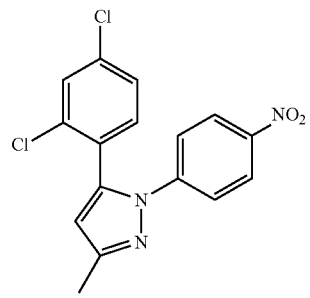 [SMILES: Cc1cc(-c2ccc(Cl)cc2Cl)n(-c2ccc([N+](=O)[O-])cc2)n1]

The titled compound was prepared by the reaction of Step 1 intermediate (503 mg, 2.17 mmol) with 4-nitrophenyl hydrazine (334 mg, 2.17 mmol) in 2,2,2,-trifluoroethanol (5.0 mL) as per the procedure described in Step 2 of Intermediate 22 to yield 498 mg of the product; $^1$H NMR (300 MHz, DMSO-d$_6$) δ 2.32 (s, 3H), 6.55 (s, 1H), 7.41 (d, J=8.7 Hz, 2H), 7.56 (s, 2H), 7.74 (s, 1H), 8.22 (d, J=8.7 Hz, 2H); ESI-MS (m/z) 248 (M−H)$^−$.

Step 3: 4-(5-(2,4-Dichlorophenyl)-3-methyl-1H-pyrazol-1-yl)aniline

The titled compound was prepared by the reduction of Step 2 intermediate (496 mg, 1.42 mmol) using iron powder (238 mg, 4.27 mmol) and ammonium chloride (761 mg, 714.2 mmol) in a mixture of ethanol and water (10 mL, 4:1) as per the procedure described in Step 4 of Intermediate 9 to yield 210 mg of the product; $^1$H NMR (300 MHz, DMSO-$d_6$) δ 2.25 (s, 3H), 5.21 (s, 2H), 6.30 (s, 1H), 6.43 (d, J=8.7 Hz, 2H), 6.79 (d, J=8.7 Hz, 2H), 7.32 (d, J=7.8 Hz, 1H), 7.38-7.43 (m, 1H), 7.67 (d, J=9.9 Hz, 1H); ESI-MS (m/z) 318 (M+H)$^+$.

Intermediate 38

4-(3-(2-Chloro-4-fluorophenyl)pyrazin-2-yl)aniline

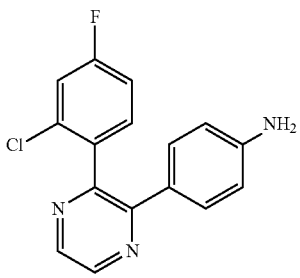

Step 1: 2-(2-Chloro-4-fluorophenyl)-3-(4-nitrophenyl)pyrazine

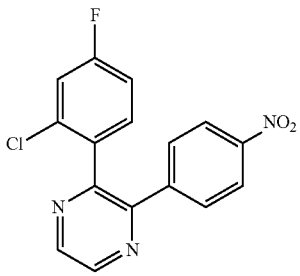 [SMILES: O=[N+]([O-])c1ccc(-c2nccnc2-c2ccc(F)cc2Cl)cc1]

The titled compound was prepared by the reaction of 2-chloro-3-(4-nitrophenyl)pyrazine (Step 1 of Intermediate 11) (1.0 g, 4.24 mmol) with 2-chloro-4-fluorophenylboronic acid (888 mg, 5.09 mmol) using sodium carbonate (1.35 g, 12.73 mmol) and [1,1'-bis(diphenylphosphino)ferrocene]dichloropalladium (II) (151 mg, 0.21 mmol) in a mixture of DMSO and water (20 mL, 3:1) as per the procedure described in Step 1 of Intermediate 1 to yield 1.14 g of the product; $^1$H NMR (300 MHz, DMSO-$d_6$) δ 7.37 (t, J=8.4 Hz, 1H), 7.48 (d, J=9.0 Hz, 1H), 7.62 (d, J=8.4 Hz, 2H), 7.64-7.69 (m, 1H), 8.20 (d, J=8.7 Hz, 2H), 8.86 (d, J=11.4 Hz, 2H); APCI-MS (m/z) 330 (M+H)$^+$.

Step 2: 4-(3-(2-Chloro-4-fluorophenyl)pyrazin-2-yl)aniline

The titled compound was prepared by the reduction of Step 1 intermediate (1.1 g, 3.34 mmol) using iron powder (559 mg, 10.0 mmol) and ammonium chloride (1.8 g, 33.36 mmol) in a mixture of ethanol and water (50 mL, 5:1) as per the procedure described in Step 4 of Intermediate 9 to yield 732 mg of the product; $^1$H NMR (300 MHz, DMSO-$d_6$) δ 5.40 (s, 2H), 6.42 (d, J=8.4 Hz, 2H), 7.03 (d, J=8.4 Hz, 2H), 7.33 (t, J=5.7 Hz, 1H), 7.43-7.53 (m, 2H), 8.54 (s, 1H), 8.67 (s, 1H).

Intermediate 39

4-(3-(2-Ethylphenyl)pyrazin-2-yl)aniline

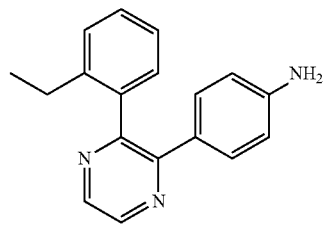

Step 1: 2-(2-Chloro-4-fluorophenyl)-3-(4-nitrophenyl)pyrazine

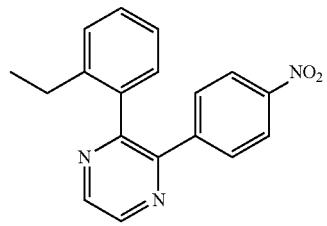 [SMILES: CCc1ccccc1-c1nccnc1-c1ccc([N+](=O)[O-])cc1]

The titled compound was prepared by the reaction of 2-chloro-3-(4-nitrophenyl)pyrazine (Step 1 of Intermediate 11) (1.0 g, 4.24 mmol) with 2-ethylphenylboronic acid (764 mg, 5.09 mmol) using sodium carbonate (1.35 g, 12.73 mmol) and [1,1'-bis(diphenylphosphino)ferrocene]dichloropalladium (II) (151 mg, 0.21 mmol) in a mixture of DMSO and water (30 mL, 3:1) as per the procedure described in Step 1 of Intermediate 1 to yield 1.23 g of the product; $^1$H NMR (300 MHz, DMSO-$d_6$) δ 0.91 (t, J=7.5 Hz, 3H), 2.33 (q, J=7.5 Hz, 2H), 7.16-7.20 (m, 2H), 7.29 (d, J=7.8 Hz, 1H), 7.35 (d, J=6.9 Hz, 1H), 7.60 (d, J=8.4 Hz, 2H), 8.13 (d, J=8.4 Hz, 2H), 8.83 (d, J=5.4 Hz, 2H); APCI-MS (m/z) 306 (M+H)$^+$.

Step 2: 4-(3-(2-Ethylphenyl)pyrazin-2-yl)aniline

The titled compound was prepared by the reduction of Step 1 intermediate (1.2 g, 3.93 mmol) using iron powder (658 mg, 11.8 mmol) and ammonium chloride (2.1 g, 39.3 mmol) in a mixture of ethanol and water (60 mL, 5:1) as per the procedure described in Step 4 of Intermediate 9 to yield 790 mg of the product; $^1$H NMR (300 MHz, DMSO-$d_6$) δ 0.84 (t, J=7.5 Hz, 3H), 2.26 (q, J=7.5 Hz, 2H), 5.35 (s, 2H), 6.36 (d, J=7.8 Hz, 2H), 7.05 (d, J=8.4 Hz, 2H), 7.17-7.34 (m, 4H), 8.51 (s, 1H), 8.61 (s, 1H); APCI-MS (m/z) 276 (M+H)$^+$.

Intermediate 40

4-(3-(4-(2-Methoxyethyl)piperazin-1-yl)pyrazin-2-yl)aniline

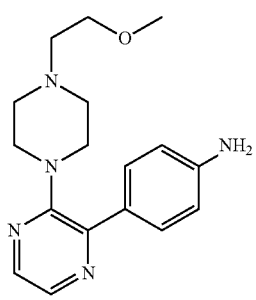 [SMILES: COCCN1CCN(c2nccnc2-c2ccc(N)cc2)CC1]

Step 1: 2-Chloro-3-(4-(2-methoxyethyl)piperazin-1-yl)pyrazine

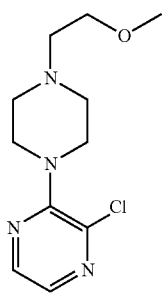 [SMILES: COCCN1CCN(c2nccnc2Cl)CC1]

The titled compound was prepared by the reaction of 2,3-dichloropyrazine (300 mg, 2.01 mmol) with 1-(2-methoxyethyl)piperazine hydrochloride (364 mg, 2.01 mmol) in the presence of potassium carbonate (556 mg, 4.03 mmol) in acetonitrile (20 mL) as per the procedure described in Step 1 of Intermediate 7 to yield 108 mg of the product; $^1$H NMR (300 MHz, CDCl$_3$) δ 2.68-2.73 (m, 6H), 3.37 (s, 3H), 3.52-3.62 (m, 6H), 7.85 (s, 1H), 8.09 (s, 1H); ESI-MS (m/z) 257 (M+H)$^+$.

Step 2: 4-(3-(4-(2-Methoxyethyl)piperazin-1-yl)pyrazin-2-yl)aniline

The titled compound was prepared by the reaction of Step 1 intermediate (100 mg, 0.39 mmol) with 4-aminophenylboronic acid pinacol ester (102 mg, 0.46 mmol) using potassium carbonate (161 mg, 1.17 mmol) and [1,1'-bis(diphenylphosphino)ferrocene]dichloropalladium (II). dichloromethane complex (16 mg, 0.02 mmol) in a mixture of DMSO and water (12 mL, 3:1) as per the procedure described in Step 1 of Intermediate 1 to yield 98 mg of the product; $^1$H NMR (300 MHz, CDCl$_3$) δ 2.19-2.23 (m, 2H), 2.64-2.72 (m, 6H), 3.32-3.36 (m, 7H), 3.60 (br s, 2H), 6.74 (d, J=8.4 Hz, 2H), 7.75 (d, J=8.4 Hz, 2H), 7.99 (s, 1H), 8.10 (s, 1H).

Intermediate 41

1-(4-(3-(4-Aminophenyl)pyrazin-2-yl)-3-methylpiperazin-1-yl)ethanone

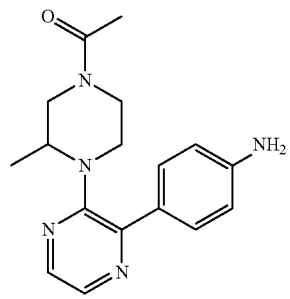 [SMILES: CC(=O)N1CCN(c2nccnc2-c2ccc(N)cc2)C(C)C1]

Step 1: 1-(4-(3-Chloropyrazin-2-yl)-3-methylpiperazin-1-yl)ethanone

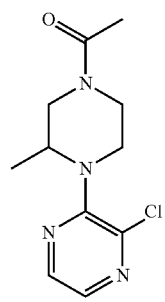 [SMILES: CC(=O)N1CCN(c2nccnc2Cl)C(C)C1]

The titled compound was prepared by the reaction of 2,3-dichloropyrazine (100 mg, 0.67 mmol) with 1-(3-methylpiperazin-1-yl)ethanone (119 mg, 0.84 mmol) in the presence of cesium carbonate (437 mg, 1.34 mmol) in acetonitrile (5.0 mL) as per the procedure described in Step 1 of Intermediate 7 to yield 46 mg of the product; APCI-MS (m/z) 255 (M+H)$^+$.

Step 2: 1-(3-Methyl-4-(3-(4-nitrophenyl)pyrazin-2-yl)piperazin-1-yl)ethanone

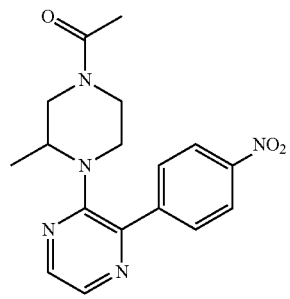

The titled compound was prepared by the reaction of Step 1 intermediate (200 mg, 0.78 mmol) with 4-nitrophenylboronic acid pinacol ester (235 mg, 0.94 mmol) using potassium carbonate (326 mg, 2.36 mmol) and [1,1'-bis(diphenylphosphino)ferrocene]dichloropalladium (II). dichloromethane complex (32 mg, 0.04 mmol) in a mixture of DMSO and water (12 mL, 3:1) as per the procedure described in Step 1 of Intermediate 1 to yield 219 mg of the product; APCI-MS (m/z) 342 (M+H)+.

Step 3: 1-(4-(3-(4-Aminophenyl)pyrazin-2-yl)-3-methylpiperazin-1-yl)ethanone

The titled compound was prepared by the reduction of Step 2 intermediate (200 mg, 0.59 mmol) using iron powder (164 mg, 2.93 mmol) and ammonium chloride (313 mg, 5.86 mmol) in a mixture of ethanol and water (18 mL, 5:1) as per the procedure described in Step 4 of Intermediate 9 to yield 147 mg of the product; $^1$H NMR (300 MHz, CDCl$_3$) δ 0.96, 1.02 (d, J=6.3 Hz, 3H, rotamer), 2.04, 2.10 (s, 3H, rotamer), 2.92-2.96 (m, 2H), 3.07-3.15 (m, 2H), 3.28-3.39 (m, 2H), 3.65-3.72 (m, 1H), 3.82-4.09 (m, 2H), 6.85 (d, J=7.8 Hz, 2H), 7.78 (d, J=5.4 Hz, 2H), 8.04 (s, 1H), 8.13 (s, 1H); APCI-MS (m/z) 312 (M+H)+.

Intermediate 42

4-(3-(Pyrimidin-5-yl)pyrazin-2-yl)aniline

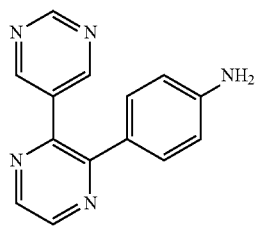

Step 1: 5-(3-Chloropyrazin-2-yl)pyrimidine

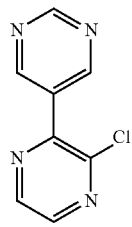 [SMILES: Clc1nccnc1-c1cncnc1]

The titled compound was prepared by the reaction of 2,3-dichloropyrazine (500 mg, 3.36 mmol) with pyrimidine-5-boronic acid (499 mg, 4.03 mmol) in the presence of potassium carbonate (1.39 g, 10.1 mmol) and [1,1'-bis(diphenylphosphino)ferrocene]dichloropalladium (II). dichloromethane complex (137 mg, 0.17 mmol) in a mixture of DMSO and water (20 mL, 3:1) as per the procedure described in Step 1 of Intermediate 1 to yield 147 mg of the product; $^1$H NMR (300 MHz, DMSO-d$_6$) δ 8.61 (s, 1H), 8.83 (s, 1H), 9.20 (s, 2H), 9.31 (s, 1H); APCI-MS (m/z) 193 (M+H)+.

Step 2: 5-(3-(4-Nitrophenyl)pyrazin-2-yl)pyrimidine

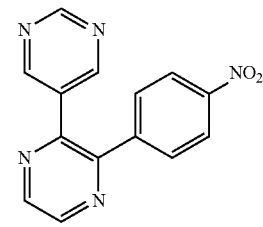 [SMILES: O=[N+]([O-])c1ccc(-c2nccnc2-c2cncnc2)cc1]

The titled compound was prepared by the reaction of Step 1 intermediate (140 mg, 0.73 mmol) with 4-nitrophenylboronic acid pinacol ester (217 mg, 0.87 mmol) using potassium carbonate (301 mg, 2.18 mmol) and [1,1'-bis(diphenylphosphino)ferrocene]dichloropalladium (II). dichloromethane complex (30 mg, 0.04 mmol) in a mixture of DMSO and water (12 mL, 3:1) as per the procedure described in Step 1 of Intermediate 1 to yield 156 mg of the product; $^1$H NMR (300 MHz, CDCl$_3$) δ 7.65 (d, J=8.7 Hz, 2H), 8.25 (d, J=7.2 Hz, 2H), 8.77 (s, 2H), 8.83 (s, 2H), 9.22 (s, 1H); APCI-MS (m/z) 280 (M+H)+.

Step 3: 4-(3-(Pyrimidin-5-yl)pyrazin-2-yl)aniline

The titled compound was prepared by the reduction of Step 2 intermediate (150 mg, 0.54 mmol) using iron powder (150 mg, 2.69 mmol) and ammonium chloride (287 mg, 5.37 mmol) in a mixture of ethanol and water (18 mL, 5:1) as per the procedure described in Step 4 of Intermediate 9 to yield 97 mg of the product; $^1$H NMR (300 MHz, CDCl$_3$) δ 3.23 (br s, 2H), 6.71 (d, J=7.8 Hz, 2H), 7.25 (d, J=7.2 Hz, 2H), 8.60 (d, J=12.9 Hz, 2H), 8.85 (s, 2H), 9.15 (s, 1H); APCI-MS (m/z) 250 (M+H)+.

Intermediate 43

4-(3-(4-Fluoro-2-methylphenyl)pyrazin-2-yl)aniline

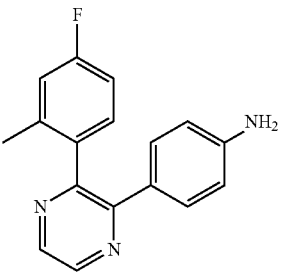 [SMILES: Cc1cc(F)ccc1-c1nccnc1-c1ccc(N)cc1]

Step 1: 2-(4-Fluoro-2-methylphenyl)-3-(4-nitrophenyl)pyrazine

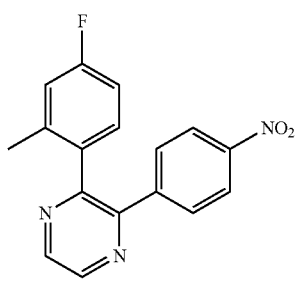 [SMILES: Cc1cc(F)ccc1-c1nccnc1-c1ccc([N+](=O)[O-])cc1]

The titled compound was prepared by the reaction of 2-chloro-3-(4-nitrophenyl)pyrazine (Step 1 of Intermediate 11) (300 mg, 1.27 mmol) with 4-fluoro-2-methylphenylboronic acid (294 mg, 1.90 mmol) using potassium carbonate (528 mg, 13.8 mmol) and [1,1'-bis(diphenylphosphino)ferrocene]dichloropalladium(II). dichloromethane complex (52 mg, 0.06 mmol) in a mixture of DMSO and water (12 mL, 3:1) as per the procedure described in Step 1 of Intermediate 1 to yield 223 mg of the product; $^1$H NMR (300 MHz, DMSO-$d_6$) δ 1.98 (s, 3H), 7.01 (t, J=8.1 Hz, 1H), 7.09 (d, J=9.0 Hz, 1H), 7.21 (t, J=8.1 Hz, 1H), 7.57 (d, J=8.4 Hz, 2H), 8.13 (d, J=8.7 Hz, 2H), 8.80 (d, J=5.1 Hz, 2H).

Step 2: 4-(3-(4-Fluoro-2-methylphenyl)pyrazin-2-yl)aniline

The titled compound was prepared by the reduction of Step 1 intermediate (215 mg, 0.69 mmol) using iron powder (194 mg, 3.47 mmol) and ammonium chloride (372 mg, 6.95 mmol) in a mixture of ethanol and water (18 mL, 5:1) as per the procedure described in Step 4 of Intermediate 9 to yield 163 mg of the product; $^1$H NMR (300 MHz, DMSO-$d_6$) δ 1.90 (s, 3H), 5.38 (s, 2H), 6.40 (d, J=8.4 Hz, 2H), 7.00-7.10 (m, 4H), 7.21-7.26 (m, 1H), 8.53 (s 1H), 8.63 (s, 1H); ESI-MS (m/z) 280 (M+H)$^+$.

Intermediate 44

4-(3-(4-Chlorophenyl)pyridin-4-yl)aniline

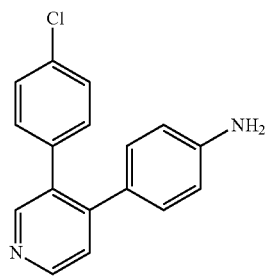 [SMILES: O=[N+]([O-])c1ccc(-c2ccncc2-c2ccc(Cl)cc2)cc1]

Step 1: 3-Bromo-4-(4-nitrophenyl)pyridine

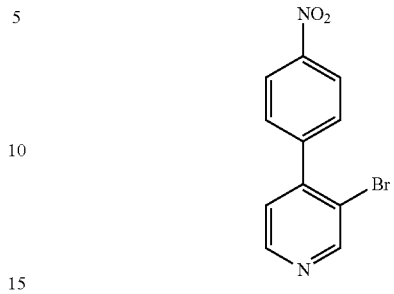

The titled compound was prepared by the reaction of 3,4-dibromopyridine (1.01 g, 4.26 mmol) with 4-nitrophenylboronic acid pinacol ester (1.06 g, 4.26 mmol) using cesium carbonate (2.07 g, 6.39 mmol) and [1,1'-bis(diphenylphosphino)ferrocene]dichloropalladium (II) (155 mg, 0.21 mmol) in a mixture of DMSO and water (20 mL, 3:1) as per the procedure described in Step 1 of Intermediate 1 to yield 455 mg of the product; $^1$H NMR (300 MHz, CDCl$_3$) δ 7.33 (d, J=4.8 Hz, 1H), 7.63 (d, J=8.7 Hz, 2H), 8.35 (d, J=8.7 Hz, 2H), 8.64 (d, J=5.1 Hz, 1H), 8.89 (s, 1H); ESI-MS (m/z) 281 (M+2H)$^+$.

Step 2: 3-(4-Chlorophenyl)-4-(4-nitrophenyl)pyridine

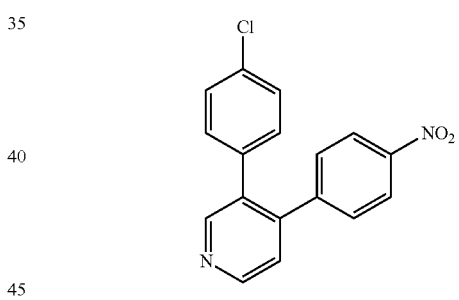

The titled compound was prepared by the reaction of Step 1 intermediate (451 mg, 1.62 mmol) with 4-chlorophenylboronic acid (253 mg, 1.62 mmol) using sodium carbonate (514 mg, 4.85 mmol) and [1,1'-bis(diphenylphosphino)ferrocene]dichloropalladium (II) (59 mg, 0.08 mmol) in a mixture of DMSO and water (10 mL, 4:1) at RT as per the procedure described in Step 1 of Intermediate 1 to yield 279 mg of the product; APCI-MS (m/z) 311 (M+H)$^+$.

Step 3: 4-(3-(4-Chlorophenyl)pyridin-4-yl)aniline

The titled compound was prepared by the reduction of Step 2 intermediate (221 mg, 0.71 mmol) using iron powder (119 mg, 2.13 mmol) and ammonium chloride (380 mg, 7.11 mmol) in a mixture of ethanol and water (10 mL, 3:1) as per the procedure described in Step 4 of Intermediate 9 to yield 113 mg of the product; $^1$H NMR (300 MHz, DMSO-$d_6$) δ 5.28 (s, 2H), 6.43 (d, J=8.1 Hz, 2H), 6.79 (d, J=8.1 Hz, 2H), 7.16 (d, J=8.4 Hz, 2H), 7.31-7.38 (m, 3H), 8.42 (s, 1H), 8.49 (d, J=5.4 Hz, 1H); APCI-MS (m/z) 281 (M+H)$^+$.

Intermediate 45

4-(3-(2,4-Dimethylphenyl)pyrazin-2-yl)aniline

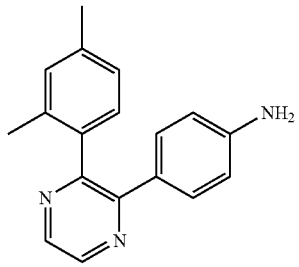 [SMILES: Cc1ccc(-c2nccnc2-c2ccc([N+](=O)[O-])cc2)c(C)c1]

Step 1:
2-(2,4-Dimethylphenyl)-3-(4-nitrophenyl)pyrazine

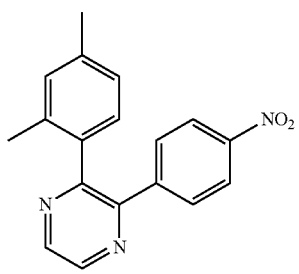

The titled compound was prepared by the reaction of 2-chloro-3-(4-nitrophenyl)pyrazine (Step 1 of intermediate 11) (300 mg, 1.27 mmol) with 2,4-dimethylphenylboronic acid (286 mg, 1.91 mmol) using potassium carbonate (528 mg, 3.81 mmol) and [1,1'-bis(diphenylphosphino)ferrocene]dichloropalladium (II). dichloromethane complex (52 mg, 0.06 mmol) in a mixture of DMSO and water (12 mL, 3:1) as per the procedure described in Step 1 of Intermediate 1 to yield 298 mg of the product; $^1$H NMR (300 MHz, CDCl$_3$) δ 1.97 (s, 3H), 2.34 (s, 3H), 6.99-7.07 (s, 3H), 7.59 (d, J=8.1 Hz, 2H), 8.10 (d, J=8.7 Hz, 2H), 8.68 (s, 2H); APCI-MS (m/z) 306 (M+H)$^+$.

Step 2:
4-(3-(2,4-Dimethylphenyl)pyrazin-2-yl)aniline

The titled compound was prepared by the reduction of Step 1 intermediate (290 mg, 0.95 mmol) using iron powder (265 mg, 4.75 mmol) and ammonium chloride (508 mg, 9.5 mmol) in a mixture of ethanol and water (24 mL, 5:1) as per the procedure described in Step 4 of Intermediate 9 to yield 243 mg of the product; $^1$H NMR (300 MHz, DMSO-d$_6$) δ 1.92 (s, 3H), 2.33 (s, 3H), 3.75 (br s, 2H), 6.53 (d, J=8.1 Hz, 2H), 6.96 (s, 1H), 7.02 (d, J=8.1 Hz, 1H), 7.15 (d, J=7.8 Hz, 1H), 7.20-7.27 (m, 2H), 8.49 (s, 1H), 8.55 (s, 1H); APCI-MS (m/z) 276 (M+H)$^+$.

Intermediate 46

4-(3-(2-Fluoro-4-methylphenyl)pyrazin-2-yl)aniline

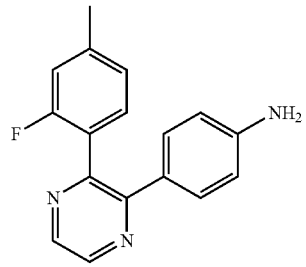 [SMILES: Cc1ccc(-c2nccnc2-c2ccc(N)cc2)c(F)c1]

Step 1: 2-(2-Fluoro-4-methylphenyl)-3-(4-nitrophenyl)pyrazine

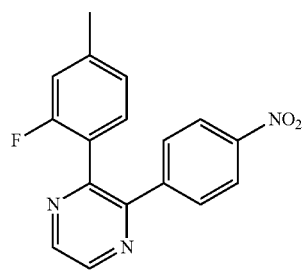 [SMILES: Cc1ccc(-c2nccnc2-c2ccc([N+](=O)[O-])cc2)c(F)c1]

The titled compound was prepared by the reaction of 2-chloro-3-(4-nitrophenyl)pyrazine (Step 1 of Intermediate 11) (300 mg, 1.27 mmol) with 2-fluoro-4-methylphenylboronic acid (294 mg, 1.90 mmol) using potassium carbonate (528 mg, 13.8 mmol) and [1,1'-bis(diphenylphosphino)ferrocene]dichloropalladium (II). dichloromethane complex (52 mg, 0.06 mmol) in a mixture of DMSO and water (12 mL, 3:1) as per the procedure described in Step 1 of Intermediate 1 to yield 298 mg of the product; $^1$H NMR (300 MHz, DMSO-d$_6$) δ 2.33 (s, 3H), 6.95 (d, J=11.4 Hz, 1H), 7.15 (d, J=7.8 Hz, 1H), 7.54 (t, J=7.8 Hz, 1H), 6.65 (d, J=8.7 Hz, 2H), 8.18 (d, J=9.0 Hz, 2H), 8.83 (s, 2H); ESI-MS (m/z) 310 (M+H)$^+$.

Step 2: 4-(3-(2-Fluoro-4-methylphenyl)pyrazin-2-yl)aniline

The titled compound was prepared by the reduction of Step 1 intermediate (290 mg, 0.94 mmol) using iron powder (262 mg, 4.69 mmol) and ammonium chloride (501 mg, 9.38 mmol) in a mixture of ethanol and water (18 mL, 5:1) as per the procedure described in Step 4 of Intermediate 9 to yield 163 mg of the product; $^1$H NMR (300 MHz, DMSO-d$_6$) δ 2.34 (s, 3H), 5.36 (s, 2H), 6.42 (d, J=8.1 Hz, 2H), 6.96 (d, J=11.1 Hz, 1H), 7.05-7.10 (m, 3H), 7.41 (t, J=7.8 Hz, 1H), 8.53 (s, 1H), 8.61 (s, 1H); ESI-MS (m/z) 280 (M+H)$^+$.

Intermediate 47

2-(4-Aminophenyl)-3-(2-chloro-4-fluorophenyl)pyrimidin-4(3H)-one

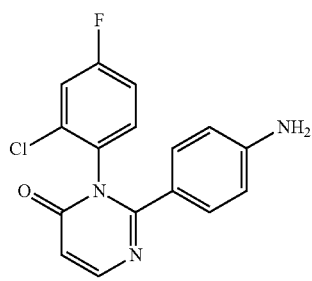

Step 1: (N)—N'-(2-Chloro-4-fluorophenyl)-N-((dimethylamino)methylene)-4-nitrobenzimidamide

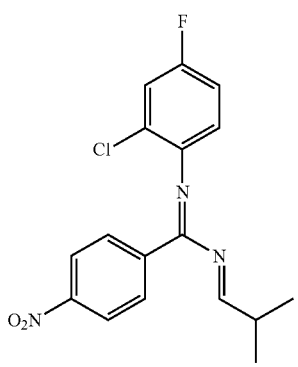 [SMILES: CC(C)/C=N/C(=Nc1ccc(F)cc1Cl)c1ccc([N+](=O)[O-])cc1]

A mixture of 4-nitrobenzonitrile (250 mg, 1.69 mmol), 2-chloro-4-fluoroaniline (243 µL, 2.02 mmol) and aluminum chloride (247 mg, 1.86 mmol) in THF (10 mL) was heated at 100° C. overnight. The reaction mixture was quenched with water and concentrated hydrochloric acid before the product was extracted with ethyl acetate (2×50 mL). The combined organic layers were washed with brine and concentrated under reduced pressure. The residue was dissolved in THF (10 mL) and added DMF-DMA (338 µL, 2.53 mmol) at RT. The mixture was refluxed overnight before cooled down to RT and concentrated to yield 537 mg of the crude product which was as such used in the next step.

Step 2: 3-(2-Chloro-4-fluorophenyl)-2-(4-nitrophenyl)pyrimidin-4(3H)-one

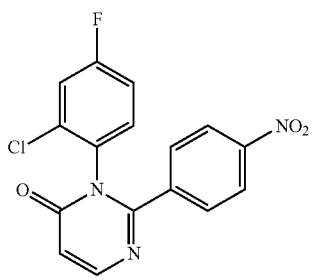 [SMILES: O=c1ccnc(-c2ccc([N+](=O)[O-])cc2)n1-c1ccc(F)cc1Cl]

To a stirred solution of Step 1 intermediate (537 mg, 1.54 mmol) in ethyl acetate (10 mL) was added (trimethylsilyl)ketene (527 mg, 4.62 mmol) and the mixture was refluxed overnight. The reaction mixture was cooled to RT and concentrated under reduced pressure. The residue thus obtained was purified by flash column chromatography to afford 236 mg of the desired product; $^1$H NMR (300 MHz, DMSO-$d_6$) δ 6.68 (d, J=6.9 Hz, 1H), 7.31 (t, J=6.9 Hz, 1H), 7.56 (d, J=5.4 Hz, 1H), 7.64 (d, J=8.7 Hz, 2H), 7.75-7.82 (m, 1H), 8.13-8.20 (m, 3H); APCI-MS (m/z) 346 (M+H)$^+$.

Step 3: 2-(4-Aminophenyl)-3-(2-chloro-4-fluorophenyl)pyrimidin-4(3H)-one

The titled compound was prepared by the reduction of Step 2 intermediate (151 mg, 0.44 mmol) using iron powder (73 mg, 1.30 mmol) and ammonium chloride (234 mg, 4.37 mmol) in a mixture of ethanol and water (10 mL, 5:1) as per the procedure described in Step 4 of Intermediate 9 to yield 102 mg of the product; $^1$H NMR (300 MHz, DMSO-$d_6$) δ 5.59 (s, 2H), 6.34 (d, J=7.2 Hz, 2H), 6.43 (d, J=6.3 Hz, 1H), 6.99 (d, J=8.4 Hz, 2H), 7.28-7.32 (m, 1H), 7.50-7.63 (m, 2H), 8.05 (d, J=6.3 Hz, 1H); APCI-MS (m/z) 316 (M+H)$^+$.

Intermediate 48

4-(3-(2,4-Dichlorophenyl)pyrazin-2-yl)aniline

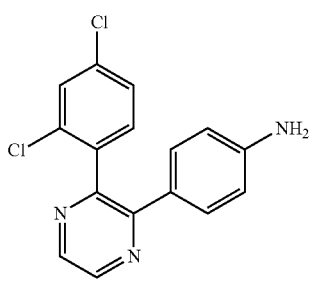 [SMILES: Nc1ccc(-c2nccnc2-c2ccc(Cl)cc2Cl)cc1]

Step 1:
2-(2,4-Dichlorophenyl)-3-(4-nitrophenyl)pyrazine

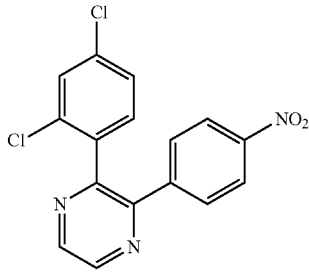 [SMILES: O=[N+]([O-])c1ccc(-c2nccnc2-c2ccc(Cl)cc2Cl)cc1]

The titled compound was prepared by the reaction of 2-chloro-3-(4-nitrophenyl)pyrazine (Step 1 of intermediate 11) (300 mg, 1.27 mmol) with 2,4-dichlorophenylboronic acid (364 mg, 1.91 mmol) using potassium carbonate (528 mg, 3.81 mmol) and [1,1'-bis(diphenylphosphino)ferrocene]dichloropalladium (II). dichloromethane complex (52 mg, 0.06 mmol) in a mixture of DMSO and water (12 mL, 3:1) as per the procedure described in Step 1 of Intermediate 1 to yield 223 mg of the product; $^1$H NMR (300 MHz, DMSO-$d_6$) δ 7.55-7.68 (m, 5H), 8.20 (d, J=8.7 Hz, 2H), 8.88 (d, J=11.1 Hz, 2H); APCI-MS (m/z) 346 (M+H)$^+$.

Step 2:
4-(3-(2,4-Dichlorophenyl)pyrazin-2-yl)aniline

The titled compound was prepared by the reduction of Step 1 intermediate (220 mg, 0.64 mmol) using iron powder (177 mg, 3.18 mmol) and ammonium chloride (339 mg, 6.36 mmol) in a mixture of ethanol and water (18 mL, 5:1) as per the procedure described in Step 4 of Intermediate 9 to yield 162 mg of the product; $^1$H NMR (300 MHz, DMSO-$d_6$) δ 5.41 (s, 2H), 6.42 (d, J=8.7 Hz, 2H), 7.03 (d, J=7.8 Hz, 2H), 7.51 (s, 2H), 7.64 (s, 1H), 8.55 (s, 1H), 8.68 (s, 1H); APCI-MS (m/z) 316 (M+H)$^+$.

Intermediate 49

(4-(3-(4-Aminophenyl)pyrazin-2-yl)piperazin-1-yl)(cyclopropyl)methanone

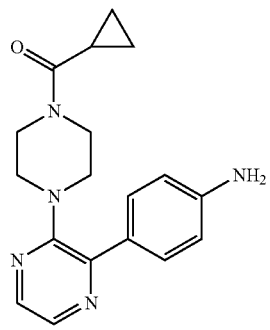 [SMILES: Nc1ccc(-c2nccnc2N2CCN(C(=O)C3CC3)CC2)cc1]

Step 1: (4-(3-Chloropyrazin-2-yl)piperazin-1-yl)(cyclopropyl)methanone

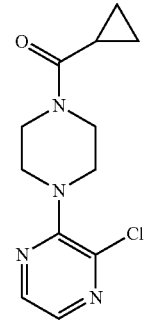 [SMILES: O=C(C1CC1)N1CCN(c2nccnc2Cl)CC1]

The titled compound was prepared by the reaction of 2,3-dichloropyrazine (100 mg, 0.67 mmol) with cyclopropyl(piperazin-1-yl)methanone trifluoroacetate salt (180 mg, 0.67 mmol) using potassium carbonate (93 mg, 0.67 mmol) in acetonitrile (15 mL) at 80° C. as per the procedure described in Step 1 of Intermediate 7 to yield 49 mg of the product; $^1$H NMR (300 MHz, CDCl$_3$) δ 0.78-0.82 (m, 2H), 0.98-1.03 (m, 2H), 1.75-1.79 (m, 1H), 3.46-3.550 (m, 4H), 3.80-3.84 (m, 4H), 7.93 (s, 1H), 8.13 (s, 1H).

Step 2. (4-(3-(4-Aminophenyl)pyrazin-2-yl)piperazin-1-yl)(cyclopropyl)methanone The titled compound was prepared by the reaction of Step 1 intermediate (250 mg, 0.93 mmol) with 4-aminophenylboronic acid pinacol ester (246 mg, 1.13 mmol) using potassium carbonate (389 mg, 2.81 mmol) and [1,1'-bis(diphenylphosphino)ferrocene]dichloropalladium (II). dichloromethane complex (77 mg, 0.09 mmol) in a mixture of DMSO and water (16 mL, 3:1) as per the procedure described in Step 1 of Intermediate 1 to yield 198 mg of the product; $^1$H NMR (300 MHz, DMSO-$d_6$) δ 0.68-0.72 (m, 4H), 1.95-1.99 (m, 1H), 3.07-3.12 (m, 4H), 3.51-3.55 (m, 2H), 3.70-3.74 (m, 2H), 5.46 (s, 2H), 6.62 (d, J=6.9 Hz, 2H), 7.71 (d, J=6.9 Hz, 2H), 8.02 (s, 1H), 8.12 (s, 1H); APCI-MS (m/z) 324 (M+H)$^+$.

Intermediate 50

3-(4-Aminophenyl)-N-(4-chlorophenyl)-N-methyl-pyrazin-2-amine

Step 1:
3-Chloro-N-(4-chlorophenyl)pyrazin-2-amine

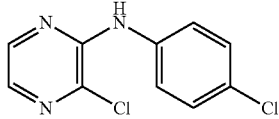 [SMILES: Clc1ccc(Nc2nccnc2Cl)cc1]

To a stirred solution of 4-chloroaniline (645 mg, 5.06 mmol) in THF (5.0 mL) was added sodium bis(trimethylsilyl)amide (1M, 5.0 mL, 5.06 mmol) at 0° C. and the mixture was stirred for 30 min at the same temperature. A solution of 2,3-dichloropyrazine (503 mg, 3.38 mmol) in THF (5.0 mL) was slowly added to the reaction mixture at 0° C. The mixture was stirred overnight at RT. The reaction mixture was quenched with aqueous ammonium chloride solution (10 mL) and diluted with water (10 mL). The aqueous mixture was extracted with ethyl acetate (2×20 mL). The combined organic layers were washed with brine (25 mL) and dried over anhydrous sodium sulfate. The solvent was removed under reduced pressure and the residue obtained was purified by silica gel column chromatography to yield 63 mg of the titled product; $^1$H NMR (300 MHz, DMSO-$d_6$) δ 7.36 (d, J=8.7 Hz, 2H), 7.72 (d, J=8.7 Hz, 2H), 7.84 (s, 1H), 8.13 (s, 1H), 8.92 (s, 1H); APCI-MS (m z) 240 (M+H)$^+$, 242 (M+2H)$^+$.

Step 2: 3-Chloro-N-(4-chlorophenyl)-N-methyl-pyrazin-2-amine

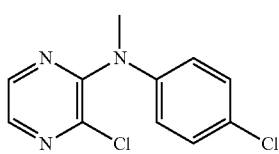 [SMILES: CN(c1ccc(Cl)cc1)c1nccnc1Cl]

To a stirred suspension of Step 1 intermediate (1.06 g, 4.43 mmol) in DMF (5.0 mL) was added sodium hydride (60% w/w, 213 mg, 5.32 mmol) at 0° C. and the mixture was stirred for 10-15 min at RT. Methyl iodide (333 μL, 5.32 mmol) was added to the reaction mixture and stirred for 2 h at RT. The reaction mixture was quenched with aqueous ammonium chloride solution (20 mL) and diluted with water (10 mL). The aqueous mixture was extracted with ethyl acetate (2×30 mL). The combined organic layers were washed with brine (30 mL) and dried over anhydrous sodium sulfate. The solvent was removed under reduced pressure to yield 723 mg of the titled product; $^1$H NMR (300 MHz, DMSO-$d_6$) δ 3.38 (s, 3H), 7.02 (d, J=9.0 Hz, 2H), 7.35 (d, J=8.4 Hz, 2H), 8.13 (s, 1H), 8.43 (s, 1H); ESI-MS (m/z) 254 (M)$^+$.

Step 3: 3-(4-Aminophenyl)-N-(4-chlorophenyl)-N-methylpyrazin-2-amine

The titled compound was prepared by the reaction of Step 2 intermediate (203 mg, 0.78 mmol) with 4-aminophenylboronic acid (280 mg, 0.96 mmol) using sodium carbonate (254 mg, 2.39 mmol) and [1,1'-bis(diphenylphosphino)ferrocene]dichloropalladium (II) (59 mg, 0.08 mmol) in a mixture of DMSO and water (10 mL, 4:1) as per the procedure described in Step 1 of Intermediate 1 to yield 143 mg of the product; $^1$H NMR (300 MHz, DMSO-$d_6$) δ 3.22 (s, 3H), 5.40 (br s, 2H), 6.43 (d, J=8.1 Hz, 2H), 6.70 (d, J=8.4 Hz, 2H), 7.10 (d, J=8.7 Hz, 2H), 7.40 (d, J=8.4 Hz, 2H), 8.23 (s, 1H), 8.38 (s, 1H); APCI-MS (m/z) 311 (M+H)$^+$.

Intermediate 51

3-(4-Aminophenyl)-N-benzyl-N-methylpyrazin-2-amine

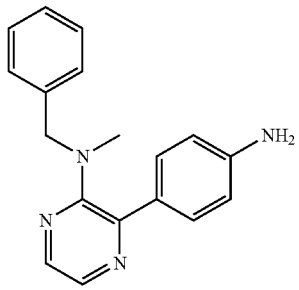 [SMILES: CN(Cc1ccccc1)c1nccnc1-c1ccc(N)cc1]

Step 1: N-Benzyl-3-chloropyrazin-2-amine

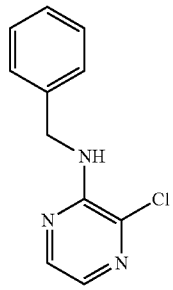

To a stirred solution of 2,3-dichloropyrazine (1.0 g, 6.71 mmol) and benzyl amine (880 μL, 8.05 mmol) in 1,4-dioxane (20 mL) was added triethylamine (1.4 mL, 10.07 mmol) and the mixture was heated overnight at 100° C. The reaction mixture was cooled to RT and diluted with ethyl acetate (50 mL). The organic extract was washed with 1N HCl (50 mL) followed by brine (30 mL). The organic layer was concentrated under reduced pressure and the residue thus obtained was purified by silica gel column chromatography to yield 613 mg of the titled product; $^1$H NMR (300 MHz, DMSO-$d_6$) δ 4.57 (d, J=6.3 Hz, 2H), 7.19-7.31 (m, 5H), 7.55 (s, 1H), 7.65-7.72 (m, 1H), 7.96 (s, 1H); APCI-MS (m/z) 220 (M+H)$^+$.

Step 2:
N-Benzyl-3-chloro-N-methylpyrazin-2-amine

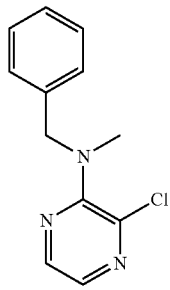 [SMILES: CN(Cc1ccccc1)c1nccnc1Cl]

The titled compound was prepared by the reaction of step 1 intermediate (599 mg, 2.72 mmol) with methyl iodide (205 µL, 3.27 mmol) in the presence of sodium hydride (60% w/w, 130 mg, 3.27 mmol) as per the procedure described in Step 2 of Intermediate 50 to yield 573 mg of the product; $^1$H NMR (300 MHz, DMSO-$d_6$) δ 3.92 (s, 3H), 4.66 (s, 2H), 7.25-7.38 (m, 5H), 7.91 (s, 1H), 8.21 (s, 1H); APCI-MS (m/z) 234 (M+H)$^+$.

Step 3:
3-(4-Aminophenyl)-N-benzyl-N-methylpyrazin-2-amine

The titled compound was prepared by the reaction of Step 2 intermediate (333 mg, 1.42 mmol) with 4-aminophenyl-boronic acid pinacol ester (498 mg, 1.71 mmol) using sodium carbonate (452 mg, 4.27 mmol) and [1,1'-bis(diphenylphosphino)ferrocene]dichloropalladium (II) (52 mg, 0.07 mmol) in a mixture of DMSO and water (10 mL, 3:1) as per the procedure described in Step 1 of Intermediate 1 to yield 270 mg of the product; $^1$H NMR (300 MHz, DMSO-$d_6$) δ 2.59 (s, 3H), 4.38 (s, 2H), 5.41 (s, 2H), 6.60 (d, J=8.4 Hz, 2H), 7.10 (d, J=7.2 Hz, 2H), 7.22-7.28 (m, 3H), 7.53 (d, J=8.1 Hz, 2H), 7.96 (s, 1H), 8.03 (s, 1H).

Intermediate 52

3-(4-Aminophenyl)-N-benzylpyrazin-2-amine

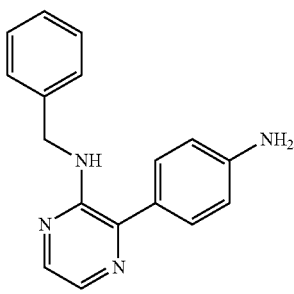 [SMILES: Nc1ccc(-c2nccnc2NCc2ccccc2)cc1]

The titled compound was prepared by the reaction of N-benzyl-3-chloropyrazin-2-amine (Step 1 of Intermediate 51) (203 mg, 0.92 mmol) with 4-aminophenylboronic acid pinacol ester (323 mg, 1.10 mmol) using sodium carbonate (294 mg, 2.77 mmol) and [1,1'-bis(diphenylphosphino)ferrocene]dichloropalladium (II) (66 mg, 0.09 mmol) in a mixture of DMSO and water (8.0 mL, 3:1) as per the procedure described in Step 1 of Intermediate 1 to yield 152 mg of the product; $^1$H NMR (300 MHz, DMSO-$d_6$) δ 4.51 (d, J=6.0 Hz, 2H), 5.46 (br s, 2H), 6.67 (d, J=8.1 Hz, 2H), 6.74-6.78 (m, 1H), 7.16-7.20 (m, 1H), 7.28-7.32 (m, 4H), 7.40 (d, J=8.4 Hz, 2H), 7.73 (s, 1H), 7.79 (s, 1H); ESI-MS (m/z) 277 (M+H)$^+$.

Intermediate 53

3-(4-Aminophenyl)-N-(1-phenylethyl)pyrazin-2-amine

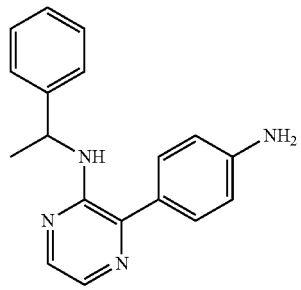 [SMILES: CC(Nc1nccnc1-c1ccc(N)cc1)c1ccccc1]

Step 1: 3-Chloro-N-(1-phenylethyl)pyrazin-2-amine

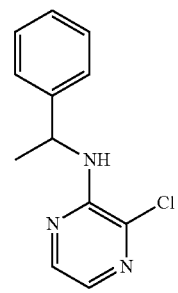 [SMILES: CC(Nc1nccnc1Cl)c1ccccc1]

The titled compound was prepared by the reaction of 2,3-dichloropyrazine (2.3 g, 15.4 mmol) with DL-1-phenylethanamine (2.16 mL, 17.0 mmol) using N,N-diisopropylethylamine (7.9 mL, 46 mmol) in 1,4-dioxane (40 mL) as per the procedure described in Step 1 of Intermediate 51 to yield 353 mg of the product; $^1$H NMR (300 MHz, DMSO-$d_6$) δ 1.53 (d, J=6.9 Hz, 3H), 5.19-5.23 (m, 1H), 7.17-7.32 (m, 3H), 7.39 (d, J=7.5 Hz, 2H), 7.53 (s, 1H), 7.94 (s, 1H), 8.56 (s, 1H).

Step 2: 3-(4-Aminophenyl)-N-(1-phenylethyl) pyrazin-2-amine

The titled compound was prepared by the reaction of Step 1 intermediate (206 mg, 0.88 mmol) with 4-aminophenyl-boronic acid pinacol ester (308 mg, 1.06 mmol) using sodium carbonate (280 mg, 2.64 mmol) and [1,1'-bis(diphenylphosphino)ferrocene]dichloropalladium (II) (63 mg, 0.08 mmol) in a mixture of DMSO and water (10 mL, 4:1) as per the procedure described in Step 1 of Intermediate 1 to yield 105 mg of the product; $^1$H NMR (300 MHz, DMSO-$d_6$) δ 1.44 (d, J=5.4 Hz, 3H), 5.11-5.12 (m, 1H), 5.55 (s, 2H), 6.06-6.10 (m, 1H), 6.67 (d, J=7.8 Hz, 2H), 7.19-7.41 (m, 6H), 7.72 (s, 1H), 7.77 (s, 1H).

Intermediate 54

(R)-3-(4-Aminophenyl)-N-(1-phenylethyl)pyrazin-2-amine

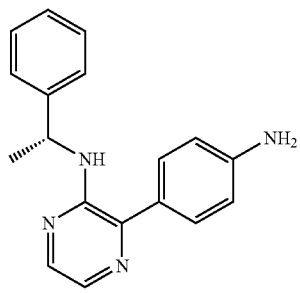 [SMILES: C[C@@H](Nc1nccnc1-c1ccc(N)cc1)c1ccccc1]

Step 1: (R)-3-Chloro-N-(1-phenylethyl)pyrazin-2-amine

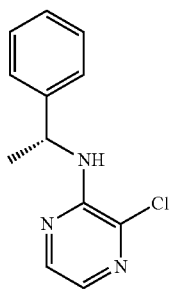 [SMILES: C[C@@H](Nc1nccnc1Cl)c1ccccc1]

The titled compound was prepared by the reaction of 2,3-dichloropyrazine (503 mg, 3.37 mmol) with (R)-(+)-α-methylbenzylamine (430 μL, 3.37 mmol) using potassium carbonate (1.4 g, 10.1 mmol) in DMF (10 mL) as per the procedure described in Step 1 of Intermediate 51 to yield 243 mg of the product; $^1$H NMR (300 MHz, DMSO-$d_6$) δ 1.53 (d, J=6.9 Hz, 3H), 5.17-5.23 (m, 1H), 7.17-7.32 (m, 4H), 7.39 (d, J=7.2 Hz, 2H), 7.53 (s, 1H), 7.94 (s, 1H); APCI-MS (m/z) 234 (M+H)$^+$.

Step 2: (R)-3-(4-Aminophenyl)-N-(1-phenylethyl)pyrazin-2-amine

The titled compound was prepared by the reaction of Step 1 intermediate (232 mg, 0.99 mmol) with 4-aminophenylboronic acid pinacol ester (435 mg, 1.49 mmol) using sodium carbonate (370 mg, 3.49 mmol) and [1,1'-bis(diphenylphosphino)ferrocene]dichloropalladium (II) (71 mg, 0.09 mmol) in a mixture of DMSO and water (10 mL, 4:1) as per the procedure described in Step 1 of Intermediate 1 to yield 210 mg of the product; $^1$H NMR (300 MHz, DMSO-$d_6$) δ 1.45 (d, J=6.6 Hz, 3H), 5.12-5.18 (m, 1H), 5.46 (s, 2H), 6.09 (d, J=6.9 Hz, 1H), 6.67 (d, J=8.1 Hz, 2H), 7.18 (d, J=7.2 Hz, 1H), 7.28 (t, J=7.2 Hz, 2H), 7.34-7.44 (m, 4H), 7.72 (s, 1H), 7.77 (s, 1H); APCI-MS (m/z) 291 (M+H)$^+$.

Intermediate 55

(R)-3-(4-Aminophenyl)-N-methyl-N-(1-phenylethyl)pyrazin-2-amine

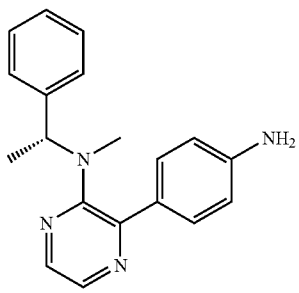 [SMILES: C[C@H](c1ccccc1)N(C)c1nccnc1-c1ccc(N)cc1]

Step 1: (R)-3-Chloro-N-methyl-N-(1-phenylethyl)pyrazin-2-amine

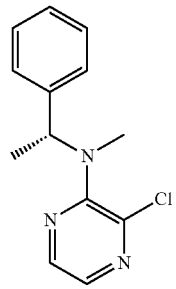 [SMILES: C[C@H](c1ccccc1)N(C)c1nccnc1Cl]

The titled compound was prepared by the reaction of (R)-3-chloro-N-(1-phenylethyl)pyrazin-2-amine (Step 1 of Intermediate 54) (503 mg, 2.15 mmol) with methyl iodide (180 μL, 2.79 mmol) in the presence of sodium hydride (60% w/w, 103 mg, 2.58 mmol) in DMF (10 mL) as per the procedure described in Step 2 of Intermediate 50 to yield 323 mg of the product; $^1$H NMR (300 MHz, DMSO-$d_6$) δ 1.56 (d, J=6.9 Hz, 3H), 2.66 (s, 3H), 5.40-5.44 (m, 1H), 7.30-7.36 (m, 5H), 7.93 (s, 1H), 8.31 (s, 1H); ESI-MS (m/z) 248 (M+H)$^+$.

Step 2: (R)-3-(4-Aminophenyl)-N-methyl-N-(1-phenylethyl)pyrazin-2-amine

The titled compound was prepared by the reaction of Step 2 intermediate (302 mg, 1.22 mmol) with 4-aminophenylboronic acid pinacol ester (530 mg, 1.82 mmol) using sodium carbonate (388 mg, 3.65 mmol) and [1,1'-bis(diphenylphosphino)ferrocene]dichloropalladium (II) (44 mg, 0.06 mmol) in a mixture of DMSO and water (10 mL, 3:1) as per the procedure described in Step 1 of Intermediate 1 to yield 183 mg of the product; $^1$H NMR (300 MHz, DMSO-$d_6$) δ 1.42 (d, J=6.9 Hz, 3H), 2.38 (s, 3H), 5.22-5.26 (m, 1H), 5.36 (s, 2H), 6.60 (d, J=8.4 Hz, 2H), 7.12 (d, J=5.7 Hz, 2H), 7.19-7.28 (m, 3H), 7.48 (d, J=8.4 Hz, 2H), 7.95 (s, 1H), 8.02 (s, 1H); APCI-MS (m/z) 305 (M+H)$^+$.

Intermediate 56

(S)-3-(4-Aminophenyl)-N-(1-phenylethyl)pyrazin-2-amine

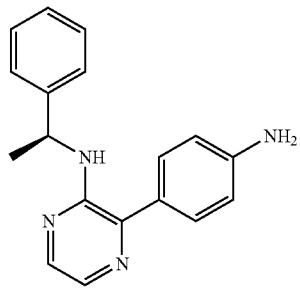 [SMILES: C[C@H](Nc1nccnc1-c1ccc(N)cc1)c1ccccc1]

Step 1: (S)-3-Chloro-N-(1-phenylethyl)pyrazin-2-amine

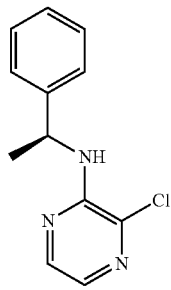

The titled compound was prepared by the reaction of 2,3-dichloropyrazine (2.0 g, 13.4 mmol) with (S)-(−)-α-methylbenzylamine (4.56 mL, 20.13 mmol) using potassium carbonate (5.56 g, 40.2 mmol) in DMF (30 mL) as per the procedure described in Step 1 of Intermediate 51 to yield 2.3 g of the product; $^1$H NMR (300 MHz, DMSO-$d_6$) δ 1.53 (d, J=6.9 Hz, 3H), 5.16-5.23 (m, 1H), 7.17-7.32 (m, 4H), 7.39 (d, J=7.5 Hz, 2H), 7.53 (s, 1H), 7.94 (s, 1H); APCI-MS (m/z) 234 (M+H)$^+$.

Step 2: (S)-3-(4-Aminophenyl)-N-(1-phenylethyl)pyrazin-2-amine

The titled compound was prepared by the reaction of Step 1 intermediate (250 mg, 1.07 mmol) with 4-aminophenylboronic acid pinacol ester (374 mg, 1.28 mmol) using sodium carbonate (340 mg, 3.20 mmol) and [1,1'-bis(diphenylphosphino)ferrocene]dichloropalladium (II) (38 mg, 0.05 mmol) in a mixture of DMSO and water (10 mL, 4:1) as per the procedure described in Step 1 of Intermediate 1 to yield 190 mg of the product; $^1$H NMR (300 MHz, DMSO-$d_6$) δ 1.45 (d, J=6.6 Hz, 3H), 5.12-5.16 (m, 1H), 5.45 (s, 2H), 6.12 (d, J=6.9 Hz, 1H), 6.67 (d, J=8.7 Hz, 2H), 7.19 (d, J=7.8 Hz, 1H), 7.28 (t, J=8.7 Hz, 2H), 7.35-7.44 (m, 3H), 7.72 (s, 1H), 7.78 (s, 1H); APCI-MS (m/z) 291 (M+H)$^+$.

Intermediate 57

(S)-3-(4-Aminophenyl)-N-methyl-N-(1-phenylethyl)pyrazin-2-amine

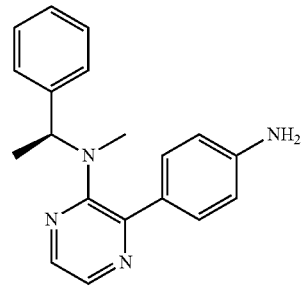 [SMILES: C[C@@H](c1ccccc1)N(C)c1nccnc1-c1ccc(N)cc1]

Step 1: (S)-3-Chloro-N-methyl-N-(1-phenylethyl)pyrazin-2-amine

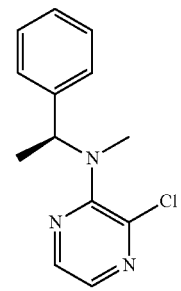 [SMILES: C[C@@H](c1ccccc1)N(C)c1nccnc1Cl]

The titled compound was prepared by the reaction of (S)-3-chloro-N-(1-phenylethyl)pyrazin-2-amine (Step 1 of Intermediate 56) (503 mg, 2.15 mmol) with methyl iodide (180 μL, 2.79 mmol) in the presence of sodium hydride (60% w/w, 103 mg, 2.58 mmol) in DMF (10 mL) as per the procedure described in Step 2 of Intermediate 50 to yield 402 mg of the product; $^1$H NMR (300 MHz, DMSO-$d_6$) δ 1.53 (d, J=6.9 Hz, 3H), 2.63 (s, 3H), 5.37-5.42 (m, 1H), 7.28-7.33 (m, 5H), 7.91 (s, 1H), 8.19 (s, 1H); APCI-MS (m/z) 248 (M+H)$^+$.

Step 2: (S)-3-(4-Aminophenyl)-N-methyl-N-(1-phenylethyl)pyrazin-2-amine

The titled compound was prepared by the reaction of Step 2 intermediate (302 mg, 1.22 mmol) with 4-aminophenylboronic acid pinacol ester (425 mg, 1.46 mmol) using sodium carbonate (388 mg, 3.65 mmol) and [1,1'-bis(diphenylphosphino)ferrocene]dichloropalladium (II) (44 mg, 0.06 mmol) in a mixture of DMSO and water (10 mL, 3:1) as per the procedure described in Step 1 of Intermediate 1 to yield 230 mg of the product; $^1$H NMR (300 MHz, DMSO-$d_6$) δ 1.42 (d, J=6.9 Hz, 3H), 2.38 (s, 3H), 5.22-5.28 (m, 1H), 5.37 (s, 2H), 6.60 (d, J=8.1 Hz, 2H), 7.12 (d, J=6.9 Hz, 2H), 7.20-7.28 (m, 3H), 7.50 (d, J=8.4 Hz, 2H), 7.95 (s, 1H), 8.02 (s, 1H); ESI-MS (m/z) 305 (M+H)$^+$.

Intermediate 58

(S)-3-(4-Aminophenyl)-N-(1-(4-chlorophenyl)ethyl)pyrazin-2-amine

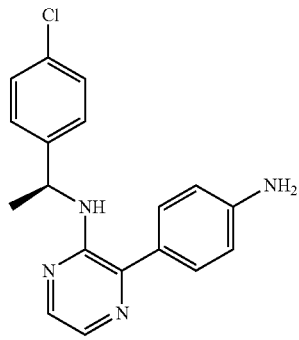 [SMILES: C[C@H](Nc1nccnc1-c1ccc(N)cc1)c1ccc(Cl)cc1]

Step 1: (S)-3-Chloro-N-(1-(4-chlorophenyl)ethyl)pyrazin-2-amine

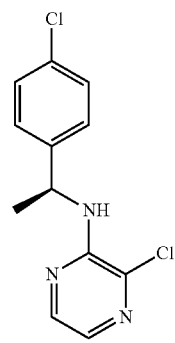 [SMILES: C[C@H](Nc1nccnc1Cl)c1ccc(Cl)cc1]

The titled compound was prepared by the reaction of 2,3-dichloropyrazine (320 mg, 2.15 mmol) with (S)-1-(4-chlorophenyl)ethanamine (456 µL, 3.22 mmol) using potassium carbonate (890 mg, 6.44 mmol) in DMF (10 mL) as per the procedure described in Step 1 of Intermediate 51 to yield 243 mg of the product; $^1$H NMR (300 MHz, DMSO-$d_6$) δ 1.49 (d, J=7.2 Hz, 3H), 5.13-5.17 (m, 1H), 7.32 (d, J=8.7 Hz, 2H), 7.39 (d, J=7.8 Hz, 2H), 7.52 (s, 1H), 7.91 (s, 1H), 8.54 (s, 1H); APCI-MS (m/z) 269 (M+H)$^+$.

Step 2: (S)-3-(4-Aminophenyl)-N-(1-(4-chlorophenyl)ethyl)pyrazin-2-amine

The titled compound was prepared by the reaction of Step 1 intermediate (253 mg, 0.94 mmol) with 4-aminophenylboronic acid pinacol ester (330 mg, 1.13 mmol) using sodium carbonate (300 mg, 2.83 mmol) and [1,1'-bis(diphenylphosphino)ferrocene]dichloropalladium (II) (67 mg, 0.09 mmol) in a mixture of DMSO and water (10 mL, 4:1) as per the procedure described in Step 1 of Intermediate 1 to yield 162 mg of the product; $^1$H NMR (300 MHz, DMSO-$d_6$) δ 1.43 (d, J=6.9 Hz, 3H), 5.08-5.12 (m, 1H), 5.45 (s, 2H), 6.24 (d, J=6.9 Hz, 1H), 6.65 (d, J=8.4 Hz, 2H), 7.18 (d, J=7.8 Hz, 1H), 7.32 (d, J=8.7 Hz, 2H), 7.43 (d, J=8.7 Hz, 2H), 7.73 (d, J=7.5 Hz, 2H), 8.31 (s, 1H); APCI-MS (m/z) 325 (M+H)$^+$.

Intermediate 59

(S)-3-(4-Aminophenyl)-N-(1-(3-chlorophenyl)ethyl)pyrazin-2-amine

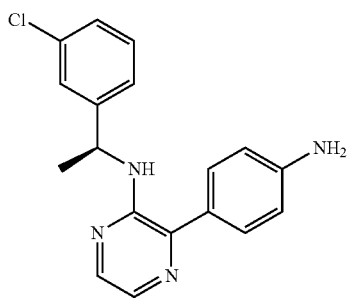 [SMILES: C[C@H](Nc1nccnc1-c1ccc([N+](=O)[O-])cc1)c1cccc(Cl)c1]

Step 1: (S)—N-(1-(3-Chlorophenyl)ethyl)-3-(4-nitrophenyl)pyrazin-2-amine

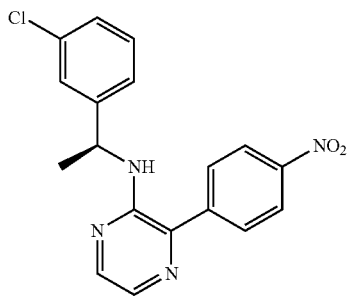

The titled compound was prepared by the reaction of 2-chloro-3-(4-nitrophenyl)pyrazine (Step 1 of intermediate 11) (101 mg, 0.43 mmol) with (S)-1-(3-chlorophenyl)ethanamine hydrochloride (82 mg, 0.43 mmol) using cesium fluoride (268 mg, 1.71 mmol) in DMSO (6.0 mL) as per procedure described in Step 1 of Intermediate 51 to yield 106 mg of the product; $^1$H NMR (300 MHz, DMSO-$d_6$) δ 1.45 (d, J=6.6 Hz, 3H), 5.17-5.21 (m, 1H), 6.95-6.99 (m, 1H), 7.23-7.35 (m, 3H), 7.45 (s, 1H), 7.88 (s, 1H), 8.02 (d, J=9.6 Hz, 3H), 8.37 (d, J=8.7 Hz, 2H).

Step 2: (S)-3-(4-Aminophenyl)-N-(1-(3-chlorophenyl)ethyl)pyrazin-2-amine

The titled compound was prepared by the reduction of Step 1 intermediate (101 mg, 0.28 mmol) using iron powder (48 mg, 0.85 mmol) and ammonium chloride (152 mg, 2.85 mmol) in a mixture of ethanol and water (10 mL, 5:1) as per the procedure described in Step 4 of Intermediate 9 to yield 79 mg of the product; $^1$H NMR (300 MHz, DMSO-$d_6$) δ 1.42 (d, J=6.6 Hz, 3H), 5.08-5.12 (m, 1H), 5.44 (s, 2H), 6.28-6.33 (m, 1H), 6.65-7.69 (m, 2H), 7.21-7.32 (m, 3H), 7.41-7.45 (m, 3H), 7.74 (d, J=7.8 Hz, 2H)

Intermediate 60

(S)-3-(4-Aminophenyl)-N-(1-(4-chlorophenyl)ethyl)-N-methylpyrazin-2-amine

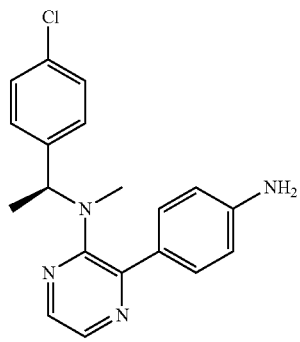 [SMILES: C[C@@H](c1ccc(Cl)cc1)N(C)c1nccnc1-c1ccc(N)cc1]

Step 1: (S)-3-Chloro-N-(1-(4-chlorophenyl)ethyl)-N-methylpyrazin-2-amine

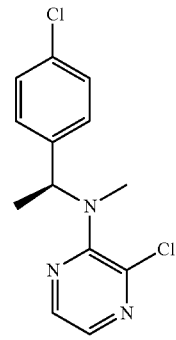 [SMILES: C[C@@H](c1ccc(Cl)cc1)N(C)c1nccnc1Cl]

The titled compound was prepared by the reaction of (S)-3-Chloro-N-(1-(4-chlorophenyl)ethyl)pyrazin-2-amine (Step 1 of Intermediate 51) (371 mg, 1.38 mmol) with methyl iodide (130 μL, 2.08 mmol) in the presence of sodium hydride (60% w/w, 83 mg, 2.08 mmol) as per the procedure described in Step 2 of Intermediate 50 to yield 352 mg of the product; $^1$H NMR (300 MHz, DMSO-$d_6$) δ 1.54 (d, J=6.9 Hz, 3H), 2.66 (s, 3H), 5.35-5.40 (m, 1H), 7.34 (d, J=8.4 Hz, 2H), 7.40 (d, J=8.4 Hz, 2H), 7.94 (s, 1H), 8.22 (s, 1H); APCI-MS (m/z) 283 (M+H)$^+$.

Step 2: (S)-3-(4-Aminophenyl)-N-(1-(4-chlorophenyl)ethyl)-N-methylpyrazin-2-amine The titled compound was prepared by the reaction of Step 1 intermediate (341 mg, 1.20 mmol) with 4-aminophenylboronic acid pinacol ester (422 mg, 1.45 mmol) using sodium carbonate (381 mg, 3.60 mmol) and [1,1'-bis(diphenylphosphino)ferrocene]dichloropalladium(II) (43 mg, 0.06 mmol) in DMSO (10 mL) as per the procedure described in Step 1 of Intermediate 1 to yield 162 mg of the product $^1$H NMR (300 MHz, DMSO-$d_6$) δ 1.40 (d, J=6.9 Hz, 3H), 2.36 (s, 3H), 5.25-5.28 (m, 1H), 5.36 (s, 2H), 6.58 (d, J=7.8 Hz, 2H), 7.14 (d, J=7.8 Hz, 2H), 7.32 (d, J=7.8 Hz, 2H), 7.46 (d, J=7.8 Hz, 2H), 7.95 (s, 1H), 8.02 (s, 1H); APCI-MS (m/z) 338 (M+H)$^+$.

Intermediate 61

(S)-3-(4-Aminophenyl)-N-(1-(2-chlorophenyl)ethyl)pyrazin-2-amine

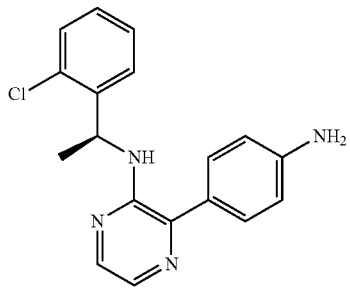 [SMILES: C[C@H](Nc1nccnc1-c1ccc(N)cc1)c1ccccc1Cl]

Step 1: (S)—N-(1-(2-Chlorophenyl)ethyl)-3-(4-nitrophenyl)pyrazin-2-amine

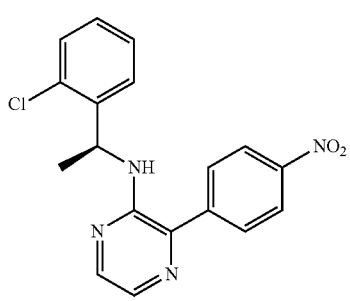 [SMILES: C[C@H](Nc1nccnc1-c1ccc([N+](=O)[O-])cc1)c1ccccc1Cl]

The titled compound was prepared by the reaction of 2-chloro-3-(4-nitrophenyl)pyrazine (Step 1 of intermediate 11) (202 mg, 0.86 mmol) with (S)-1-(2-chlorophenyl)ethanamine hydrochloride (198 mg, 1.03 mmol) using cesium fluoride (390 mg, 2.57 mmol) in DMSO (8.0 mL) as per the procedure described in Step 1 of Intermediate 51 to yield 219 mg of the product; $^1$H NMR (300 MHz, DMSO-$d_6$) δ 1.42 (d, J=6.9 Hz, 3H), 5.42-5.49 (m, 1H), 7.05 (d, J=8.7 Hz, 1H), 7.19-7.26 (m, 1H), 7.38 (d, J=8.4 Hz, 1H), 7.48 (d, J=6.0 Hz, 1H), 7.87 (s, 1H), 7.97 (s, 1H), 8.03 (d, J=8.7 Hz, 3H), 8.37 (d, J=8.7 Hz, 2H).

Step 2: (S)-3-(4-Aminophenyl)-N-(1-(2-chlorophenyl)ethyl)pyrazin-2-amine

The titled compound was prepared by the reduction of Step 1 intermediate (192 mg, 0.54 mmol) using iron powder (90 mg, 1.62 mmol) and ammonium chloride (290 mg, 5.41 mmol) in a mixture of ethanol and water (10 mL, 5:1) as per the procedure described in Step 4 of Intermediate 9 to yield 140 mg of the product; $^1$H NMR (300 MHz, DMSO-$d_6$) δ 1.43 (d, J=6.9 Hz, 3H), 5.37-5.45 (m, 1H), 5.47 (s, 2H), 6.33 (d, J=6.9 Hz, 1H), 6.68 (d, J=8.4 Hz, 2H), 7.19-7.26 (m, 2H), 7.38 (d, J=7.8 Hz, 2H), 7.46 (d, J=8.4 Hz, 2H), 7.73 (d, J=5.1 Hz, 2H); APCI-MS (m/z) 325 (M+H)$^+$.

Intermediate 62

(S)-3-(4-Aminophenyl)-N-(1-(4-fluoro-2-methylphenyl)ethyl)pyrazin-2-amine

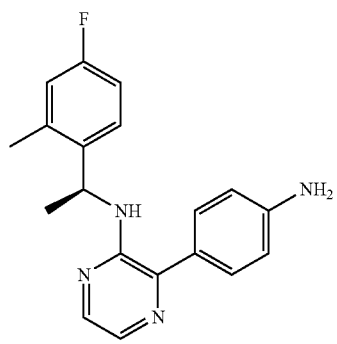 [SMILES: Cc1cc(F)ccc1[C@H](C)Nc1nccnc1-c1ccc([N+](=O)[O-])cc1]

Step 1: (S)—N-(1-(4-Fluoro-2-methylphenyl)ethyl)-3-(4-nitrophenyl)pyrazin-2-amine

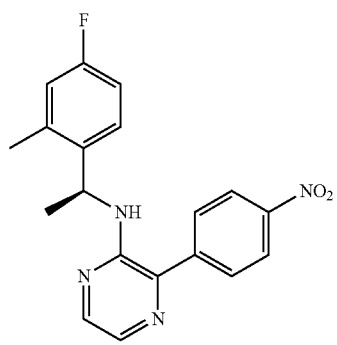

The titled compound was prepared by the reaction of 2-chloro-3-(4-nitrophenyl)pyrazine (Step 1 of intermediate 11) (203 mg, 0.86 mmol) with (S)-1-(4-fluoro-2-methylphenyl)ethanamine hydrochloride (197 mg, 1.03 mmol) using cesium fluoride (523 mg, 3.44 mmol) in DMSO (10 mL) as per the procedure described in Step 1 of Intermediate 51 to yield 190 mg of the product; $^1$H NMR (300 MHz, DMSO-$d_6$) δ 1.37 (d, J=7.5 Hz, 3H), 2.42 (s, 3H), 5.26-5.30 (m, 1H), 6.88-6.95 (m, 3H), 7.38-7.45 (m, 1H), 7.85 (s, 1H), 7.95-8.01 (m, 3H), 8.36 (d, J=8.7 Hz, 2H); ESI-MS (m/z) 353 (M+H)$^+$.

Step 2: (S)-3-(4-Aminophenyl)-N-(1-(4-fluoro-2-methylphenyl)ethyl)pyrazin-2-amine The titled compound was prepared by the reduction of Step 1 intermediate (181 mg, 0.51 mmol) using iron powder (86 mg, 1.54 mmol) and ammonium chloride (275 mg, 5.14 mmol) in a mixture of ethanol and water (10 mL, 5:1) as per the procedure described in Step 4 of Intermediate 9 to yield 130 mg of the product; $^1$H NMR (300 MHz, DMSO-$d_6$) δ 1.37 (d, J=6.6 Hz, 3H), 2.38 (s, 3H), 5.18-5.22 (m, 1H), 5.47 (s, 2H), 6.16 (d, J=7.8 Hz, 1H), 6.64 (d, J=8.4 Hz, 2H), 6.91-6.95 (m, 2H), 7.39 (d, J=8.1 Hz, 1H), 7.69 (s, 1H), 7.75 (s, 1H); APCI-MS (m/z) 323 (M+H)$^+$.

Intermediate 63

(S)-3-(4-Aminophenyl)-N-(1-(2,4-dimethylphen)ethyl)pyrazin-2-amine

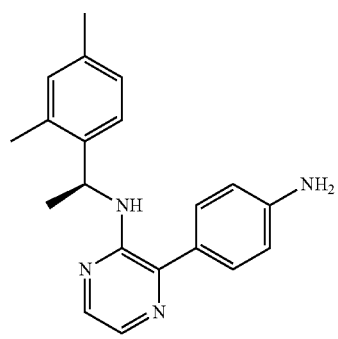

Step 1: (S)—N-(1-(2,4-Dimethylphenyl)ethyl)-3-(4-nitrophenyl)pyrazin-2-amine

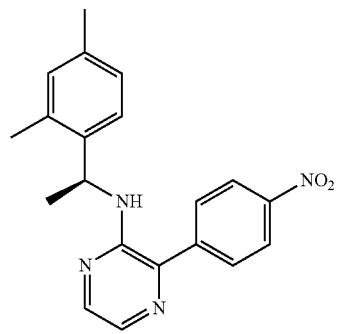 [SMILES: Cc1ccc([C@H](C)Nc2nccnc2-c2ccc([N+](=O)[O-])cc2)c(C)c1]

The titled compound was prepared by the reaction of 2-chloro-3-(4-nitrophenyl)pyrazine (Step 1 of intermediate 11) (203 mg, 0.86 mmol) with (S)-1-(2,4-dimethylphenyl)ethanamine hydrochloride (176 mg, 0.95 mmol) using cesium fluoride (523 mg, 3.44 mmol) in DMSO (8.0 mL) as per the procedure described in Step 1 of Intermediate 51 to yield 216 mg of the product; $^1$H NMR (300 MHz, DMSO-$d_6$) δ 1.36 (d, J=6.3 Hz, 3H), 2.19 (s, 3H), 2.36 (s, 3H), 5.26-5.30 (m, 1H), 6.82-6.92 (m, 3H), 7.26 (d, J=8.4 Hz, 1H), 7.84 (s, 1H), 7.96 (d, J=8.7 Hz, 3H), 8.36 (d, J=8.4 Hz, 2H); APCI-MS (m/z) 349 (M+H)$^+$.

Step 2: (S)-3-(4-Aminophenyl)-N-(1-(2,4-dimethylphenyl)ethyl)pyrazin-2-amine The titled compound was prepared by the reduction of Step 1 intermediate (209 mg, 0.60 mmol) using iron powder (100 mg, 1.80 mmol) and ammonium chloride (320 mg, 5.99 mmol) in a mixture of ethanol and water (10 mL, 5:1) as per the procedure described in Step 4 of Intermediate 9 to yield 140 mg of the product; $^1$H NMR (300 MHz, DMSO-$d_6$) δ 1.37 (d, J=6.6 Hz, 3H), 2.19 (s, 3H), 2.33 (s, 3H), 5.20-5.24 (m, 1H), 5.56 (br s, 2H), 5.97-6.02 (m, 1H), 6.67 (d, J=8.4 Hz, 2H), 6.92 (s, 2H), 7.23 (d, J=7.8 Hz, 1H), 7.38 (d, J=8.1 Hz, 2H), 7.70 (s, 1H), 7.78 (s, 1H); APCI-MS (m/z) 319 (M+H)$^+$.

115

Intermediate 64

(S)-3-(4-Aminophenyl)-N-(1-(2-chloro-4-fluorophenyl)ethyl)pyrazin-2-amine

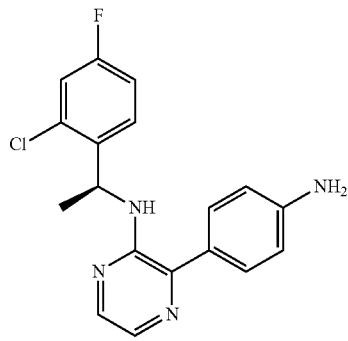

Step 1: (S)—N-(1-(2-Chloro-4-fluorophenyl)ethyl)-3-(4-nitrophenyl)pyrazin-2-amine

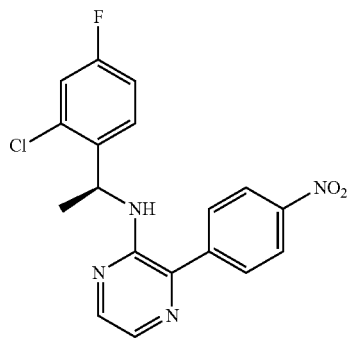 [SMILES: C[C@H](Nc1nccnc1-c1ccc(N)cc1)c1ccc(F)cc1Cl]

The titled compound was prepared by the reaction of 2-chloro-3-(4-nitrophenyl)pyrazine (Step 1 of intermediate 11) (203 mg, 0.86 mmol) with (S)-1-(2-chloro-4-fluorophenyl)ethanamine hydrochloride (217 mg, 1.03 mmol) using cesium fluoride (524 mg, 3.44 mmol) in DMSO (8.0 mL) as per the procedure described in Step 1 of Intermediate 51 to yield 103 mg of the product. The product was as such taken for the next step without characterization.

Step 2: (S)-3-(4-Aminophenyl)-N-(1-(2-chloro-4-fluorophenyl)ethyl)pyrazin-2-amine

The titled compound was prepared by the reduction of Step 1 intermediate (98 mg, 0.26 mmol) using iron powder (44 mg, 0.79 mmol) and ammonium chloride (140 mg, 2.63 mmol) in a mixture of ethanol and water (10 mL, 5:1) as per the procedure described in Step 4 of Intermediate 9 to yield 62 mg of the product. The product was as such taken for the next step without characterization.

116

Intermediate 65

3-(4-Aminophenyl)-N-(cyclohexylmethyl)pyrazin-2-amine

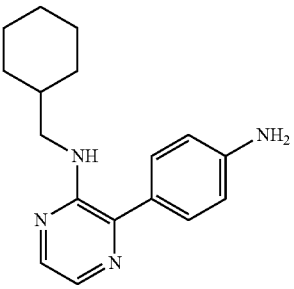 [SMILES: O=[N+]([O-])c1ccc(-c2nccnc2NCC2CCCCC2)cc1]

Step 1: N-(Cyclohexylmethyl)-3-(4-nitrophenyl)pyrazin-2-amine

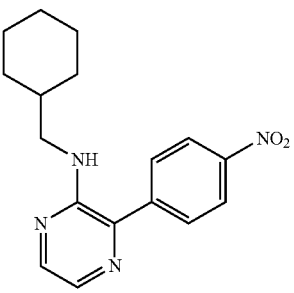

The titled compound was prepared by the reaction of 2-chloro-3-(4-nitrophenyl)pyrazine (Step 1 of intermediate 11) (203 mg, 0.86 mmol) with cyclohexylmethanamine (146 mg, 1.29 mmol) using cesium fluoride (392 mg, 2.58 mmol) in DMSO (8.0 mL) as per the procedure described in Step 1 of Intermediate 51 to yield 121 mg of the product; $^1$H NMR (300 MHz, DMSO-$d_6$) δ 0.85-0.95 (m, 2H), 1.07-1.17 (m, 3H), 1.51-1.80 (m, 6H), 3.14 (t, J=6.6 Hz, 2H), 6.64-6.68 (m, 1H), 7.84 (s, 1H), 7.90 (d, J=8.7 Hz, 2H), 8.05 (s, 1H), 8.33 (d, J=8.1 Hz, 2H); APCI-MS (m/z) 311 (M–H)$^-$.

Step 2: 3-(4-Aminophenyl)-N-(cyclohexylmethyl)pyrazin-2-amine

The titled compound was prepared by the reduction of Step 1 intermediate (115 mg, 0.37 mmol) using iron powder (62 mg, 1.10 mmol) and ammonium chloride (197 mg, 3.68 mmol) in a mixture of ethanol and water (12 mL, 5:1) as per the procedure described in Step 4 of Intermediate 9 to yield 84 mg of the product; $^1$H NMR (300 MHz, DMSO-$d_6$) δ 0.88-0.93 (m, 3H), 1.12-1.18 (m, 3H), 1.60-1.76 (m, 5H), 3.12 (t, J=5.7 Hz, 2H), 5.42 (s, 2H), 6.02-6.06 (m, 1H), 6.64 (d, J=8.4 Hz, 2H), 7.33 (d, J=9.0 Hz, 2H), 7.69 (s, 1H), 7.82 (s, 1H); ESI-MS (m/z) 283 (M+H)$^+$.

Intermediate 66

(S)-3-(4-Amino-3-fluorophenyl)-N-(1-(2-chlorophenyl)ethyl)pyrazin-2-amine

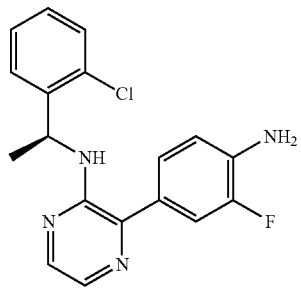 [SMILES: C[C@H](Nc1nccnc1-c1ccc(N)c(F)c1)c1ccccc1Cl]

Step 1: (S)-3-Chloro-N-(1-(2-chlorophenyl)ethyl)pyrazin-2-amine

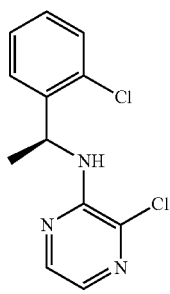 [SMILES: C[C@H](Nc1nccnc1Cl)c1ccccc1Cl]

The titled compound was prepared by the reaction of 2,3-dichloropyrazine (130 mg, 0.87 mmol) with (S)-1-(2-chlorophenyl)ethanamine hydrochloride (250 mg, 1.31 mmol) using cesium fluoride (530 mg, 3.48 mmol) in DMSO (8.0 mL) as per the procedure described in Step 1 of Intermediate 51 to yield 159 mg of the product; $^1$H NMR (300 MHz, DMSO-$d_6$) δ 1.51 (d, J=6.9 Hz, 3H), 5.42-5.47 (m, 1H), 7.21-7.30 (m, 3H), 7.37-7.42 (m, 2H), 7.48-7.56 (m, 2H), 7.92 (s, 1H).

Step 2: (S)-3-(4-Amino-3-fluorophenyl)-N-(1-(2-chlorophenyl)ethyl)pyrazin-2-amine The titled compound was prepared by the reaction of Step 1 intermediate (151 mg, 0.56 mmol) with 4-amino-3-fluorophenylboronic acid pinacol ester (160 mg, 0.68 mmol) using sodium carbonate (180 mg, 1.69 mmol) and [1,1'-bis(diphenylphosphino)ferrocene]dichloropalladium (II) (46 mg, 0.06 mmol) in a mixture of DMSO and water (8.0 mL, 3:1) as per the procedure described in Step 1 of Intermediate 1 to yield 159 mg of the product; $^1$H NMR (300 MHz DMSO-$d_6$) δ 1.43 (d, J=6.6 Hz, 3H), 3.94 (s, 1H), 5.38-5.42 (m, 1H), 5.51 (s, 2H), 6.60 (d, J=6.6 Hz, 1H), 6.83-6.91 (m, 1H), 7.19-7.25 (m, 2H), 7.36-7.41 (m, 2H), 7.46 (d, J=5.7 Hz, 1H), 7.72-7.78 (m, 2H); ESI-MS (m/z) 343 (M+H)$^+$.

Intermediate 67

(S)-3-(4-Amino-2-fluorophenyl)-N-(1-(2-chlorophenyl)ethyl)pyrazin-2-amine

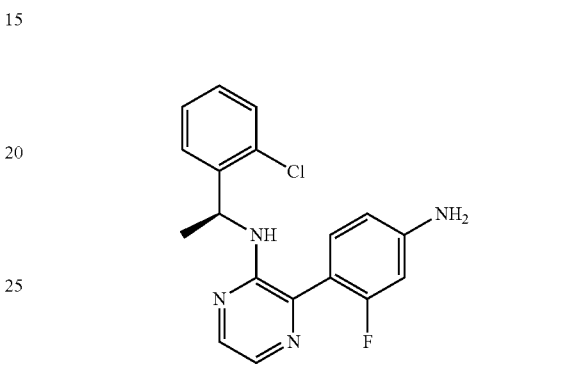

The titled compound was prepared by the reaction of (S)-3-chloro-N-(1-(2-chlorophenyl)ethyl)pyrazin-2-amine (Step 1 of Intermediate 66) (206 mg, 0.77 mmol) with 4-amino-2-fluorophenylboronic acid pinacol ester (273 mg, 1.15 mmol) using sodium carbonate (244 mg, 2.30 mmol) and [1,1'-bis(diphenylphosphino)ferrocene]dichloropalladium (II) (63 mg, 0.08 mmol) in a mixture of DMSO and water (10 mL, 3:1) as per the procedure described in Step 1 of Intermediate 1 to yield 149 mg of the product; $^1$H NMR (300 MHz DMSO-$d_6$) δ 1.37 (d, J=6.9 Hz, 3H), 5.38-5.43 (m, 1H), 5.69 (s, 2H), 6.27 (d, J=6.6 Hz, 1H), 6.39-6.51 (m, 2H), 7.09-7.23 (m, 3H), 7.35 (d, J=6.0 Hz, 1H), 7.41-7.45 (m, 1H), 7.71 (s, 1H), 7.81 (s, 1H); ESI-MS (m/z) 343 (M+H)$^+$.

Intermediate 68

4-(3-(Benzyloxy)pyrazin-2-yl)aniline

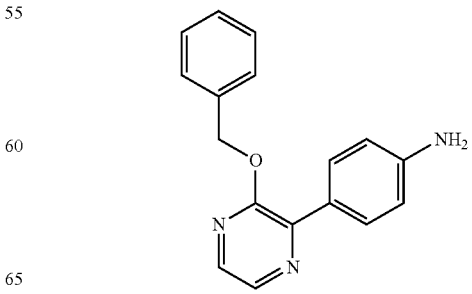

Step 1: 2-(Benzyloxy)-3-(4-nitrophenyl)pyrazine

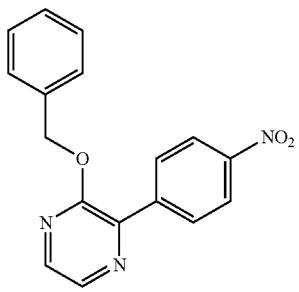

The titled compound was prepared by the reaction of 2-chloro-3-(4-nitrophenyl)pyrazine (Step 1 of intermediate 11) (109 mg, 0.46 mmol) with benzyl alcohol (72 μL, 0.69 mmol) using cesium fluoride (280 mg, 1.84 mmol) in DMSO (8.0 mL) as per the procedure described in Step 1 of Intermediate 51 to yield 96 mg of the product; $^1$H NMR (300 MHz, DMSO-$d_6$) δ 5.52 (s, 2H), 7.36-7.40 (m, 3H), 7.45-7.49 (m, 2H), 8.31-8.35 (m, 5H), 8.44 (s, 1H); APCI-MS (m/z) 308 (M+H)$^+$.

Step 2: 4-(3-(Benzyloxy)pyrazin-2-yl)aniline

The titled compound was prepared by the reduction of Step 1 intermediate (89 mg, 0.29 mmol) using iron powder (49 mg, 0.87 mmol) and ammonium chloride (155 mg, 2.89 mmol) in a mixture of ethanol and water (12 mL, 5:1) as per the procedure described in Step 4 of Intermediate 9 to yield 72 mg of the product; $^1$H NMR (300 MHz, DMSO-$d_6$) δ 5.46 (s, 2H), 5.53 (s, 2H), 6.58 (d, J=8.1 Hz, 2H), 7.36-7.41 (m, 3H), 7.43-7.48 (m, 2H), 7.85 (d, J=8.4 Hz, 2H), 8.01 (s, 1H), 8.20 (s, 1H); APCI-MS (m/z) 278 (M+H)$^+$.

Intermediate 69

4-(3-(1-Phenylethoxy)pyrazin-2-yl)aniline

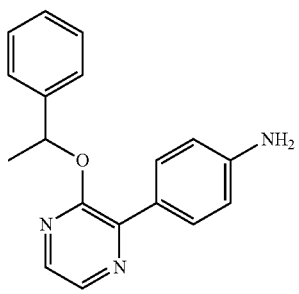

Step 1: 2-(4-Nitrophenyl)-3-(1-phenylethoxy)pyrazine

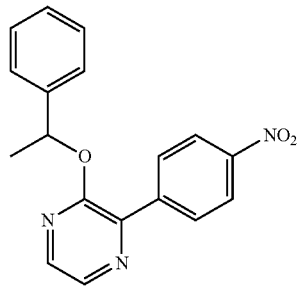 [SMILES: CC(Oc1nccnc1-c1ccc([N+](=O)[O-])cc1)c1ccccc1]

The titled compound was prepared by the reaction of 2-chloro-3-(4-nitrophenyl)pyrazine (Step 1 of intermediate 11) (203 mg, 0.86 mmol) with 1-phenylethanol (156 μL, 1.29 mmol) using cesium fluoride (392 mg, 2.58 mmol) in DMSO (10 mL) as per the procedure described in Step 1 of Intermediate 51 to yield 196 mg of the product; $^1$H NMR (300 MHz, DMSO-$d_6$) δ 1.64 (d, J=6.3 Hz, 3H), 6.28-6.32 (m, 1H), 7.26-7.34 (m, 3H), 7.42 (d, J=6.9 Hz, 2H), 8.24 (s, 1H), 8.35 (s, 5H); APCI-MS (m/z) 322 (M+H)$^+$.

Step 2: 4-(3-(1-Phenylethoxy)pyrazin-2-yl)aniline

The titled compound was prepared by the reduction of Step 1 intermediate (189 mg, 0.59 mmol) using iron powder (99 mg, 1.76 mmol) and ammonium chloride (315 mg, 5.88 mmol) in a mixture of ethanol and water (10 mL, 5:1) as per the procedure described in Step 4 of Intermediate 9 to yield 141 mg of the product; $^1$H NMR (300 MHz, DMSO-$d_6$) δ 1.63 (d, J=6.3 Hz, 3H), 5.67 (br s, 2H), 6.25 (d, J=6.3 Hz, 1H), 6.64 (d, J=8.7 Hz, 2H), 7.24-7.43 (m, 5H), 7.92 (d, J=8.4 Hz, 3H), 8.14 (s, 1H); APCI-MS (m/z) 292 (M+H)$^+$.

Intermediate 70

4-(3-((2-Chloro-4-fluorobenzyl)oxy)pyrazin-2-yl)aniline

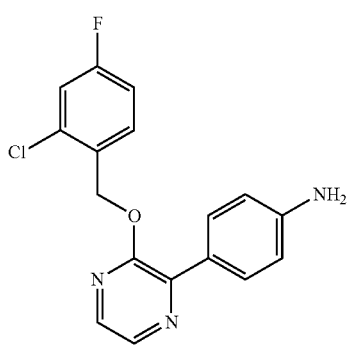 [SMILES: O=[N+]([O-])c1ccc(-c2nccnc2OCc2ccc(F)cc2Cl)cc1]

121

Step 1: 2-((2-Chloro-4-fluorobenzyl)oxy)-3-(4-nitrophenyl)pyrazine

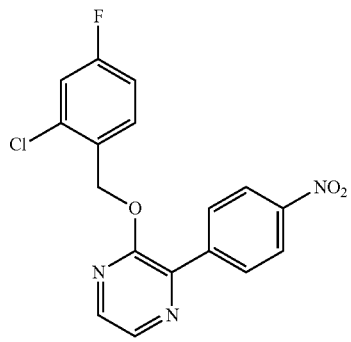

The titled compound was prepared by the reaction of 2-chloro-3-(4-nitrophenyl)pyrazine (Step 1 of intermediate 11) (203 mg, 0.86 mmol) with 2-chloro-4-fluorobenzylalcohol (152 µL, 0.94 mmol) using cesium fluoride (261 mg, 1.72 mmol) in DMSO (10 mL) as per the procedure described in Step 1 of Intermediate 51 to yield 261 mg of the product; $^1$H NMR (300 MHz, DMSO-$d_6$) δ 5.56 (s, 2H), 7.25-7.29 (m, 1H), 7.53 (d, J=9.3 Hz, 1H), 7.62-7.68 (m, 1H), 8.28-8.37 (m, 5H), 8.46 (s, 1H); APCI-MS (m/z) 360 (M+H)$^+$.

Step 2: 4-(3-((2-Chloro-4-fluorobenzyl)oxy)pyrazin-2-yl)aniline

The titled compound was prepared by the reduction of Step 1 intermediate (249 mg, 0.69 mmol) using iron powder (116 mg, 2.08 mmol) and ammonium chloride (370 mg, 6.92 mmol) in a mixture of ethanol and water (10 mL, 5:1) as per the procedure described in Step 4 of Intermediate 9 to yield 120 mg of the product; $^1$H NMR (300 MHz, DMSO-$d_6$) δ 5.49 (s, 2H), 5.58 (br s, 2H), 6.58 (d, J=8.1 Hz, 2H), 7.25-7.29 (m, 1H), 7.56 (d, J=8.7 Hz, 1H), 7.64 (t, J=8.1 Hz, 1H), 7.82 (d, J=8.1 Hz, 2H), 8.03 (s, 1H), 8.23 (s, 1H); APCI-MS (m/z) 330 (M+H)$^+$.

Intermediate 71

(R)-4-(3-(1-Phenylethoxy)pyrazin-2-yl)aniline

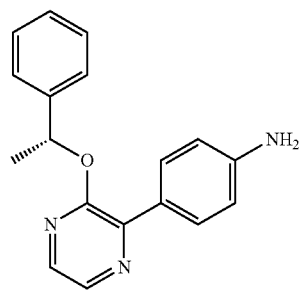 [SMILES: C[C@@H](Oc1nccnc1-c1ccc([N+](=O)[O-])cc1)c1ccccc1]

122

Step 1: (R)-2-(4-nitrophenyl)-3-(1-phenylethoxy)pyrazine

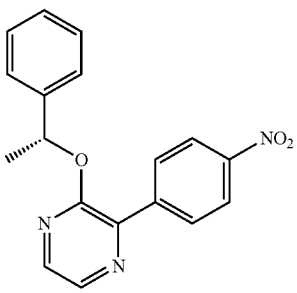

The titled compound was prepared by the reaction of 2-chloro-3-(4-nitrophenyl)pyrazine (Step 1 of intermediate 11) (203 mg, 0.86 mmol) with (R)-1-phenylethanol (109 µL, 0.95 mmol) using cesium fluoride (326 mg, 2.15 mmol) in DMSO (8.0 mL) as per the procedure described in Step 1 of Intermediate 51 to yield 211 mg of the product; $^1$H NMR (300 MHz, DMSO-$d_6$) δ 1.64 (d, J=6.3 Hz, 3H), 6.29 (d, J=6.3 Hz, 1H), 7.23-7.36 (m, 3H), 7.42 (d, J=6.9 Hz, 2H), 8.24 (s, 1H), 8.35 (s, 5H).

Step 2: (R)-4-(3-(1-Phenylethoxy)pyrazin-2-yl)aniline

The titled compound was prepared by the reduction of Step 1 intermediate (204 mg, 0.70 mmol) using iron powder (118 mg, 2.10 mmol) and ammonium chloride (374 mg, 70.0 mmol) in a mixture of ethanol and water (10 mL, 5:1) as per the procedure described in Step 4 of Intermediate 9 to yield 142 mg of the product; $^1$H NMR (300 MHz, DMSO-$d_6$) δ 1.64 (d, J=6.3 Hz, 3H), 5.56 (br s, 2H), 6.25 (d, J=6.9 Hz, 1H), 6.63 (d, J=8.4 Hz, 2H), 7.24-7.44 (m, 5H), 7.89-7.93 (m, 3H), 8.14 (s, 1H); APCI-MS (m/z) 292 (M+H)$^+$.

Intermediate 72

(S)-4-(3-(1-Phenyl ethoxy)pyrazin-2-yl)aniline

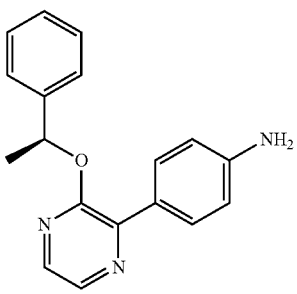 [SMILES: C[C@H](Oc1nccnc1-c1ccc(N)cc1)c1ccccc1]

123

Step 1: (S)-2-(4-nitrophenyl)-3-(1-phenylethoxy)pyrazine

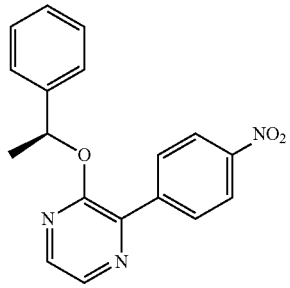 [SMILES: C[C@H](Oc1nccnc1-c1ccc([N+](=O)[O-])cc1)c1ccccc1]

The titled compound was prepared by the reaction of 2-chloro-3-(4-nitrophenyl)pyrazine (Step 1 of intermediate 11) (203 mg, 0.86 mmol) with (S)-1-phenylethanol (114 μL, 0.91 mmol) using cesium fluoride (325 mg, 2.15 mmol) in DMSO (8.0 mL) as per the procedure described in Step 1 of Intermediate 51 to yield 130 mg of the product; $^1$H NMR (300 MHz, DMSO-$d_6$) δ 1.66 (d, J=6.3 Hz, 3H), 6.29-6.33 (m, 1H), 7.28 (d, J=6.9 Hz, 1H), 7.35 (t, J=6.9 Hz, 2H), 7.44 (d, J=7.2 Hz, 2H), 8.26 (s, 1H), 8.37 (s, 5H); APCI-MS (m/z) 322 (M+H)$^+$.

Step 2: (S)-4-(3-(1-Phenylethoxy)pyrazin-2-yl)aniline

The titled compound was prepared by the reduction of Step 1 intermediate (120 mg, 0.41 mmol) using iron powder (69 mg, 1.23 mmol) and ammonium chloride (220 mg, 4.11 mmol) in a mixture of ethanol and water (10 mL, 5:1) as per the procedure described in Step 4 of Intermediate 9 to yield 87 mg of the product; $^1$H NMR (300 MHz, DMSO-$d_6$) δ 1.63 (d, J=6.3 Hz, 3H), 5.56 (s, 2H), 6.23-6.27 (m, 1H), 6.63 (d, J=9.0 Hz, 2H), 7.26 (d, J=6.9 Hz, 1H), 7.34 (t, J=7.2 Hz, 2H), 7.42 (d, J=7.2 Hz, 2H), 7.89-7.93 (m, 3H), 8.14 (s, 1H); APCI-MS (m/z) 292 (M+H)$^+$.

Intermediate 73

4-(3-(1-(2-Cyclopropylphenyl)ethoxy)pyrazin-2-yl)aniline

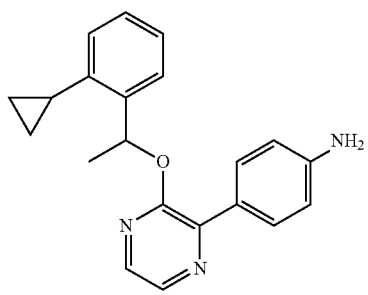

124

Step 1: 2-(1-(2-Cyclopropylphenyl)ethoxy)-3-(4-nitrophenyl)pyrazine

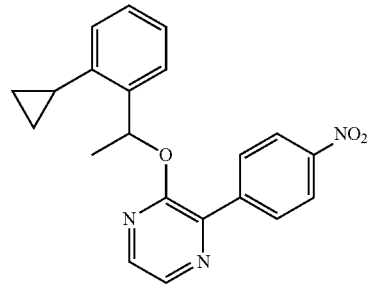 [SMILES: CC(Oc1nccnc1-c1ccc([N+](=O)[O-])cc1)c1ccccc1C1CC1]

The titled compound was prepared by the reaction of 2-chloro-3-(4-nitrophenyl)pyrazine (Step 1 of intermediate 11) (400 mg, 1.69 mmol) with 1-(2-cyclopropylphenyl)ethanol (275 mg, 1.69 mmol) using cesium fluoride (770 mg, 5.07 mmol) in DMSO (15 mL) as per the procedure described in Step 1 of Intermediate 51 to yield 260 mg of the product; $^1$H NMR (300 MHz, DMSO-$d_6$) δ 0.59-0.63 (m, 1H), 0.73-0.77 (m, 1H), 0.89-0.94 (m, 2H), 1.67 (d, J=6.3 Hz, 3H), 2.09-2.13 (m, 1H), 6.76-6.81 (m, 1H), 7.00-7.03 (m, 1H), 7.11-7.15 (m, 2H), 7.31-7.35 (m, 1H), 8.22 (s, 1H), 8.33-8.37 (m, 5H); APCI-MS (m/z) 362 (M+H)$^+$.

Step 2: 4-(3-(1-(2-Cyclopropylphenyl)ethoxy)pyrazin-2-yl)aniline

The titled compound was prepared by the reduction of Step 1 intermediate (200 mg, 0.55 mmol) using iron powder (92 mg, 1.65 mmol) and ammonium chloride (296 mg, 5.53 mmol) in a mixture of ethanol and water (18 mL, 5:1) as per the procedure described in Step 4 of Intermediate 9 to yield 140 mg of the product; $^1$H NMR (300 MHz, DMSO-$d_6$) δ 0.60-0.64 (m, 1H), 0.74-0.78 (m, 1H), 0.90-0.95 (m, 2H), 1.64 (d, J=6.3 Hz, 3H), 2.11-2.15 (m, 1H), 5.55 (s, 2H), 6.64 (d, J=8.7 Hz, 2H), 6.72-6.76 (m, 1H), 7.01-7.05 (m, 1H), 7.11-7.17 (m, 2H), 7.34-7.38 (m, 1H), 7.89-7.96 (m, 3H), 8.12 (s, 1H); APCI-MS (m/z) 332 (M+H)$^+$.

Intermediate 74

4-(3-(1-Phenylcyclopropoxy)pyrazin-2-yl)aniline

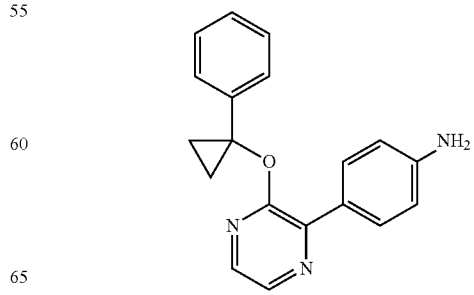

Step 1:
2-(4-Nitrophenyl)-3-(1-phenylcyclopropoxy)pyrazine

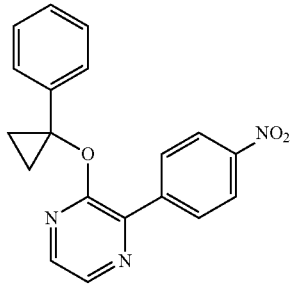 [SMILES: O=[N+]([O-])c1ccc(-c2nccnc2OC2(c3ccccc3)CC2)cc1]

The titled compound was prepared by the reaction of 2-chloro-3-(4-nitrophenyl)pyrazine (Step 1 of intermediate 11) (151 mg, 0.64 mmol) with 1-phenylcyclopropanol (129 mg, 0.96 mmol) using cesium fluoride (389 mg, 2.56 mmol) in DMSO (10 mL) as per the procedure described in Step 1 of Intermediate 51 to yield 76 mg of the product; $^1$H NMR (300 MHz, DMSO-$d_6$) δ 1.39-1.43 (m, 2H), 1.49-1.53 (m, 2H), 7.20-7.28 (m, 5H), 8.21 (s, 1H), 8.30-8.41 (m, 5H).

Step 2:
4-(3-(1-Phenylcyclopropoxy)pyrazin-2-yl)aniline

The titled compound was prepared by the reduction of Step 1 intermediate (72 mg, 0.22 mmol) using iron powder (36 mg, 0.64 mmol) and ammonium chloride (116 mg, 2.16 mmol) in a mixture of ethanol and water (10 mL, 5:1) as per the procedure described in Step 4 of Intermediate 9 to yield 65 mg of the product. The product was as such taken for the next step without characterization.

Intermediate 75

(R)-4-(3-(1-(2-chlorophenyl)ethoxy)pyrazin-2-yl)aniline

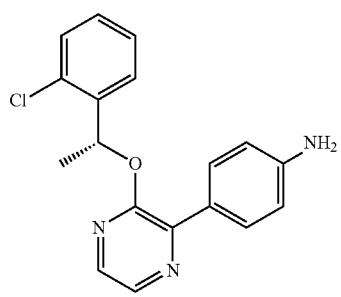 [SMILES: C[C@@H](Oc1nccnc1-c1ccc(N)cc1)c1ccccc1Cl]

Step 1: (R)-2-(1-(2-Chlorophenyl)ethoxy)-3-(4-nitrophenyl)pyrazine

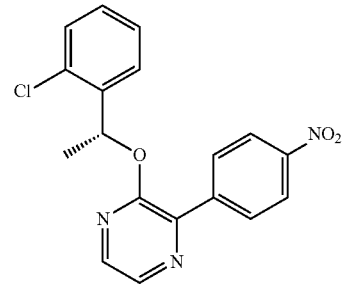 [SMILES: C[C@@H](Oc1nccnc1-c1ccc([N+](=O)[O-])cc1)c1ccccc1Cl]

The titled compound was prepared by the reaction of 2-chloro-3-(4-nitrophenyl)pyrazine (Step 1 of intermediate 11) (300 mg, 1.27 mmol) with (R)-1-(2-chlorophenyl)ethanol (209 mg, 1.33 mmol) using cesium fluoride (580 mg, 3.82 mmol) in DMSO (10 mL) as per the procedure described in Step 1 of Intermediate 51 to yield 374 mg of the product; $^1$H NMR (300 MHz, DMSO-$d_6$) δ 1.66 (d, J=6.3 Hz, 3H), 6.50-6.54 (m, 1H), 7.29-7.36 (m, 3H), 7.44-7.49 (m, 2H), 8.25 (s, 1H), 8.38 (s, 4H).

Step 2: (R)-4-(3-(1-(2-chlorophenyl)ethoxy)pyrazin-2-yl)aniline

The titled compound was prepared by the reduction of Step 1 intermediate (366 mg, 1.03 mmol) using iron powder (172 mg, 3.08 mmol) and ammonium chloride (550 mg, 10.28 mmol) in a mixture of ethanol and water (25 mL, 5:1) as per the procedure described in Step 4 of Intermediate 9 to yield 230 mg of the product; $^1$H NMR (300 MHz, DMSO-$d_6$) δ 1.64 (d, J=6.3 Hz, 3H), 5.58 (s, 2H), 6.45-6.50 (m, 1H), 6.64 (d, J=8.7 Hz, 2H), 7.29-7.32 (m, 2H), 7.43-7.47 (m, 2H), 7.90-7.95 (m, 3H), 8.15 (s, 1H).

Intermediate 76

(S)-4-(3-(1-(2-chlorophenyl)ethoxy)pyrazin-2-yl)aniline

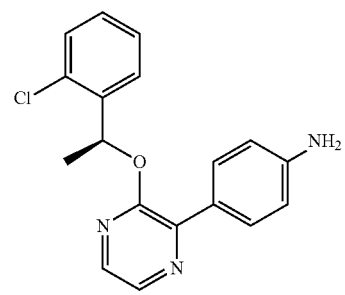 [SMILES: C[C@H](Oc1nccnc1-c1ccc(N)cc1)c1ccccc1Cl]

Step 1: (S)-2-(1-(2-Chlorophenyl)ethoxy)-3-(4-nitrophenyl)pyrazine

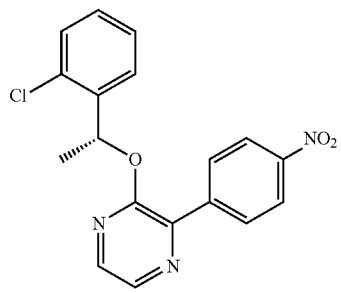 [SMILES: C[C@@H](Oc1nccnc1-c1ccc([N+](=O)[O-])cc1)c1ccccc1Cl]

The titled compound was prepared by the reaction of 2-chloro-3-(4-nitrophenyl)pyrazine (Step 1 of intermediate 11) (300 mg, 1.27 mmol) with (S)-1-(2-chlorophenyl)ethanol (209 mg, 1.33 mmol) using cesium fluoride (580 mg, 3.82 mmol) in DMSO (10 mL) as per the procedure described in Step 1 of Intermediate 51 to yield 398 mg of the product; $^1$H NMR (300 MHz, DMSO-d$_6$) δ 1.66 (d, J=6.3 Hz, 3H), 6.50-6.54 (m, 1H), 7.30-7.34 (m, 2H), 7.43-7.47 (m, 2H), 8.25 (s, 1H), 8.38 (s, 5H).

Step 2: (S)-4-(3-(1-(2-chlorophenyl)ethoxy)pyrazin-2-yl)aniline

The titled compound was prepared by the reduction of Step 1 intermediate (392 mg, 1.10 mmol) using iron powder (185 mg, 3.30 mmol) and ammonium chloride (589 mg, 11.01 mmol) in a mixture of ethanol and water (10 mL, 5:1) as per the procedure described in Step 4 of Intermediate 9 to yield 246 mg of the product; $^1$H NMR (300 MHz, DMSO-d$_6$) δ 1.64 (d, J=6.3 Hz, 3H), 5.57 (s, 2H), 6.44-6.48 (m, 1H), 6.64 (d, J=8.4 Hz, 2H), 7.28-7.32 (m, 2H), 7.42-7.46 (m, 2H), 7.89-7.95 (m, 3H), 8.14 (s, 1H).

Intermediate 77

4-(3-(2-Chlorophenoxy)pyrazin-2-yl)aniline

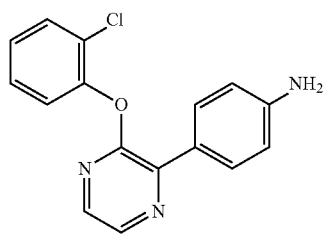 [SMILES: Nc1ccc(-c2nccnc2Oc2ccccc2Cl)cc1]

Step 1: 2-(2-chlorophenoxy)-3-(4-nitrophenyl)pyrazine

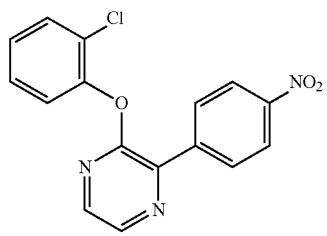 [SMILES: O=[N+]([O-])c1ccc(-c2nccnc2Oc2ccccc2Cl)cc1]

The titled compound was prepared by the reaction of 2-chloro-3-(4-nitrophenyl)pyrazine (Step 1 of intermediate 11) (200 mg, 0.85 mmol) with 2-chlorophenol (131 mg, 1.02 mmol) using cesium carbonate (415 mg, 1.27 mmol) in DMSO (5.0 mL) as per the procedure described in Step 1 of Intermediate 51 to yield 151 mg of the product; $^1$H NMR (300 MHz, DMSO-d$_6$) δ 7.34-7.40 (m, 1H), 7.45-7.52 (m, 2H), 7.63 (d, J=7.2 Hz, 1H), 8.26 (s, 1H), 8.41 (s, 4H), 8.60 (s, 1H).

Step 2: 4-(3-(2-Chlorophenoxy)pyrazin-2-yl)aniline

The titled compound was prepared by the reduction of Step 1 intermediate (151 mg, 0.46 mmol) using iron powder (129 mg, 2.30 mmol) and ammonium chloride (247 mg, 4.61 mmol) in a mixture of ethanol and water (18 mL, 5:1) as per the procedure described in Step 4 of Intermediate 9 to yield 89 mg of the product; $^1$H NMR (300 MHz, DMSO-d$_6$) δ 5.62 (s, 2H), 6.66 (d, J=8.1 Hz, 2H), 7.29-7.33 (m, 1H), 7.39-7.43 (m, 2H), 7.61 (d, J=8.1 Hz, 1H), 7.90-7.97 (m, 3H), 8.35 (s, 1H); APCI-MS (m/z) 298 (M+H)$^+$.

Intermediate 78

(R)-4-(3-(1-(2-Chloro-4-methylphenyl)ethoxy)pyrazin-2-yl)aniline

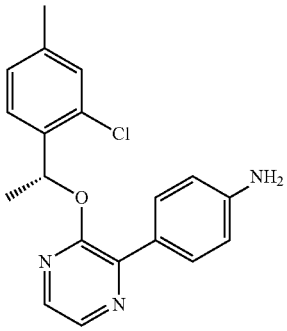 [SMILES: Cc1ccc([C@@H](C)Oc2nccnc2-c2ccc(N)cc2)c(Cl)c1]

Step 1: (R)-2-(1-(2-Chloro-4-methylphenyl)ethoxy)-3-(4-nitrophenyl)pyrazine

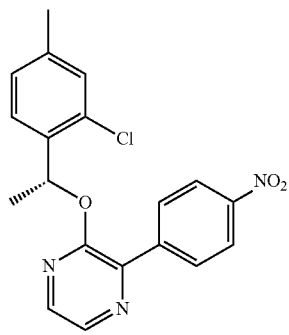 [SMILES: Cc1ccc([C@@H](C)Oc2nccnc2-c2ccc([N+](=O)[O-])cc2)c(Cl)c1]

The titled compound was prepared by the reaction of 2-chloro-3-(4-nitrophenyl)pyrazine (Step 1 of intermediate 11) (203 mg, 0.86 mmol) with (R)-1-(2-chloro-4-methylphenyl)ethanol (147 mg, 0.86 mmol) using cesium fluoride (392 mg, 2.58 mmol) in DMSO (8.0 mL) as per the procedure described in Step 1 of Intermediate 51 to yield 161 mg of the product; 1H NMR (300 MHz, DMSO-$d_6$) δ 1.64 (d, J=6.3 Hz, 3H), 2.26 (s, 3H), 6.46-6.50 (m, 1H), 7.12-7.16 (m, 1H), 7.28-7.34 (m, 2H), 8.24 (s, 1H), 8.37 (s, 5H); APCI-MS (m/z) 370 (M+H)$^+$.

Step 2: (R)-4-(3-(1-(2-Chloro-4-methylphenyl)ethoxy)pyrazin-2-yl)aniline

The titled compound was prepared by the reduction of Step 1 intermediate (188 mg, 0.51 mmol) using iron powder (85 mg, 1.52 mmol) and ammonium chloride (272 mg, 5.08 mmol) in a mixture of ethanol and water (12 mL, 5:1) as per the procedure described in Step 4 of Intermediate 9 to yield 140 mg of the product; $^1$H NMR (300 MHz, DMSO-$d_6$) δ 1.61 (d, J=6.3 Hz, 3H), 2.25 (s, 3H), 5.55 (s, 2H), 6.41-6.45 (m, 1H), 6.63 (d, J=6.9 Hz, 2H), 7.12 (d, J=8.4 Hz, 1H), 7.26-7.34 (m, 2H), 7.87-7.91 (m, 3H), 8.13 (s, 1H); APCI-MS (m/z) 340 (M+H)$^+$.

Intermediate 79

4-(3-((3,5-Dimethylisoxazol-4-yl)methoxy)pyrazin-2-yl)aniline

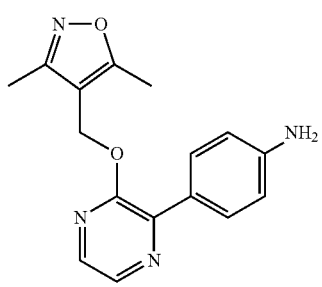 [SMILES: Cc1noc(C)c1COc1nccnc1-c1ccc([N+](=O)[O-])cc1]

Step 1: 3,5-Dimethyl-4-(((3-(4-nitrophenyl)pyrazin-2-yl)oxy)methyl)isoxazole

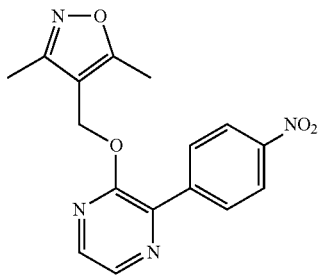

The titled compound was prepared by the reaction of 2-chloro-3-(4-nitrophenyl)pyrazine (Step 1 of intermediate 11) (112 mg, 0.48 mmol) with (3,5-dimethylisoxazol-4-yl)methanol (61 mg, 0.48 mmol) using cesium fluoride (216 mg, 1.43 mmol) in DMSO (8.0 mL) as per the procedure described in Step 1 of Intermediate 51 to yield 109 mg of the product; $^1$H NMR (300 MHz, DMSO-$d_6$) δ 2.22 (s, 3H), 2.45 (s, 3H), 5.33 (s, 2H), 8.22 (d, J=8.7 Hz, 2H), 8.32-8.38 (m, 3H), 8.43 (s, 1H).

Step 2: 4-(3-((3,5-Dimethylisoxazol-4-yl)methoxy)pyrazin-2-yl)aniline

The titled compound was prepared by the reduction of Step 1 intermediate (102 mg, 0.31 mmol) using iron powder (52 mg, 0.94 mmol) and ammonium chloride (167 mg, 3.13 mmol) in a mixture of ethanol and water (12 mL, 5:1) as per the procedure described in Step 4 of Intermediate 9 to yield 56 mg of the product; $^1$H NMR (300 MHz, DMSO-$d_6$) δ 2.23 (s, 3H), 2.43 (s, 3H), 5.27 (s, 2H), 5.53 (s, 2H), 6.57 (d, J=8.1 Hz, 2H), 7.79 (d, J=8.7 Hz, 2H), 8.03 (s, 1H), 8.21 (s, 1H).

Intermediate 80

4-(3-(2-(3,5-Dimethylisoxazol-4-yl)ethoxy)pyrazin-2-yl)aniline

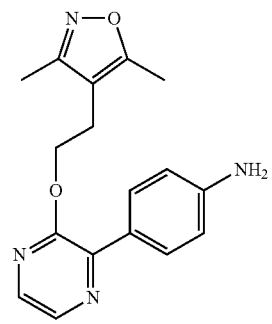

131

Step 1: 3,5-Dimethyl-4-(2-((3-(4-nitrophenyl)
pyrazin-2-yl)oxy)ethyl)isoxazole

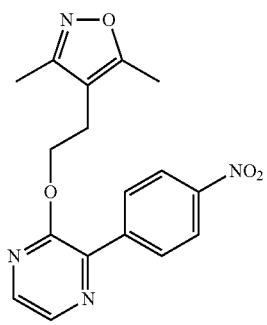 [SMILES: Cc1noc(C)c1CCOc1nccnc1-c1ccc([N+](=O)[O-])cc1]

The titled compound was prepared by the reaction of 2-chloro-3-(4-nitrophenyl)pyrazine (Step 1 of intermediate 11) (203 mg, 0.86 mmol) with 2-(3,5-dimethylisoxazol-4-yl)ethanol (121 mg, 0.86 mmol) using cesium fluoride (392 mg, 2.58 mmol) in DMSO (8.0 mL) as per the procedure described in Step 1 of Intermediate 51 to yield 149 mg of the product; $^1$H NMR (300 MHz, DMSO-$d_6$) δ 2.10 (s, 3H), 2.19 (s, 3H), 2.84 (t, J=6.6 Hz, 2H), 4.51 (t, J=6.6 Hz, 2H), 8.18 (d, J=8.7 Hz, 2H), 8.28-8.33 (m, 3H), 8.40 (s, 1H).

Step 2: 4-(3-(2-(3,5-Dimethylisoxazol-4-yl)ethoxy)
pyrazin-2-yl)aniline

The titled compound was prepared by the reduction of Step 1 intermediate (141 mg, 0.41 mmol) using iron powder (70 mg, 1.24 mmol) and ammonium chloride (221 mg, 4.14 mmol) in a mixture of ethanol and water (12 mL, 5:1) as per the procedure described in Step 4 of Intermediate 9 to yield 121 mg of the product; $^1$H NMR (300 MHz, DMSO-$d_6$) δ 2.14 (s, 3H), 2.24 (s, 3H), 2.83 (t, J=6.6 Hz, 2H), 4.45 (t, J=6.6 Hz, 2H), 5.53 (s, 2H), 6.58 (d, J=8.1 Hz, 2H), 7.71 (d, J=8.4 Hz, 2H), 7.97 (s, 1H), 8.16 (s, 1H); ESI-MS (m/z) 311 (M+H)$^+$.

Intermediate 81

4-(3-((2-Chlorobenzyl)oxy)pyrazin-2-yl)aniline

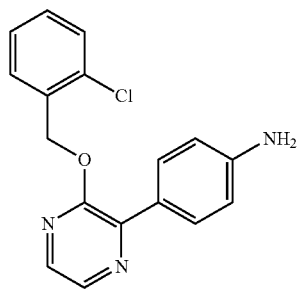 [SMILES: Nc1ccc(-c2nccnc2OCc2ccccc2Cl)cc1]

132

Step 1: 2-((2-Chlorobenzyl)oxy)-3-(4-nitrophenyl)
pyrazine

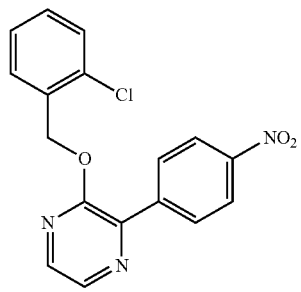 [SMILES: O=[N+]([O-])c1ccc(-c2nccnc2OCc2ccccc2Cl)cc1]

The titled compound was prepared by the reaction of 2-chloro-3-(4-nitrophenyl)pyrazine (Step 1 of intermediate 11) (203 mg, 0.86 mmol) with 2-chlorobenzylalcohol (123 mg, 0.86 mmol) using cesium fluoride (392 mg, 2.58 mmol) in DMSO (8.0 mL) as per the procedure described in Step 1 of Intermediate 51 to yield 110 mg of the product; $^1$H NMR (300 MHz, DMSO-$d_6$) δ 5.59 (s, 2H), 7.38-7.42 (m, 2H), 7.49-7.53 (m, 2H), 8.28-8.32 (m, 5H), 8.46 (s, 1H).

Step 2: 4-(3-((2-Chlorobenzyl)oxy)pyrazin-2-yl)
aniline

The titled compound was prepared by the reduction of Step 1 intermediate (101 mg, 0.29 mmol) using iron powder (49 mg, 0.88 mmol) and ammonium chloride (158 mg, 2.95 mmol) in a mixture of ethanol and water (12 mL, 5:1) as per the procedure described in Step 4 of Intermediate 9 to yield 78 mg of the product; $^1$H NMR (300 MHz, DMSO-$d_6$) δ 5.52 (s, 4H), 6.58 (d, J=7.8 Hz, 2H), 7.37-7.41 (m, 2H), 7.53-7.57 (m, 2H), 7.83 (d, J=8.4 Hz, 2H), 8.02 (s, 1H), 8.22 (s, 1H); ESI-MS (m/z) 312 (M+H)$^+$.

Intermediate 82

4-(3-(2-(4-Methylthiazol-5-yl)ethoxy)pyrazin-2-yl)
aniline

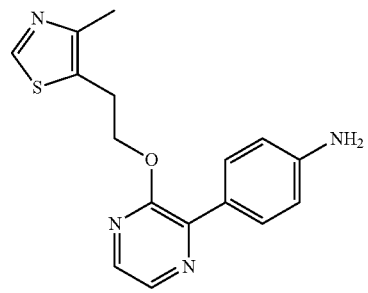

Step 1: 5-(2-((3-Chloropyrazin-2-yl)oxy)ethyl)-4-methylthiazole

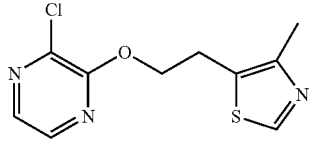 [SMILES: Cc1ncsc1CCOc1nccnc1Cl]

The titled compound was prepared by the reaction of 2,3-dichloropyrazine (200 mg, 1.34 mmol) with 2-(4-methylthiazol-5-yl)ethanol (230 mg, 1.61 mmol) using cesium fluoride (612 mg, 4.01 mmol) in DMSO (10 mL) as per the procedure described in Step 1 of Intermediate 51 to yield 326 mg of the product; $^1$H NMR (300 MHz, CDCl$_3$) δ 2.46 (s, 3H), 3.31 (t, J=6.3 Hz, 2H), 4.55 (t, J=6.3 Hz, 2H), 7.93-8.01 (m, 2H), 8.63 (s, 1H).

Step 2: 4-Methyl-5-(2-((3-(4-nitrophenyl)pyrazin-2-yl)oxy)ethyl)thiazole

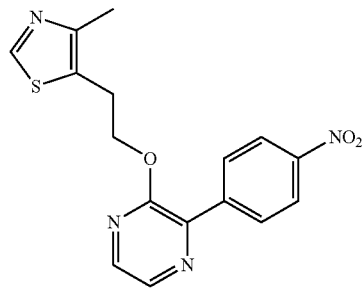 [SMILES: Cc1ncsc1CCOc1nccnc1-c1ccc([N+](=O)[O-])cc1]

The titled compound was prepared by the reaction of Step 1 intermediate (160 mg, 0.63 mmol) with 4-nitrophenylboronic acid pinacol ester (187 mg, 0.75 mmol) using potassium carbonate (259 mg, 1.88 mmol) and [1,1'-bis(diphenylphosphino)ferrocene]dichloropalladium (II). dichloromethane complex (26 mg, 0.03 mmol) in a mixture of DMSO and water (12 mL, 3:1) at RT as per the procedure described in Step 1 of Intermediate 1 to yield 96 mg of the product; $^1$H NMR (300 MHz, DMSO-d$_6$) δ 2.27 (s, 3H), 3.32 (t, J=6.3 Hz, 2H), 4.61 (t, J=6.3 Hz, 2H), 8.16 (d, J=8.7 Hz, 2H), 8.26-8.33 (m, 3H), 8.41 (s, 1H), 8.83 (s, 1H); ESI-MS (m/z) 343 (M+H)$^+$.

Step 3: 4-(3-(2-(4-Methylthiazol-5-yl)ethoxy)pyrazin-2-yl)aniline

The titled compound was prepared by the reduction of Step 2 intermediate (90 mg, 0.26 mmol) using iron powder (73 mg, 1.31 mmol) and ammonium chloride (141 mg, 2.63 mmol) in a mixture of ethanol and water (18 mL, 5:1) as per the procedure described in Step 4 of Intermediate 9 to yield 56 mg of the product; $^1$H NMR (300 MHz, DMSO-d$_6$) δ 2.32 (s, 3H), 3.31 (t, J=6.3 Hz, 2H), 4.54 (t, J=6.3 Hz, 2H), 5.53 (s, 2H), 6.56 (d, J=8.7 Hz, 2H), 7.73 (d, J=9.0 Hz, 2H), 7.98 (s, 1H), 8.18 (s, 1H), 8.84 (s, 1H); ESI-MS (m/z) 313 (M+H)$^+$.

Intermediate 83

4-(3-(Cyclohexylmethoxy)pyrazin-2-yl)aniline

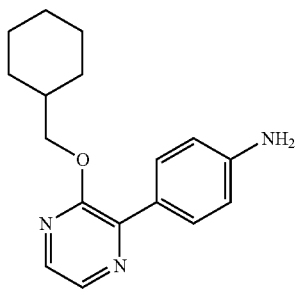

Step 1: 2-(Cyclohexylmethoxy)-3-(4-nitrophenyl)pyrazine

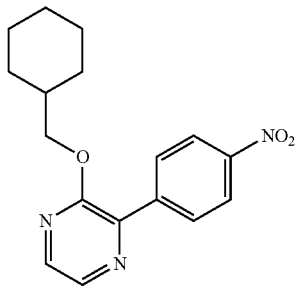 [SMILES: O=[N+]([O-])c1ccc(-c2nccnc2OCC2CCCCC2)cc1]

The titled compound was prepared by the reaction of 2-chloro-3-(4-nitrophenyl)pyrazine (Step 1 of intermediate 11) (203 mg, 0.86 mmol) with cyclohexylmethanol (99 mg, 0.86 mmol) using cesium fluoride (392 mg, 2.58 mmol) in DMSO (8.0 mL) as per the procedure described in Step 1 of Intermediate 51 to yield 141 mg of the product; $^1$H NMR (300 MHz, DMSO-d$_6$) δ 1.03-1.28 (m, 5H), 1.68-1.81 (m, 6H), 4.24 (d, J=5.7 Hz, 2H), 8.25-8.32 (m, 2H), 8.33-8.41 (m, 4H).

Step 2: 4-(3-(Cyclohexylmethoxy)pyrazin-2-yl)aniline

The titled compound was prepared by the reduction of Step 1 intermediate (132 mg, 0.42 mmol) using iron powder (70 mg, 1.26 mmol) and ammonium chloride (225 mg, 4.21 mmol) in a mixture of ethanol and water (10 mL, 5:1) as per the procedure described in Step 4 of Intermediate 9 to yield 103 mg of the product; $^1$H NMR (300 MHz, DMSO-d$_6$) δ 1.00-1.24 (m, 5H), 1.68-1.81 (m, 5H), 3.15-3.21 (m, 1H), 4.16 (d, J=3.9 Hz, 2H), 5.51 (s, 2H), 6.61 (d, J=8.7 Hz, 2H), 7.83 (d, J=7.2 Hz, 2H), 7.96 (s, 1H), 8.15 (s, 1H); ESI-MS (m/z) 282 (M−H)$^−$.

Intermediate 84

4-(3-(3-(Benzyloxy)azetidin-1-yl)pyrazin-2-yl)aniline

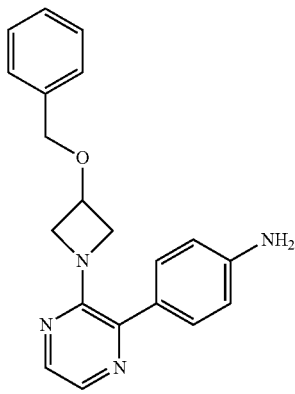

Step 1: 2-(3-(Benzyloxy)azetidin-1-yl)-3-(4-nitrophenyl)pyrazine

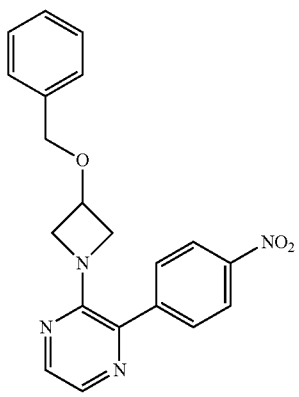 [SMILES: O=[N+]([O-])c1ccc(-c2nccnc2N2CC(OCc3ccccc3)C2)cc1]

The titled compound was prepared by the reaction of 2-chloro-3-(4-nitrophenyl)pyrazine (Step 1 of intermediate 11) (162 mg, 0.69 mmol) with 3-(benzyloxy)azetidine hydrochloride (151 mg, 0.76 mmol) using cesium fluoride (418 mg, 2.75 mmol) in DMSO (8.0 mL) as per the procedure described in Step 1 of Intermediate 51 to yield 217 mg of the product; $^1$H NMR (300 MHz, DMSO-$d_6$) δ 3.52-3.59 (m, 2H), 3.84-3.92 (m, 2H), 4.33-4.39 (m, 3H), 7.27-7.31 (m, 5H), 7.83 (d, J=8.1 Hz, 2H), 8.13 (s, 1H), 8.21 (s, 1H), 8.31 (d, J=8.4 Hz, 2H); ESI-MS (m/z) 363 (M+H)$^+$.

Step 2: 4-(3-(3-(Benzyloxy)azetidin-1-yl)pyrazin-2-yl)aniline

The titled compound was prepared by the reduction of Step 1 intermediate (209 mg, 0.57 mmol) using iron powder (97 mg, 1.72 mmol) and ammonium chloride (308 mg, 5.76 mmol) in a mixture of ethanol and water (10 mL, 5:1) as per the procedure described in Step 4 of Intermediate 9 to yield 161 mg of the product; $^1$H NMR (300 MHz, DMSO-$d_6$) δ 3.32-3.57 (m, 2H), 3.86-3.91 (m, 2H), 4.34-4.37 (m, 1H), 4.38 (s, 2H), 5.40 (s, 2H), 6.61 (d, J=8.4 Hz, 2H), 7.28-7.32 (m, 7H), 7.96 (s, 2H); ESI-MS (m/z) 333 (M+H)$^+$.

Intermediate 85

2-((3-(4-Aminophenyl)pyrazin-2-yl)amino)-2-phenylethanol

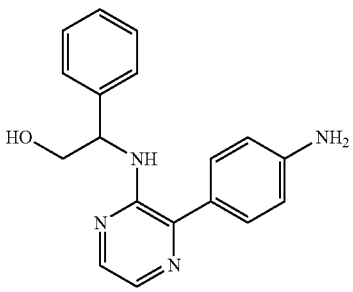 [SMILES: Nc1ccc(-c2nccnc2NC(CO)c2ccccc2)cc1]

Step 1: 2-((3-Chloropyrazin-2-yl)amino)-2-phenylethanol

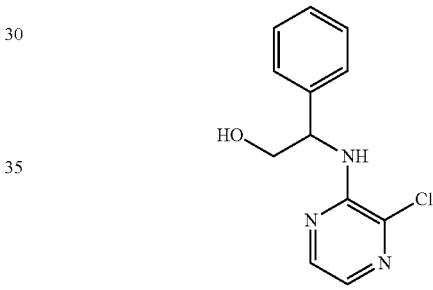

A mixture of 2,3-dichloropyrazine (1.0 g, 6.71 mmol) and (+)-2-amino-2-phenylethanol (1.02 g, 7.45 mmol) in 1,4-dioxane (15 mL) was refluxed overnight. The mixture was cooled to RT and concentrated under vacuum. The residue obtained was diluted with ethyl acetate (30 mL) and washed with water (30 mL) followed by brine (40 mL). The organic layer was dried over anhydrous sodium sulfate and concentrated under reduced pressure. The residue obtained was purified by silica gel column chromatography to yield 548 mg of the desired product; $^1$H NMR (300 MHz, CDCl$_3$) δ 3.60-3.65 (m, 1H), 3.86-3.91 (m, 1H), 4.96-5.02 (m, 1H), 5.63 (br s, 1H), 7.28-7.41 (m, 5H), 7.62 (s, 1H), 7.93 (s, 1H).

Step 2: 2-((3-(4-Aminophenyl)pyrazin-2-yl)amino)-2-phenylethanol

The titled compound was prepared by the reaction of Step 1 intermediate (200 mg, 0.80 mmol) with 4-aminophenylboronic acid pinacol ester (210 mg, 0.96 mmol) using sodium carbonate (255 mg, 2.40 mmol) and [1,1'-bis(diphenylphosphino)ferrocene]dichloropalladium (II). dichloromethane complex (65 mg, 0.08 mmol) in a mixture of DMSO and water (12 mL, 3:1) at 80° C. as per the procedure described in Step 1 of Intermediate 1 to yield 127 mg of the product; $^1$H NMR (300 MHz, DMSO-$d_6$) δ 3.34-3.42 (m, 1H), 3.56-3.62 (m, 1H), 4.80-4.84 (m, 1H), 5.43 (s, 2H), 5.56-5.58 (m, 1H), 6.01 (br s, 1H), 6.62 (d, J=8.4 Hz, 2H), 7.29 (d, J=8.7 Hz, 2H), 7.32-7.36 (m, 5H), 7.75 (s, 1H), 7.86 (s, 1H).

Intermediate 86

(R)-4-(3-(1-(2,4-Dimethylphenyl)ethoxy)pyrazin-2-yl)aniline

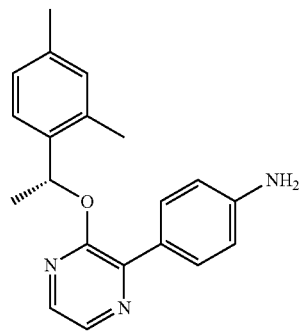 [SMILES: Cc1ccc([C@@H](C)Oc2nccnc2-c2ccc(N)cc2)c(C)c1]

Step 1: (R)-2-(1-(2,4-Dimethylphenyl)ethoxy)-3-(4-nitrophenyl)pyrazine

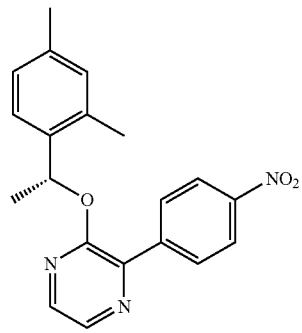 [SMILES: Cc1ccc([C@@H](C)Oc2nccnc2-c2ccc([N+](=O)[O-])cc2)c(C)c1]

The titled compound was prepared by the reaction of 2-chloro-3-(4-nitrophenyl)pyrazine (Step 1 of intermediate 11) (203 mg, 0.85 mmol) with (R)-1-(2,4-dimethylphenyl)ethanol (128 mg, 0.85 mmol) using cesium fluoride (386 mg, 2.54 mmol) in DMSO (8.0 mL) as per the procedure described in Step 1 of Intermediate 51 to yield 123 mg of the product; $^1$H NMR (300 MHz, DMSO-$d_6$) δ 1.60 (d, J=6.3 Hz, 3H), 2.19 (s, 3H), 2.35 (s, 3H), 6.35-6.42 (m, 1H), 6.91-6.96 (m, 2H), 7.23 (d, J=7.8 Hz, 1H), 8.22 (s, 1H), 8.29-8.36 (m, 5H); APCI-MS (m/z) 350 (M+H)$^+$.

Step 2: (R)-4-(3-(1-(2,4-Dimethylphenyl)ethoxy) pyrazin-2-yl)aniline

The titled compound was prepared by the reduction of Step 1 intermediate (117 mg, 0.33 mmol) using iron powder (56 mg, 1.00 mmol) and ammonium chloride (180 mg, 3.34 mmol) in a mixture of ethanol and water (12 mL, 5:1) as per the procedure described in Step 4 of Intermediate 9 to yield 72 mg of the product; $^1$H NMR (300 MHz, DMSO-$d_6$) δ 1.58 (d, J=6.3 Hz, 3H), 2.20 (s, 3H), 2.35 (s, 3H), 5.52 (s, 2H), 6.33-6.37 (m, 1H), 6.63 (d, J=8.1 Hz, 2H), 6.93-6.99 (m, 2H), 7.21-7.27 (m, 2H), 7.90 (s, 1H), 7.92 (s, 1H), 8.10 (s, 1H).

Intermediate 87

4-(3-(4-(Oxetan-3-yl)piperazin-1-yl)pyrazin-2-yl)aniline

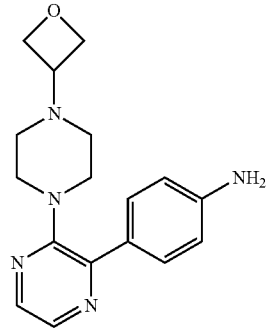 [SMILES: Nc1ccc(-c2nccnc2N2CCN(C3COC3)CC2)cc1]

Step 1: tert-Butyl 4-(3-Chloropyrazin-2-yl)piperazine-1-carboxylate

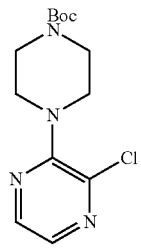 [SMILES: CC(C)(C)OC(=O)N1CCN(c2nccnc2Cl)CC1]

The titled compound was prepared by the reaction of 2,3-dichloropyrazine (500 mg, 3.35 mmol) with tert-butyl piperazine-1-carboxylate (625 mg, 3.35 mmol) in dimethylacetamide (10 mL) as per the procedure described in Step 1 of Intermediate 7 to yield 882 mg of the product; $^1$H NMR (300 MHz, CDCl$_3$) δ 1.48 (s, 9H), 3.39-3.45 (m, 4H), 3.57-3.60 (m, 4H), 7.91 (s, 1H), 8.11 (s, 1H).

Step 2: 2-Chloro-3-(piperazin-1-yl)pyrazine

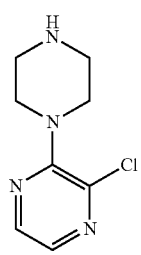 [SMILES: Clc1nccnc1N1CCNCC1]

To a stirred solution of Step 1 intermediate (870 mg, 2.92 mmol) in dichloromethane (10 mL) was added trifluoroacetic acid (4.0 mL) at 0° C. and the mixture was stirred for 6 h at RT. The reaction mixture was basified (pH 10) with 50% aqueous solution of sodium hydroxide and the aqueous mixture was extracted with dichloromethane (2×100 mL). The combined organic layers were washed with water (100 mL) and brine (50 mL). The solvent was removed under vacuum to obtain 378 mg of the titled product; APCI-MS (m/z) 199 (M+H)⁺.

Step 3: 2-Chloro-3-(4-(oxetan-3-yl)piperazin-1-yl) pyrazine

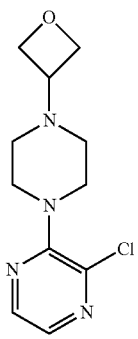 [SMILES: Clc1nccnc1N1CCN(C2COC2)CC1]

A mixture of Step 2 intermediate (378 mg, 1.90 mmol), 3-oxetanone (205 mg, 2.85 mmol) and catalytic amount of acetic acid in 1,2-dichloroethane (10 mL) was stirred for 2 h at RT. Sodium triacetoxyborohydride (806 mg, 3.85 mmol) was added to the reaction mixture and allowed to stir overnight at RT. The reaction mixture was diluted with ethyl acetate (100 mL) and washed with saturated aqueous sodium bicarbonate solution (2×30 mL) followed by brine (50 mL). The organic layer was dried over anhydrous sodium sulfate and concentrated under reduced pressure. The residue obtained was purified by silica gel column chromatography to yield 273 mg of the titled product; $^1$H NMR (300 MHz, CDCl$_3$) δ 2.52-2.56 (m, 4H), 3.52-3.62 (m, 5H), 4.65-3.73 (m, 3H), 7.89 (s, 1H), 8.11 (s, 2H); APCI-MS (m/z) 255 (M+H)⁺.

Step 4: 4-(3-(4-(Oxetan-3-yl)piperazin-1-yl)pyrazin-2-yl)aniline

The titled compound was prepared by the reaction of Step 3 intermediate (255 mg, 1.00 mmol) with 4-aminophenyl-boronic acid pinacol ester (263 mg, 1.20 mmol) using potassium carbonate (415 mg, 3.00 mmol) and [1,1'-bis(diphenylphosphino)ferrocene]dichloropalladium (II) (82 mg, 0.10 mmol) in a mixture of DMSO and water (12 mL, 3:1) at 80° C. as per the procedure described in Step 1 of Intermediate 1 to yield 123 mg of the product; $^1$H NMR (300 MHz, DMSO-d$_6$) δ 2.28-2.32 (m, 3H), 3.08-3.12 (m, 4H), 3.37-3.46 (m, 2H), 4.41 (t, J=5.7 Hz, 2H), 4.52 (t, J=6.3 Hz, 2H), 5.42 (br s, 2H), 6.60 (d, J=8.7 Hz, 2H), 7.65 (d, J=8.1 Hz, 2H), 8.01 (s, 1H), 8.09 (s, 1H); ESI-MS (m/z) 312 (M+H)⁺.

EXAMPLES

The examples were prepared by following the methods described below:

Method A

Preparation of N-(4-(3-(4-chlorophenyl)pyrazin-2-yl)phenyl)-2-(4-(1,1-difluoropropyl)phenyl) acetamide (Example 1)

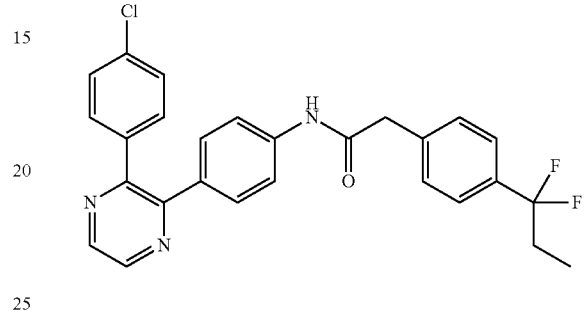

To a stirred solution of Intermediate 1 (92 mg, 0.32 mmol) and Intermediate 2 (70 mg, 0.32 mmol) in DMF (5.0 mL) at 0° C. was added N,N'-diisopropylethylamine (160 µL, 0.97 mmol) followed by propylphosphonic anhydride (50% in EtOAc, 194 µL, 0.65 mmol). The mixture was stirred overnight at RT. The reaction mixture was diluted with water (20 mL) and extracted with ethyl acetate (75 mL×2). The combined organic layer was washed with brine (100 mL), dried over anhydrous sodium sulfate and concentrated under reduced pressure. The crude material obtained was purified by silica gel column chromatography to obtain 53 mg of the product; H NMR (300 MHz, DMSO-d$_6$) δ 0.88 (t, J=7.2 Hz, 3H), 2.15-2.26 (m, 2H), 3.69 (s, 2H), 7.29-7.45 (m, 10H), 7.56 (d, J=8.7 Hz, 2H), 8.66 (d, J=8.7 Hz, 2H), 10.32 (s, 1H); APCI-MS (m/z) 477 (M+H)⁺.

Method B

Preparation of N-(4-(3-(4-chlorophenyl)pyrazin-2-yl)phenyl)-2-(4-(1,1-difluoro-2-hydroxy propyl) phenyl)acetamide (Example 2)

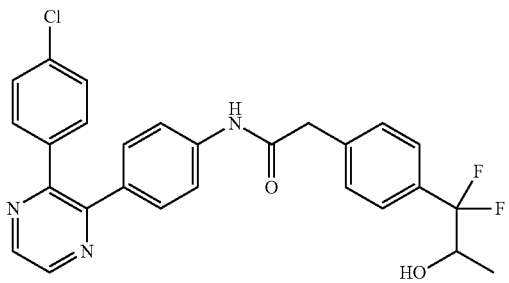 [SMILES: CC(O)C(F)(F)c1ccc(CC(=O)Nc2ccc(-c3nccnc3-c3ccc(Cl)cc3)cc2)cc1]

141

Step 1: N-(4-(3-(4-Chlorophenyl)pyrazin-2-yl)phenyl)-2-(4-(1,1-difluoro-2-oxopropyl)phenyl)acetamide

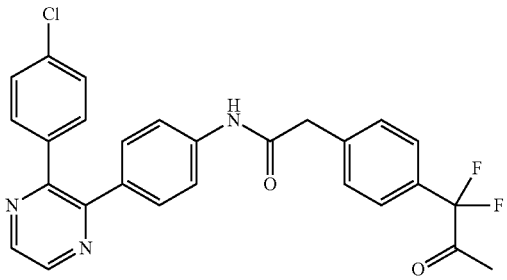 [SMILES: CC(=O)C(F)(F)c1ccc(CC(=O)Nc2ccc(-c3nccnc3-c3ccc(Cl)cc3)cc2)cc1]

The titled compound was prepared by the reaction of Intermediate 1 (133 mg, 0.47 mmol) and Intermediate 3 (120 mg, 0.52 mmol) using N,N'-diisopropylethylamine (269 µL, 1.57 mmol) and propylphosphonic anhydride (50% in EtOAc, 624 µL, 1.05 mmol) in DMF (5.0 mL) at RT as per the procedure described in Method A to give 143 mg of the product; APCI-MS (m/z) 492 (M+H)$^+$.

Step 2: N-(4-(3-(4-Chlorophenyl)pyrazin-2-yl)phenyl)-2-(4-(1,1-difluoro-2-hydroxypropyl)phenyl)acetamide To a stirred solution of step 1 intermediate (134 mg, 0.27 mmol) in methanol (5.0 mL) at 0° C. was added sodium borohydride (125 mg, 0.32 mmol). The reaction mixture was stirred at 0° C. for 1 h. The mixture was quenched with aq. ammonium chloride (20 mL), poured into water (20 mL) and extracted with ethyl acetate (70 mL×2). The combined organic layer was dried over anhydrous sodium sulfate and concentrated under reduced pressure. The crude material obtained was purified by silica gel column chromatography to obtain 64 mg of the product; $^1$H NMR (300 MHz, DMSO-d$_6$) δ 1.07 (d, J=5.7 Hz, 3H), 3.70 (s, 2H), 3.99-4.06 (m, 1H), 5.51 (d, J=6.0 Hz, 1H), 7.34 (d, J=8.1 Hz, 3H), 7.39-7.45 (m, 7H), 7.56 (d, J=8.1 Hz, 2H), 8.67 (d, J=3.9 Hz, 2H), 10.34 (s, 1H); ESI-MS (m/z) 494 (M+H)$^+$.

Method C

Preparation of (S)-2-(4-(1,1-difluoro-2-hydroxypropyl)phenyl)-N-(4-(3-(2-ethylphenyl)pyrazin-2-yl)phenyl)acetamide (Example 52)

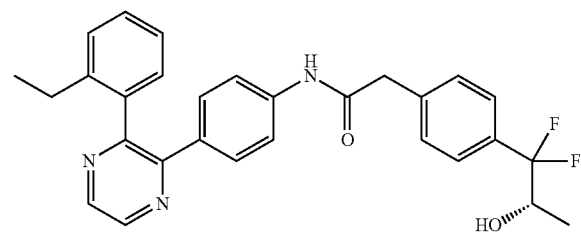

142

Step 1: 2-(4-(1,1-Difluoro-2-oxopropyl)phenyl)-N-(4-(3-(2-ethylphenyl)pyrazin-2-yl)phenyl)acetamide

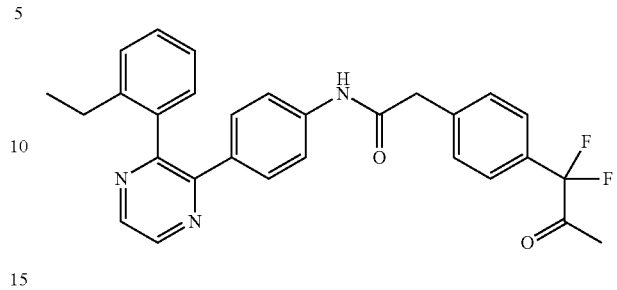

The titled compound was prepared by the reaction of Intermediate 39 (60 mg, 0.22 mmol) and Intermediate 3 (50 mg, 0.22 mmol) using N,N'-diisopropylethylamine (113 µL, 0.66 mmol) and propylphosphonic anhydride (50% in EtOAc, 263 µL, 0.44 mmol) in DMF (6.0 mL) as per the procedure described in Method A to yield 103 mg of the product; $^1$H NMR (300 MHz, DMSO-d$_6$) δ 0.85 (t, J=7.2 Hz, 3H), 2.26 (q, J=7.2 Hz, 2H), 2.35 (s, 3H), 3.70 (s, 2H), 7.16-7.30 (m, 5H), 7.43-7.52 (m, 5H), 7.95 (s, 2H), 8.66 (s, 1H), 8.72 (s, 1H), 10.29 (s, 1H).

Step 2: (S)-2-(4-(1,1-Difluoro-2-hydroxypropyl)phenyl)-N-(4-(3-(2-ethylphenyl)pyrazin-2-yl)phenyl)acetamide (Crude)

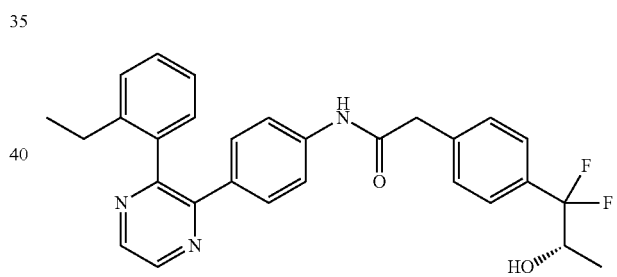

To a stirred solution of (R)-(+)-2-methyl-CBS-oxaborolidine (1M in toluene, 0.41 mL) [Ref: (i) Corey, E. J; Helal, C. J. Angew. Chem. Int. Ed. 1998, 37, 1986-2012 (ii) Corey, E. J.; Bakshi, R. K.; Shibata, S. J Am. Chem. Soc. 1987, 109 (18), 5551-5553] in anhydrous THF (10 mL) was added borane dimethyl sulfide complex (86 µL, 0.91 mmol) at 0° C. and the mixture was stirred for 20 min at the same temperature. A solution of Step 1 Intermediate (400 mg, 0.82 mmol) in THF (10 mL) was drop wise added to the reaction mixture over a period of 10 min at 0° C. The resultant mixture was stirred at RT for 30 min. The reaction mixture was quenched with methanol (10 mL) and concentrated under reduced pressure. The residue obtained was purified by flash silica gel column chromatography to yield 371 mg of the titled product; $^1$H NMR (300 MHz, DMSO-d$_6$) δ 0.85 (t, J=7.2 Hz, 3H), 1.06 (d, J=6.3 Hz, 3H), 2.26 (q, J=7.2 Hz, 2H), 3.67 (s, 2H), 4.01-4.05 (m, 1H), 5.50 (d, J=6.0 Hz, 1H), 7.14-7.34 (m, 6H), 7.36-7.49 (m, 6H), 8.67 (s, 1H), 8.73 (s, 1H), 10.28 (s, 1H); APCI-MS (m/z) 488 (M+H)$^+$; chiral HPLC purity: 84.85%.

Step 3: (S)—(S)-1-(4-(2-((4-(3-(2-ethylphenyl) pyrazin-2-yl)phenyl)amino)-2-oxoethyl)phenyl)-1,1-difluoropropan-2-yl 2-(((benzyloxy)carbonyl)amino)-3-phenylpropanoate

Preparation of (R)-2-(4-(1,1-difluoro-2-hydroxypropyl)phenyl)-N-(4-(3-(2-ethylphenyl) pyrazin-2-yl) phenyl)acetamide (Example 53)

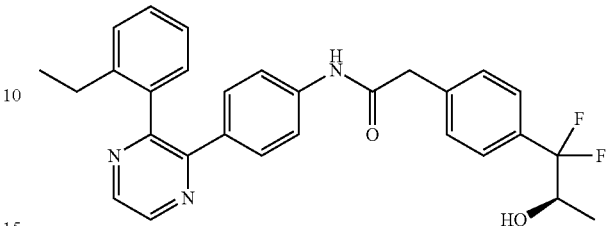

Step 1: 2-(4-(1,1-Difluoro-2-oxopropyl)phenyl)-N-(4-(3-(2-ethylphenyl)pyrazin-2-yl)phenyl)acetamide

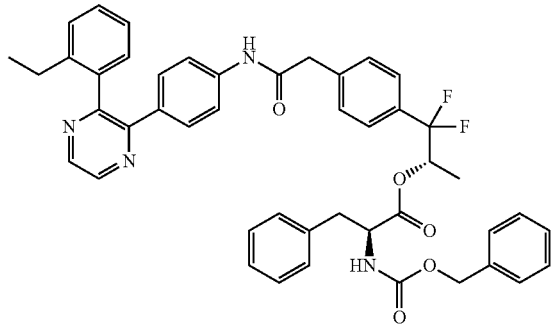 [SMILES: CCc1ccccc1-c1nccnc1-c1ccc(NC(=O)Cc2ccc(C(F)(F)[C@H](C)OC(=O)[C@H](Cc3ccccc3)NC(=O)OCc3ccccc3)cc2)cc1]

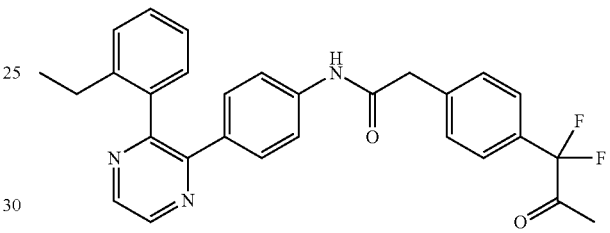

To a stirred solution of Step 2 product (300 mg, 0.62 mmol), N-benzyloxycarbonyl-L-phenylalanine (239 mg, 0.80 mmol) and DIPEA (0.3 mL, 1.84 mmol) in dichloromethane (10 mL) were added BOP (354 mg, 0.80 mmol) and DMAP (38 mg, 0.31 mmol) at 0° C. The resultant mixture was warmed up to RT and stirred for 16 h. The reaction mixture was diluted with ethyl acetate (200 mL) and washed with saturated aqueous solution of ammonium chloride (100 mL), saturated aqueous sodium bicarbonate solution (100 mL), water (100 mL) and brine (100 mL). The organic layer was dried over anhydrous sodium sulfate, concentrated and the residue thus obtained was purified by flash silica gel column chromatography to yield 738 mg of the titled product; APCI-MS (m/z) 769 (M+H)$^+$.

The titled compound was prepared by the reaction of Intermediate 39 (60 mg, 0.22 mmol) and Intermediate 3 (50 mg, 0.22 mmol) using N,N'-diisopropylethylamine (113 μL, 0.66 mmol) and propylphosphonic anhydride (50% in EtOAc, 263 μL, 0.44 mmol) in DMF (6.0 mL) as per the procedure described in Method A to yield 103 mg of the product as solid; $^1$H NMR (300 MHz, DMSO-d$_6$) δ δ 0.85 (t, J=7.2 Hz, 3H), 2.26 (q, J=7.2 Hz, 2H), 2.35 (s, 3H), 3.70 (s, 2H), 7.16-7.30 (m, 5H), 7.43-7.52 (m, 5H), 7.95 (s, 2H), 8.66 (s, 1H), 8.72 (s, 1H), 10.29 (s, 1H).

Step 2: (R)-2-(4-(1,1-Difluoro-2-hydroxypropyl) phenyl)-N-(4-(3-(2-ethylphenyl)pyrazin-2-yl)phenyl) acetamide (Crude)

Step 4: (S)-2-(4-(1,1-Difluoro-2-hydroxypropyl) phenyl)-N-(4-(3-(2-ethylphenyl)pyrazin-2-yl)phenyl) acetamide To a stirred solution of Step 3 Intermediate (96 mg, 0.13 mmol) in a mixture of THF (3.0 mL), methanol (1.0 mL) and water (1.0 mL) was added lithium hydroxide monohydrate (16 mg, 0.38 mmol) and the mixture was stirred at RT for 30 min. The reaction mixture was quenched with saturated aqueous solution of ammonium chloride (10 mL) and the product was extracted in ethyl acetate (2×20 mL). The combined organic layers were washed with water (20 mL) and brine (10 mL). The organic layer was dried over anhydrous sodium sulfate and concentrated under reduced pressure. The residue obtained was purified by flash silica gel column chromatography to yield 38 mg of the titled product; $^1$H NMR (300 MHz, DMSO-d$_6$) δ 0.85 (t, J=7.2 Hz, 3H), 1.05 (d, J=6.3 Hz, 3H), 2.26 (q, J=7.2 Hz, 2H), 3.67 (s, 2H), 4.02-4.05 (m, 1H), 5.49 (d, J=6.0 Hz, 1H), 7.16-7.34 (m, 6H), 7.39-7.49 (m, 6H), 8.66 (s, 1H), 8.72 (s, 1H), 10.27 (s, 1H); APCI-MS (m/z) 488 (M+H)$^+$; Chiral HPLC purity: 97.34%.

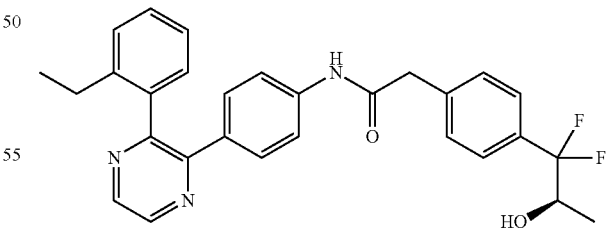

To a stirred solution of (S)-(+)-2-methyl-CBS-oxaborolidine (1M in toluene, 0.36 mL) [Ref: (i) Corey, E. J; Helal, C. J. Angew. Chem. Int. Ed. 1998, 37, 1986-2012 (ii) Corey, E. J.; Bakshi, R. K.; Shibata, S. J Am. Chem. Soc. 1987, 109 (18), 5551-5553] in anhydrous THF (10 mL) was added borane dimethyl sulfide complex (75 μL, 0.79 mmol) at 0° C. and the mixture was stirred for 20 min at the same temperature. A solution of Step 1 Intermediate (350 mg, 0.72 mmol) in THF (5.0 mL) was drop wise added to the reaction mixture over a period of 10 min at 0° C. The resultant mixture was stirred at RT for 30 min. The reaction mixture was quenched with methanol (10 mL) and concentrated under reduced pressure. The residue obtained was purified by flash silica gel column chromatography to yield 338 mg of the titled product; $^1$H NMR (300 MHz, DMSO-$d_6$) δ 0.85 (t, J=7.2 Hz, 3H), 1.06 (d, J=6.3 Hz, 3H), 2.26 (q, J=7.2 Hz, 2H), 3.67 (s, 2H), 4.01-4.05 (m, 1H), 5.50 (d, J=6.0 Hz, 1H), 7.14-7.34 (m, 6H), 7.36-7.49 (m, 6H), 8.67 (s, 1H), 8.73 (s, 1H), 10.28 (s, 1H); APCI-MS (m/z) 488 (M+H)$^+$; chiral HPLC purity: 84.85%.

Step 3: (S)—(R)-1-(4-(2-((4-(3-(2-Ethylphenyl) pyrazin-2-yl)phenyl)amino)-2-oxoethyl)phenyl)-1,1-difluoropropan-2-yl 2-(((benzyloxy)carbonyl)amino)-3-phenylpropanoate

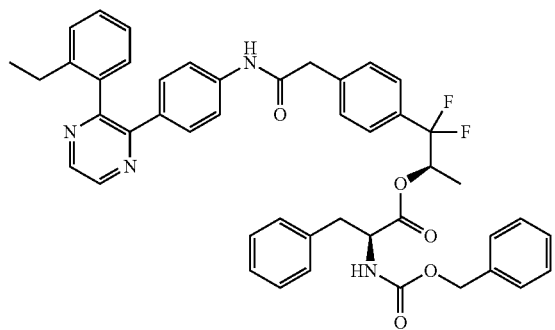 [SMILES: CCc1ccccc1-c1nccnc1-c1ccc(NC(=O)Cc2ccc(C(F)(F)[C@@H](C)OC(=O)[C@H](Cc3ccccc3)NC(=O)OCc3ccccc3)cc2)cc1]

To a stirred solution of Step 2 product (150 mg, 0.30 mmol), N-benzyloxycarbonyl-L-phenylalanine (120 mg, 0.40 mmol) and DIPEA (0.16 mL, 0.92 mmol) in dichloromethane (15 mL) were added BOP (177 mg, 0.40 mmol) and DMAP (19 mg, 0.15 mmol) at 0° C. The resultant mixture was warmed up to RT and stirred for 16 h. The reaction mixture was diluted with ethyl acetate (50 mL) and washed with saturated aqueous solution of ammonium chloride (50 mL), saturated aqueous sodium bicarbonate solution (50 mL), water (50 mL) and brine (50 mL). The organic layer was dried over anhydrous sodium sulfate, concentrated and the residue thus obtained was purified by flash silica gel column chromatography to yield 108 mg of the titled product; APCI-MS (m/z) 769 (M+H)$^+$.

Step 4: (R)-2-(4-(1,1-Difluoro-2-hydroxypropyl) phenyl)-N-(4-(3-(2-ethylphenyl)pyrazin-2-yl)phenyl) acetamide To a stirred solution of Step 3 Intermediate (105 mg, 0.14 mmol) in a mixture of THF (3.0 mL), methanol (1.0 mL) and water (1.0 mL) was added lithium hydroxide monohydrate (17 mg, 0.40 mmol) and the mixture was stirred at RT for 30 min. The reaction mixture was quenched with saturated aqueous solution of ammonium chloride (10 mL) and the product was extracted in ethyl acetate (2×20 mL). The combined organic layers were washed with water (20 mL) and brine (10 mL). The organic layer was dried over anhydrous sodium sulfate and concentrated under reduced pressure. The residue obtained was purified by flash silica gel column chromatography to yield 48 mg of the titled product as solid; $^1$H NMR (300 MHz, DMSO-$d_6$) δ 0.84 (t, J=7.8 Hz, 3H), 1.06 (d, J=6.3 Hz, 3H), 2.26 (q, J=7.8 Hz, 2H), 3.67 (s, 2H), 4.01-4.05 (m, 1H), 5.50 (d, J=6.0 Hz, 1H), 7.14-7.34 (m, 6H), 7.40-7.49 (m, 6H), 8.66 (s, 1H), 8.73 (s, 1H), 10.28 (s, 1H); APCI-MS (m/z) 488 (M+H)$^+$; Chiral HPLC purity: 95.86%.

Chemical name, structure Intermediate No., method of preparation and analytical data of Example 3-51 & 54-99 are given below in Table 1.

TABLE 1

Chemical name, structure Intermediate No., method of preparation and analytical data of Example 3-51 & 54-99

| Example No. | Chemical Name and Structure | Intermediate/ Method | Analytical Data |
|---|---|---|---|
| Example 3 | N-(4-(3-(4-Chlorophenyl)pyrazin-2-yl)phenyl)-2-(4-(1,1-difluoro-2-methoxyethyl)phenyl)acetamide | Intermediate 1 and Intermediate 10 Method A | $^1$H NMR (300 MHz, DMSO-$d_6$) δ 3.35 (s, 3H), 3.71 (s, 2H), 3.88 (t, J = 13.8 Hz, 2H), 7.34 (d, J = 8.1 Hz, 2H), 7.39-7.52 (m, 7H), 7.56 (d, J = 8.1 Hz, 3H), 8.67 (d, J = 3.9 Hz, 2H), 10.35 (s, 1H); APCI-MS (m/z) 494 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 4 | 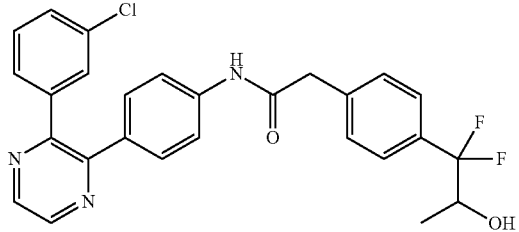 [SMILES: CC(O)C(F)(F)c1ccc(CC(=O)Nc2ccc(-c3nccnc3-c3cccc(Cl)c3)cc2)cc1]<br>N-(4-(3-(3-Chlorophenyl)pyrazin-2-yl)phenyl)-2-(4-(1,1-difluoro-2-hydroxypropyl)phenyl)acetamide | Intermediate 3 and Intermediate 4 Method B | $^1$H NMR (300 MHz, DMSO-$d_6$) δ 1.07 (d, J = 6.3 Hz, 3H), 3.70 (s, 2H), 3.99-4.05 (m, 1H), 5.49 (d, J = 6.0 Hz, 1H), 7.21-7.43 (m, 8H), 7.42-7.57 (m, 4H), 8.68 (d, J = 8.1 Hz, 2H), 10.33 (s, 1H). APCI-MS (m/z) 494 (M + H)$^+$. |
| Example 5 | 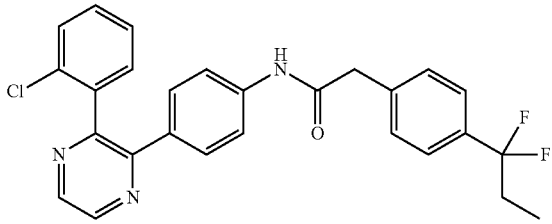 [SMILES: CCC(F)(F)c1ccc(CC(=O)Nc2ccc(-c3nccnc3-c3ccccc3Cl)cc2)cc1]<br>N-(4-(3-(2-Chlorophenyl)pyrazin-2-yl)phenyl)-2-(4-(1,1-difluoropropyl)phenyl)acetamide | Intermediate 2 and Intermediate 11 Method A | $^1$H NMR (300 MHz, DMSO-$d_6$) δ 0.87 (t, J = 7.2 Hz, 3H), 2.13-2.20 (m, 2H), 3.66 (s, 2H), 7.26 (d, J = 8.7 Hz, 2H), 7.40-7.51 (m, 10H), 8.67 (s, 1H), 8.75 (s, 1H), 10.27 (s, 1H); ESI-MS (m/z) 479 (M + H)$^+$. |
| Example 6 | 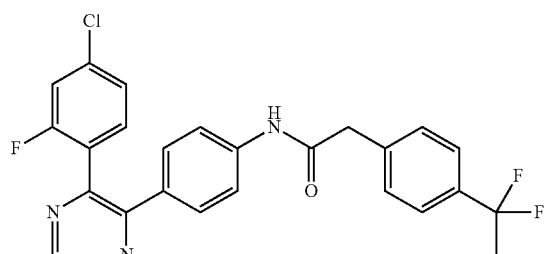<br>N-(4-(3-(4-Chloro-2-fluorophenyl)pyrazin-2-yl)phenyl)-2-(4-(1,1-difluoropropyl)phenyl)acetamide | Intermediate 2 and Intermediate 12 Method A | $^1$H NMR (300 MHz, DMSO-$d_6$) δ 0.89 (t, J = 7.2 Hz, 3H), 2.15-2.22 (m, 2H), 3.70 (s, 2H), 7.30-7.45 (m, 8H), 7.52-7.64 (m, 3H), 8.71 (s, 1H), 8.76 (s, 1H), 10.33 (s, 1H); APCI-MS (m/z) 497 (M + H)$^+$. |
| Example 7 | 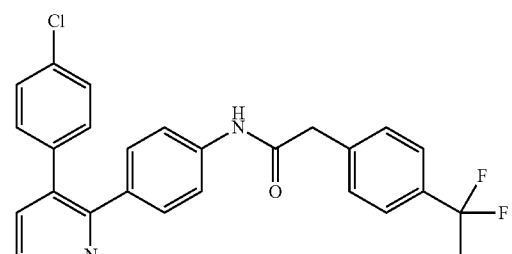<br>N-(4-(3-(4-Chlorophenyl)pyridin-2-yl)phenyl)-2-(4-(1,1-difluoropropyl)phenyl)acetamide | Intermediate 2 and Intermediate 14 Method A | $^1$H NMR (300 MHz, DMSO-$d_6$) δ 0.87 (t, J = 6.9 Hz, 3H), 2.12-2.19 (m, 2H), 3.67 (s, 2H), 7.14-7.20 (m, 4H), 7.33-7.45 (m, 9H), 7.74-7.77 (m, 1H), 8.63 (br s, 1H), 10.25 (s, 1H); APCI-MS (m/z) 477 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 8 | 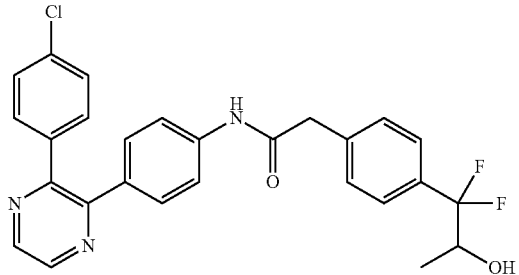<br>2-(4-(1,1-Difluoro-2-hydroxypropyl)phenyl)-N-(4-(3-(4-fluorophenyl)pyrazin-2-yl)phenyl)acetamide | Intermediate 3 and Intermediate 5 Method B | $^1$H NMR (300 MHz, DMSO-$d_6$) δ 1.05 (d, J = 6.3 Hz, 3H), 3.68 (s, 2H), 3.99-4.04 (m, 1H), 5.48 (d, J = 6.3 Hz, 1H), 7.15 (t, J = 8.7 Hz, 2H), 7.29-7.42 (m, 7H), 7.54 (d, J = 8.4 Hz, 2H), 8.64 (d, J = 3.3 Hz, 2H), 10.31 (s, 1H); APCI-MS (m/z) 478 (M + H)$^+$. |
| Example 9 | 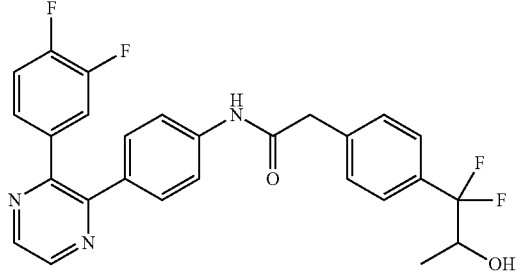 [SMILES: CC(O)C(F)(F)c1ccc(CC(=O)Nc2ccc(-c3nccnc3-c3ccc(F)c(F)c3)cc2)cc1]<br>2-(4-(1,1-Difluoro-2-hydroxypropyl)phenyl)-N-(4-(3-(3,4-difluorophenyl)pyrazin-2-yl)phenyl)acetamide | Intermediate 3 and Intermediate 6 Method B | $^1$H NMR (300 MHz, DMSO-$d_6$) δ 1.05 (d, J = 6.3 Hz, 3H), 3.68 (s, 2H), 3.99-4.05 (m, 1H), 5.49 (d, J = 6.0 Hz, 1H), 7.14-7.17 (m, 2H), 7.32-7.42 (m, 7H), 7.56 (d, J = 8.7 Hz, 2H), 8.66 (s, 1H), 8.69 (s, 1H), 10.33 (s, 1H); APCI-MS (m/z) 496 (M + H)$^+$. |
| Example 10 | 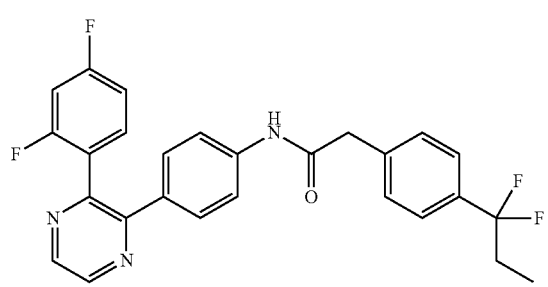<br>N-(4-(3-(2,4-Difluorophenyl)pyrazin-2-yl)phenyl)-2-(4-(1,1-difluoropropyl)phenyl)acetamide | Intermediate 2 and Intermediate 13 Method A | $^1$H NMR (300 MHz, DMSO-$d_6$) δ 0.87 (t, J = 7.5 Hz, 3H), 2.09-2.20 (m, 2H), 3.68 (s, 2H), 7.13-7.22 (m, 2H), 7.30 (d, J = 8.7 Hz, 2H), 7.42 (d, J = 3.3 Hz, 4H), 7.53 (d, J = 8.1 Hz, 2H), 7.61-7.65 (m, 1H), 8.69 (s, 1H), 8.73 (s, 1H), 10.31 (s, 1H); ESI-MS (m/z) 480 (M + H)$^+$. |
| Example 11 | 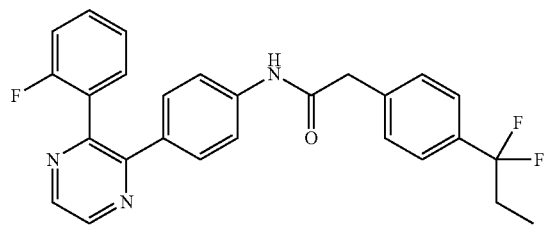 [SMILES: CCC(F)(F)c1ccc(CC(=O)Nc2ccc(-c3nccnc3-c3ccccc3F)cc2)cc1]<br>2-(4-(1,1-Difluoropropyl)phenyl)-N-(4-(3-(2-fluorophenyl)pyrazin-2-yl)phenyl)acetamide | Intermediate 2 and Intermediate 15 Method A | $^1$H NMR (300 MHz, DMSO-$d_6$) δ 1.89 (t, J = 7.8 Hz, 3H), 2.11-2.27 (m, 2H), 3.69 (s, 2H), 7.11 (t, J = 8.7 Hz, 1H), 7.31 (d, J = 8.1 Hz, 3H), 7.43-7.59 (m, 8H), 8.71 (s, 1H), 8.74 (s, 1H), 10.31 (s, 1H); ESI-MS (m/z) 462 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 12 | 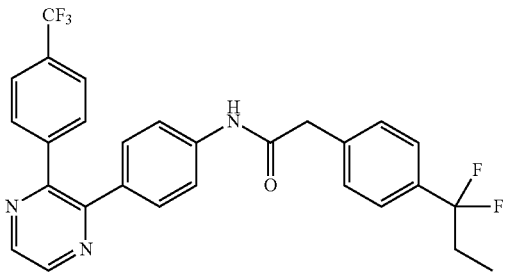<br>2-(4-(1,1-Difluoropropyl)phenyl)-N-(4-(3-(4-(trifluoromethyl)phenyl)pyrazin-2-yl)phenyl)acetamide | Intermediate 2 and Intermediate 16 Method A | $^1$H NMR (300 MHz, DMSO-$d_6$) δ 1.89 (t, J = 7.2 Hz, 3H), 2.14-2.19 (m, 2H), 3.70 (s, 2H), 7.34 (d, J = 8.4 Hz, 2H), 7.49 (br s, 4H), 7.54-7.64 (m, 4H), 7.72 (d, J = 8.1 Hz, 2H), 8.73 (d, J = 6.0 Hz, 2H), 10.34 (s, 1H); ESI-MS (m/z) 512 (M + H)$^+$. |
| Example 13 | 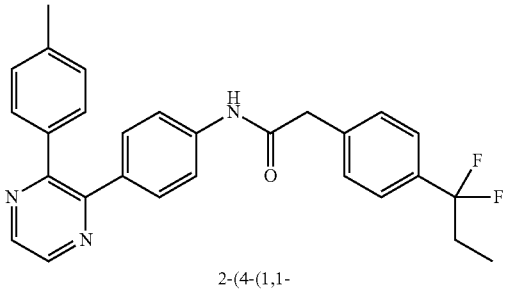<br>2-(4-(1,1-Difluoropropyl)phenyl)-N-(4-(3-(p-tolyl)pyrazin-2-yl)phenyl)acetamide | Intermediate 2 and Intermediate 17 Method A | $^1$H NMR (300 MHz, DMSO-$d_6$) δ 0.90 (t, J = 7.5 Hz, 3H), 2.16-2.23 (m, 2H), 2.29 (s, 3H), 3.70 (s, 2H), 7.13 (d, J = 7.8 Hz, 2H), 7.26-7.35 (m, 4H), 7.45 (d, J = 3.6 Hz, 4H), 7.54 (d, J = 8.4 Hz, 2H), 8.63 (s, 2H), 10.32 (s, 1H). |
| Example 14 | 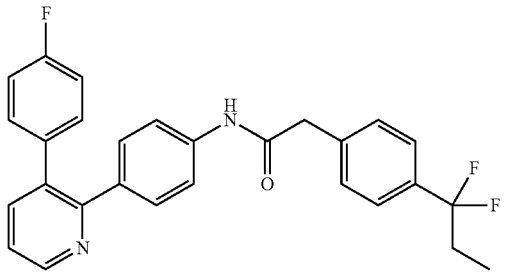 [SMILES: CCC(F)(F)c1ccc(CC(=O)Nc2ccc(-c3ncccc3-c3ccc(F)cc3)cc2)cc1]<br>2-(4-(1,1-Difluoropropyl)phenyl)-N-(4-(3-(4-fluorophenyl)pyridin-2-yl)phenyl)acetamide | Intermediate 2 and Intermediate 18 Method A | $^1$H NMR (300 MHz, CDCl$_3$) δ 0.99 (t, J = 7.2 Hz, 3H), 2.10-2.15 (m, 2H), 3.74 (s, 2H), 6.99 (t, J = 9.0 Hz, 2H), 7.09-7.12 (m, 2H), 7.27 (d, J = 8.7 Hz, 3H), 7.38 (d, J = 9.3 Hz, 5H), 7.47 (d, J = 7.8 Hz, 2H), 7.69 (d, J = 7.8 Hz, 1H), 8.67 (s, 1H); APCI-MS (m/z) 461 (M + H)$^+$. |
| Example 15 | 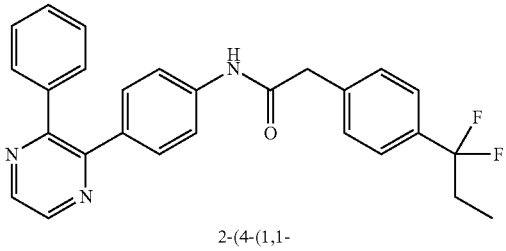<br>2-(4-(1,1-Difluoropropyl)phenyl)-N-(4-(3-phenylpyrazin-2-yl)phenyl)acetamide | Intermediate 2 and Intermediate 19 Method A | $^1$H NMR (300 MHz, DMSO-$d_6$) δ 0.89 (t, J = 7.2 Hz, 3H), 2.15- 2.22 (m, 2H), 3.70 (s, 2H), 7.33-7.57 (m, 13H), 8.67 (s, 2H), 10.32 (s, 1H); ESI-MS (m/z) 444 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 16 | 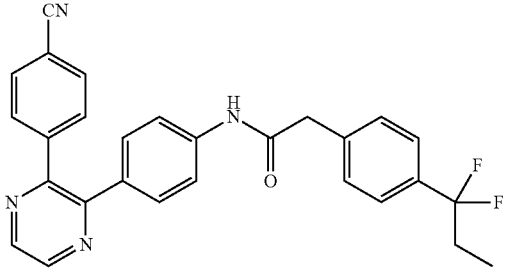 [SMILES: CCC(F)(F)c1ccc(CC(=O)Nc2ccc(-c3nccnc3-c3ccc(C#N)cc3)cc2)cc1]<br>N-(4-(3-(4-Cyanophenyl)pyrazin-2-yl)phenyl)-2-(4-(1,1-difluoropropyl)phenyl)acetamide | Intermediate 2 and Intermediate 20 Method A | $^1$H NMR (300 MHz, DMSO-d$_6$) δ 0.90 (t, J = 7.2 Hz, 3H), 2.16-2.23 (m, 2H), 3.71 (s, 2H), 7.33 (d, J = 8.4 Hz, 2H), 7.45 (s, 4H), 7.57 (d, J = 8.1 Hz, 4H), 7.82 (d, J = 7.8 Hz, 2H), 8.72 (d, J = 6.6 Hz, 2H), 10.35 (s, 1H); ESI-MS (m/z) 469 (M + H)$^+$. |
| Example 17 | 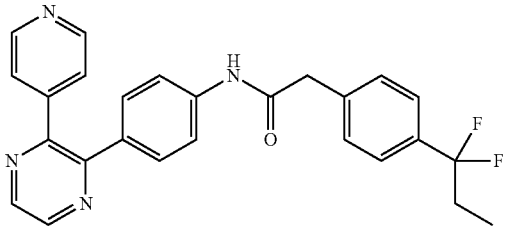 [SMILES: CCC(F)(F)c1ccc(CC(=O)Nc2ccc(-c3nccnc3-c3ccncc3)cc2)cc1]<br>2-(4-(1,1-Difluoropropyl)phenyl)-N-(4-(3-(pyridin-4-yl)pyrazin-2-yl)phenyl)acetamide | Intermediate 2 and Intermediate 21 Method A | $^1$H NMR (300 MHz, DMSO-d$_6$) δ 0.89 (t, J = 5.7 Hz, 3H), 2.18-2.22 (m, 2H), 3.36 (br s, 2H), 7.32-7.47 (m, 8H), 7.56 (d, J = 8.1 Hz, 2H), 8.55 (s, 2H), 8.74 (d, J = 9.6 Hz, 2H), 10.36 (s, 1H); ESI-MS (m/z) 445 (M + H)$^+$. |
| Example 18 | 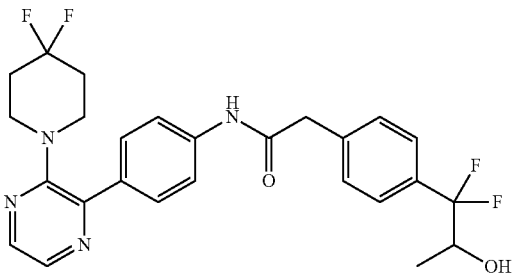 [SMILES: CC(O)C(F)(F)c1ccc(CC(=O)Nc2ccc(-c3nccnc3N3CCC(F)(F)CC3)cc2)cc1]<br>2-(4-(1,1-Difluoro-2-hydroxypropyl)phenyl)-N-(4-(3-(4,4-difluoropiperidin-1-yl)pyrazin-2-yl)phenyl)acetamide | Intermediate 3 and Intermediate 7 Method B | $^1$H NMR (300 MHz, DMSO-d$_6$) δ 1.05 (d, J = 7.5 Hz, 3H), 1.94-2.07 (m, 4H), 3.19 (s, 4H), 3.71 (s, 2H), 4.02 (m, 1H), 5.49 (d, J = 6 Hz, 1H), 7.43 (s, 4H), 7.70 (d, J = 7.8 Hz, 2H), 7.87 (d, J = 7.8 Hz, 2H), 8.12 (s, 1H), 8.18 (s, 1H), 10.37 (br s, 1H); ESI-MS (m/z) 503 (M + H)$^+$. |
| Example 19 | 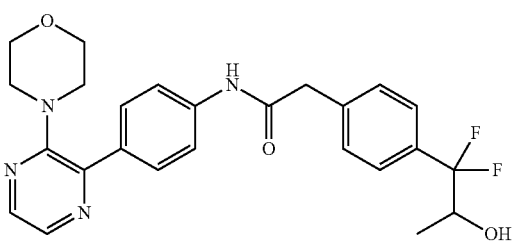 [SMILES: CC(O)C(F)(F)c1ccc(CC(=O)Nc2ccc(-c3nccnc3N3CCOCC3)cc2)cc1]<br>2-(4-(1,1-Difluoro-2-hydroxypropyl)phenyl)-N-(4-(3-morpholinopyrazin-2-yl)phenyl)acetamide | Intermediate 3 and Intermediate 8 Method B | $^1$H NMR (300 MHz, DMSO-d$_6$) δ 1.08 (d, J = 6.9 Hz, 3H), 3.06 (br s, 4H), 3.61 (br s, 4H), 3.73 (s, 2H), 4.00-4.07 (m, 1H), 5.51 (d, J = 5.1 Hz, 1H), 7.44 (s, 4H), 7.72 (d, J = 8.7 Hz, 2H), 7.89 (d, J = 9.0 Hz, 2H), 8.14 (s, 1H), 8.18 (s, 1H), 10.38 (s, 1H) APCI-MS (m/z) 469 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 20 | 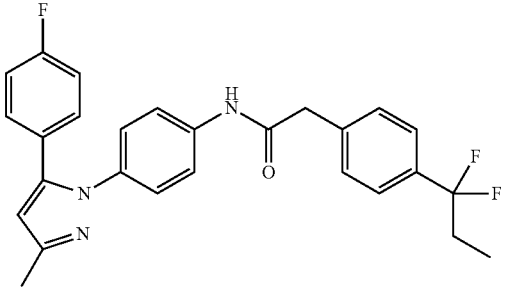 [SMILES: CCC(F)(F)c1ccc(CC(=O)Nc2ccc(N/C(=C\C(C)=N)c3ccc(F)cc3)cc2)cc1]<br>2-(4-(1,1-Difluoropropyl)phenyl)-N-(4-(5-(4-fluorophenyl)-3-methyl-1H-pyrazol-1-yl)phenyl)acetamide | Intermediate 2 and Intermediate 22 Method A | $^1$H NMR (300 MHz, DMSO-$d_6$) δ 0.90 (t, J = 7.5 Hz, 3H), 2.25 (s, 5H), 3.70 (s, 2H), 6.42 (s, 1H), 7.14-7.22 (m, 6H), 7.45 (s, 4H), 7.60 (d, J = 7.2 Hz, 1H), 10.36 (s, 1H); ESI-MS (m/z) 464 (M + H)$^+$. |
| Example 21 | 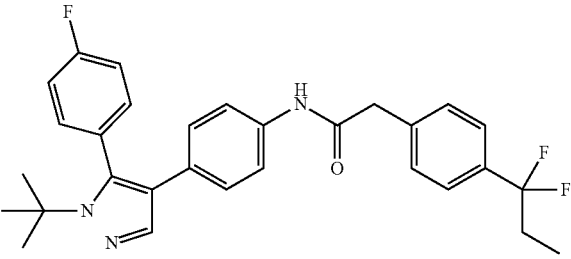<br>N-(4-(1-(tert-Butyl)-5-(4-fluorophenyl)-1H-pyrazol-4-yl)phenyl)-2-(4-(1,1-difluoropropyl)phenyl)acetamide | Intermediate 2 and Intermediate 9 Method A | $^1$H NMR (300 MHz, DMSO-$d_6$) δ 0.88 (t, J = 7.5 Hz, 3H), 1.38 (s, 9H), 2.14-2.20 (m, 2H), 3.64 (s, 2H), 6.94 (d, J = 8.1 Hz, 2H), 7.27-7.44 (m, 10H), 7.70 (s, 1H), 10.11 (s, 1H); ESI-MS (m/z) 505 (M + H)$^+$. |
| Example 22 | 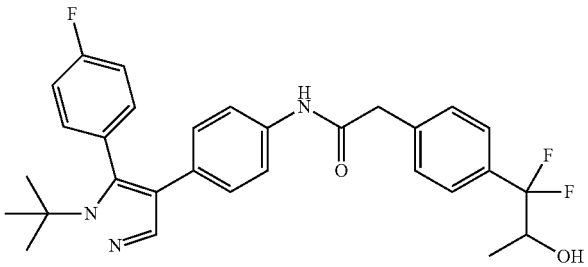 [SMILES: CC(O)C(F)(F)c1ccc(CC(=O)Nc2ccc(/C(C=N)=C(/NC(C)(C)C)c3ccc(F)cc3)cc2)cc1]<br>N-(4-(1-(tert-Butyl)-5-(4-fluorophenyl)-1H-pyrazol-4-yl)phenyl)-2-(4-(1,1-difluoro-2-hydroxypropyl)phenyl)acetamide | Intermediate 3 and Intermediate 9 Method B | '$^1$H NMR (300 MHz, DMSO-$d_6$) δ 1.05 (d, J = 7.5 Hz, 3H), 1.38 (s, 9H), 3.63 (s, 2H), 4.01 (m, 1H), 5.49 (d, J = 6.0 Hz, 1H), 6.94 (d, J = 8.1 Hz, 2H), 7.24-7.41 (m, 10H), 7.70 (s, 1H), 10.11 (s, 1H); ESI-MS (m/z) 522 (M + H)$^+$. |
| Example 23 | 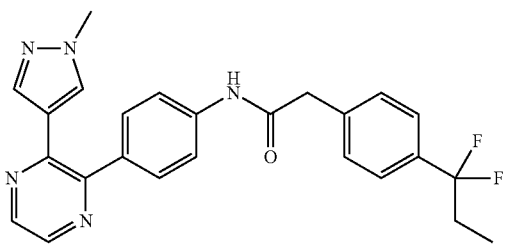 [SMILES: CCC(F)(F)c1ccc(CC(=O)Nc2ccc(-c3nccnc3-c3cnn(C)c3)cc2)cc1]<br>2-(4-1,1-Difluoropropyl)phenyl)-N-(4-(3-(1-methyl-1H-pyrazol-4-yl)pyrazin-2-yl)phenyl)acetamide | Intermediate 2 and Intermediate 23 Method A | $^1$H NMR (300 MHz, DMSO-$d_6$) δ 0.90 (t, J = 5.7 Hz, 3H), 2.18-2.23 (m, 2H), 3.77 (s, 5H), 7.11 (s, 1H), 7.44-7.48 (m, 6H), 7.68-7.75 (m, 3H), 8.48 (s, 1H), 8.55 (s, 1H), 10.41 (s, 1H); ESI-MS (m/z) 448 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 24 | 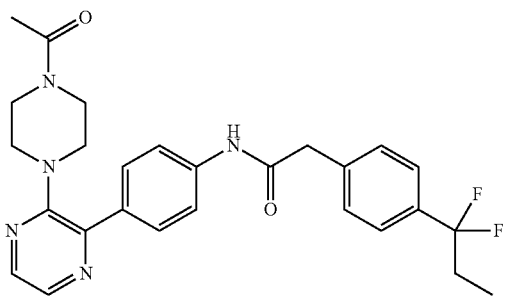 [SMILES: CCC(F)(F)c1ccc(CC(=O)Nc2ccc(-c3nccnc3N3CCN(C(C)=O)CC3)cc2)cc1]<br>N-(4-(3-(4-Acetylpiperazin-1-yl)pyrazin-2-yl)phenyl)-2-(4-(1,1-difluoropropyl)phenyl)acetamide | Intermediate 2 and Intermediate 24 Method A | $^1$H NMR (300 MHz, CDCl$_3$) δ 0.99 (t, J = 7.5 Hz, 3H), 2.07 (s, 3H), 2.15 (q, J = 9.3 Hz, 2H), 3.10-3.19 (m, 4H), 3.44 (br s, 2H), 3.57 (br s, 2H), 3.78 (s, 2H), 7.26 (s, 1H), 7.40-7.57 (m, 6H), 7.87 (d, J = 8.4 Hz, 2H), 8.07 (s, 1H), 8.17 (s, 1H); ESI-MS (m/z) 494 (M + H)$^+$. |
| Example 25 | 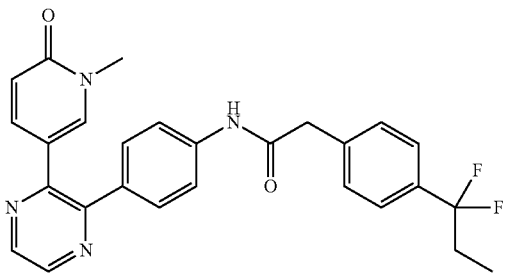 [SMILES: CCC(F)(F)c1ccc(CC(=O)Nc2ccc(-c3nccnc3-c3ccc(=O)n(C)c3)cc2)cc1]<br>2-(4-(1,1-Difluoropropyl)phenyl)-N-(4-(3-(1-methyl-6-oxo-1,6-dihydropyridin-3-yl)pyrazin-2-yl)phenyl)acetamide | Intermediate 2 and Intermediate 25 Method A | $^1$H NMR (300 MHz, CDCl$_3$) δ 0.98 (t, J = 7.2 Hz, 3H), 2.10-2.20 (m, 2H), 3.56 (s, 3H), 3.77 (s, 2H), 6.36 (d, J = 9.3 Hz, 1H), 7.15 (d, J = 9.3 Hz, 1H), 7.26-7.53 (m, 7H), 7.66 (s, 1H), 7.80 (s, 1H), 8.49 (s, 1H), 8.53 (s, 1H); APCI-MS (m/z) 475 (M + H)$^+$. |
| Example 26 | 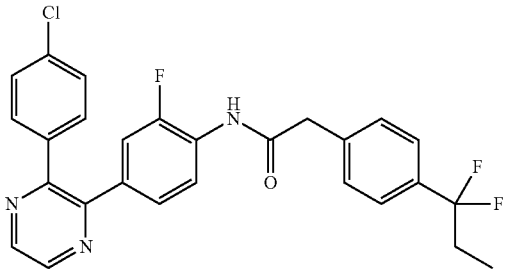<br>N-(4-(3-(4-Chlorophenyl)pyrazin-2-yl)-2-fluorophenyl)-2-(4-(1,1-difluoropropyl)phenyl)acetamide | Intermediate 2 and Intermediate 26 Method A | $^1$H NMR (300 MHz, CDCl$_3$) δ 0.99 (t, J = 7.2 Hz, 3H), 2.10-2.17 (m, 2H), 3.80 (s, 2H), 7.20-7.40 (m, 9H), 7.49 (s, 2H), 8.29-8.31 (m, 1H), 8.59 (s, 2H); APCI-MS (m/z) 496 (M + H)$^+$. |
| Example 27 | 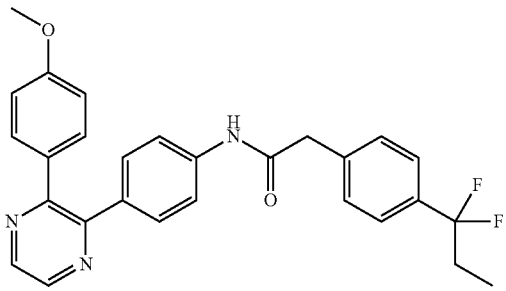 [SMILES: CCC(F)(F)c1ccc(CC(=O)Nc2ccc(-c3nccnc3-c3ccc(OC)cc3)cc2)cc1]<br>2-(4-(1,1-Difluoropropyl)phenyl)-N-(4-(3-(4-methoxyphenyl)pyrazin-2-yl)phenyl)acetamide | Intermediate 2 and Intermediate 27 Method A | $^1$H NMR (300 MHz, CDCl$_3$) δ 0.90 (t, J = 7.2 Hz, 3H), 2.15-2.23 (m, 2H), 3.70-3.76 (m, 5H), 6.89 (d, J = 7.2 Hz, 2H), 7.35 (d, J = 7.8 Hz, 4H), 7.46 (s, 4H), 7.56 (d, J = 7.8 Hz, 2H), 8.61 (s, 2H), 10.33 (s, 1H); APCI-MS (m/z) 474 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 28 | 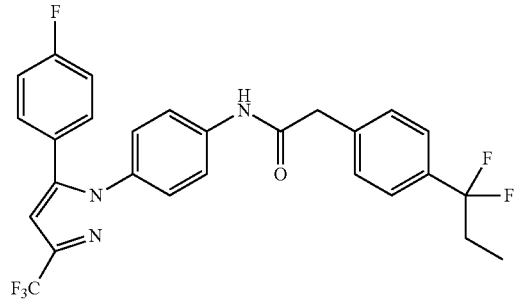 [SMILES: CCC(F)(F)c1ccc(CC(=O)Nc2ccc(N/C(=C\C(=N)C(F)(F)F)c3ccc(F)cc3)cc2)cc1]<br>2-(4-(1,1-Difluoropropyl)phenyl)-N-(4-(5-(4-fluorophenyl)-3-(trifluoromethyl)-1H-pyrazol-1-yl)phenyl)acetamide | Intermediate 2 and Intermediate 28 Method A | $^1$H NMR (300 MHz, DMSO-$d_6$) δ 0.90 (t, J = 7.2 Hz, 3H), 2.17-2.22 (m, 2H), 3.72 (s, 2H), 7.18-7.31 (m, 7H), 7.46 (br s, 4H), 6.67 (d, J = 7.8 Hz, 2H), 10.45 (s, 1H). |
| Example 29 | 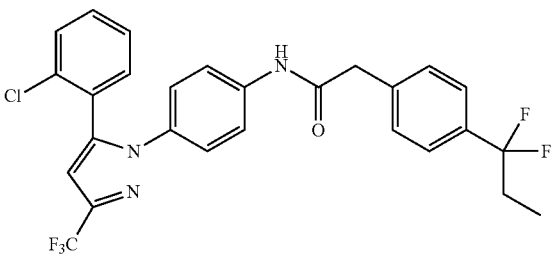 [SMILES: CCC(F)(F)c1ccc(CC(=O)Nc2ccc(N/C(=C\C(=N)C(F)(F)F)c3ccccc3Cl)cc2)cc1]<br>N-(4-(5-(2-Chlorophenyl)-3-(trifluoromethyl)-1H-pyrazol-1-yl)phenyl)-2-(4-(1,1-difluoropropyl)phenyl)acetamide | Intermediate 2 and Intermediate 29 Method A | $^1$H NMR (300 MHz, DMSO-$d_6$) δ 0.98 (t, J = 7.2 Hz, 3H), 2.10-2.20 (m, 2H), 3.69 (s, 2H), 7.14 (s, 1H), 7.20 (d, J = 8.4 Hz, 2H), 7.42-7.60 (m, 10H), 10.38 (s, 1H). |
| Example 30 | 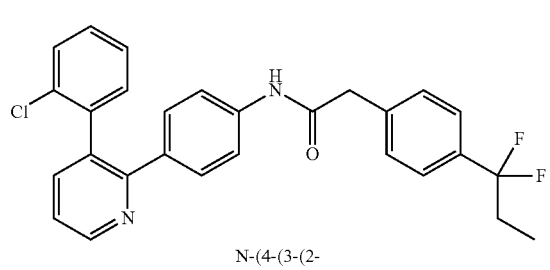<br>N-(4-(3-(2-Chlorophenyl)pyridin-2-yl)phenyl)-2-(4-(1,1-difluoropropyl)phenyl)acetamide | Intermediate 2 and Intermediate 30 Method A | $^1$H NMR (300 MHz, CDCl$_3$) δ 0.99 (t, J = 7.2 Hz, 3H), 2.08-2.22 (m, 2H), 3.72 (s, 2H), 7.12-7.38 (m, 12H), 7.47 (d, J = 8.4 Hz, 2H), 7.66 (d, J = 7.5Hz, 1H), 8.71 (s, 1H); APCI-MS (m/z) 477 (M + H)$^+$. |
| Example 31 | 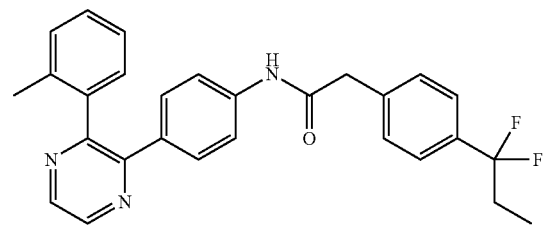 [SMILES: CCC(F)(F)c1ccc(CC(=O)Nc2ccc(-c3nccnc3-c3ccccc3C)cc2)cc1]<br>2-(4-(1,1-Difluoropropyl)phenyl)-N-(4-(3-(o-tolyl)pyrazin-2-2-yl)phenyl)acetamide | Intermediate 2 and Intermediate 31 Method A | $^1$H NMR (300 MHz, DMSO-$d_6$) δ 0.89 (t, J = 7.2 Hz, 3H), 1.90 (s, 3H), 2.15-2.24 (m, 2H), 3.68 (s, 2H), 7.20-7.29 (m, 6H), 7.42-7.49 (m, 6H), 8.67 (s, 1H), 8.72 (s, 1H), 10.28 (s, 1H); APCI-MS (m/z) 458 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 32 | 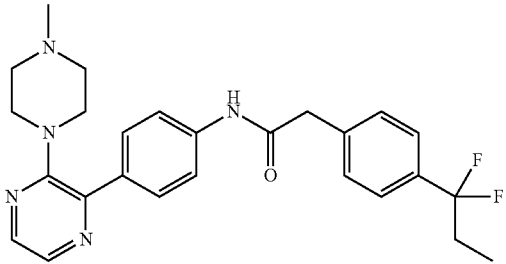 [SMILES: CCC(F)(F)c1ccc(CC(=O)Nc2ccc(-c3nccnc3N3CCN(C)CC3)cc2)cc1]<br>2-(4-(1,1-Difluoropropyl)phenyl)-N-(4-(3-(4-methylpiperazin-1-yl)pyrazin-2-yl)phenyl)acetamide | Intermediate 2 and Intermediate 32 Method A | $^1$H NMR (300 MHz, CDCl$_3$) δ 0.98 (t, J = 7.2 Hz, 3H), 2.06-2.22 (m, 2H), 2.50 (s, 3H), 2.72 (s, 4H), 3.39 (s, 4H), 3.79 (s, 2H), 7.42-7.48 (m, 3H), 7.59 (d, J = 8.1 Hz, 2H), 7.73 (s, 1H), 7.82 (d, J = 8.7 Hz, 2H), 8.05 (d, J = 1.8 Hz, 1H), 8.16 (d, J = 2.1 Hz, 1H); APCI-MS (m/z) 466 (M + H)$^+$. |
| Example 33 | 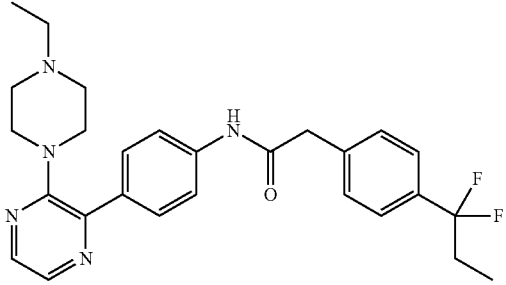 [SMILES: CCN1CCN(c2nccnc2-c2ccc(NC(=O)Cc3ccc(C(F)(F)CC)cc3)cc2)CC1]<br>2-(4-(1,1-Difluoropropyl)phenyl)-N-(4-(3-(4-ethylpiperazin-1-yl)pyrazin-2-yl)phenyl)acetamide | Intermediate 2 and Intermediate 33 Method A | $^1$H NMR (300 MHz, CDCl$_3$) δ 0.98 (t, J = 7.2 Hz, 3H), 1.23 (t, J = 6.9 Hz, 3H), 2.07-2.20 (m, 2H), 2.62-2.73 (m, 6H), 3.40 (s, 4H), 3.79 (s, 2H), 7.43-7.47 (m, 3H), 7.58 (d, J = 8.4 Hz, 2H), 7.69 (s, 1H), 7.83 (d, J = 8.4 Hz, 2H), 8.05 (s, 1H), 8.15 (s, 1H); APCI-MS (m/z) 480 (M + H)$^+$. |
| Example 34 | 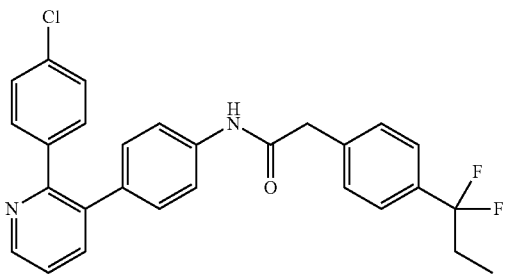<br>N-(4-(2-(4-Chlorophenyl)pyridin-3-yl)phenyl)-2-(4-(1,1-difluoropropyl)phenyl)acetamide | Intermediate 2 and Intermediate 34 Method A | $^1$H NMR (300 MHz, DMSO-d$_6$) δ 0.90 (t, J = 7.2 Hz, 3H), 2.11-2.27 (m, 2H), 3.70 (s, 2H), 7.11 (d, J = 8.4 Hz, 2H), 7.29 (d, J = 8.4 Hz, 2H), 7.33 (d, J = 8.1 Hz, 2H), 7.44-7.49 (m, 5H), 7.55 (d, J = 8.1 Hz, 2H), 7.80 (d, J = 7.8 Hz, 1H), 8.64 (d, J = 4.2 Hz, 1H), 10.28 (s, 1H); APCI-MS (m/z) 477 (M + H)$^+$. |
| Example 35 | 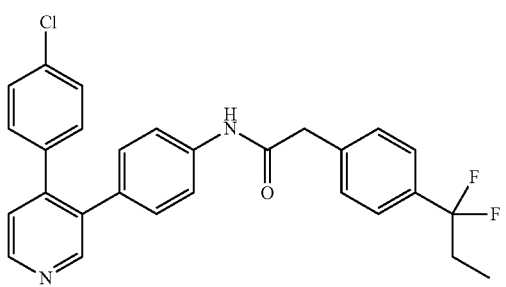 [SMILES: CCC(F)(F)c1ccc(CC(=O)Nc2ccc(-c3cnccc3-c3ccc(Cl)cc3)cc2)cc1]<br>N-(4-(4-(4-Chlorophenyl)pyridin-3-yl)phenyl)-2-(4-(1,1-difluoropropyl)phenyl)acetamide | Intermediate 2 and Intermediate 35 Method A | $^1$H NMR (300 MHz, DMSO-d$_6$) δ 0.90 (t, J = 6.9 Hz, 3H), 2.17-2.23 (m, 2H), 3.69 (s, 2H), 7.09 (d, J = 7.8 Hz, 2H), 7.18 (d, J = 7.2 Hz, 2H), 7.36-7.46 (m, 7H), 7.55 (d, J = 8.4 Hz, 2H), 8.57 (s, 1H), 8.61 (d, J = 4.8 Hz, 1H), 10.27 (s, 1H); APCI-MS (m/z) 477 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 36 | 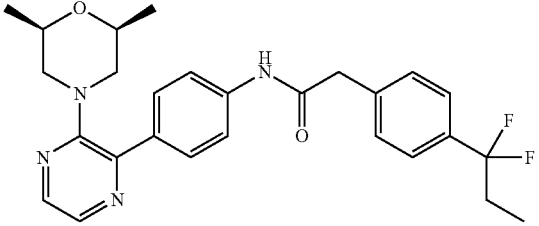 [SMILES: CCC(F)(F)c1ccc(CC(=O)Nc2ccc(-c3nccnc3N3C[C@@H](C)O[C@@H](C)C3)cc2)cc1]<br>2-(4-(1,1-Difluoropropyl)phenyl)-N-(4-(3-((2S,6R)-2,6-dimethylmorpholino)pyrazin-2-yl)phenyl)acetamide | Intermediate 2 and Intermediate 36 Method A | $^1$H NMR (300 MHz, CDCl$_3$) δ 0.99 (t, J = 7.2 Hz, 3H), 1.08 (d, J = 6.3 Hz, 6H), 2.07-2.22 (m, 2H), 2.45 (t, J = 11.1 Hz, 2H), 3.42 (d, J = 12.3 Hz, 2H), 2.62-2.72 (m, 2H), 3.78 (s, 2H), 7.31 (s, 1H), 7.41 (d, J = 7.8 Hz, 2H), 7.47-7.57 (m, 4H), 7.86 (d, J = 8.4 Hz, 2H), 8.07 (s, 1H), 8.11 (s, 1H); APCI-MS (m/z) 481 (M + H)$^+$. |
| Example 37 | 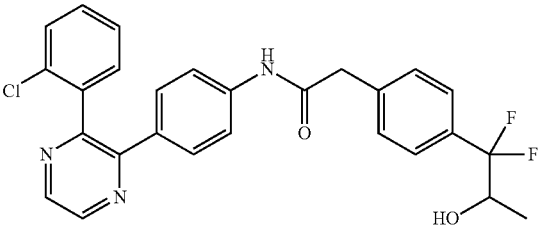 [SMILES: CC(O)C(F)(F)c1ccc(CC(=O)Nc2ccc(-c3nccnc3-c3ccccc3Cl)cc2)cc1]<br>N-(4-(3-(2-Chlorophenyl)pyrazin-2-yl)phenyl)-2-(4-(1,1-difluoro-2-hydroxypropyl)phenyl)acetamide | Intermediate 3 and Intermediate 11 Method B | $^1$H NMR (300 MHz, DMSO-d$_6$) δ 1.06 (d, J = 6.3 Hz, 3H), 3.68 (s, 2H), 4.01-4.05 (m, 1H), 5.49 (d, J = 6.0 Hz, 1H), 7.28 (d, J = 8.4 Hz, 2H), 7.39-7.45 (m, 8H), 7.49 (d, J = 7.8 Hz, 2H), 8.69 (s, 1H), 8.77 (s, 1H), 10.29 (s, 1H); ESI-MS (m/z) 494 (M + H)$^+$. |
| Example 38 | 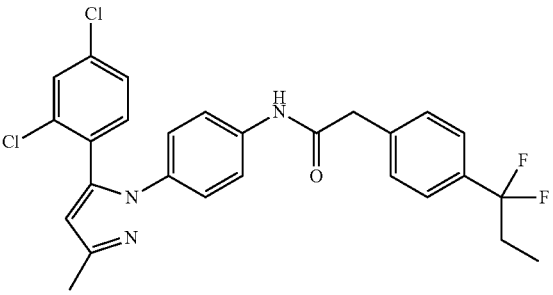 [SMILES: CCC(F)(F)c1ccc(CC(=O)Nc2ccc(N/C(=C\C(C)=N)c3ccc(Cl)cc3Cl)cc2)cc1]<br>N-(4-(5-(2,4-Dichlorophenyl)-3-methyl-1H-pyrazol-1-yl)phenyl)-2-(4-(1,1-difluoropropyl)phenyl)acetamide | Intermediate 2 and Intermediate 37 Method A | $^1$H NMR (300 MHz, DMSO-d$_6$) δ 0.89 (t, J = 7.2 Hz, 3H), 2.15-2.22 (m, 2H), 2.28 (s, 3H), 3.68 (s, 2H), 6.39 (s, 1H), 7.08 (d, J = 9.0 Hz, 2H), 7.44-7.53 (m, 8H), 7.66 (s, 1H), 10.30 (s, 1H); ESI-MS (m/z) 514 (M)$^+$. |
| Example 39 | 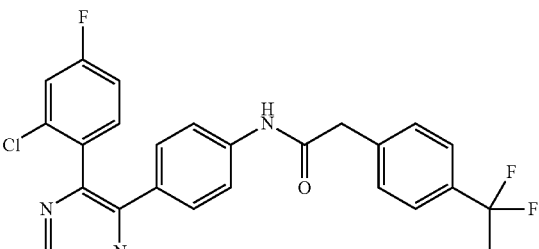<br>N-(4-(3-(2-Chloro-4-fluorophenyl)pyrazin-2-yl)phenyl)-2-(4-(1,1-difluoro-2-hydroxypropyl)phenyl)acetamide | Intermediate 2 and Intermediate 38 Method B | $^1$H NMR (300 MHz, DMSO-d$_6$) δ 1.06 (d, J = 6.6 Hz, 3H), 3.68 (s, 2H), 4.00-4.05 (m, 1H), 5.49 (d, J = 5.1 Hz, 1H), 7.25-7.54 (m, 11H), 8.69 (s, 1H), 8.77 (s, 1H), 10.30 (s, 1H). |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 40 | 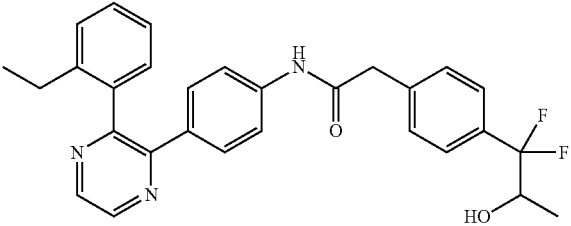<br>2-(4-(1,1-Difluoro-2-hydroxypropyl)phenyl)-N-(4-(3-(2-ethylphenyl)pyrazin-2-yl)phenyl)acetamide | Intermediate 2 and Intermediate 39 Method B | $^1$H NMR (300 MHz, DMSO-$d_6$) δ 0.85 (t, J = 6.9 Hz, 3H), 1.06 (d, J = 6.0 Hz, 3H), 2.27 (q, J = 6.9 Hz, 2H), 3.67 (s, 2H), 4.03-4.07 (m, 1H), 5.49 (br s, 1H), 7.17-7.49 (m, 12H), 8.66 (s, 1H), 8.72 (s, 1H), 10.27 (s, 1H); APCI-MS (m/z) 488 (M + H)$^+$. |
| Example 41 | 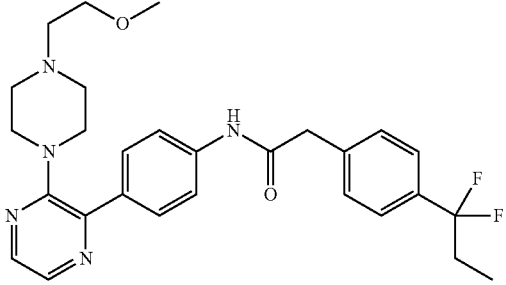 [SMILES: CCC(F)(F)c1ccc(CC(=O)Nc2ccc(-c3nccnc3N3CCN(CCOC)CC3)cc2)cc1]<br>2-(4-(1,1-Difluoropropyl)phenyl)-N-(4-(3-(4-(2-methoxyethyl)piperazin-1-yl)pyrazin-2-yl)phenyl)acetamide | Intermediate 2 and Intermediate 40 Method A | $^1$H NMR (300 MHz, CDCl$_3$) δ 1.00 (t, J = 7.8 Hz, 3H), 2.08-2.21 (m, 3H), 2.65-2.71 (m, 6H), 3.33 (s, 6H), 3.60-3.64 (m, 2H), 3.80 (s, 2H), 7.43 (d, J = 8.4 Hz, 3H), 7.50 (d, J = 7.8 Hz, 2H), 7.56 (d, J = 8.4 Hz, 2H), 7.86 (d, J = 8.4 Hz, 2H), 8.06 (s, 1H), 8.15 (s, 1H); APCI-MS (m/z) 510 (M + H)$^+$. |
| Example 42 | 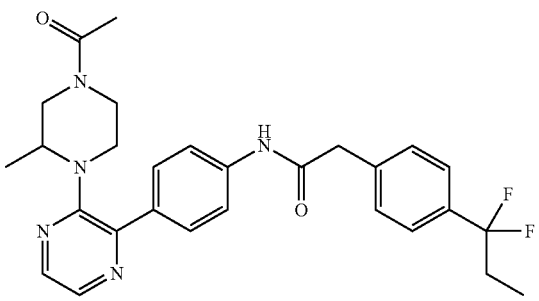 [SMILES: CCC(F)(F)c1ccc(CC(=O)Nc2ccc(-c3nccnc3N3CCN(C(C)=O)CC3C)cc2)cc1]<br>N-(4-(3-(4-Acetyl-2-methylpiperazin-1-yl)pyrazin-2-yl)phenyl)-2-(4-(1,1-difluoropropyl)phenyl)acetamide | Intermediate 2 and Intermediate 41 Method A | $^1$H NMR (300 MHz, DMSO-$d_6$) δ 0.90 (t, J =7.5 Hz, 3H), 2.19-2.23 (m, 2H), 2.94-3.10 (m, 2H), 3.20-3.35 (m, 9H), 3.73 (s, 2H), 3.74-3.84 (m, 2H), 7.47 (s, 4H), 7.72 (d, J = 7.8 Hz, 2H), 7.88 (d, J = 7.8 Hz, 2H), 8.16 (d, J = 11.1 Hz, 2H), 10.38 (s, 1H); APCI-MS (m/z) 508 (M + H)$^+$. |
| Example 43 | 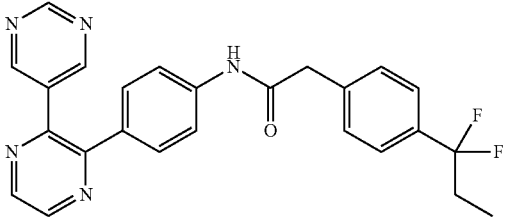 [SMILES: CCC(F)(F)c1ccc(CC(=O)Nc2ccc(-c3nccnc3-c3cncnc3)cc2)cc1]<br>2-(4-(1,1-Difluoropropyl)phenyl)-N-(4-(3-(pyrimidin-5-yl)pyrazin-2-yl)phenyl)acetamide | Intermediate 2 and Intermediate 42 Method A | $^1$H NMR (300 MHz, CDCl$_3$) δ 0.99 (t, J = 7.8 Hz, 3H), 2.07-2.22 (m, 2H), 3.77 (s, 2H), 7.34-7.41 (m, 6H), 7.49 (d, J = 7.8 Hz, 2H), 8.66 (d, J = 4.8 Hz, 2H), 8.82 (s, 2H), 9.15 (s, 1H); ESI-MS (m/z) 446 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 44 | 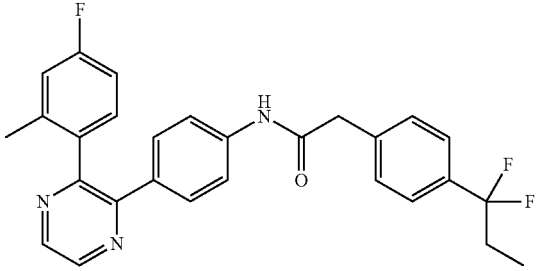 [SMILES: CCC(F)(F)c1ccc(CC(=O)Nc2ccc(-c3nccnc3-c3ccc(F)cc3C)cc2)cc1]<br>2-(4-(1,1-Difluoropropyl)phenyl)-N-(4-(3-(4-fluoro-2-methylphenyl)pyrazin-2-yl)phenyl)acetamide | Intermediate 2 and Intermediate 43 Method A | $^1$H NMR (300 MHz, DMSO-$d_6$) δ 0.89 (t, J = 7.8 Hz, 3H), 1.91 (s, 3H), 2.16-2.18 (m, 2H), 3.69 (s, 2H), 7.03-7.07 (m, 2H), 7.04-7.29 (m, 3H), 7.42-7.53 (m, 5H), 8.67 (s, 1H), 8.72 (s, 1H), 10.30 (s, 1H); APCI-MS (m/z) 476 (M + H)$^+$. |
| Example 45 | 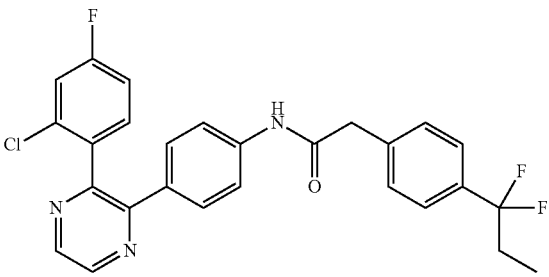 [SMILES: CCC(F)(F)c1ccc(CC(=O)Nc2ccc(-c3nccnc3-c3ccc(F)cc3Cl)cc2)cc1]<br>N-(4-(3-(2-Chloro-4-fluorophenyl)pyrazin-2-yl)phenyl)-2-(4-(1,1-difluoropropyl)phenyl)acetamide | Intermediate 2 and Intermediate 38 Method A | $^1$H NMR (300 MHz, DMSO-$d_6$) δ 0.89 (t, J = 6.9 Hz, 3H), 2.16-2.22 (m, 2H), 3.69 (s, 2H), 7.28 (d, J = 8.4 Hz, 2H), 7.30-7.60 (m, 9H), 8.69 (s, 1H), 8.77 (s, 1H), 10.31 (s, 1H); APCI-MS (m/z) 496 (M + H)$^+$. |
| Example 46 | 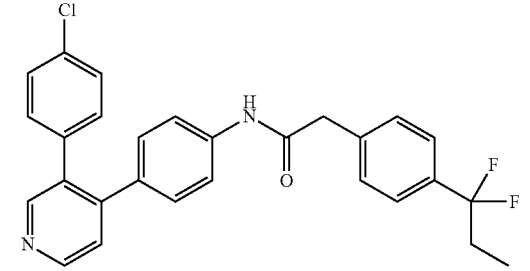<br>N-(4-(3-(4-Chlorophenyl)pyridin-4-yl)phenyl)-2-(4-(1,1-difluoropropyl)phenyl)acetamide | Intermediate 2 and Intermediate 44 Method A | $^1$H NMR (300 MHz, DMSO-$d_6$) δ 0.89 (t, J = 7.2 Hz, 3H), 2.15-2.19 (m, 2H), 3.69 (s, 2H), 7.08-7.18 (m, 4H), 7.36-7.53 (m, 9H), 8.54 (s, 1H), 8.60 (s, 1H), 10.24 (s, 1H); APCI-MS (m/z) 477 (M + H)$^+$. |
| Example 47 | 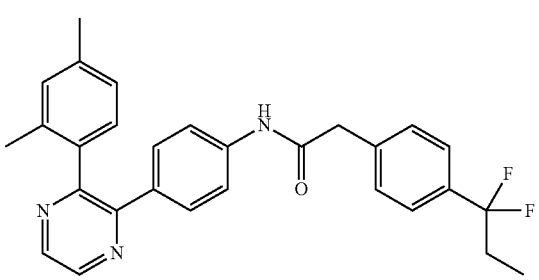 [SMILES: CCC(F)(F)c1ccc(CC(=O)Nc2ccc(-c3nccnc3-c3ccc(C)cc3C)cc2)cc1]<br>2-(4-(1,1-Difluoropropyl)phenyl)-N-(4-(3-(2,4-dimethylphenyl)pyrazin-2-yl)phenyl)acetamide | Intermediate 2 and Intermediate 45 Method A | $^1$H NMR (300 MHz, CDCl$_3$) δ 0.99 (t, J = 7.2 Hz, 3H), 1.90 (s, 3H), 2.07-2.22 (m, 2H), 2.31 (s, 3H), 3.73 (s, 2H), 6.94-7.01 (m, 2H), 7.06-7.12 (m, 2H), 7.34-7.39 (m, 5H), 7.49 (d, J = 7.8 Hz, 2H), 8.56 (s, 1H), 8.59 (s, 1H); APCI-MS (m/z) 472 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 48 | 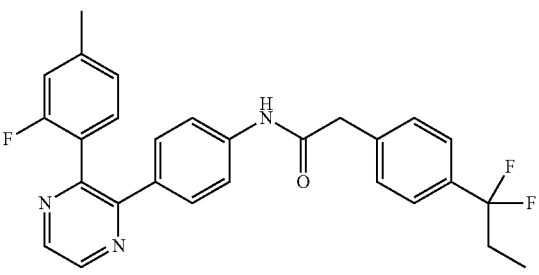 [SMILES: CCC(F)(F)c1ccc(CC(=O)Nc2ccc(-c3nccnc3-c3ccc(C)cc3F)cc2)cc1]<br>2-(4-(1,1-Difluoropropyl)phenyl)-N-(4-(3-(2-fluoro-4-methylphenyl)pyrazin-2-yl)phenyl)acetamide | Intermediate 2 and Intermediate 46 Method A | $^1$H NMR (300 MHz, DMSO-$d_6$) δ 0.90 (t, J = 7.8 Hz, 3H), 2.17-2.25 (m, 2H), 2.33 (s, 3H), 3.69 (s, 2H), 6.91-6.97 (m, 1H), 7.12 (d, J = 7.2 Hz, 1H), 7.32 (d, J = 8.4 Hz, 2H), 7.43-7.55 (m, 7H), 8.70 (d, J = 9.3 Hz, 2H), 10.31 (s, 1H); APCI-MS (m/z) 476 (M + H)$^+$. |
| Example 49 | 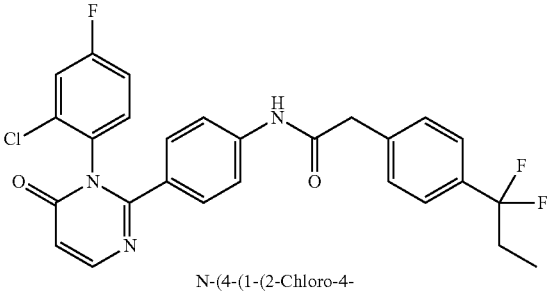<br>N-(4-(1-(2-Chloro-4-fluorophenyl)-6-oxo-1,6-dihydropyrimidin-2-yl)phenyl)-2-(4-(1,1-difluoropropyl)phenyl)acetamide | Intermediate 2 and Intermediate 47 Method A | $^1$H NMR (300 MHz, DMSO-$d_6$) δ 0.88 (t, J = 7.2 Hz, 3H), 2.15-2.39 (m, 2H), 3.67 (s, 2H), 6.56 (d, J = 6.3 Hz, 1H), 7.24-7.30 (m, 4H), 7.40-7.50 (m, 6H), 7.70 (s, 1H), 8.11 (d, J = 5.7 Hz, 1H), 10.33 (s, 1H); APCI-MS (m/z) 512 (M + H)$^+$. |
| Example 50 | 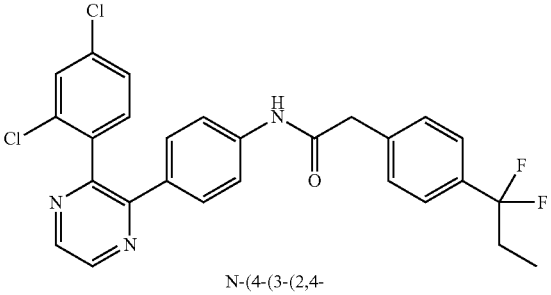<br>N-(4-(3-(2,4-Dichlorophenyl)pyrazin-2-yl)phenyl)-2-(4-(1,1-difluoropropyl)phenyl)acetamide | Intermediate 2 and Intermediate 48 Method A | $^1$H NMR (300 MHz, DMSO-$d_6$) δ 0.89 (t, J = 7.8 Hz, 3H), 2.16-2.22 (m, 2H), 3.69 (s, 2H), 7.29 (d, J = 8.1 Hz, 2H), 7.42-7.55 (m, 7H), 7.63 (s, 1H), 8.70 (s, 1H), 8.79 (s, 1H), 10.32 (s, 1H): APCI-MS (m/z) 512 (M + H)$^+$. |
| Example 51 | 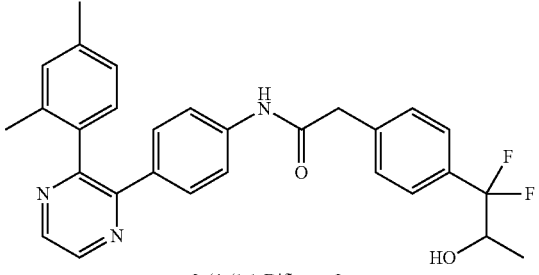<br>2-(4-(1,1-Difluoro-2-hydroxypropyl)phenyl)-N-(4-(3-(2,4-dimethylphenyl)pyrazin-2-yl)phenyl)acetamide | Intermediate 3 and Intermediate 45 Method B | $^1$H NMR (300 MHz, CDCl$_3$) δ 1.23 (d, J = 5.7 Hz, 3H), 1.91 (s, 3H), 2.31 (s, 3H), 3.72 (s, 2H), 4.13-4.17 (m, 1H), 6.95 (s, 1H), 6.99 (d, J = 6.9 Hz, 1H), 7 10 (d, J = 7.8 Hz, 1H), 7.19 (s, 1H), 7.35-7.40 (m, 5H), 7.50 (d, J = 8 1 Hz, 2H), 8.59 (d, J = 8.7 Hz, 2H); APCI-MS (m/z) 488 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 54 | 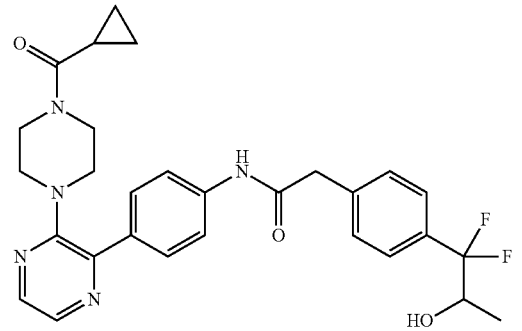 [SMILES: CC(O)C(F)(F)c1ccc(CC(=O)Nc2ccc(-c3nccnc3N3CCN(C(=O)C4CC4)CC3)cc2)cc1]<br>N-(4-(3-(4-(Cyclopropanecarbonyl)piperazin-1-yl)pyrazin-2-yl)phenyl)-2-(4-(1,1-difluoro-2-hydroxypropyl)phenyl)acetamide | Intermediate 3 and Intermediate 49 Method B | $^1$H NMR (300 MHz, DMSO-$d_6$) δ 0.63-0.70 (m, 4H), 1.07 (d, J = 6.3 Hz, 3H), 1.91-1.95 (m, 1H), 3.08-3.12 (m, 4H), 3.49-3.53 (m, 2H), 3.68-3.72 (m, 2H), 3.73 (s, 2H), 4.02-4.06 (m, 1H), 5.47-5.51 (m, 1H), 7.44 (s, 4H), 7.73 (d, J = 8.4 Hz, 2H), 7.90 (d, J = 7.2 Hz, 2H), 8.14 (s, 1H), 8.19 (s, 1H), 10.38 (s, 1H); ESI-MS (m/z) 536 (M + H)$^+$. |
| Example 55 | 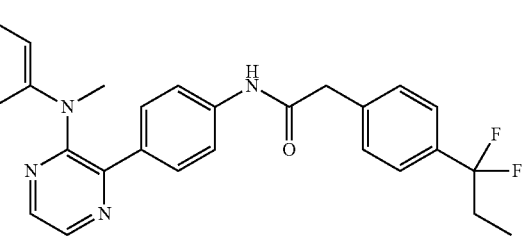<br>N-(4-(3-((4-Chlorophenyl)(methyl)amino)pyrazin-2-yl)phenyl)-2-(4-(1,1-difluoropropyl)phenyl)acetamide | Intermediate 2 and Intermediate 50 Method A | $^1$H NMR (300 MHz, DMSO-$d_6$) δ 0.88 (t, J = 7.2 Hz, 3H), 2.15-2.21 (m, 2H), 3.27 (s, 3H), 3.68 (s, 2H), 6.72-6.76 (m, 2H), 7.06 (d, J = 6.3 Hz, 2H), 7.42-7.55 (m, 8H), 8.34-8.43 (m, 2H), 10.24 (s, 1H); APCI-MS (m/z) 507 (M + H)$^+$. |
| Example 56 | 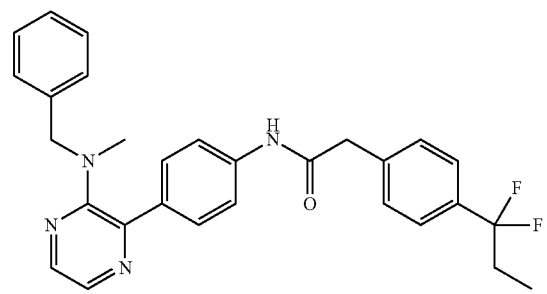 [SMILES: CCC(F)(F)c1ccc(CC(=O)Nc2ccc(-c3nccnc3N(C)Cc3ccccc3)cc2)cc1]<br>N-(4-(3-(Benzyl(methyl)amino)pyrazin-2-yl)phenyl)-2-(4-(1,1-difluoropropyl)phenyl)acetamide | Intermediate 2 and Intermediate 51 Method A | $^1$H NMR (300 MHz, DMSO-$d_6$) δ 0.89 (t, J = 7.2 Hz, 3H), 2.15-2.23 (m, 2H), 2.57 (s, 3H), 3.72 (s, 2H), 4.42 (s, 2H), 7.12 (d, J = 6.9 Hz, 2H), 7.23-7.31 (m, 3H), 7.44-7.48 (m, 4H), 7.70 (s, 4H), 8.08 (d, J = 6.3 Hz, 2H), 10.36 (s, 1H); APCI-MS (m/z) 487 (M + H)$^+$. |
| Example 57 | 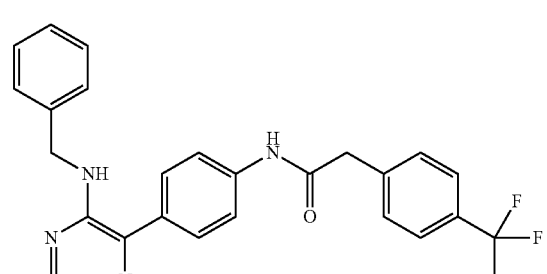<br>N-(4-(3-(Benzylamino)pyrazin-2-yl)phenyl)-2-(4-(1,1-difluoropropyl)phenyl)acetamide | Intermediate 2 and Intermediate 52 Method A | $^1$H NMR (300 MHz, DMSO-$d_6$) δ 0.89 (t, J = 7.2 Hz, 3H), 2.18-2.22 (m, 2H), 3.74 (s, 2H), 4.50 (s, 2H), 6.90-6.95 (m, 1H), 7.25-7.32 (m, 5H), 7.44-7.48 (m, 4H), 7.64 (d, J = 7.2 Hz, 2H), 7.68-7.74 (m, 3H), 7.89 (s, 1H), 10.39 (s, 1H); APCI-MS (m/z) 473 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 58 | 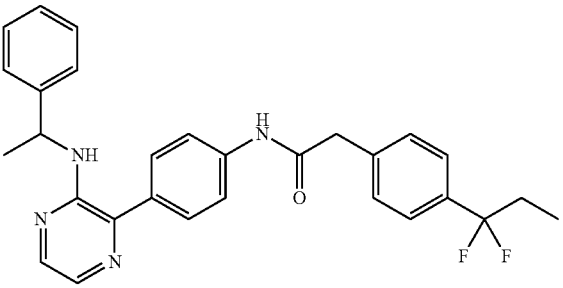 [SMILES: CCC(F)(F)c1ccc(CC(=O)Nc2ccc(-c3nccnc3NC(C)c3ccccc3)cc2)cc1]<br>2-(4-(1,1-Difluoropropyl)phenyl)-N-(4-(3-((1-phenylethyl)amino)pyrazin-2-yl)phenyl)acetamide | Intermediate 2 and Intermediate 53 Method A | $^1$H NMR (300 MHz, DMSO-$d_6$) δ 0.90 (t, J = 7.2 Hz, 3H), 1.43 (d, J = 7.2 Hz, 3H), 2.18-2.23 (m, 2H), 3.74 (s, 2H), 5.14-5.18 (m, 1H), 6.31-6.35 (m, 1H), 7.17 (d, J = 6.3 Hz, 1H), 7.25-7.37 (m, 4H), 7.45-7.49 (m, 4H), 7.65 (d, J = 7.2 Hz, 2H), 7.70-7.75 (m, 3H), 7.86 (s, 1H), 10.40 (s, 1H); APCI-MS (m/z) 487 (M + H)$^+$. |
| Example 59 | 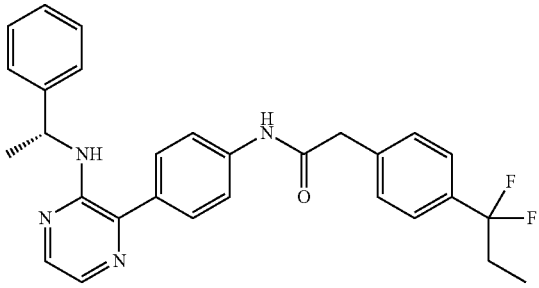 [SMILES: CCC(F)(F)c1ccc(CC(=O)Nc2ccc(-c3nccnc3N[C@H](C)c3ccccc3)cc2)cc1]<br>(R)-2-(4-(1,1-Difluoropropyl)phenyl)-N-(4-(3-((1-phenylethyl)amino)pyrazin-2-yl)phenyl)acetamide | Intermediate 2 and Intermediate 54 Method A | $^1$H NMR (300 MHz, DMSO-$d_6$) δ 0.90 (t, J = 7.8 Hz, 3H), 1.43 (d, J = 6.6 Hz, 3H), 2.18-2.25 (m, 2H), 3.74 (s, 2H), 5.14-5.18 (m, 1H), 6.32-6.36 (m, 1H), 7.17 (d, J = 7.2 Hz, 1H), 7.27 (t, J = 7.8 Hz, 2H), 7.35 (d, J = 7.2 Hz, 2H), 7.45-7.49 (m, 4H), 7.65 (d, J = 8.4 Hz, 2H), 7.72-7.78 (m, 3H), 7.86 (s, 1H), 10.41 (s, 1H); APCI-MS (m/z) 487 (M + H)$^+$. |
| Example 60 | 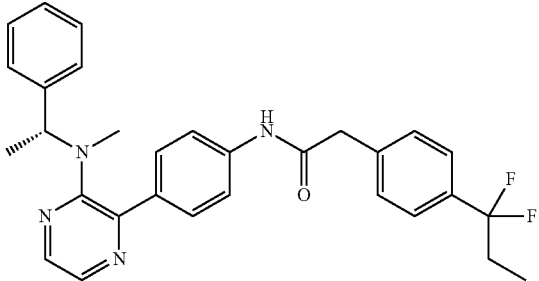 [SMILES: CCC(F)(F)c1ccc(CC(=O)Nc2ccc(-c3nccnc3N(C)[C@H](C)c3ccccc3)cc2)cc1]<br>(R)-2-(4-(1,1-Difluoropropyl)phenyl)-N-(4-(3-(methyl(1-phenylethyl)amino)pyrazin-2-yl)phenyl)acetamide | Intermediate 2 and Intermediate 55 Method A | $^1$H NMR (300 MHz, DMSO-$d_6$) δ 0.87 (t, J = 7.5 Hz, 3H), 1.41 (d, J = 6.9 Hz, 3H), 2.13-2.17 (m, 2H), 2.31 (s, 3H), 3.69 (s, 2H), 5.25-5.29 (m, 1H), 7.13 (d, J = 7.2 Hz, 2H), 7.18-7.27 (m, 3H), 7.41-7.45 (m, 4H), 7.65 (s, 4H), 8.05 (s, 2H), 10.32 (s, 1H); APCI-MS (m/z) 501 (M + H)$^+$. |
| Example 61 | 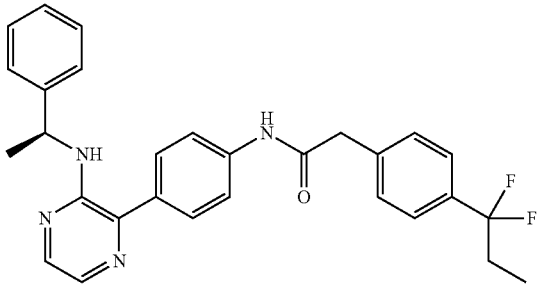 [SMILES: CCC(F)(F)c1ccc(CC(=O)Nc2ccc(-c3nccnc3N[C@@H](C)c3ccccc3)cc2)cc1]<br>(S)-2-(4-(1,1-Difluoropropyl)phenyl)-N-(4-(3-((1-phenylethyl)amino)pyrazin- | Intermediate 2 and Intermediate 56 Method A | $^1$H NMR (300 MHz, DMSO-$d_6$) δ 0.90 (t, J = 7.2 Hz, 3H), 1.43 (d, J = 7.2 Hz, 3H), 2.16-2.25 (m, 2H), 3.74 (s, 2H), 5.14-5.18 (m, 1H), 6.35 (d, J = 7.8 Hz, 1H), 7.17 (t, J = 7.2 Hz, 1H), 7.27 (d, J = 7.8 Hz, 2H), 7.36 (d, J = 7.2 Hz, 2H), 7.45-7.49 (m, 4H), 7.65 (d, J = 9.0 Hz, 2H), 7.72-7.79 (m, 3H), 7.87 (s, 1H), 10.41 (s, 1H); APCI-MS (m/z) 487 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| | 2-yl)phenyl)acetamide | | |
| Example 62 | 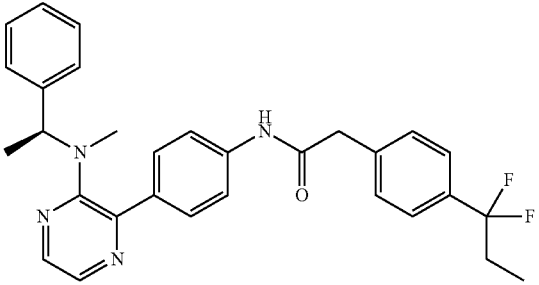 [SMILES: CCC(F)(F)c1ccc(CC(=O)Nc2ccc(-c3nccnc3N(C)[C@@H](C)c3ccccc3)cc2)cc1]<br>(S)-2-(4-(1,1-Difluoropropyl)phenyl)-N-(4-(3-(methyl(1-phenylethyl)amino)pyrazin-2-yl)phenyl)acetamide | Intermediate 2 and Intermediate 57 Method A | $^1$H NMR (300 MHz, DMSO-$d_6$) δ 0.89 (t, J = 7.2 Hz, 3H), 1.43 (d, J = 6.3 Hz, 3H), 2.16-2.25 (m, 2H), 2.33 (s, 3H), 3.72 (s, 2H), 5.29-5.35 (m, 1H), 7.16 (d, J = 7.2 Hz, 2H), 7.22-7.29 (m, 3H)-7.44-7.48 (m, 4H), 7.67 (s, 4H), 8.08 (s, 2H), 10.34 (s, 1H); APCI-MS (m/z) 501 (M + H)$^+$. |
| Example 63 | 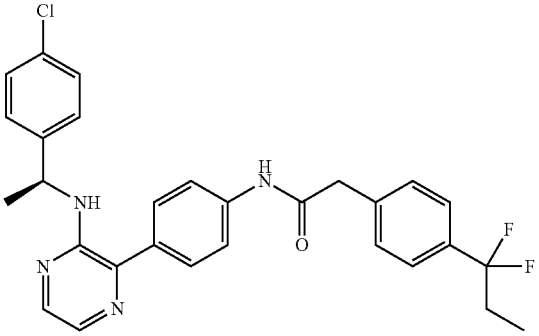 [SMILES: CCC(F)(F)c1ccc(CC(=O)Nc2ccc(-c3nccnc3N[C@@H](C)c3ccc(Cl)cc3)cc2)cc1]<br>(S)-N-(4-(3-((1-(4-Chlorophenyl)ethyl)amino)pyrazin-2-yl)phenyl)-2-(4-(1,1-difluoropropyl)phenyl)acetamide | Intermediate 2 and Intermediate 58 Method A | $^1$H NMR (300 MHz, DMSO-$d_6$) δ 0.90 (t, J = 7.5 Hz, 3H), 1.42 (d, J = 6.3 Hz, 3H), 2.17-2.31 (m, 2H), 3.74 (s, 2H), 5.13 (t, J = 6.3 Hz, 1H), 6.48 (d, J = 7.5 Hz, 1H), 7.32 (d, J= 7.8 Hz, 2H), 7.39 (d, J = 7.8 Hz, 2H), 7.45-7.49 (m, 4H), 7.65 (d, J = 7.8 Hz, 2H), 7.72-7.78 (m, 3H), 7.85 (s, 1H), 10.42 (s, 1H); APCI-MS (m/z) 521 (M + H)$^+$. |
| Example 64 | 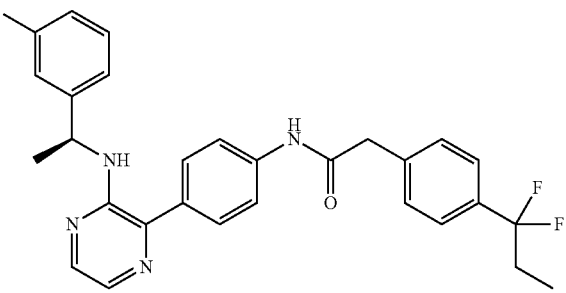<br>(S)-N-(4-(3-((1-(3-Chlorophenyl)ethyl)amino)pyrazin-2-yl)phenyl)-2-(4-(1,1-difluoropropyl)phenyl)acetamide | Intermediate 2 and Intermediate 59 Method A | $^1$H NMR (300 MHz, DMSO-$d_6$) δ 0.90 (t, J = 7.2 Hz, 3H), 1.43(d, J = 6.3 Hz, 3H), 2.18-2.32 (m, 2H), 3.75 (s, 2H), 5.14 (t, J = 6.3 Hz, 1H), 6.55 (d, J = 7.5 Hz, 1H), 7.22 (d, J = 7.8 Hz, 2H), 7.28-7.35 (m, 2H), 7.42-7.50 (m, 4H), 7.67 (d, J = 8.4 Hz, 2H), 7.73-7.79 (m, 3H), 7.86 (s, 1H), 10.42 (s, 1H); APCI-MS (m/z) 521 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 65 | 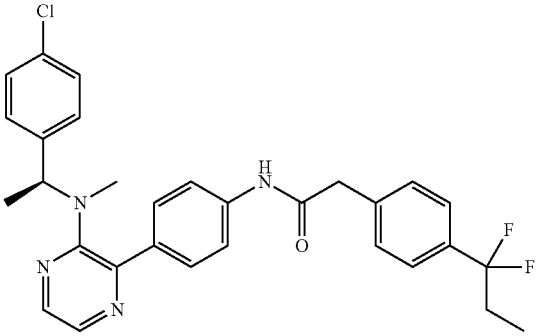 [SMILES: CCC(F)(F)c1ccc(CC(=O)Nc2ccc(-c3nccnc3N(C)[C@@H](C)c3ccc(Cl)cc3)cc2)cc1]<br>(S)-N-(4-(3-((1-(4-Chlorophenyl)ethyl)(methyl)amino)pyrazin-2-yl)phenyl)-2-(4-(1,1-difluoropropyl)phenyl)acetamide | Intermediate 2 and Intermediate 60 Method A | $^1$H NMR (300 MHz, DMSO-$d_6$) δ 0.89 (t, J = 7.2 Hz, 3H), 1.43 (d, J = 6.3 Hz, 3H), 2.18-2.22 (m, 2H), 2.32 (s, 3H), 3.72 (s, 2H), 5.26-5.31 (m, 1H), 7.19 (d, J = 7.8 Hz, 2H), 7.34 (d, J = 8.4 Hz, 2H), 7.44-7.48 (m, 4H), 7.65-7.69 (m, 4H), 8.08 (d, J = 5.1 Hz, 2H), 10.35 (s, 1H). |
| Example 66 | 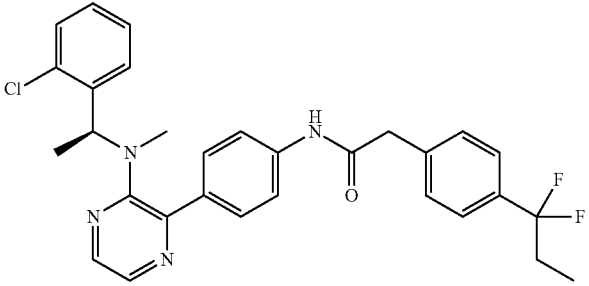<br>(S)-N-(4-(3-((1-(2-Chlorophenyl)ethyl)amino)pyrazin-2-yl)phenyl)-2-(4-(1,1-difluoropropyl)phenyl)acetamide | Intermediate 2 and Intermediate 61 Method A | $^1$H NMR (300 MHz, DMSO-$d_6$) δ 0.90 (t, J = 7.2 Hz, 3H), 1.41 (d, J = 6.9 Hz, 3H), 2.13-2.23 (m, 2H), 3.75 (s, 2H), 5.39-5.43 (m, 1H), 6.57 (d, J = 7.5 Hz, 1H), 7.21-7.25 (m, 2H), 7.38 (d, J = 7.2 Hz, 1H), 7.45-7.49 (m, 5H), 7.70-7.84 (m, 6H), 10.42 (s, 1H); APCI-MS (m/z) 520 (M)$^+$. |
| Example 67 | 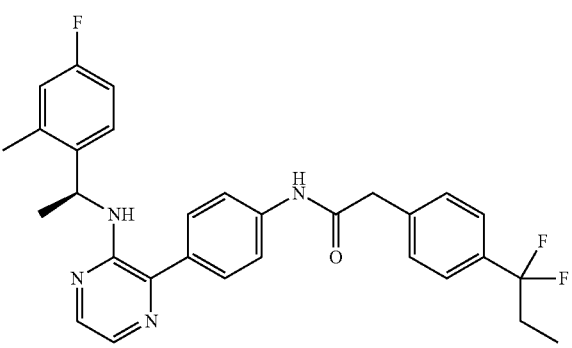 [SMILES: CCC(F)(F)c1ccc(CC(=O)Nc2ccc(-c3nccnc3N[C@@H](C)c3ccc(F)cc3C)cc2)cc1]<br>(S)-2-(4-(1,1-Difluoropropyl)phenyl)-N-(4-(3-((1-(4-fluoro-2-methylphenyl)ethyl)amino)pyrazin-2-yl)phenyl)acetamide | Intermediate 2 and Intermediate 62 Method A | $^1$H NMR (300 MHz, DMSO-$d_6$) δ 0.90 (t, J = 7.2 Hz, 3H), 1.36 (d, J = 6.3 Hz, 3H), 2.18-2.25 (m, 2H), 2.40 (s, 3H), 3.74 (s, 2H), 5.21-5.25 (m, 1H), 6.44 (d, J = 6.3 Hz, 1H), 6.92-7.01 (m, 2H), 7.39-7.50 (m, 5H), 7.63 (d, J = 8.4 Hz, 2H), 7.74 (d, J = 8.4 Hz, 3H), 7.86 (s, 1H), 10.42 (s, 1H). |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 68 | 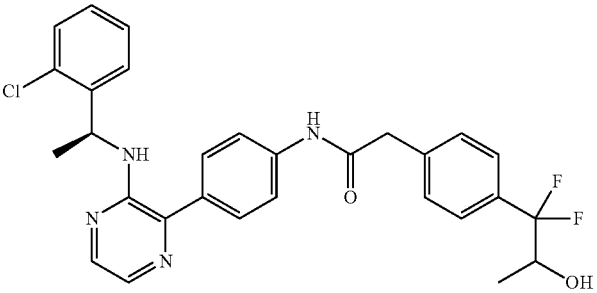 [SMILES: CC(O)C(F)(F)c1ccc(CC(=O)Nc2ccc(-c3nccnc3N[C@@H](C)c3ccccc3Cl)cc2)cc1]<br>N-(4-(3-(((S)-1-(2-Chlorophenyl)ethyl)amino)pyrazin-2-yl)phenyl)-2-(4-(1,1-difluoro-2-hydroxypropyl)phenyl)acetamide | Intermediate 3 and Intermediate 61 Method B | $^1$H NMR (300 MHz, DMSO-$d_6$) δ 1.07 (d, J = 6.9 Hz, 3H), 1.41 (d, J = 6.9 Hz, 3H), 3.74 (s, 2H), 4.06 (br s, 1H), 5.39-5.43 (m, 1H), 6.57 (d, J = 6.9 Hz, 1H), 7.21-7.26 (m, 3H), 7.36-7.46 (m, 6H), 7.70 (d, J = 8.4 Hz, 2H), 7.77 (d, J = 8.4 Hz, 2H), 7.84 (s, 1H), 10.42 (s, 1H); APCI-MS (m/z) 537 (M + H)$^+$. |
| Example 69 | 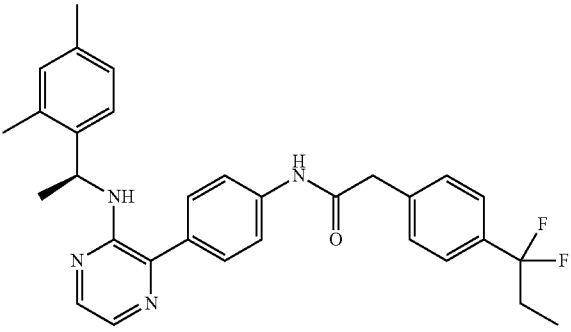 [SMILES: CCC(F)(F)c1ccc(CC(=O)Nc2ccc(-c3nccnc3N[C@@H](C)c3ccc(C)cc3C)cc2)cc1]<br>(S)-2-(4-(1,1-Difluoropropyl)pheny)-N-(4-(3-((1-(2-4-dimethylphenyl)ethyl)amino)pyrazin-2-yl)phenyl)acetamide | Intermediate 2 and Intermediate 63 Method A | $^1$H NMR (300 MHz, DMSO-$d_6$) δ 0.88 (t, J = 7.2 Hz, 3H), 1.34 (d, J = 5.7 Hz, 3H), 2.15-2.25 (m, 5H), 2.32 (s, 3H), 3.73 (s, 2H), 5.21-5.25 (m, 1H), 6.24 (d, J = 6.3 Hz, 1H), 6.88-6.90 (m, 2H), 7.21 (d, J = 7.8 Hz, 1H), 7.45-7.47 (m, 4H), 7.60 (d, J = 7.8 Hz, 2H), 7.73 (d, J = 8.4 Hz, 3H), 7.85 (s, 1H), 10.39 (s, 1H); APCI-MS (m/z) 513 (M − H)$^-$. |
| Example 70 | 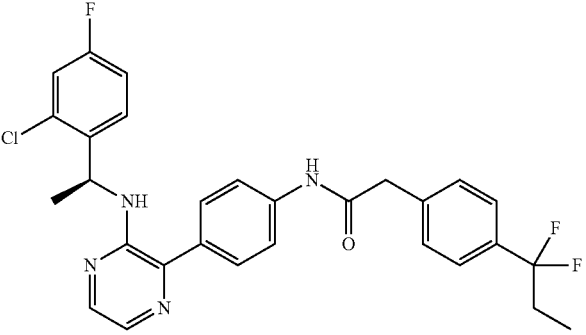 [SMILES: CCC(F)(F)c1ccc(CC(=O)Nc2ccc(-c3nccnc3N[C@@H](C)c3ccc(F)cc3Cl)cc2)cc1]<br>(S)-N-(4-(3-((1-(2-Chloro-4-fluorophenyl)ethyl)amino)pyrazin-2-yl)phenyl)-2-(4-(1,1-difluoropropyl)phenyl)acetamide | Intermediate 2 and Intermediate 64 Method A | $^1$H NMR (300 MHz, DMSO-$d_6$) δ 0.90 (t, J = 7.2 Hz, 3H), 1.40 (d, J = 6.9 Hz, 3H), 2.18-2.25 (m, 2H), 3.75 (s, 2H), 5.35-5.39 (m, 1H), 6.62-6.65 (m, 1H), 7.11-7.15 (m, 2H), 7.35 (d, J = 8.7 Hz, 1H), 7.45-7.49 (m, 5H), 7.67-7.85 (m, 5H), 10.42 (s, 1H); APCI-MS (m/z) 539 (M + H)$^+$ |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 71 | 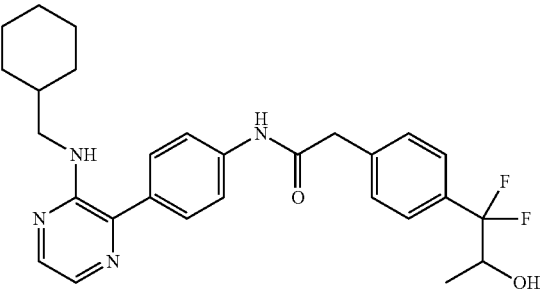 [SMILES: CC(O)C(F)(F)c1ccc(CC(=O)Nc2ccc(-c3nccnc3NCC3CCCCC3)cc2)cc1]<br>N-(4-(3-((Cyclohexylmethyl)amino)pyrazin-2-yl)phenyl)-2-(4-(1,1-difluoro-2-hydroxypropyl)phenyl)acetamide | Intermediate 3 and Intermediate 65 Method B | $^1$H NMR (300 MHz, DMSO-$d_6$) δ 0.83-0.88 (m, 2H), 1.07 (d, J = 6.3 Hz, 3H), 1.11-1.15 (m, 2H), 1.62-1.72 (m, 5H), 2.99-3.13 (m, 2H), 3.10-3.15 (m, 3H), 3.73 (s, 2H), 4.03 (br s, 1H), 5.52 (d, J = 5.7 Hz, 1H), 6.25 (br s, 1H), 7.42-7.46 (m, 3H), 7.57 (d, J = 8.4 Hz, 2H), 7.69-7.75 (m, 3H), 77.91 (s, 1H), 10.39 (s, 1H). |
| Example 72 | 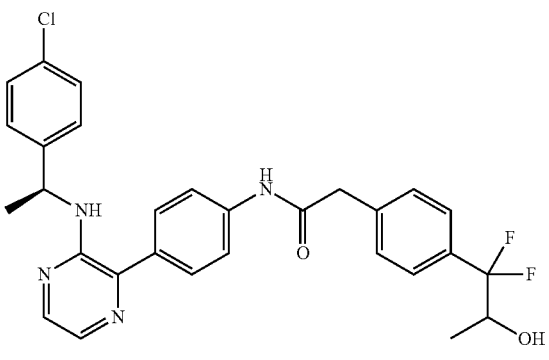 [SMILES: CC(O)C(F)(F)c1ccc(CC(=O)Nc2ccc(-c3nccnc3N[C@@H](C)c3ccc(Cl)cc3)cc2)cc1]<br>N-(4-(3-(((S)-1-(4-Chlorophenyl)ethyl)amino)pyrazin-2-yl)phenyl)-2-(4-(1,1-difluoro-2-hydroxypropyl)phenyl)acetamide | Intermediate 3 and Intermediate 58 Method B | $^1$H NMR (300 MHz, DMSO-$d_6$) δ 1.07 (d, J = 6.9 Hz, 3H), 1.42 (d, J = 6.3 Hz, 3H), 3.74 (s, 2H), 4.05 (br s, 1H), 5.11-5.15 (m, 1H), 5.49-5.53 (m, 1H), 6.49 (d, J = 7.5 Hz, 1H), 7.32-7.40 (m, 7H), 7.65 (d, J = 8.4 Hz, 2H), 7.72-7.76 (m, 3H), 7.82-7.86 (m, 2H), 10.41 (s, 1H). |
| Example 73 | 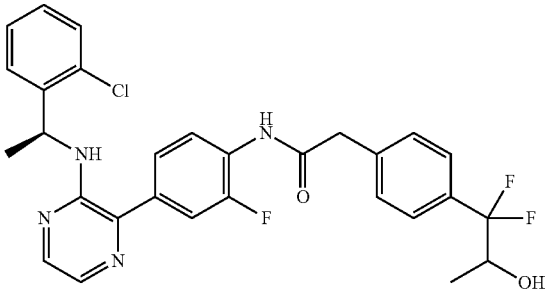 [SMILES: CC(O)C(F)(F)c1ccc(CC(=O)Nc2ccc(-c3nccnc3N[C@@H](C)c3ccccc3Cl)cc2F)cc1]<br>N-(4-(3-(((S)-1-(2-Chlorophenyl)ethyl)amino)pyrazin-2-yl)-2-fluorophenyl)-2-(4-(1,1-difluoro-2-hydroxypropyl)phenyl)acetamide | Intermediate 3 and Intermediate 66 Method B | $^1$H NMR (300 MHz, DMSO-$d_6$) δ 1.07 (d, J = 6.3 Hz, 3H), 1.42 (d, J = 6.6 Hz, 3H), 3.85 (s, 2H), 4.05 (br s, 1H), 5.39-5.46 (m, 1H), 5.52 (d, J = 6.0 Hz, 1H), 683 (d, J = 6.9 Hz, 1H), 7.18-7.25 (m, 2H), 7.38 (d, J = 7.8 Hz, 1H), 7.45 (s, 4H), 7.56-7.65 (m. 2H), 7.79 (s, 1H), 7.87 (s, 1H), 8.12 (t, J = 7.8 Hz, 2H), 10.19 (s, 1H); ESI-MS (m/z) 555 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 74 | 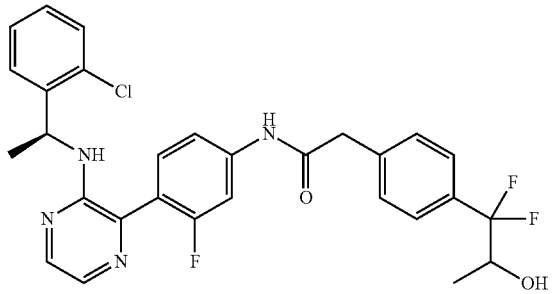 [SMILES: CC(O)C(F)(F)c1ccc(CC(=O)Nc2ccc(-c3nccnc3N[C@@H](C)c3ccccc3Cl)c(F)c2)cc1]<br><br>N-(4-(3-(((S)-1-(2-Chlorophenyl)ethyl)amino)pyrazin-2-yl)-3-fluorophenyl)-2-(4-(1,1-difluoro-2-hydroxypropyl)phenyl)acetamide | Intermediate 3 and Intermediate 67 Method B | $^1$H NMR (300 MHz, DMSO-$d_6$) δ 1.07 (d, J = 6.9 Hz, 3H), 1.37 (d, J = 6.6 Hz, 3H), 3.76 (s, 2H), 4.05 (br s, 1H), 5.40-5.45 (m, 1H), 5.52 (d, J = 6.0 Hz, 1H), 6.62 (d, J = 7.2 Hz, 1H), 7.18-7.25 (m, 3H), 7.37 (d, J =7.2 Hz, 1H), 7.45 (s, 6H), 7.73-7.78 (m, 2H), 7.90 (s, 1H), 10.61 (s, 1H); ESI-MS (m/z) 555 (M + H)$^+$. |
| Example 75 | 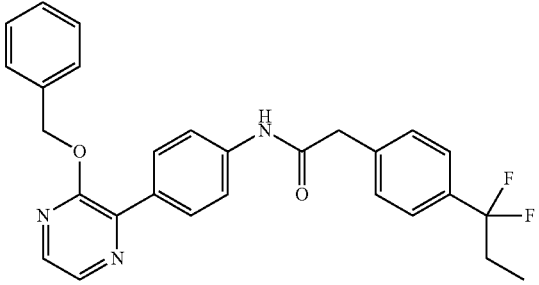 [SMILES: CCC(F)(F)c1ccc(CC(=O)Nc2ccc(-c3nccnc3OCc3ccccc3)cc2)cc1]<br><br>N-(4-(3-(Benzyloxy)pyrazin-2-yl)phenyl)-2-(4-(1,1-difluoropropyl)phenyl)acetamide | Intermediate 2 and Intermediate 68 Method A | $^1$H NMR (300 MHz, DMSO-$d_6$) δ 0.89 (t, J = 7.2 Hz, 3H), 2.18-2.25 (m, 2H), 3.73 (s, 2H), 5.48 (s, 2H), 6.01 (br s, 1H), 7.35-7.47 (m, 8H), 7.69 (d, J = 8.4 Hz, 2H), 8.03 (d, J = 8.7 Hz, 2H), 8.17 (s, 1H), 8.31 (s, 1H), 10.40 (s, 1H); APCI-MS (m/z) 474 (M + H)$^+$. |
| Example 76 | 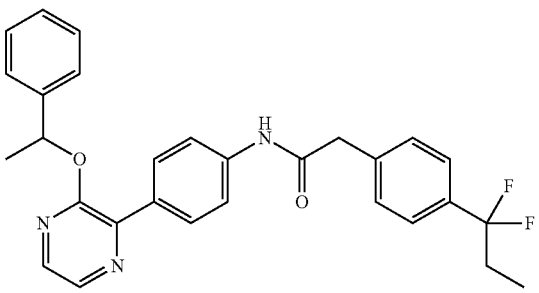 [SMILES: CCC(F)(F)c1ccc(CC(=O)Nc2ccc(-c3nccnc3OC(C)c3ccccc3)cc2)cc1]<br><br>2-(4-(1,1-Difluoropropyl)phenyl)-N-(4-(3-(1-phenylethoxy)pyrazin-2-yl)phenyl)acetamide | Intermediate 2 and Intermediate 69 Method A | $^1$H NMR (300 MHz, DMSO-$d_6$) δ 0.90 (t, J = 7.2 Hz, 3H), 1.63 (d, J = 6.3 Hz, 3H), 2.16-2.25 (m, 2H), 3.75 (s, 2H), 6.21-6.26 (m, 1H), 7.30-7.35 (m, 3H), 7.40-7.50 (m, 6H), 7.73 (d, J = 8.7 Hz, 2H), 8.06-8.12 (m, 3H), 8.25 (s, 1H), 10.43 (s, 1H); APCI-MS (m/z) 488 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 77 | 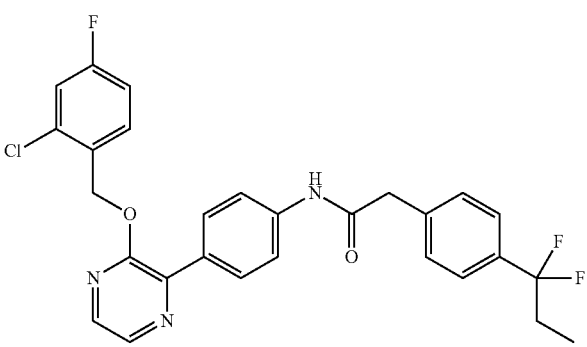 [SMILES: CCC(F)(F)c1ccc(CC(=O)Nc2ccc(-c3nccnc3OCc3ccc(F)cc3Cl)cc2)cc1]  N-(4-(3-((2-Chloro-4-fluorobenzyl)oxy)pyrazin-2-yl)phenyl)-2-(4-(1,1-difluoropropyl)phenyl)acetamide | Intermediate 2 and Intermediate 70 Method A | $^1$H NMR (300 MHz, DMSO-$d_6$) δ 0.89 (t, J = 7.2 Hz, 3H), 2.16-2.21 (m, 2H), 3.73 (s, 2H), 5.51 (s, 2H), 7.24-7.27 (m, 1H), 7.44-7.48 (m, 4H), 7.55 (d, J = 8.7 Hz, 1H), 7.65-7.70 (m, 3H), 8.00 (d, J = 9.0 Hz, 2H), 8.19 (s, 1H), 8.34 (s, 1H), 10.39 (s, 1H); APCI-MS (m/z) 526 (M + H)$^+$. |
| Example 78 | 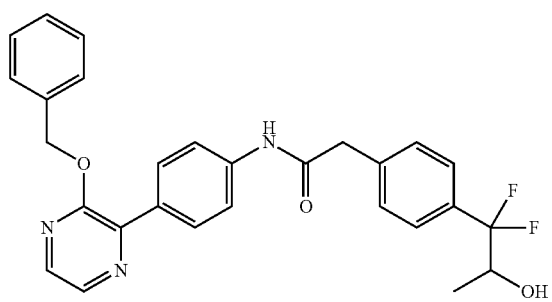 [SMILES: CC(O)C(F)(F)c1ccc(CC(=O)Nc2ccc(-c3nccnc3OCc3ccccc3)cc2)cc1]  N-(4-(3-(Benzyloxy)pyrazin-2-yl)phenyl)-2-(4-(1,1-difluoro-2-hydroxypropyl)phenyl)acetamide | Intermediate 3 and Intermediate 68 Method B | $^1$H NMR (300 MHz, DMSO-$d_6$) δ 1.06 (d, J = 6.9 Hz, 3H), 3.72 (s, 2H), 4.03 (br s, 1H), 5.46-5.60 (m, 3H), 7.37-7.50 (m, 9H), 7.70 (d, J = 7.2 Hz, 2H), 8.03 (d, J = 8.4 Hz, 2H), 8.17 (s, 1H), 8.32 (s, 1H), 10.39 (s, 1H); APCI-MS (m/z) 490 (M + H)$^+$. |
| Example 79 | 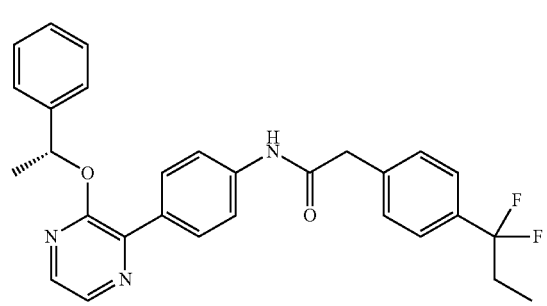 [SMILES: CCC(F)(F)c1ccc(CC(=O)Nc2ccc(-c3nccnc3O[C@H](C)c3ccccc3)cc2)cc1]  (R)-2-(4-(1,1-Difluoropropyl)phenyl)-N-(4-(3-(1-phenylethoxy)pyrazin-2-yl)phenyl)acetamide | Intermediate 2 and Intermediate 71 Method A | $^1$H NMR (300 MHz, DMSO-$d_6$) δ 0.90 (t, J = 7.2 Hz, 3H), 1.63 (d, J = 6.3 Hz, 3H), 2.12-2.26 (m, 2H), 3.75 (s, 2H), 6.24-6.28 (m, 1H), 7.24-7.49 (m, 9H), 7.73 (d, J = 8.4 Hz, 2H), 8.05-8.09 (m, 3H), 8.25 (s, 1H), 10.44 (s, 1H); APCI-MS (m/z) 488 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 80 | 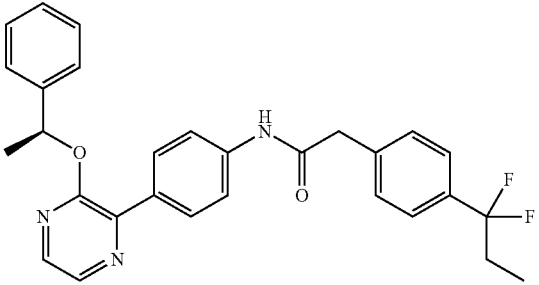 [SMILES: CCC(F)(F)c1ccc(CC(=O)Nc2ccc(-c3nccnc3O[C@@H](C)c3ccccc3)cc2)cc1]<br>(S)-2-(4-(1,1-Difluoropropyl)phenyl)-N-(4-(3-(1-phenylethoxy)pyrazin-2-yl)phenyl)acetamide | Intermediate 2 and Intermediate 72 Method A | $^1$H NMR (300 MHz, DMSO-$d_6$) δ 0.90 (t, J = 7.2 Hz, 3H), 1.64 (d, J = 6.3 Hz, 3H), 2.16-2.25 (m, 2H), 3.75 (s, 2H), 6.25-6.29 (m, 1H), 7.27-7.35 (m, 4H), 7.39-7.48 (m, 5H), 7.73 (d, J = 8.7 Hz, 2H), 8.05-8.09 (m, 3H), 8.24 (s, 1H), 10.43 (s, 1H); APCI-MS (m/z) 488 (M + H)$^+$. |
| Example 81 | 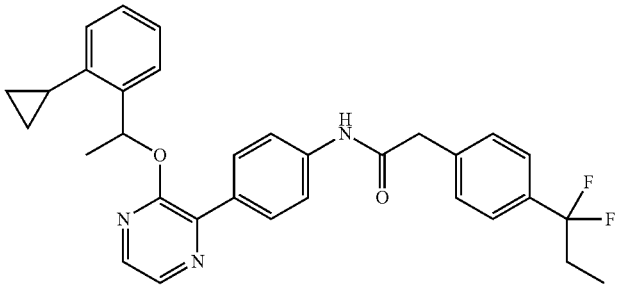 [SMILES: CCC(F)(F)c1ccc(CC(=O)Nc2ccc(-c3nccnc3OC(C)c3ccccc3C3CC3)cc2)cc1]<br>N-(4-(3-(1-(2-Cyclopropylphenyl)ethoxy)pyrazin-2-yl)phenyl)-2-(4-(1,1-difluoropropyl)phenyl)acetamide | Intermediate 2 and Intermediate 73 Method A | $^1$H NMR (300 MHz, DMSO-$d_6$) δ 0.88-0.93 (m, 5H), 1.20-1.25 (m, 1H), 1.66 (d, J = 6.6 Hz, 3H), 2.14-2.18 (m, 4H), 3.75 (s, 2H), 6.73-6.77 (m, 1H), 7.01-7.05 (m, 1H), 7.12-7.16 (m, 2H), 7.32-7.36 (m, 2H), 7.45-7.49 (m, 3H), 7.75 (d, J = 8.7 Hz, 2H), 8.08-8.14 (m, 3H), 8.22 (s, 1H), 10.42 (s, 1H); APCI-MS (m/z) 528 (M + H)$^+$. |
| Example 82 | 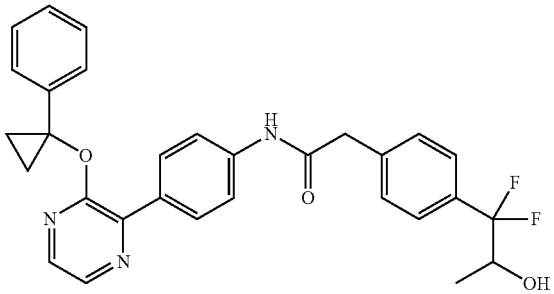 [SMILES: CC(O)C(F)(F)c1ccc(CC(=O)Nc2ccc(-c3nccnc3OC3(c4ccccc4)CC3)cc2)cc1]<br>2-(4-(1,1-Difluoro-2-hydroxypropyl)phenyl)-N-(4-(3-1-phenylcyclopropoxy)pyrazin-2-yl)phenyl)acetamide | Intermediate 3 and Intermediate 74 Method B | $^1$H NMR (300 MHz, DMSO-$d_6$) δ 1.07 (d, J = 6.9 Hz, 3H), 1.39-1.46 (m, 4H), 3.74 (s, 2H), 4.03 (br s, 1H), 5.51-5.55 (m, 1H), 7.17 (d, J = 6.9 Hz, 2H), 7.25 (d, J = 6.9 Hz, 2H), 7.45 (s, 5H), 7.75 (d, J = 8.7 Hz, 2H), 8.03-8.08 (m, 3H), 8.26 (s, 1H), 10.44 (s, 1H); APCI-MS (m/z) 516 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 83 | (R)-N-(4-(3-(1-(2-Chlorophenyl)ethoxy)pyrazin-2-yl)phenyl)-2-(4-(1,1-difluoropropyl)phenyl)acetamide | Intermediate 2 and Intermediate 75 Method A | $^1$H NMR (300 MHz, DMSO-$d_6$) δ 0.90 (t, J = 7.2 Hz, 3H), 1.64 (d, J = 6.9 Hz, 3H), 2.18-2.23 (m, 2H), 3.75 (s, 2H), 6.47-6.51 (m, 1H), 7.29-7.32 (m, 3H), 7.45-7.49 (m, 5H), 7.74 (d, J = 8.7 Hz, 2H), 8.06-8.12 (m, 3H), 8.26 (s, 1H), 10.44 (s, 1H); APCI-MS (m/z) 522 (M + H)$^+$. |
| Example 84 | N-(4-(3-((R)-1-(2-Chlorophenyl)ethoxy)pyrazin-2-yl)phenyl)-2-(4-(1,1-difluoro-2-hydroxypropyl)phenyl)acetamide | Intermediate 3 and Intermediate 75 Method B | $^1$H NMR (300 MHz, DMSO-$d_6$) δ 1.07 (d, J = 6.9 Hz, 3H), 1.64 (d, J = 6.3 Hz, 3H), 3.75 (s, 2H), 4.04 (br s, 1H), 5.52 (d, J = 5.7 Hz, 1H), 6.47-6.51 (m, 1H), 7.29-7.32 (m, 3H), 7.45 (s, 5H), 7.75 (d, J = 8.7 Hz, 2H), 8.06-8.12 (m, 3H), 8.26 (s, 1H), 10.44 (s, 1H); APCI-MS (m/z) 538 (M + H)$^+$. |
| Example 85 | (S)-N-(4-(3-(1-(2-Chlorophenyl)ethoxy)pyrazin-2-yl)phenyl)-2-(4-(1,1-difluoropropyl)phenyl)acetamide | Intermediate 2 and Intermediate 76 Method A | $^1$H NMR (300 MHz, DMSO-$d_6$) δ 0.90 (t, J = 7.2 Hz, 3H), 1.64 (d, J = 6.3 Hz, 3H), 2.12-2.27 (m, 2H), 3.75 (s, 2H), 6.46-6.52 (m, 1H), 7.27-7.32 (m, 3H), 7.42-7.45 (m, 5H), 7.74 (d, J = 5.7 Hz, 2H), 8.07-8.12 (m, 3H), 8.26 (s, 1H), 10.45 (s, 1H); APCI-MS (m/z) 520 (M − H)$^-$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 86 | 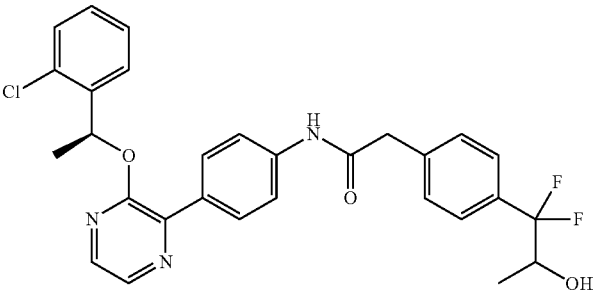 [SMILES: CC(O)C(F)(F)c1ccc(CC(=O)Nc2ccc(-c3nccnc3O[C@@H](C)c3ccccc3Cl)cc2)cc1]<br>N-(4-(3-((S)-1-(2-Chlorophenyl)ethoxy)pyrazin-2-yl)phenyl)-2-(4-(1,1-difluoro-2-hydroxypropyl)phenyl)acetamide | Intermediate 3 and Intermediate 76 Method B | $^1$H NMR (300 MHz, DMSO-$d_6$) δ 1.07 (d, J = 6.3 Hz, 3H), 1.64 (d, J = 6.9 Hz, 3H), 3.75 (s, 2H), 4.05 (br s, 1H), 5.52 (d, J = 6.3 Hz, 1H), 6.47-6.51 (m, 1H), 7.29-7.32 (m, 3H), 7.45 (s, 5H), 7.75 (d, J = 9.0 Hz, 2H), 8.07-8.12 (m, 3H), 8.27 (s, 1H), 10.45 (s, 1H); APCI-MS (m/z) 538 (M + H)$^+$. |
| Example 87 | 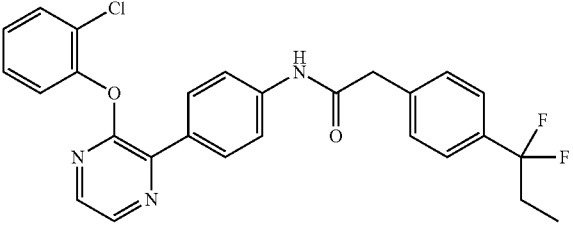 [SMILES: CCC(F)(F)c1ccc(CC(=O)Nc2ccc(-c3nccnc3Oc3ccccc3Cl)cc2)cc1]<br>N-(4-(3-(2-Chlorophenoxy)pyrazin-2-yl)phenyl)-2-(4-(1,1-difluoropropyl)phenyl)acetamide | Intermediate 2 and Intermediate 77 Method A | $^1$H NMR (300 MHz, DMSO-$d_6$) δ 1.89 (t, J = 7.2 Hz, 3H), 2.16-2.21 (m, 2H), 3.75 (s, 2H), 7.28-7.35 (m, 2H), 7.43-7.47 (m, 5H), 7.62 (d, J = 7.8 Hz, 1H), 7.76 (d, J = 8.7 Hz, 2H), 8.06-8.16 (m, 3H), 8.46 (s, 1H), 10.47 (s, 1H); ESI-MS (m/z) 494 (M + H)$^+$. |
| Example 88 | 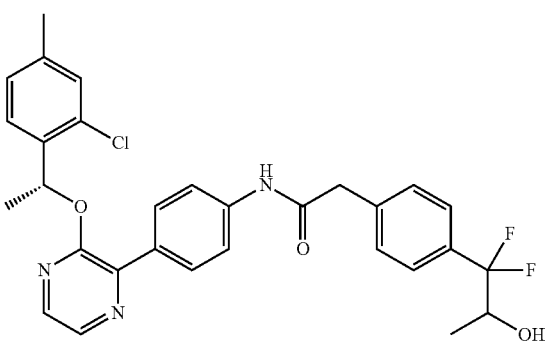 [SMILES: Cc1ccc([C@@H](C)Oc2nccnc2-c2ccc(NC(=O)Cc3ccc(C(F)(F)C(C)O)cc3)cc2)c(Cl)c1]<br>N-(4-(3-((R)-1-(2-Chloro-4-methylphenyl)ethoxy)pyrazin-2-yl)phenyl)-2-(4-(1,1-difluoro-2-hydroxypropyl)phenyl)acetamide | Intermediate 3 and Intermediate 78 Method B | $^1$H NMR (300 MHz, DMSO-$d_6$) δ 1.07 (d, J = 6.6 Hz, 3H), 1.62 (d, J = 6.3 Hz, 3H), 2.25 (s, 3H), 3.74 (s, 2H), 4.04 (br s, 1H), 5.52 (d, J = 5.7 Hz, 1H), 6.43-6.47 (m, 1H), 7.10 (d, J = 7.8 Hz, 1H), 7.27-7.34 (m, 2H), 7.45 (s, 4H), 7.74 (d, J = 9.0 Hz, 2H), 8.05-8.11 (m, 3H), 8.24 (s, 1H), 10.44 (s, 1H); APCI-MS (m/z) 553 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 89 | 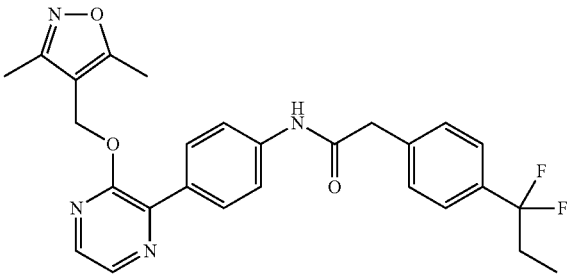 [SMILES: CCC(F)(F)c1ccc(CC(=O)Nc2ccc(-c3nccnc3OCc3c(C)noc3C)cc2)cc1]<br>2-(4-(1,1-Difluoropropyl)phenyl)-N-(4-(3-((3,5-dimethylisoxazol-4-yl)methoxy)pyrazin-2-yl)phenyl)acetamide | Intermediate 2 and Intermediate 79 Method A | $^1$H NMR (300 MHz, DMSO-$d_6$) δ 0.89 (t, J = 7.2 Hz, 3H), 2.11-2.19 (m, 2H), 2.21 (s, 3H), 2.43 (s, 3H), 3.73 (s, 2H), 5.29 (s, 2H), 7.43-7.48 (m, 4H), 7.68 (d, J = 8.7 Hz, 2H), 7.95 (d, J = 8.7 Hz, 2H), 8.19 (s, 1H), 8.31 (s, 1H), 10.40 (s, 1H); ESI-MS (m/z) 493 (M + H)$^+$. |
| Example 90 | 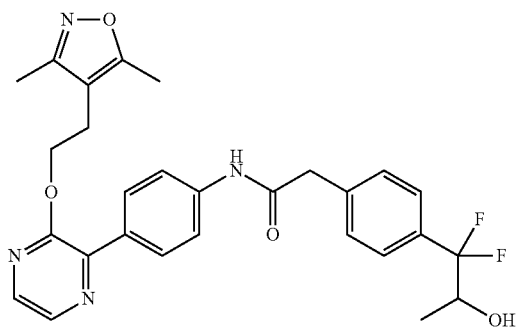 [SMILES: Cc1noc(C)c1CCOc1nccnc1-c1ccc(NC(=O)Cc2ccc(C(F)(F)C(C)O)cc2)cc1]<br>2-(4-(1,1-Difluoro-2-hydroxypropyl)phenyl)-N-(4-(3-(2-(3,5-dimethylisoxazol-4-yl)ethoxy)pyrazin-2-yl)phenyl)acetamide | Intermediate 3 and Intermediate 80 Method B | $^1$H NMR (300 MHz, DMSO-$d_6$) δ 1.07 (d, J = 5.7 Hz, 3H), 2.12 (s, 3H), 2.21 (s, 3H), 2.84 (t, J = 6.3 Hz, 2H), 3.74 (s, 2H), 4.04 (br s, 1H), 4.48 (d, J = 6.3 Hz, 2H), 5.51 (d, J = 6.0 Hz, 1H), 7.44 (s, 4H), 7.69 (d, J = 8.4 Hz, 2H), 7.89 (d, J = 8.1 Hz, 2H), 8.14 (s, 1H), 8.27 (s, 1H), 10.41 (s, 1H); ESI-MS (m/z) 523 (M + H)$^+$. |
| Example 91 | 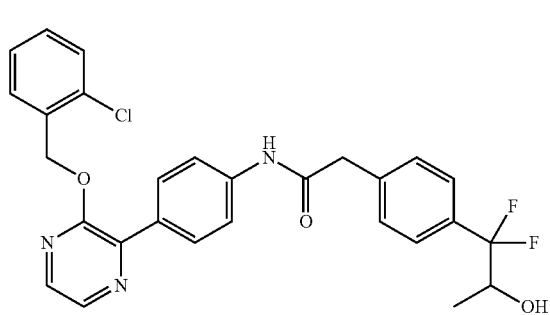 [SMILES: CC(O)C(F)(F)c1ccc(CC(=O)Nc2ccc(-c3nccnc3OCc3ccccc3Cl)cc2)cc1]<br>N-(4-(3-((2-Chlorobenzyl)oxy)pyrazin-2-yl)phenyl)-2-(4-(1,1-difluoro-2-hydroxypropyl)phenyl)acetamide | Intermediate 3 and Intermediate 81 Method B | $^1$H NMR (300 MHz, DMSO-$d_6$) δ 1.04 (d, J = 6.3 Hz, 3H), 3.70 (s, 2H), 4.00 (br s, 1H), 5.53 (s, 2H), 7.36-7.42 (m, 6H), 7.50-7.54 (m, 2H), 7.66 (d, J = 8.1 Hz, 2H), 8.00 (d, J = 8.4 Hz, 2H), 8.17(s, 1H), 8.31 (s, 1H), 10.38 (s, 1H); APCI-MS (m/z) 524 (M + H)$^+$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 92 | 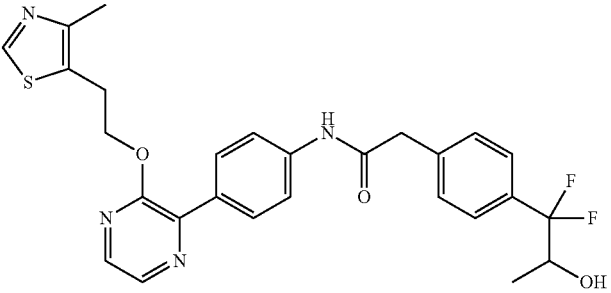 [SMILES: Cc1ncsc1CCOc1nccnc1-c1ccc(NC(=O)Cc2ccc(C(F)(F)C(C)O)cc2)cc1]<br>2-(4-(1,1-Difluoro-2-hydroxypropyl)phenyl)-N-(4-(3-(2-(4-methylthiazol-5-yl)ethoxy)pyrazin-2-yl)phenyl)acetamide | Intermediate 3 and Intermediate 82 Method B | $^1$H NMR (300 MHz, DMSO-$d_6$) δ 1.07 (d, J = 6.0 Hz, 3H), 2.30 (s, 3H), 3.32 (s, 2H), 3.74 (s, 2H), 4.05 (br s, 1H), 4.57 (br s, 2H), 5.52 (d, J = 6.0 Hz, 1H), 7.44 (s, 4H), 7.67 (d, J = 8.4 Hz, 2H), 7.90 (d, J = 8.4 Hz, 2H), 8.14 (s, 1H), 8.28 (s, 1H), 8.84 (s, 1H), 10.41 (s, 1H); ESI-MS (m/z) 525 (M + H)$^+$. |
| Example 93 | 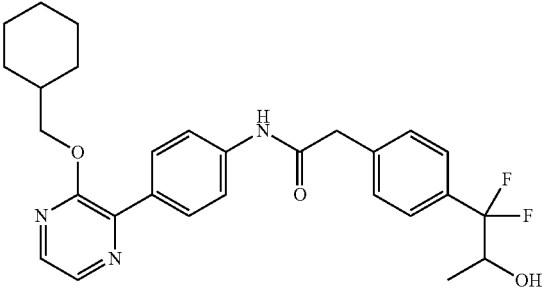 [SMILES: CC(O)C(F)(F)c1ccc(CC(=O)Nc2ccc(-c3nccnc3OCC3CCCCC3)cc2)cc1]<br>N-(4-(3-(Cyclohexylmethoxy)pyrazin-2-yl)phenyl)-2-(4-(1,1-difluoro-2-hydroxypropyl)phenyl)acetamide | Intermediate 3 and Intermediate 83 Method B | $^1$H NMR (300 MHz, DMSO-$d_6$) δ 1.07 (d, J = 6.6 Hz, 3H), 1.18-1.45 (m, 6H), 1.72-1.82 (m, 5H), 3.73 (s, 2H), 4.06 (br s, 1H), 4.19 (d, J = 6.0 Hz, 2H), 5.49 (d, J = 6.0 Hz, 1H), 7.44 (s, 4H), 7.71 (d, J = 9.0 Hz, 2H), 8.02 (d, J = 8.7 Hz, 2H), 8.12 (m, 1H), 8.26 (s, 1H), 10.39 (s, 1H); ESI-MS (m/z) 496 (M + H)$^+$. |
| Example 94 | 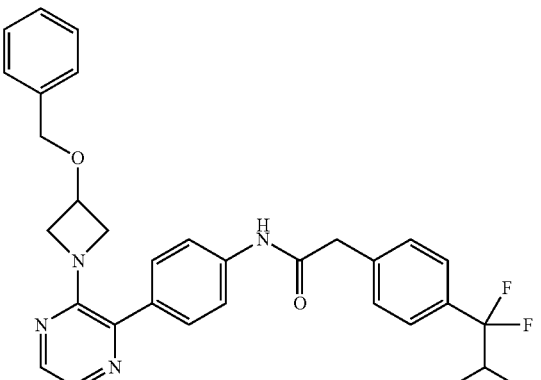<br>N-(4-(3-(3-(Benzyloxy)azetidin-1-yl)pyrazin-2-yl)phenyl)-2-(4-(1,1-difluoro-2-hydroxypropyl)phenyl)acetamide | Intermediate 3 and Intermediate 84 Method B | $^1$H NMR (300 MHz, DMSO-$d_6$) δ 1.07 (d, J = 5.7 Hz, 3H), 3.50-3.55 (m, 2H), 3.73 (s, 2H), 3.84-3.88 (m, 2H), 4.05 (br s, 1H), 4.30-4.35 (m, 1H), 4.36 (s, 2H), 5.47-5.51 (m, 1H), 7.26-7.30 (m, 5H), 7.45 (s, 4H), 7.53 (d, J = 8.4 Hz, 2H), 7.69 (d, J = 8.4 Hz, 2H), 8.02 (s, 1H), 8.07 (s, 1H), 10.37 (s, 1H); ESI-MS (m/z) 543 (M − H)$^−$. |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 95 | 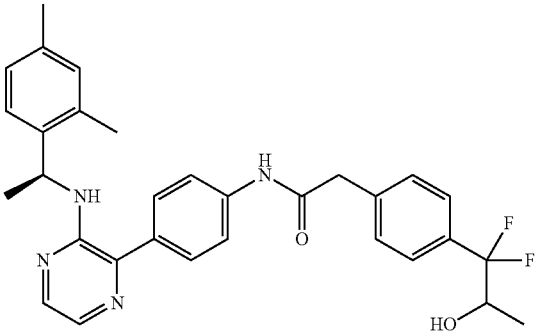 [SMILES: Cc1ccc([C@H](C)Nc2nccnc2-c2ccc(NC(=O)Cc3ccc(C(F)(F)C(C)O)cc3)cc2)c(C)c1]<br>2-(4-(1,1-Difluoro-2-hydroxypropyl)phenyl)-N-(4-(3-(((S)-1-(2,4-dimethylphenyl)ethyl)amino)pyrazin-2-yl)phenyl)acetamide | Intermediate 3 and Intermediate 63 Method B | $^1$H NMR (300 MHz, DMSO-$d_6$) δ 1.07 (d, J = 6.6 Hz, 3H), 1.36 (d, J = 6.9 Hz, 3H), 2.19 (s, 3H), 2.19 (s, 3H), 3.74 (s, 2H), 4.08 (br s, 1H), 5.23-5.27 (m, 1H), 5.48-5.52 (m, 1H), 6.20-6.24 (m, 1H), 6.89-6.93 (m, 2H), 7.21-7.26 (m, 2H), 7.45 (s, 4H), 7.62 (d, J = 9.0 Hz, 2H), 7.74 (d, J = 7.2 Hz, 2H), 7.87 (s, 1H), 10.39 (s, 1H); APCI-MS (m/z) 531 (M + H)$^+$. |
| Example 96 | 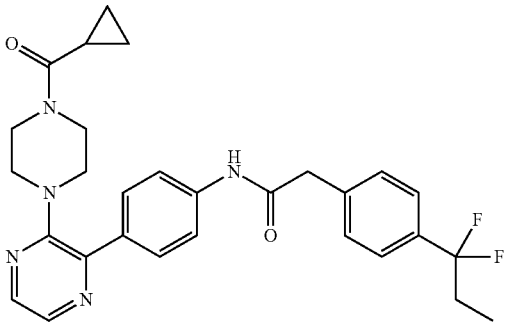 [SMILES: CCC(F)(F)c1ccc(CC(=O)Nc2ccc(-c3nccnc3N3CCN(C(=O)C4CC4)CC3)cc2)cc1]<br>N-(4-(3-(4-(Cyclopropanecarbony)piperazin-1-yl)pyrazin-2-yl)phenyl)-2-(4-(1,1-difluoropropyl)phenyl)acetamide | Intermediate 2 and Intermediate 49 Method A | $^1$H NMR (300 MHz, DMSO-$d_6$) δ 0.66-0.76 (m, 4H), 0.90 (t, J = 7.2 Hz, 3H), 1.91-1.95 (m, 1H), 2.19-2.46 (m, 2H), 3.08-3.12 (m, 4H), 3.48-3.52 (m, 2H), 3.65-3.72 (m, 2H), 3.74 (s, 2H), 7.47 (s, 4H), 7.73 (d, J = 8.4 Hz, 2H), 7.90 (d, J = 9.0 Hz, 2H), 8.15 (s, 1H), 8.20 (s, 1H), 10.39 (s, 1H). |
| Example 97 | 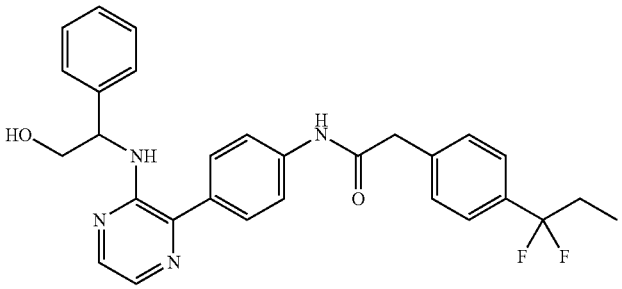 [SMILES: CCC(F)(F)c1ccc(CC(=O)Nc2ccc(-c3nccnc3NC(CO)c3ccccc3)cc2)cc1]<br>2-(4-(1,1-Difluoropropyl)phenyl)-N-(4-(3-((2-hydroxy-1-phenylethyl)amino)pyrazin-2-yl)phenyl)acetamide | Intermediate 2 and Intermediate 85 Method A | $^1$H NMR (300 MHz, DMSO-$d_6$) δ 0.90 (t, J = 7.2 Hz, 3H), 2.14-2.25 (m, 2H), 3.34-3.38 (m, 1H), 3.56-3.61 (m, 1H), 3.74 (s, 2H), 4.83 (br s, 1H), 5.52 (br s, 1H), 6.02 (d, J = 4.8 Hz, 1H), 7.25-7.35 (m, 6H), 7.47 (s, 3H), 7.53 (d, J = 8.7 Hz, 2H), 7.71 (d, J = 8.7 Hz, 2H), 7.81 (s, 1H), 7.96 (s, 1H), 10.39 (s, 1H). |

TABLE 1-continued

Chemical name, structure Intermediate No., method of preparation and analytical data of Example 3-51 & 54-99

| Example No. | Chemical Name and Structure | Intermediate/ Method | Analytical Data |
|---|---|---|---|
| Example 98 | 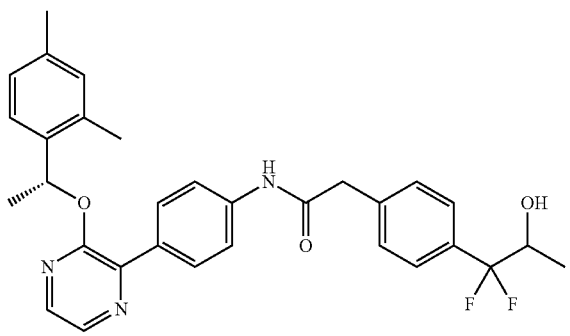 [SMILES: Cc1ccc([C@@H](C)Oc2nccnc2-c2ccc(NC(=O)Cc3ccc(C(F)(F)C(C)O)cc3)cc2)c(C)c1]<br>2-(4-(1,1-Difluoro-2-hydroxypropyl)phenyl)-N-(4-(3-((R)-1-(2,4-dimethylphenyl)ethoxy)pyrazin-2-yl)phenyl)acetamide | Intermediate 3 and Intermediate 86 Method B | $^1$H NMR (300 MHz, DMSO-$d_6$) δ 1.07 (d, J = 6.3 Hz, 3H), 1.59 (d, J = 6.3 Hz, 3H), 2.20 (s, 3H), 2.34 (s, 3H), 3.56 (s, 1H), 3.74 (s, 2H), 4.04 (br s, 1H), 5.50 (d, J = 6.3 Hz, 1H), 6.35 (d, J = 6.9 Hz, 1H), 6.91-6.98 (m, 2H), 7.23 (d, J = 7.8 Hz, 1H), 7.45 (s, 4H), 7.73 (d, J = 8.1 Hz, 2H), 8.08 (d, J = 8.1 Hz, 2H), 8.22 (s, 1H), 10.41 (s, 1H). |
| Example 99 | 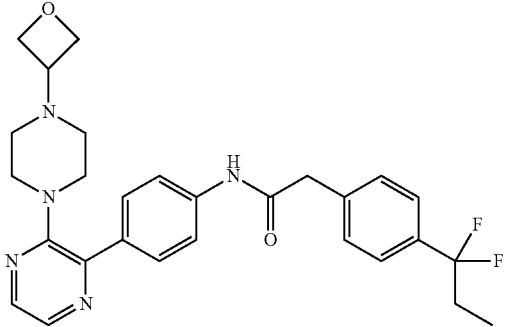 [SMILES: CCC(F)(F)c1ccc(CC(=O)Nc2ccc(-c3nccnc3N3CCN(C4COC4)CC3)cc2)cc1]<br>2-(4-(1,1-Difluoropropyl)phenyl)-N-(4-(3-(4-(oxetan-3-yl)piperazin-1-yl)pyrazin-2-yl)phenyl)acetamide | Intermediate 2 and Intermediate 87 Method A | $^1$H NMR (300 MHz, DMSO-$d_6$) δ 0.90 (t, J = 7.5 Hz, 3H), 2.18-2.28 (m, 6H), 3.08-3.12 (m, 4H), 3.34-3.44 (m, 1H), 3.73 (s, 2H), 4.39 (t, J = 6.3 Hz, 2H), 4.50 (t, J = 6.3 Hz, 2H), 7.46-7.50 (m, 4H), 7.70 (d, J = 8.7 Hz, 2H), 7.85 (d, J = 8.1 Hz, 2H), 8.12 (s, 1H), 8.16 (s, 1H), 10.37 (s, 1H); APCI-MS (m/z) 508 (M + H)$^+$. |

Pharmacological Activity

Biological Assay

The compounds described herein were screened for ROR gamma modulator activity using the TR-FRET assay (LanthaScreen™ available from Invitrogen of Carlsbad, Calif.) as described in JBC 2011, 286, 26: 22707-10; and *Drug Metabolism and Disposition* 2009, 37, 10: 2069-78.

TR-FRET Assay for ROR Gamma

The assay is based on the principle that binding of the agonist to the ROR gamma causes a conformational change around helix 12 in the ligand binding domain, resulting in higher affinity for the co-activator peptide. ROR gamma being constitutively active, the Fluorescein-D22 co-activator peptide used in the assay is recruited in the absence of a ligand. Binding of the co-activator peptide, causes an increase in the TR-FRET signal while binding of an antagonist decreases the recruitment of the co-activator peptide, causing a decrease in the TR-FRET signal compared to control with no compound. The assay was performed using a two-step procedure, pre-incubation step with the compound followed by the detection step on addition of the anti-GST tagged terbium (Tb) and fluorescein tagged fluorophores as the acceptor.

Test compounds or reference compounds such as T0901317 (Calbiochem) were dissolved in dimethylsulfoxide (DMSO) to prepare 10.0 mM stock solutions and diluted to the desired concentration. The final concentration of DMSO in the reaction was 4% (v/v). The assay mixture was prepared by mixing 10 nM of the GST-tagged ROR gamma ligand binding domain (LBD) in the assay buffer containing 25 mM HEPES (pH 7.4), 100 mM NaCl, 5 mM DTT and 0.01% BSA with or without the desired concentration of the compound. The reaction was incubated at 22° C. for 1 hour. The pre-incubation step was terminated by addition of the detection mixture containing 300 nM Fluorescein-D22 co-activator peptide and 10 nM lantha screen Tb-anti GST antibody into the reaction mixture. After shaking for 5 minutes the reaction was further incubated for 1 hour at room temperature and read at 4° C. on an Infinite F500 reader as per the kit instructions (Invitrogen). The inhibition of test compound was calculated based on the TR-FRET ratio of 520/495. The activity was calculated as a percent of control reaction. $IC_{50}$ values were calculated from dose response curve by nonlinear regression analysis using GraphPad Prism software.

The compounds prepared were tested using the above assay procedure and the results obtained are given in Table 1. Percentage inhibition at concentrations of 1.0 µM and 10.0 µM are given in the table along with $IC_{50}$ (nM) details for selected examples. The compounds were found to have $IC_{50}$ less than 500 nM, preferably less than 100 nM, more preferably less than 50 nM.

The $IC_{50}$ (nM) values are set forth in Table 1 wherein "A" refers to an $IC_{50}$ value of less than 50 nM; "B" refers to $IC_{50}$ value in range of 50.01 to 100.0 nM; "C" refers to $IC_{50}$ values more than 100.01 to 500.0 nM and "D" refers to $IC_{50}$ values more than 500 nM.

TABLE 2

| | | In-vitro screening results | | |
|---|---|---|---|---|
| | | % Inhibition at | | |
| S. N. | Example No. | 1 µM | 10 µM | $IC_{50}$ range |
| 1. | Example 1 | 80.93 | 81.51 | A |
| 2. | Example 2 | 76.07 | 82.71 | A |
| 3. | Example 3 | 73.97 | 84.76 | B |
| 4. | Example 4 | 60.73 | 77.81 | D |
| 5. | Example 5 | 81.48 | 84.41 | A |
| 6. | Example 6 | 87.42 | 86.39 | A |
| 7. | Example 7 | 82.98 | 86.21 | A |
| 8. | Example 8 | 73.56 | 85.3 | C |
| 9. | Example 9 | 55.24 | 72.12 | D |
| 10. | Example 10 | 78.16 | 82.96 | B |
| 11. | Example 11 | 78.76 | 83.8 | A |
| 12. | Example 12 | 85.57 | 83.01 | A |
| 13. | Example 13 | 82.69 | 84.39 | A |
| 14. | Example 14 | 74.44 | 83.84 | C |
| 15. | Example 15 | 72.19 | 80.64 | C |
| 16. | Example 16 | 69.91 | 60.55 | — |
| 17. | Example 17 | 60.46 | 74.44 | — |
| 18. | Example 18 | 32.41 | 71.16 | — |
| 19. | Example 19 | 42.16 | 48.79 | — |
| 20. | Example 20 | 65.47 | 78.01 | — |
| 21. | Example 21 | 37.41 | 38.32 | — |
| 22. | Example 22 | 46.68 | 56.2 | — |
| 23. | Example 23 | 36.56 | 68.59 | — |
| 24. | Example 24 | 61.61 | 83.62 | — |
| 25. | Example 25 | 18.89 | 59.74 | — |
| 26. | Example 26 | 71.91 | 79.57 | C |
| 27. | Example 27 | 78.57 | 83.46 | A |
| 28. | Example 28 | 73.7 | 77.57 | C |
| 29. | Example 29 | 77.07 | 79.83 | A |
| 30. | Example 30 | 81.32 | 82.48 | A |
| 31. | Example 31 | 77.74 | 81.65 | A |
| 32. | Example 32 | 15.29 | 65.07 | — |
| 33. | Example 33 | 27.32 | 75.76 | — |
| 34. | Example 34 | 57.91 | 66.83 | — |
| 35. | Example 35 | 72.79 | 73.32 | C |
| 36. | Example 36 | 2.6 | 8.3 | — |
| 37. | Example 37 | 71.1 | 73.5 | A |
| 38. | Example 38 | 70.7 | 74.9 | C |
| 39. | Example 39 | 65.5 | 72.8 | — |
| 40. | Example 40 | 71.4 | 76.9 | A |
| 41. | Example 41 | 4.2 | 48.7 | — |
| 42. | Example 42 | 51.9 | 76.1 | — |
| 43. | Example 43 | 12.21 | 33.58 | — |
| 44. | Example 44 | 76.87 | 84.14 | A |
| 45. | Example 45 | 81.09 | 80.8 | A |
| 46. | Example 46 | 69.96 | 77.08 | — |
| 47. | Example 47 | 82.32 | 82.33 | A |
| 48. | Example 48 | 79.22 | 84.07 | A |
| 49. | Example 49 | 83.95 | 88.78 | A |
| 50. | Example 50 | 83.15 | 82.98 | A |
| 51. | Example 51 | 73.23 | 81.03 | A |
| 52. | Example 52 | 78.62 | 84 | A |
| 53. | Example 53 | 70.49 | 77.01 | A |
| 54. | Example 54 | 23.1 | 42.4 | — |
| 55. | Example 55 | 56.5 | 64.6 | — |
| 56. | Example 56 | 73.44 | 85.81 | C |
| 57. | Example 57 | 69.4 | 85.2 | — |
| 58. | Example 58 | 80.3 | 90.7 | C |
| 59. | Example 59 | 58.65 | 79.73 | — |
| 60. | Example 60 | 69.57 | 82.97 | C |
| 61. | Example 61 | 84.15 | 91.38 | B |
| 62. | Example 62 | 65.6 | 84.79 | — |
| 63. | Example 63 | 86.85 | 91.23 | B |
| 64. | Example 64 | 76.23 | 84.93 | C |
| 65. | Example 65 | 76.06 | 83.2 | C |
| 66. | Example 66 | 88.41 | 90.15 | A |
| 67. | Example 67 | 87.89 | 92.37 | A |
| 68. | Example 68 | 93.52 | 96.9 | A |
| 69. | Example 69 | 97.05 | 97.09 | A |
| 70. | Example 70 | 94.1 | 93.75 | A |
| 71. | Example 71 | 20.49 | 73.7 | — |
| 72. | Example 72 | 86.9 | 93.39 | A |
| 73. | Example 73 | 78.51 | 89.22 | C |
| 74. | Example 74 | 79.25 | 89.87 | B |
| 75. | Example 75 | 75.7 | 84.25 | B |
| 76. | Example 76 | 78.06 | 87.5 | C |
| 77. | Example 77 | 80.49 | 73.7 | A |
| 78. | Example 78 | 89.59 | 93.87 | A |
| 79. | Example 79 | 69.54 | 85.85 | C |
| 80. | Example 80 | 69.47 | 86.27 | C |
| 81. | Example 81 | 83.18 | 88.3 | C |
| 82. | Example 82 | 37.88 | 80.06 | — |
| 83. | Example 83 | 79.67 | 78.18 | B |
| 84. | Example 84 | 83.77 | 81.93 | B |
| 85. | Example 85 | 74.77 | 79.6 | C |
| 86. | Example 86 | 84.51 | 86.05 | B |
| 87. | Example 87 | 16.28 | 32.43 | — |
| 88. | Example 88 | 87.37 | 85.55 | A |
| 89. | Example 89 | 58.75 | 74.57 | — |
| 90. | Example 90 | 90.71 | 93.86 | A |
| 91. | Example 91 | 79.34 | 82.61 | A |
| 92. | Example 92 | 83.54 | 88.04 | B |
| 93. | Example 93 | 86.56 | 94.07 | C |
| 94. | Example 94 | 15.85 | 45.59 | — |
| 95. | Example 95 | 93.66 | 95.43 | A |
| 96. | Example 96 | 47.68 | 77.2 | — |
| 97. | Example 97 | 22.5 | 46.22 | — |
| 98. | Example 98 | 89.55 | 89.01 | A |
| 99. | Example 99 | 79.16 | 91.88 | B |

(—): Not determined

What is claimed is:

1. A compound of formula (I)

or a tautomer thereof, stereoisomer thereof, or a pharmaceutically acceptable salt thereof, wherein
Ring A is selected from

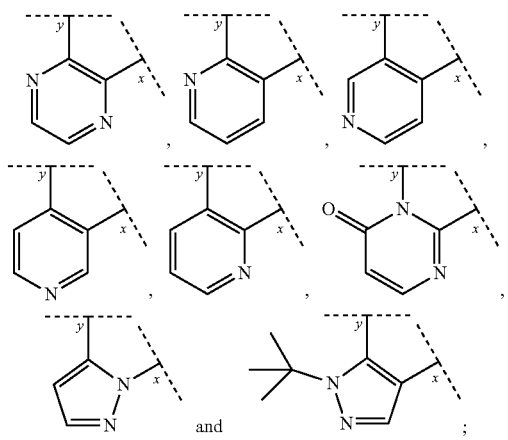

Ring B is selected from $C_{3-6}$cycloalkyl, $C_{6-14}$aryl, 3-15 membered heterocyclyl and 5 to 14 membered heteroaryl;

L is absent or is $_y*-X-(CR^xR^y)_t-*_z$; X is selected from O, $NR^{x1}$ and

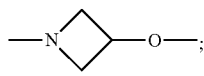

each of x, y and z represents a point of attachment;
$R^1$ is selected from hydroxyl, $C_{1-8}$alkyl and $C_{1-8}$alkoxy;
each occurrence of $R^2$ is independently selected from cyano, halogen, hydroxyl, $C_{1-8}$alkyl, $C_{1-8}$alkoxy, $C_{1-8}$alkoxy$C_{1-8}$alkyl, halo$C_{1-8}$alkyl, halo$C_{1-8}$alkoxy, hydroxy$C_{1-8}$alkyl, $C(O)C_{1-8}$alkyl, $C_{3-6}$cycloalkyl, $C(O)C_{3-6}$cycloalkyl and 3 to 15 membered heterocyclic ring;
each occurrence of $R^3$ is independently selected from halogen, cyano, $C_{1-8}$alkyl, halo$C_{1-8}$alkyl and $C_{3-6}$cycloalkyl;
each occurrence of $R^4$ is independently selected from halogen, cyano, $C_{1-8}$alkyl, halo$C_{1-8}$alkyl and $C_{3-6}$cycloalkyl;
each occurrence of $R^5$ is independently selected from halogen, cyano, $C_{1-8}$alkyl, halo$C_{1-8}$alkyl and $C_{3-6}$cycloalkyl;
$R^a$ and $R^b$, which may be the same or different, are each independently selected from hydrogen and $C_{1-8}$alkyl;
$R^x$ and $R^y$ which may be the same or different, are each independently selected from hydrogen, $C_{1-8}$alkyl and hydroxy$C_{1-8}$alkyl; or $R^x$ and $R^y$ together with the carbon atom to which they are attached, form a 3 to 6 membered cycloalkyl ring;
$R^{x1}$ is selected from hydrogen or $C_{1-8}$alkyl;
'n' is 0, 1, 2 or 3;
'm' is 0, 1 or 2;
'p' is 0, 1 or 2;
'q' is 0, 1, 2 or 3 and
't' is 0, 1, 2 or 3.

2. The compound according to claim 1, wherein ring B is cyclohexyl, phenyl, 6-oxo-1,6-dihydropyridinyl, piperidinyl, piperazinyl, morpholinyl, isoxazolyl, pyrazolyl, thiazolyl, pyridinyl or pyrimidinyl.

3. The compound according to claim 1, wherein L is absent.

4. The compound according to claim 1, wherein L is

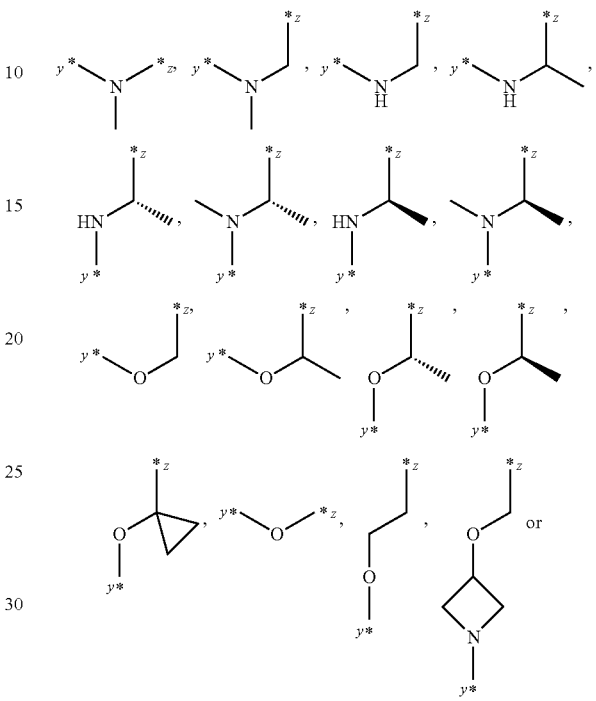

5. The compound according to claim 1, wherein $R^1$ is hydroxyl, methyl or methoxy.

6. The compound according to claim 1, wherein 'n' is 0.

7. The compound according to claim 1, wherein each $R^2$ is independently cyano, F, Cl, methyl, ethyl, methoxy, methoxyethyl, trifluoromethyl, cyclopropyl, C(O)methyl, C(O)cyclopropyl or oxetan-3-yl and 'n' is 1 or 2.

8. The compound according to claim 1, wherein 'm' is 0.

9. The compound according to claim 1, wherein $R^3$ is methyl, tert-butyl or trifluoromethyl and 'm' is 1.

10. The compound according to claim 1, wherein 'p' is 0.

11. The compound according to claim 1, wherein one of $R^a$ and $R^b$ is hydrogen and the other is hydrogen or methyl.

12. The compound according to claim 1, wherein $R^1$ is methyl; $R^a$ is hydrogen and $R^b$ is hydrogen.

13. The compound according to claim 1, wherein $R^1$ is hydroxyl; $R^a$ is hydrogen and $R^b$ is methyl.

14. The compound according to claim 1, wherein

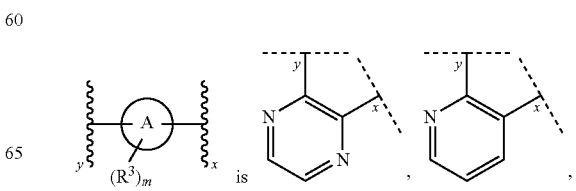

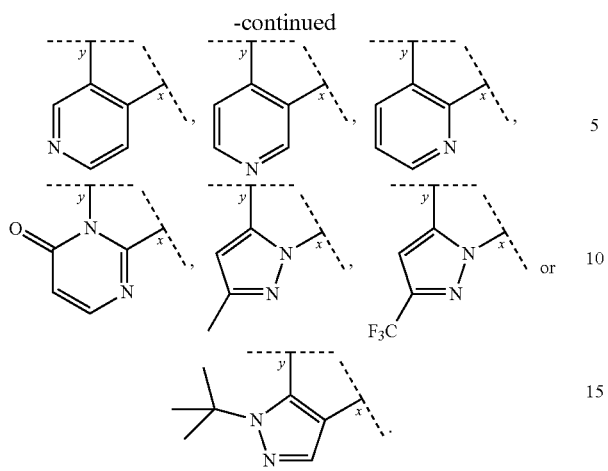

15. The compound according to claim 1, wherein

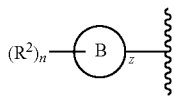

is cyclohexyl, phenyl, 2-chlorophenyl, 3-chlorophenyl, 4-chlorophenyl, 4-cyanophenyl, 2-cyclopropylphenyl, 2,4-dichlorophenyl, 2-chloro-4-fluorophenyl, 4-chloro-2-fluorophenyl, 2-chloro-4-methylphenyl, 2,4-difluorophenyl, 3,4-difluorophenyl, 2,4-dimethylphenyl, 2-ethylphenyl, 2-fluorophenyl, 4-fluorophenyl, 2-fluoro-4-methylphenyl, 4-fluoro-2-methylphenyl, 4-methoxyphenyl, 4-(trifluoromethyl)phenyl, o-tolyl, p-tolyl, 4-acetylpiperazin-1-yl, 4-acetyl-2-methylpiperazin-1-yl, 4-(cyclopropanecarbonyl)piperazin-1-yl, 4,4-difluoropiperidin-1-yl, 4-ethylpiperazin-1-yl, 4-methylpiperazin-1-yl, 4-(2-methoxyethyl)piperazin-1-yl, 1-methyl-6-oxo-1,6-dihydropyridin-3-yl, 4-(oxetan-3-yl)piperazin-1-yl, morpholin-4-yl, (2S,6R)-2,6-dimethylmorpholin-4-yl, 3,5-dimethylisoxazol-4-yl, 1-methyl-1H-pyrazol-4-yl, 4-methylthiazol-5-yl, pyridin-4-yl or pyrimidin-5-yl.

16. The compound according to claim 1, wherein Ring A is

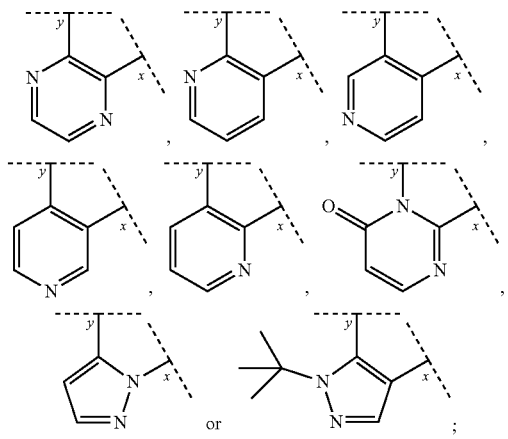

Ring B is cyclohexyl, phenyl, 6-oxo-1,6-dihydropyridinyl, piperidinyl, piperazinyl, morpholinyl, isoxazolyl, pyrazolyl, thiazolyl, pyridinyl or pyrimidinyl;

L is absent or is

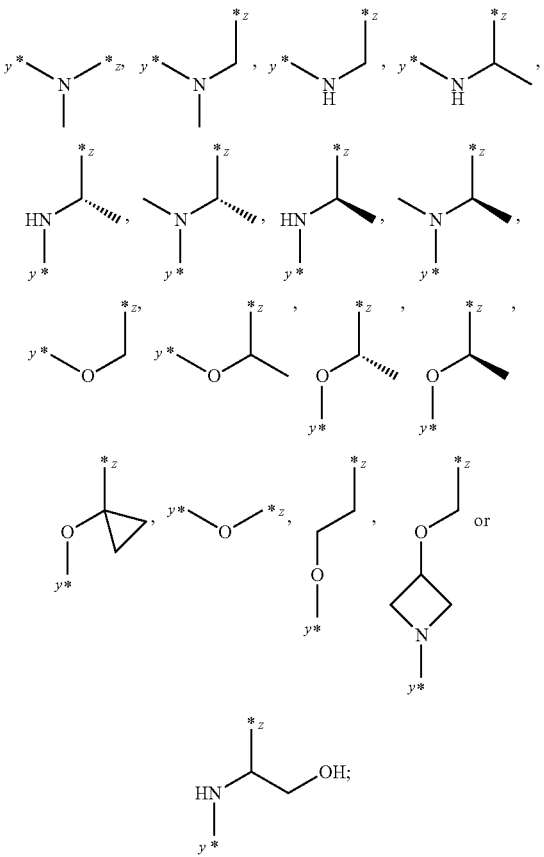

$R^1$ is hydroxyl, methyl or methoxy;

$R^2$ is cyano, F, Cl, methyl, ethyl, methoxy, methoxyethyl, trifluoromethyl, cyclopropyl, C(O)methyl, C(O)cyclopropyl or oxetan-3-yl;

$R^3$ is methyl, tert-butyl or trifluoromethyl;

$R^4$ is F;

$R^a$ is hydrogen;

$R^b$ is hydrogen or methyl;

'n' is 0, 1 or 2;

'm' is 0 or 1;

'p' is 0 or 1; and

'q' is 0.

17. The compound according to claim 1, wherein

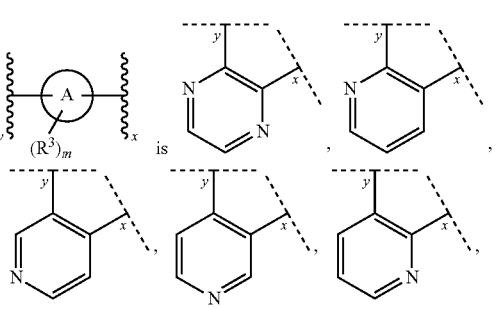

-continued

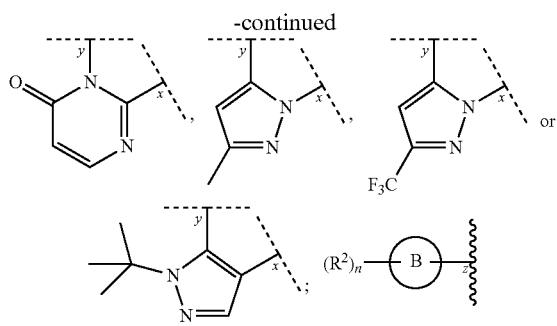

is cyclohexyl, phenyl, 2-chlorophenyl, 3-chlorophenyl, 4-chlorophenyl, 4-cyanophenyl, 2-cyclopropylphenyl, 2,4-dichlorophenyl, 2-chloro-4-fluorophenyl, 4-chloro-2-fluorophenyl, 2-chloro-4-methylphenyl, 2,4-difluorophenyl, 3,4-difluorophenyl, 2,4-dimethylphenyl, 2-ethylphenyl, 2-fluorophenyl, 4-fluorophenyl, 2-fluoro-4-methylphenyl, 4-fluoro-2-methylphenyl, 4-methoxyphenyl, 4-(trifluoromethyl)phenyl, o-tolyl, p-tolyl, 4-acetylpiperazin-1-yl, 4-acetyl-2-methylpiperazin-1-yl, 4-(cyclopropanecarbonyl)piperazin-1-yl, 4,4-difluoropiperidin-1-yl, 4-ethylpiperazin-1-yl, 4-methylpiperazin-1-yl, 4-(2-methoxyethyl)piperazin-1-yl, 1-methyl-6-oxo-1,6-dihydropyridin-3-yl, 4-(oxetan-3-yl)piperazin-1-yl, morpholin-4-yl, (2S,6R)-2,6-dimethylmorpholin-4-yl, 3,5-dimethylisoxazol-4-yl, 1-methyl-1H-pyrazol-4-yl, 4-methylthiazol-5-yl, pyridin-4-yl or pyrimidin-5-yl;

L is absent or is

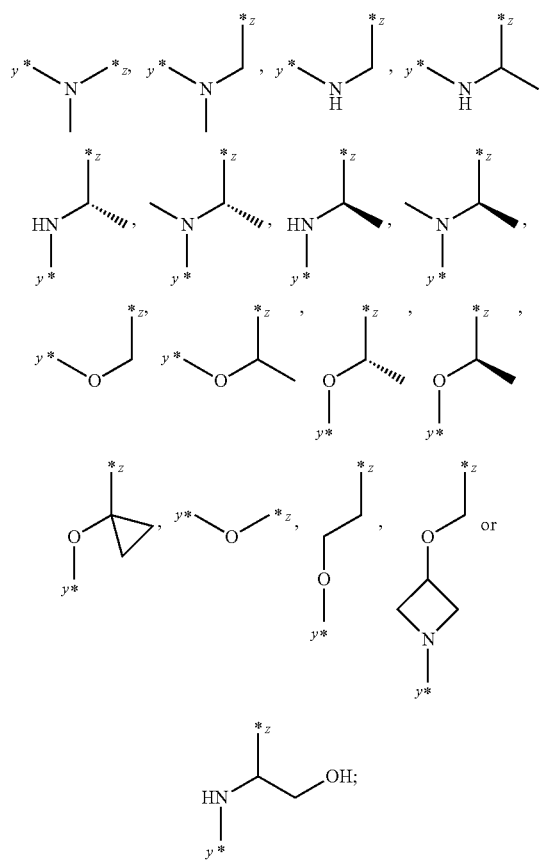

$R^1$ is hydroxyl, methyl or methoxy;
$R^4$ is F;
$R^a$ is hydrogen;
$R^b$ is hydrogen or methyl;
'p' is 0 or 1; and
'q' is 0.

18. The compound according to claim 1, represented by formula (II)

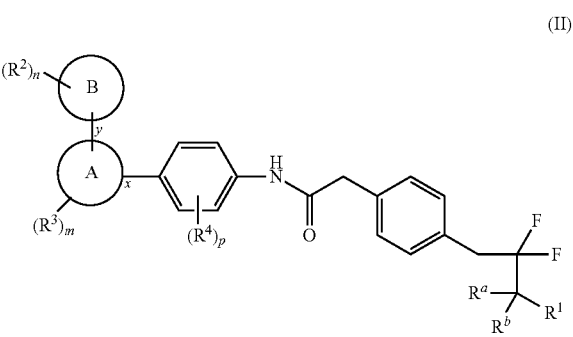

(II)

or a tautomer thereof, stereoisomer thereof or pharmaceutically acceptable salt thereof,
wherein
Ring A is selected from

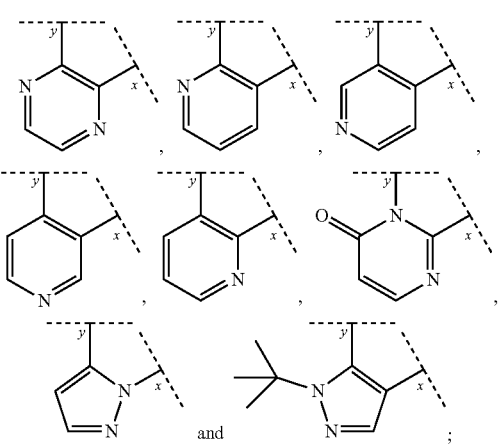

Ring B is selected from $C_{3-6}$cycloalkyl, $C_{6-14}$aryl, 3-15 membered heterocycyl and 5 to 14 membered heteroaryl;
each of x and y represents point of attachment;
$R^1$ is selected from hydroxyl, $C_{1-8}$alkyl and $C_{1-8}$alkoxy;
each occurrence of $R^2$ is independently selected from cyano, halogen, hydroxyl, $C_{1-8}$alkyl, $C_{1-8}$alkoxy, $C_{1-8}$alkoxyC$_{1-8}$alkyl, haloC$_{1-8}$alkyl, haloC$_{1-8}$alkoxy, hydroxyC$_{1-8}$alkyl, C(O)C$_{1-8}$alkyl, $C_{3-6}$cycloalkyl, C(O)C$_{3-6}$cycloalkyl and 3 to 15 membered heterocyclic ring;
each occurrence of $R^3$ is independently selected from halogen, cyano, $C_{1-8}$alkyl, haloC$_{1-8}$alkyl and $C_{3-6}$cycloalkyl;
each occurrence of $R^4$ is independently selected from halogen, cyano, $C_{1-8}$alkyl, haloC$_{1-8}$alkyl and $C_{3-6}$cycloalkyl;
$R^a$ and $R^b$, which may be same or different, are each independently selected from hydrogen and $C_{1-8}$alkyl;

'n' is 0, 1, 2 or 3;
'm' is 0, 1 or 2; and
'p' is 0, 1 or 2.

19. The compound according to claim 18, wherein

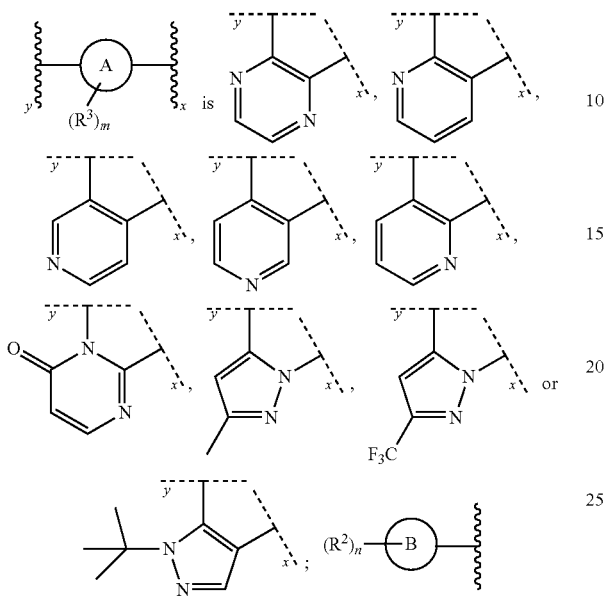

is phenyl, 2-chlorophenyl, 3-chlorophenyl, 4-chlorophenyl, 4-cyanophenyl, 2,4-dichlorophenyl, 2-chloro-4-fluorophenyl, 4-chloro-2-fluorophenyl, 2,4-difluorophenyl, 3,4-difluorophenyl, 2,4-dimethylphenyl, 2-ethylphenyl, 2-fluorophenyl, 4-fluorophenyl, 2-fluoro-4-methylphenyl, 4-fluoro-2-methylphenyl, 4-methoxyphenyl, 4-(trifluoromethyl)phenyl, o-tolyl, p-tolyl, 4-acetylpiperazin-1-yl, 4-acetyl-2-methylpiperazin-1-yl, 4-(cyclopropanecarbonyl)piperazin-1-yl, 4,4-difluoropiperidin-1-yl, 4-ethylpiperazin-1-yl, 4-methylpiperazin-1-yl, 4-(2-methoxyethyl)piperazin-1-yl, 1-methyl-6-oxo-1,6-dihydropyridin-3-yl, 4-(oxetan-3-yl)piperazin-1-yl, morpholin-4-yl, (2S,6R)-2,6-dimethylmorpholin-4-yl, 1-methyl-1H-pyrazol-4-yl, pyridin-4-yl or pyrimidin-5-yl;

$R^1$ is hydroxyl, methyl or methoxy;
$R^4$ is F;
$R^a$ is hydrogen;
$R^b$ is hydrogen or methyl; and
'p' is 0 or 1.

20. The compound according to claim 1, represented by formula (III)

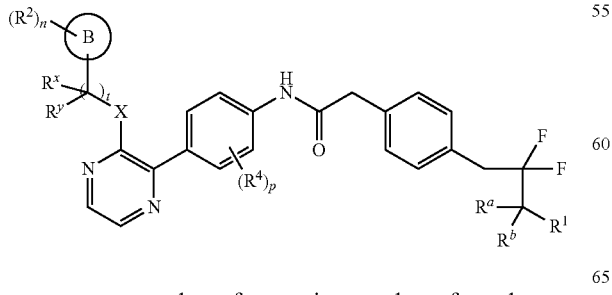

(III)

or a tautomer thereof, stereoisomer thereof or pharmaceutically acceptable salt thereof, wherein
Ring B is selected from $C_{3-6}$cycloalkyl, $C_{6-14}$aryl, 3-15 membered heterocyclyl and 5 to 14 membered heteroaryl;
X is selected from —O—, —$NR^{x1}$— and,

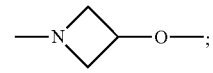

$R^1$ is selected from hydroxyl, $C_{1-8}$alkyl and $C_{1-8}$alkoxy;
each occurrence of $R^2$ is independently selected from cyano, halogen, hydroxyl, $C_{1-8}$alkyl, $C_{1-8}$alkoxy, $C_{1-8}$alkoxy$C_{1-8}$alkyl, halo$C_{1-8}$alkyl, halo$C_{1-8}$alkoxy, hydroxy$C_{1-8}$alkyl, C(O)$C_{1-8}$alkyl, $C_{3-6}$cycloalkyl, C(O)$C_{3-6}$cycloalkyl and 3 to 15 membered heterocyclic ring;
each occurrence of $R^4$ is independently selected from halogen, cyano, $C_{1-8}$alkyl, halo$C_{1-8}$alkyl and $C_{3-6}$cycloalkyl;
$R^a$ and $R^b$, which may be same or different, are each independently selected from hydrogen and $C_{1-8}$alkyl;
$R^x$ and $R^y$ which may be same or different, are each independently selected from hydrogen, $C_{1-8}$alkyl and hydroxy$C_{1-8}$alkyl; or $R^x$ and $R^y$ together with the carbon atom to which they are attached, form a 3 to 6 membered cycloalkyl ring;
$R^{x1}$ is selected from hydrogen or $C_{1-8}$alkyl;
'n' is 0, 1, 2 or 3;
'p' is 0, 1 or 2; and
't' is 0, 1, 2 or 3.

21. The compound according to claim 20, wherein

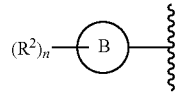

is cyclohexyl, phenyl, 2-chlorophenyl, 3-chlorophenyl, 4-chlorophenyl, 2-cyclopropylphenyl, 2-chloro-4-fluorophenyl, 2-chloro-4-methylphenyl, 2,4-dimethylphenyl, 4-fluoro-2-methylphenyl, 3,5-dimethylisoxazol-4-yl or 4-methylthiazol-5-yl;

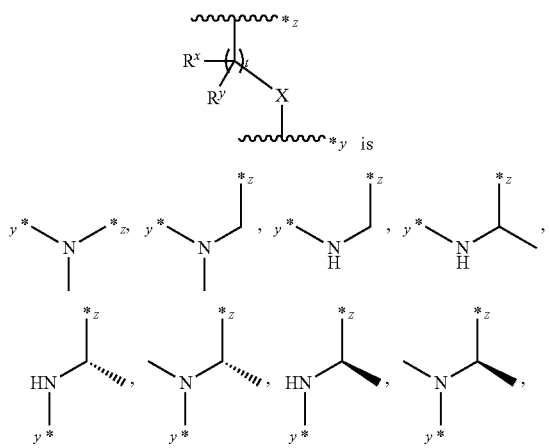

y and z represents point of attachment;
$R^1$ is hydroxyl, methyl or methoxy;
$R^4$ is F;
$R^a$ is hydrogen;
$R^b$ is hydrogen or methyl; and
'p' is 0 or 1.

22. The compound according to claim 1, selected from
N-(4-(3-(4-Chlorophenyl)pyrazin-2-yl)phenyl)-2-(4-(1,1-difluoropropyl)phenyl) acetamide;
N-(4-(3-(4-Chlorophenyl)pyrazin-2-yl)phenyl)-2-(4-(1,1-difluoro-2-hydroxy propyl)phenyl)acetamide;
N-(4-(3-(4-Chlorophenyl)pyrazin-2-yl)phenyl)-2-(4-(1,1-difluoro-2-methoxyethyl)phenyl)acetamide;
N-(4-(3-(3-Chlorophenyl)pyrazin-2-yl)phenyl)-2-(4-(1,1-difluoro-2-hydroxypropyl)phenyl)acetamide;
N-(4-(3-(2-Chlorophenyl)pyrazin-2-yl)phenyl)-2-(4-(1,1-difluoropropyl)phenyl) acetamide;
N-(4-(3-(4-Chloro-2-fluorophenyl)pyrazin-2-yl)phenyl)-2-(4-(1,1-difluoropropyl)phenyl) acetamide;
N-(4-(3-(4-Chlorophenyl)pyridin-2-yl)phenyl)-2-(4-(1,1-difluoropropyl)phenyl) acetamide;
2-(4-(1,1-Difluoro-2-hydroxypropyl)phenyl)-N-(4-(3-(4-fluorophenyl)pyrazin-2-yl)phenyl)acetamide;
2-(4-(1,1-Difluoro-2-hydroxypropyl)phenyl)-N-(4-(3-(3,4-difluorophenyl)pyrazin-2-yl)phenyl)acetamide;
N-(4-(3-(2,4-Difluorophenyl)pyrazin-2-yl)phenyl)-2-(4-(1,1-difluoropropyl)phenyl) acetamide;
2-(4-(1,1-Difluoropropyl)phenyl)-N-(4-(3-(2-fluorophenyl)pyrazin-2-yl)phenyl) acetamide;
2-(4-(1,1-Difluoropropyl)phenyl)-N-(4-(3-(4-(trifluoromethyl)phenyl)pyrazin-2-yl)phenyl)acetamide;
2-(4-(1,1-Difluoropropyl)phenyl)-N-(4-(3-(p-tolyl)pyrazin-2-yl)phenyl)acetamide;
2-(4-(1,1-Difluoropropyl)phenyl)-N-(4-(3-(4-fluorophenyl)pyridin-2-yl)phenyl)acetamide;
2-(4-(1,1-Difluoropropyl)phenyl)-N-(4-(3-phenylpyrazin-2-yl)phenyl)acetamide;
N-(4-(3-(4-Cyanophenyl)pyrazin-2-yl)phenyl)-2-(4-(1,1-difluoropropyl)phenyl) acetamide;
2-(4-(1,1-Difluoropropyl)phenyl)-N-(4-(3-(pyridin-4-yl)pyrazin-2-yl)phenyl)acetamide;
2-(4-(1,1-Difluoro-2-hydroxypropyl)phenyl)-N-(4-(3-(4,4-difluoropiperidin-1-yl)pyrazin-2-yl)phenyl)acetamide;
2-(4-(1,1-Difluoro-2-hydroxypropyl)phenyl)-N-(4-(3-morpholinopyrazin-2-yl)phenyl) acetamide;
2-(4-(1,1-Difluoropropyl)phenyl)-N-(4-(5-(4-fluorophenyl)-3-methyl-1H-pyrazol-1-yl)phenyl)acetamide;
N-(4-(1-(tert-Butyl)-5-(4-fluorophenyl)-1H-pyrazol-4-yl)phenyl)-2-(4-(1,1-difluoropropyl)phenyl)acetamide;
N-(4-(1-(tert-Butyl)-5-(4-fluorophenyl)-1H-pyrazol-4-yl)phenyl)-2-(4-(1,1-difluoro-2-hydroxypropyl)phenyl) acetamide;
2-(4-(1,1-Difluoropropyl)phenyl)-N-(4-(3-(1-methyl-1H-pyrazol-4-yl)pyrazin-2-yl)phenyl)acetamide;
N-(4-(3-(4-Acetylpiperazin-1-yl)pyrazin-2-yl)phenyl)-2-(4-(1,1-difluoropropyl)phenyl)acetamide;
2-(4-(1,1-Difluoropropyl)phenyl)-N-(4-(3-(1-methyl-6-oxo-1,6-dihydropyridin-3-yl)pyrazin-2-yl)phenyl)acetamide;
N-(4-(3-(4-Chlorophenyl)pyrazin-2-yl)-2-fluorophenyl)-2-(4-(1,1-difluoropropyl)phenyl)acetamide;
2-(4-(1,1-Difluoropropyl)phenyl)-N-(4-(3-(4-methoxyphenyl)pyrazin-2-yl)phenyl)acetamide;
2-(4-(1,1-Difluoropropyl)phenyl)-N-(4-(5-(4-fluorophenyl)-3-(trifluoromethyl)-1H-pyrazol-1-yl)phenyl)acetamide;
N-(4-(5-(2-Chlorophenyl)-3-(trifluoromethyl)-1H-pyrazol-1-yl)phenyl)-2-(4-(1,1-difluoropropyl)phenyl)acetamide;
N-(4-(3-(2-Chlorophenyl)pyridin-2-yl)phenyl)-2-(4-(1,1-difluoropropyl)phenyl) acetamide;
2-(4-(1,1-Difluoropropyl)phenyl)-N-(4-(3-(o-tolyl)pyrazin-2-yl)phenyl)acetamide;
2-(4-(1,1-Difluoropropyl)phenyl)-N-(4-(3-(4-methylpiperazin-1-yl)pyrazin-2-yl)phenyl)acetamide;
2-(4-(1,1-Difluoropropyl)phenyl)-N-(4-(3-(4-ethylpiperazin-1-yl)pyrazin-2-yl)phenyl) acetamide;
N-(4-(2-(4-Chlorophenyl)pyridin-3-yl)phenyl)-2-(4-(1,1-difluoropropyl)phenyl) acetamide;
N-(4-(4-(4-Chlorophenyl)pyridin-3-yl)phenyl)-2-(4-(1,1-difluoropropyl)phenyl) acetamide;
2-(4-(1,1-Difluoropropyl)phenyl)-N-(4-(3-((2S,6R)-2,6-dimethylmorpholino)pyrazin-2-yl)phenyl)acetamide;
N-(4-(3-(2-Chlorophenyl)pyrazin-2-yl)phenyl)-2-(4-(1,1-difluoro-2-hydroxypropyl)phenyl)acetamide;
N-(4-(5-(2,4-Dichlorophenyl)-3-methyl-1H-pyrazol-1-yl)phenyl)-2-(4-(1,1-difluoropropyl)phenyl)acetamide;
N-(4-(3-(2-Chloro-4-fluorophenyl)pyrazin-2-yl)phenyl)-2-(4-(1,1-difluoro-2-hydroxypropyl)phenyl)acetamide;
2-(4-(1,1-Difluoro-2-hydroxypropyl)phenyl)-N-(4-(3-(2-ethylphenyl)pyrazin-2-yl)phenyl)acetamide;
2-(4-(1,1-Difluoropropyl)phenyl)-N-(4-(3-(4-(2-methoxyethyl)piperazin-1-yl)pyrazin-2-yl)phenyl)acetamide;
N-(4-(3-(4-Acetyl-2-methylpiperazin-1-yl)pyrazin-2-yl)phenyl)-2-(4-(1,1-difluoropropyl)phenyl)acetamide;
2-(4-(1,1-Difluoropropyl)phenyl)-N-(4-(3-(pyrimidin-5-yl)pyrazin-2-yl)phenyl)acetamide;
2-(4-(1,1-Difluoropropyl)phenyl)-N-(4-(3-(4-fluoro-2-methylphenyl)pyrazin-2-yl)phenyl)acetamide;
N-(4-(3-(2-Chloro-4-fluorophenyl)pyrazin-2-yl)phenyl)-2-(4-(1,1-difluoropropyl)phenyl) acetamide;
N-(4-(3-(4-Chlorophenyl)pyridin-4-yl)phenyl)-2-(4-(1,1-difluoropropyl)phenyl) acetamide;
2-(4-(1,1-Difluoropropyl)phenyl)-N-(4-(3-(2,4-dimethylphenyl)pyrazin-2-yl)phenyl)acetamide;

2-(4-(1,1-Difluoropropyl)phenyl)-N-(4-(3-(2-fluoro-4-methylphenyl)pyrazin-2-yl)phenyl)acetamide;
N-(4-(1-(2-Chloro-4-fluorophenyl)-6-oxo-1,6-dihydropyrimidin-2-yl)phenyl)-2-(4-(1,1-difluoropropyl)phenyl)acetamide;
N-(4-(3-(2,4-Dichlorophenyl)pyrazin-2-yl)phenyl)-2-(4-(1,1-difluoropropyl)phenyl) acetamide;
2-(4-(1,1-Difluoro-2-hydroxypropyl)phenyl)-N-(4-(3-(2,4-dimethylphenyl)pyrazin-2-yl)phenyl)acetamide;
(S)-2-(4-(1,1-Difluoro-2-hydroxypropyl)phenyl)-N-(4-(3-(2-ethylphenyl)pyrazin-2-yl)phenyl)acetamide;
(R)-2-(4-(1,1-Difluoro-2-hydroxypropyl)phenyl)-N-(4-(3-(2-ethylphenyl)pyrazin-2-yl)phenyl)acetamide;
N-(4-(3-(4-(Cyclopropanecarbonyl)piperazin-1-yl)pyrazin-2-yl)phenyl)-2-(4-(1,1-difluoro-2-hydroxypropyl)phenyl)acetamide;
N-(4-(3-((4-Chlorophenyl)(methyl)amino)pyrazin-2-yl)phenyl)-2-(4-(1,1-difluoropropyl)phenyl)acetamide;
N-(4-(3-(Benzyl(methyl)amino)pyrazin-2-yl)phenyl)-2-(4-(1,1-difluoropropyl)phenyl) acetamide;
N-(4-(3-(Benzylamino)pyrazin-2-yl)phenyl)-2-(4-(1,1-difluoropropyl)phenyl)acetamide;
2-(4-(1,1-Difluoropropyl)phenyl)-N-(4-(3-((1-phenylethyl)amino)pyrazin-2-yl)phenyl)acetamide;
(R)-2-(4-(1,1-Difluoropropyl)phenyl)-N-(4-(3-((1-phenylethyl)amino)pyrazin-2-yl)phenyl)acetamide;
(R)-2-(4-(1,1-Difluoropropyl)phenyl)-N-(4-(3-(methyl(1-phenylethyl)amino)pyrazin-2-yl)phenyl)acetamide;
(S)-2-(4-(1,1-Difluoropropyl)phenyl)-N-(4-(3-((1-phenylethyl)amino)pyrazin-2-yl)phenyl)acetamide;
(S)-2-(4-(1,1-Difluoropropyl)phenyl)-N-(4-(3-(methyl(1-phenylethyl)amino)pyrazin-2-yl)phenyl)acetamide;
(S)—N-(4-(3-((1-(4-Chlorophenyl)ethyl)amino)pyrazin-2-yl)phenyl)-2-(4-(1,1-difluoropropyl)phenyl)acetamide;
(S)—N-(4-(3-((1-(3-Chlorophenyl)ethyl)amino)pyrazin-2-yl)phenyl)-2-(4-(1,1-difluoropropyl)phenyl)acetamide;
(S)—N-(4-(3-((1-(4-Chlorophenyl)ethyl)(methyl)amino)pyrazin-2-yl)phenyl)-2-(4-(1,1-difluoropropyl)phenyl)acetamide;
(S)—N-(4-(3-((1-(2-Chlorophenyl)ethyl)amino)pyrazin-2-yl)phenyl)-2-(4-(1,1-difluoropropyl)phenyl)acetamide;
(S)-2-(4-(1,1-Difluoropropyl)phenyl)-N-(4-(3-((1-(4-fluoro-2-methylphenyl)ethyl)amino)pyrazin-2-yl)phenyl)acetamide;
N-(4-(3-(((S)-1-(2-Chlorophenyl)ethyl)amino)pyrazin-2-yl)phenyl)-2-(4-(1,1-difluoro-2-hydroxypropyl)phenyl)acetamide;
(S)-2-(4-(1,1-Difluoropropyl)phenyl)-N-(4-(3-((1-(2,4-dimethylphenyl)ethyl)amino) pyrazin-2-yl)phenyl)acetamide;
(S)—N-(4-(3-((1-(2-Chloro-4-fluorophenyl)ethyl)amino)pyrazin-2-yl)phenyl)-2-(4-(1,1-difluoropropyl)phenyl)acetamide;
N-(4-(3-((Cyclohexylmethyl)amino)pyrazin-2-yl)phenyl)-2-(4-(1,1-difluoro-2-hydroxypropyl)phenyl)acetamide;
N-(4-(3-(((S)-1-(4-Chlorophenyl)ethyl)amino)pyrazin-2-yl)phenyl)-2-(4-(1,1-difluoro-2-hydroxypropyl)phenyl)acetamide;
N-(4-(3-(((S)-1-(2-Chlorophenyl)ethyl)amino)pyrazin-2-yl)-2-fluorophenyl)-2-(4-(1,1-difluoro-2-hydroxypropyl)phenyl)acetamide;
N-(4-(3-(((S)-1-(2-Chlorophenyl)ethyl)amino)pyrazin-2-yl)-3-fluorophenyl)-2-(4-(1,1-difluoro-2-hydroxypropyl)phenyl)acetamide;
N-(4-(3-(Benzyloxy)pyrazin-2-yl)phenyl)-2-(4-(1,1n-difluoropropyl)phenyl)acetamide;
2-(4-(1,1-Difluoropropyl)phenyl)-N-(4-(3-(1-phenylethoxy)pyrazin-2-yl)phenyl)acetamide;
N-(4-(3-((2-Chloro-4-fluorobenzyl)oxy)pyrazin-2-yl)phenyl)-2-(4-(1,1-difluoropropyl)phenyl)acetamide;
N-(4-(3-(Benzyloxy)pyrazin-2-yl)phenyl)-2-(4-(1,1-difluoro-2-hydroxypropyl)phenyl)acetamide;
(R)-2-(4-(1,1-Difluoropropyl)phenyl)-N-(4-(3-(1-phenylethoxy)pyrazin-2-yl)phenyl)acetamide;
(S)-2-(4-(1,1-Difluoropropyl)phenyl)-N-(4-(3-(1-phenylethoxy)pyrazin-2-yl)phenyl)acetamide;
N-(4-(3-(1-(2-Cyclopropylphenyl)ethoxy)pyrazin-2-yl)phenyl)-2-(4-(1,1-difluoropropyl)phenyl)acetamide;
2-(4-(1,1-Difluoro-2-hydroxypropyl)phenyl)-N-(4-(3-(1-phenylcyclopropoxy)pyrazin-2-yl)phenyl)acetamide;
(R)—N-(4-(3-(1-(2-Chlorophenyl)ethoxy)pyrazin-2-yl)phenyl)-2-(4-(1,1-difluoropropyl)phenyl)acetamide;
N-(4-(3-((R)-1-(2-Chlorophenyl)ethoxy)pyrazin-2-yl)phenyl)-2-(4-(1,1-difluoro-2-hydroxypropyl)phenyl)acetamide;
(S)—N-(4-(3-(1-(2-Chlorophenyl)ethoxy)pyrazin-2-yl)phenyl)-2-(4-(1,1-difluoropropyl)phenyl)acetamide;
N-(4-(3-((S)-1-(2-Chlorophenyl)ethoxy)pyrazin-2-yl)phenyl)-2-(4-(1,1-difluoro-2-hydroxypropyl)phenyl)acetamide;
N-(4-(3-(2-Chlorophenoxy)pyrazin-2-yl)phenyl)-2-(4-(1,1-difluoropropyl) phenyl)acetamide;
N-(4-(3-((R)-1-(2-Chloro-4-methylphenyl)ethoxy)pyrazin-2-yl)phenyl)-2-(4-(1,1-difluoro-2-hydroxypropyl)phenyl)acetamide;
2-(4-(1,1-Difluoropropyl)phenyl)-N-(4-(3-((3,5-dimethylisoxazol-4-yl)methoxy)pyrazin-2-yl)phenyl)acetamide;
2-(4-(1,1-Difluoro-2-hydroxypropyl)phenyl)-N-(4-(3-(2-(3,5-dimethylisoxazol-4-yl)ethoxy)pyrazin-2-yl)phenyl)acetamide;
N-(4-(3-((2-Chlorobenzyl)oxy)pyrazin-2-yl)phenyl)-2-(4-(1,1-difluoro-2-hydroxypropyl)phenyl)acetamide;
2-(4-(1,1-Difluoro-2-hydroxypropyl)phenyl)-N-(4-(3-(2-(4-methylthiazol-5-yl)ethoxy)pyrazin-2-yl)phenyl)acetamide;
N-(4-(3-(Cyclohexylmethoxy)pyrazin-2-yl)phenyl)-2-(4-(1,1-difluoro-2-hydroxypropyl)phenyl)acetamide;
N-(4-(3-(3-(Benzyloxy)azetidin-1-yl)pyrazin-2-yl)phenyl)-2-(4-(1,1-difluoro-2-hydroxypropyl)phenyl)acetamide;
2-(4-(1,1-Difluoro-2-hydroxypropyl)phenyl)-N-(4-(3-(((S)-1-(2,4-dimethylphenyl)ethyl)amino)pyrazin-2-yl)phenyl)acetamide;
N-(4-(3-(4-(Cyclopropanecarbonyl)piperazin-1-yl)pyrazin-2-yl)phenyl)-2-(4-(1,1-difluoropropyl)phenyl) acetamide;
2-(4-(1,1-Difluoropropyl)phenyl)-N-(4-(3-((2-hydroxy-1-phenylethyl)amino)pyrazin-2-yl)phenyl)acetamide;
2-(4-(1,1-Difluoro-2-hydroxypropyl)phenyl)-N-(4-(3-((R)-1-(2,4-dimethylphenyl)ethoxy)pyrazin-2-yl)phenyl)acetamide or 2-(4-(1,1-Difluoropropyl)phenyl)-N-(4-(3-(4-(oxetan-3-yl)piperazin-1-yl)pyrazin-2-yl)phenyl)acetamide and
pharmaceutically acceptable salts thereof.

23. A compound of formula

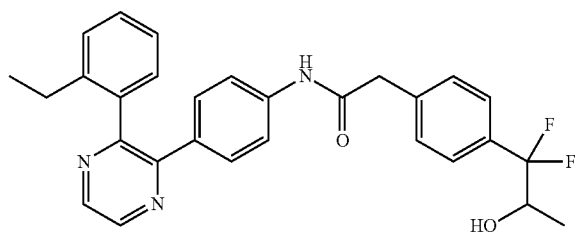 [SMILES: CCc1ccccc1-c1nccnc1-c1ccc(NC(=O)Cc2ccc(C(F)(F)C(C)O)cc2)cc1]

or a stereoisomer thereof, or a pharmaceutically acceptable salt thereof.

24. The compound according to claim 23, having formula

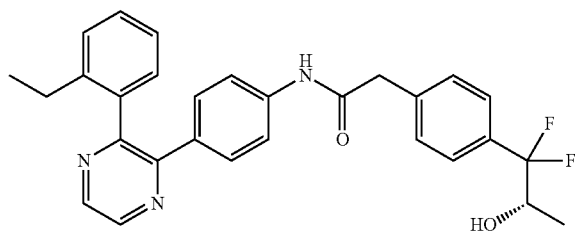

or a pharmaceutically acceptable salt thereof.

25. The compound according to claim 23, having formula

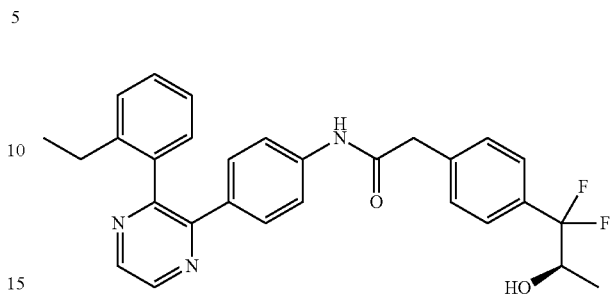

or a pharmaceutically acceptable salt thereof.

26. A pharmaceutical composition comprising a compound according to claim 1 and a pharmaceutically acceptable excipient.

27. The pharmaceutical composition according to claim 26, wherein the pharmaceutically acceptable excipient is a carrier or diluent.

* * * * *